US012583859B2

(12) United States Patent
O'Boyle et al.

(10) Patent No.: US 12,583,859 B2
(45) Date of Patent: Mar. 24, 2026

(54) PRMT5 INHIBITORS AND USES THEREOF

(71) Applicants: California Institute of Technology, Pasadena, CA (US); 1200 Pharma LLC, Culver City, CA (US); The Regents of the University of California, Oakland, CA (US)

(72) Inventors: Brendan M. O'Boyle, Monrovia, CA (US); Corey M. Reeves, San Mateo, CA (US); Justin A. Hilf, Los Angeles, CA (US); Brian M. Stoltz, San Marino, CA (US); Michael D. Bartberger, Sherman Oaks, CA (US); Steven J. Wittenberger, Sherman Oaks, CA (US); Oliver C. Loson, Culver City, CA (US); Martina S. McDermott, Los Angeles, CA (US); Neil A. O'Brien, Los Angeles, CA (US); Dennis Slamon, Los Angeles, CA (US)

(73) Assignees: California Institute of Technology, Pasadena, CA (US); 1200 Pharma LLC, Culver City, CA (US); The Regents of the University of California, Oakland, CA (US)

( * ) Notice: Subject to any disclaimer, the term of this patent is extended or adjusted under 35 U.S.C. 154(b) by 912 days.

(21) Appl. No.: 17/598,152

(22) PCT Filed: Mar. 25, 2020

(86) PCT No.: PCT/US2020/024654

§ 371 (c)(1),
(2) Date: Sep. 24, 2021

(87) PCT Pub. No.: WO2020/198323

PCT Pub. Date: Oct. 1, 2020

(65) Prior Publication Data

US 2022/0194949 A1 Jun. 23, 2022

Related U.S. Application Data

(60) Provisional application No. 62/874,773, filed on Jul. 16, 2019, provisional application No. 62/823,374, filed on Mar. 25, 2019.

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC ............................... C07D 487/04; A61P 35/00
See application file for complete search history.

(56) References Cited

U.S. PATENT DOCUMENTS

2017/0348313 A1 12/2017 Tatlock et al.

FOREIGN PATENT DOCUMENTS

| | | | |
|---|---|---|---|
| WO | WO-96/40686 | A1 | 12/1996 |
| WO | WO-2014/153226 | A1 | 9/2014 |
| WO | WO-2016/135582 | A1 | 9/2016 |
| WO | WO-2017/032840 | A1 | 3/2017 |
| WO | WO-2017/153186 | A1 | 9/2017 |
| WO | WO-2018/065365 | A1 | 4/2018 |
| WO | WO-2018/160824 | A1 | 9/2018 |
| WO | WO-2019/032859 | A1 | 2/2019 |
| WO | WO-2019/110734 | A1 | 6/2019 |
| WO | WO-2020/198323 | A1 | 10/2020 |

OTHER PUBLICATIONS

Extended European Search Report for EP Application No. 20778402.6 dated Oct. 27, 2022.
Dang et al., "Synthesis of 4'-Spironucleoside via Radical Translocation Cyclization Reaction," Chemical Research in Chinese Universities, 24(4): 473-476 (2008).
Gao et al., "Structural Determinants of A3 Adenosine Receptor Activation: Nucleoside Ligands at the Agonist/Antagonist Boundary," Journal of Medicinal Chemistry, 45(20): 4471-4484 (2002).
International Search Report and Written Opinion for International Application No. PCT/US2020/024654 mailed Jul. 15, 2020.
Paquette et al., "Conformationally Constrained Purine Mimics. Incorporation of Adenine and Guanine into Spirocyclic Nucleosides," The Journal of Organic Chemistry, 69(17): 5555-5562 (2004).

(Continued)

*Primary Examiner* — Kortney L. Klinkel
*Assistant Examiner* — Richard Grant Peckham
(74) *Attorney, Agent, or Firm* — Foley Hoag LLP; Janine S. Ladislaw; Lawrence P. Tardibono

(57) ABSTRACT

The present disclosure describes compounds of formulas (I)-(V) and methods of making the same. The compounds of the present disclosure are useful as inhibitors of PRMT5 activity and in methods of treating cancers and other diseases.

(Formula I)

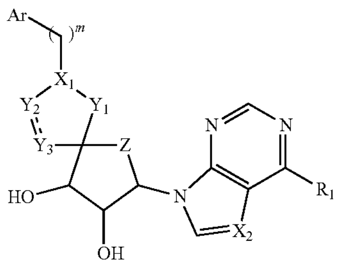

24 Claims, No Drawings

(56) References Cited

OTHER PUBLICATIONS

Srimongkolpithak., "The Search for Novel Histone Lysine Methyltransferase Inhibitors, A thesis submitted for the degree of Doctor of Philosophy," Department of Chemistry, Imperial College London: (2015).

PRMT5 INHIBITORS AND USES THEREOF

CROSS-REFERENCE TO RELATED APPLICATIONS

This application is a 371(c) national stage of PCT/US2020/024654, filed Mar. 25, 2020, which claims the benefit of U.S. Provisional Application No. 62/823,374, filed Mar. 25, 2019, and U.S. Provisional Application No. 62/874,773, filed Jul. 16, 2019, each of which is incorporated by reference herein in its entirety.

BACKGROUND

Increased protein expression of PRMT5 is implicated in its tumorigenicity because it is one of the major symmetrical arginine methyltransferases and is involved in a variety of cellular processes. Both elevated PRMT5-MEP50 protein level and cytoplasmic accumulation of this complex are also implicated in cancer tumorigenesis, and have been correlated with poor clinical outcome. There exists a need for new small-molecules (i.e., compounds) as provided herein that inhibit PRMT5 activity for treating a broad spectrum of cancers and other diseases.

SUMMARY

In certain embodiments, the invention relates to a compound having (a) the structure of Formula I.

(Formula I)

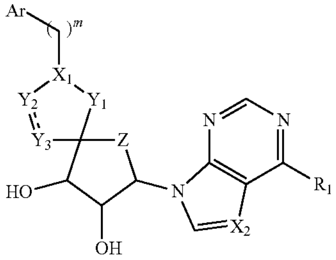

or a pharmaceutically acceptable salt thereof, wherein:

$\cdots$ is a double bond or a single bond;

Ar is an optionally substituted aryl or heteroaryl, wherein one, two, or three optional substituents are independently selected from halogen, hydroxyl, cyano, —C(O)$NH_2$, —C(O)N$(R_a)_2$, —C(O)O$(R_a)$, —C(O)$R_a$, —N$(R_a)_2$, —O$(R_a)$, $C_3$-$C_6$ cycloalkyl, $C_3$-$C_7$ heterocyclyl, optionally substituted $C_1$-$C_4$ alkyl and optionally substituted $C_2$-$C_6$ alkenyl;

$R_1$ is H, halogen, $C_1$-$C_4$ alkyl, $C_2$-$C_4$ alkenyl, —O$(R_a)$, $C_3$-$C_6$ cycloalkyl, $C_3$-$C_7$ heterocyclyl or N$(R_a)_2$;

$X_1$ and $X_2$ are each independently CH or N;

$Y_1$ is $(CH_2)_n$ or C(O), with the proviso that $Y_1$ cannot be C(O) when $Y_2$ or $Y_3$ is C(O);

$Y_2$ is $CH_2$, C(O), S, $SO_2$, O or $NR_a$, with the provisos that:

$Y_2$ cannot be C(O) when $Y_1$ or $Y_3$ is C(O); and $\cdots$ is a single bond;

$Y_3$ is $CH_2$ or C(O), with the provisos that:

$Y_3$ cannot be C(O) when $Y_1$ or $Y_2$ is C(O); and $\cdots$ is a single bond; or $Y_2$ and $Y_3$ are CH and $\cdots$ is a double bond;

Z is $CH_2$, O, S or NH;

$R_a$ in each instance is independently H, $C_1$-$C_4$ alkyl or $C_3$-$C_6$ cycloalkyl;

m is 0, 1, 2 or 3; and n is 1 or 2; or (b) the structure of Formula II:

(Formula II)

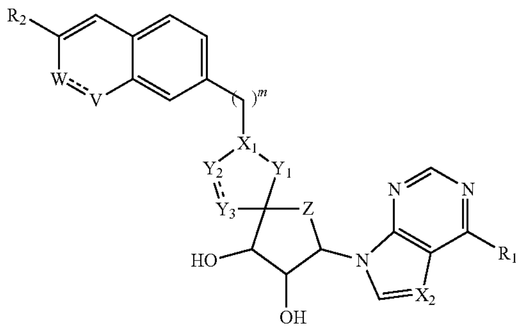

or a pharmaceutically acceptable salt thereof, wherein:

$\cdots$ in each instance is independently a double bond or a single bond;

$R_1$ is H, halogen, $C_1$-$C_4$ alkyl, $C_2$-$C_4$ alkenyl, —O$(R_a)$, $C_3$-$C_6$ cycloalkyl, $C_3$-$C_7$ heterocyclyl or N$(R_a)_2$;

$R_2$ is H, halogen, hydroxyl, cyano, —C(O)$NH_2$, —C(O)N$(R_a)_2$, —C(O)O$(R_a)$, —C(O)$R_a$, —N$(R_a)_2$, —O$(R_a)$, $C_3$-$C_6$ cycloalkyl, $C_3$-$C_7$ heterocyclyl, optionally substituted $C_1$-$C_4$ alkyl or optionally substituted $C_2$-$C_6$ alkenyl;

W is C$(R_b)$ or C(O), with the proviso that V is NH and the $\cdots$ between W and V is a single bond when W is C(O);

V is CH, NH or N, with the proviso that W is C$(R_b)$ and the $\cdots$ between W and V is a double bond when V is CH or N;

$X_1$ and $X_2$ are each independently CH or N;

$Y_1$ is $(CH_2)_n$ or C(O), with the proviso that $Y_1$ cannot be C(O) when $Y_2$ or $Y_3$ is C(O);

$Y_2$ is $CH_2$, C(O), S, $SO_2$, O or $NR_a$, with the provisos that:

$Y_2$ cannot be C(O) when $Y_1$ or $Y_3$ is C(O); and the $\cdots$ between $Y_2$ and $Y_3$ is a single bond;

$Y_3$ is $CH_2$ or C(O), with the provisos that:

$Y_3$ cannot be C(O) when $Y_1$ or $Y_2$ is C(O); and the $\cdots$ between $Y_2$ and $Y_3$ is a single bond; or $Y_2$ and $Y_3$ are CH and the $\cdots$ between $Y_2$ and $Y_3$ is a double bond;

Z is $CH_2$, O, S or NH;

$R_a$ in each instance is independently H, $C_1$-$C_4$ alkyl or $C_3$-$C_6$ cycloalkyl;

$R_b$ is H, halogen, hydroxyl, cyano, —C(O)$NH_2$, —C(O)N$(R_a)_2$, —C(O)O$(R_a)$, —C(O)$R_a$, —N$(R_a)_2$, —O$(R_a)$, $C_3$-$C_6$ cycloalkyl, $C_3$-$C_7$ heterocyclyl, optionally substituted $C_1$-$C_4$ alkyl or optionally substituted $C_2$-$C_6$ alkenyl;

m is 0, 1, 2 or 3; and n is 1 or 2; or (c) the structure of Formula III:

(Formula III)

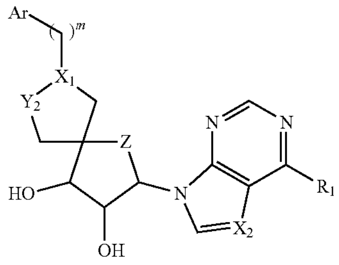

or a pharmaceutically acceptable salt thereof, wherein:

Ar is an optionally substituted aryl or heteroaryl, wherein one, two, or three optional substituents are independently selected from halogen, hydroxyl, cyano, —C(O)$NH_2$, —C(O)N$(R_a)_2$, —C(O)O($R_a$), —C(O)$R_a$, —N$(R_a)_2$, —O($R_a$), $C_3$-$C_6$ cycloalkyl, $C_3$-$C_7$ heterocyclyl, optionally substituted $C_1$-$C_4$ alkyl and optionally substituted $C_2$-$C_6$ alkenyl;

$R_1$ is H, halogen, $C_1$-$C_4$ alkyl, $C_2$-$C_4$ alkenyl, —O($R_a$), $C_3$-$C_6$ cycloalkyl, $C_3$-$C_7$ heterocyclyl or N$(R_a)_2$;

$X_1$ and $X_2$ are each independently CH or N;

$Y_2$ is $CH_2$, S, O or N($R_a$);

Z is $CH_2$, O, S or NH;

$R_a$ in each instance is independently H, $C_1$-$C_4$ alkyl or $C_3$-$C_6$ cycloalkyl; and m is 0, 1, 2 or 3; or (d) the structure of Formula IV:

(Formula IV)

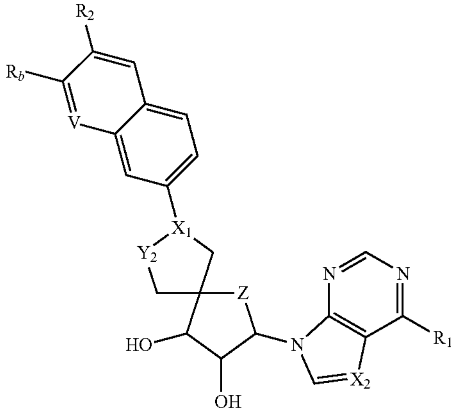

or a pharmaceutically acceptable salt thereof, wherein:

$R_1$ is H, halogen, $C_1$-$C_4$ alkyl, $C_2$-$C_4$ alkenyl, —O($R_a$), $C_3$-$C_6$ cycloalkyl, $C_3$-$C_7$ heterocyclyl or N$(R_a)_2$;

$R_2$ is H, halogen, hydroxyl, cyano, —C(O)$NH_2$, —C(O)N$(R_a)_2$, —C(O)O($R_a$), —C(O)$R_a$, —N$(R_a)_2$, —O($R_a$), $C_3$-$C_6$ cycloalkyl, $C_3$-$C_7$ heterocyclyl, optionally substituted $C_1$-$C_4$ alkyl or optionally substituted $C_2$-$C_6$ alkenyl;

$X_1$ and $X_2$ are each independently CH or N;

V is CH or N;

$Y_2$ is $CH_2$, S, O or N($R_a$);

Z is $CH_2$, O, S or NH;

$R_a$ in each instance is independently H, $C_1$-$C_4$ alkyl or $C_3$-$C_6$ cycloalkyl; and $R_b$ is H, halogen, hydroxyl, cyano, —C(O)$NH_2$, —C(O)N$(R_a)_2$, —C(O)O($R_a$), —C(O)$R_a$, —N$(R_a)_2$, —O($R_a$), $C_3$-$C_6$ cycloalkyl, $C_3$-$C_7$ heterocyclyl, optionally substituted $C_1$-$C_4$ alkyl or optionally substituted $C_2$-$C_6$ alkenyl; or (e) The structure of Formula V:

(Formula V)

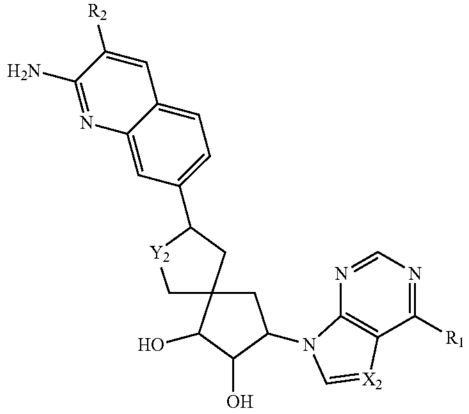

or a pharmaceutically acceptable salt thereof, wherein:

$R_1$ is H, halogen, $C_1$-$C_4$ alkyl, $C_2$-$C_4$ alkenyl, —O($R_a$), $C_3$-$C_6$ cycloalkyl, $C_3$-$C_7$ heterocyclyl or N$(R_a)_2$;

$R_2$ is H, halogen, hydroxyl, cyano, —C(O)$NH_2$, —C(O)N$(R_a)_2$, —C(O)O($R_a$), —C(O)$R_a$, —N$(R_a)_2$, —O($R_a$), $C_3$-$C_6$ cycloalkyl, $C_3$-$C_7$ heterocyclyl, optionally substituted $C_1$-$C_4$ alkyl or optionally substituted $C_2$-$C_6$ alkenyl;

$X_2$ is CH or N;

$Y_2$ is $CH_2$, S, O or N($R_a$); and $R_a$ in each instance is independently H, $C_1$-$C_4$ alkyl or $C_3$-$C_6$ cycloalkyl.

DETAILED DESCRIPTION

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g., "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y.

(1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10, or more preferably from 1 to about 3 unless otherwise defined. Examples of straight chained and branched alkyl groups include, but are not limited to methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, an oxo, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_1$-$C_6$ alkyl, $C_3$-$C_6$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

In addition, the term "alkyl" as used throughout the specification, examples, and claims is intended to be interchangeable, where valence requires, with the term "alkylene" (i.e., an alkyl diradical or a bivalent alkyl moiety).

The term "alkenyl," as used herein, refers to an aliphatic group containing at least one double bond and is intended to include both "unsubstituted alkenyls" and "substituted alkenyls" the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkynyl," as used herein, refers to an aliphatic group containing at least one triple bond and is intended to include both "unsubstituted alkynyls" and "substituted alkynyls," the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "$C_x$-$C_y$," when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. Co alkyl indicates a hydrogen where the group is in a terminal position, a bond if internal. The terms "$C_2$-$C_y$ alkenyl" and "$C_2$-$C_y$ alkynyl" refer to substituted or unsubstituted unsaturated aliphatic groups analogous in length and possible substitution to the alkyls described above, but that contain at least one double or triple bond respectively.

The term "aryl" as used herein include substituted or unsubstituted single-ring aromatic groups in which each atom of the ring is carbon. Preferably the ring is a 6- to 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, aniline, and the like.

The term "carbocycle" refers to a saturated or unsaturated ring in which each atom of the ring is carbon. The term carbocycle includes both aromatic carbocycles and non-aromatic carbocycles. Non-aromatic carbocycles include both cycloalkyl and cycloalkenyl rings. "Carbocycle" includes 5-7 membered monocyclic and 8-12 membered bicyclic rings.

Each ring of a bicyclic carbocycle may be selected from saturated, unsaturated and aromatic rings. Carbocycle includes bicyclic molecules in which one, two or three or more atoms are shared between the two rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3- to about 10-carbon atoms, from 3- to 8-carbon atoms, or more typically from 3- to 6-carbon atoms unless otherwise defined. The second ring of a bicyclic cycloalkyl may be selected from saturated, unsaturated and aromatic rings. Cycloalkyl includes bicyclic molecules in which one, two, or three or more atoms are shared between the two rings (e.g., fused bicyclic compounds, bridged bicyclic compounds, and spirocyclic compounds).

The term "fused bicyclic compound" refers to a bicyclic molecule in which two rings share two adjacent atoms. In other words, the rings share one covalent bond, i.e., the so-called bridgehead atoms are directly connected (e.g., α-thujene and decalin). For example, in a fused cycloalkyl each of the rings shares two adjacent atoms with the other ring, and the second ring of a fused bicyclic cycloalkyl may be selected from saturated, unsaturated and aromatic rings.

The term "spirocyclic compound" refers to a bicyclic molecule in which the two rings have only one single atom, the spiro atom, in common.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, quinoline, quinoxaline, naphthyridine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, preferably 3- to 7-membered rings, more preferably 5- to 6-membered rings, in some instances, most preferably a 5-membered ring, in other instances, most preferably a 6-membered ring, which ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, pyrrolidine, piperidine, piperazine, pyrrolidine, tetrahydropyran, tetrahydrofuran, morpholine, lactones, lactams, oxazolines, imidazolines and the like.

The terms "halo" and "halogen" are used interchangeably herein and mean halogen and includes chloro, fluoro, bromo, and iodo.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substitutions can be one or more and the same or different for appropriate organic compounds.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt that is suitable for or compatible with the treatment of patients.

The term "pharmaceutically acceptable acid addition salt" as used herein means any non-toxic organic or inorganic salt of any base compounds disclosed herein. Illustrative inorganic acids that form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds disclosed herein are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of the invention for laboratory use, or for subsequent conversion to a pharmaceutically acceptable acid addition salt.

The term "pharmaceutically acceptable basic addition salt" as used herein means any non-toxic organic or inorganic base addition salt of any acid compounds of the invention, or any of their intermediates. Illustrative inorganic bases that form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726. Where the absolute stereochemistry of a stereogenic center is not determined, the stereochemistry is denoted using " "—in other words, a compound having the structural formula

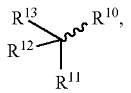

where $R^{10}$, $R^{11}$, $R^{12}$, and $R^{13}$ are different from each other, has either a R configuration or a S configuration. Where the stereochemistry at the stereogenic center is not indicated in a structure as drawn herein, the structure as drawn is intended to cover racemic or other mixtures of the enantiomeric or diastereomeric forms, as well as isolated enantiomers of any stereochemical configuration.

Furthermore, certain compounds which contain alkenyl groups may exist as Z (zusammen) or E (entgegen) isomers. In each instance, the disclosure includes both mixtures and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of the invention). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of the invention, or a pharmaceutically acceptable salt thereof. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

EXAMPLE COMPOUNDS

In certain embodiments, the invention relates to a compound having the structure of Formula I:

(Formula I)

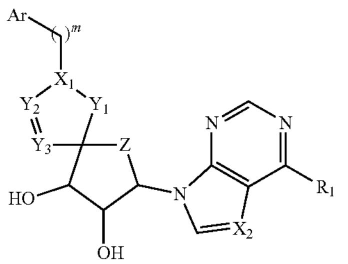

or a pharmaceutically acceptable salt thereof, wherein:

$\overline{---}$ is a double bond or a single bond;

Ar is an optionally substituted aryl or heteroaryl, wherein one, two, or three optional substituents are independently selected from halogen, hydroxyl, cyano, —C(O)$NH_2$, —C(O)$N(R_a)_2$, —C(O)O($R_a$), —C(O)$R_a$, —$N(R_a)_2$, —O($R_a$), $C_3$-$C_6$ cycloalkyl, $C_3$-$C_7$ heterocyclyl, optionally substituted $C_1$-$C_4$ alkyl and optionally substituted $C_2$-$C_6$ alkenyl;

$R_1$ is H, halogen, $C_1$-$C_4$ alkyl, $C_2$-$C_4$ alkenyl, —O($R_a$), $C_3$-$C_6$ cycloalkyl, $C_3$-$C_7$ heterocyclyl or $N(R_a)_2$;

$X_1$ and $X_2$ are each independently CH or N;

$Y_1$ is $(CH_2)_n$ or C(O), with the proviso that $Y_1$ cannot be C(O) when $Y_2$ or $Y_3$ is C(O);

$Y_2$ is $CH_2$, C(O), S, $SO_2$, O or $NR_a$, with the provisos that:

$Y_2$ cannot be C(O) when $Y_1$ or $Y_3$ is C(O); and $\overline{---}$ is a single bond;

$Y_3$ is $CH_2$ or C(O), with the provisos that:

$Y_3$ cannot be C(O) when $Y_1$ or $Y_2$ is C(O); and $\overline{---}$ is a single bond; or $Y_2$ and $Y_3$ are CH and $\overline{---}$ is a double bond;

Z is $CH_2$, O, S or NH;

$R_a$ in each instance is independently H, $C_1$-$C_4$ alkyl or $C_3$-$C_6$ cycloalkyl;

m is 0, 1, 2 or 3; and n is 1 or 2.

In other embodiments, Ar is an optionally substituted aryl or heteroaryl, wherein one, two, or three optional substituents are independently selected from F, Cl, Br, methyl, $N(R_a)_2$ and $O(R_a)$; $R_1$ is H, F, Cl, Br or $N(R_a)_2$; Z is $CH_2$, O or NH; $R_a$ in each instance is independently H or methyl; and m is 0 or 1.

In particular embodiments, the compounds of Formula I have the structure of Formula Ia:

(Formula Ia)

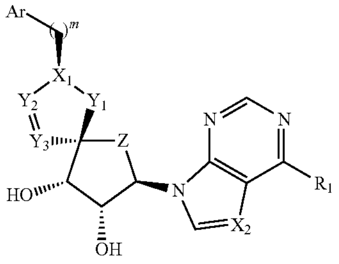

or a pharmaceutically acceptable salt thereof. Alternatively, the compounds of Formula I have the structure of Formula Ib:

(Formula Ib)

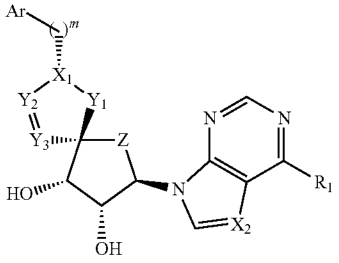

or a pharmaceutically acceptable salt thereof.

In certain embodiments, the compound of Formula I has the structure of Formula II:

(Formula II)

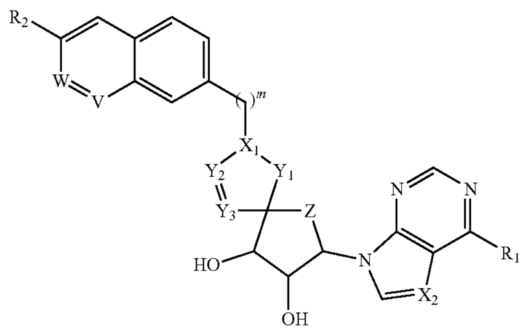

or a pharmaceutically acceptable salt thereof, wherein:

$\overline{---}$ in each instance is independently a double bond or a single bond;

$R_1$ is H, halogen, $C_1$-$C_4$ alkyl, $C_2$-$C_4$ alkenyl, —O($R_a$), $C_3$-$C_6$ cycloalkyl, $C_3$-$C_7$ heterocyclyl or $N(R_a)_2$;

$R_2$ is H, halogen, hydroxyl, cyano, —C(O)$NH_2$, —C(O)$N(R_a)_2$, —C(O)O($R_a$), —C(O)$R_a$, —$N(R_a)_2$, —O($R_a$), $C_3$-$C_6$ cycloalkyl, $C_3$-$C_7$ heterocyclyl, optionally substituted $C_1$-$C_4$ alkyl or optionally substituted $C_2$-$C_6$ alkenyl;

W is C($R_b$) or C(O), with the proviso that V is NH and $\overline{---}$ the between W and V is a single bond when W is C(O);

V is CH, NH or N, with the proviso that W is C($R_b$) and the $\overline{---}$ between W and V is a double bond when V is CH or N;

$X_1$ and $X_2$ are each independently CH or N;

$Y_1$ is $(CH_2)_n$ or C(O), with the proviso that $Y_1$ cannot be C(O) when $Y_2$ or $Y_3$ is C(O);

$Y_2$ is $CH_2$, C(O), S, $SO_2$, O or $NR_a$, with the provisos that:

$Y_2$ cannot be C(O) when $Y_1$ or $Y_3$ is C(O); and the $\overline{---}$ between $Y_2$ and $Y_3$ is a single bond;

$Y_3$ is $CH_2$ or C(O), with the provisos that:

$Y_3$ cannot be C(O) when $Y_1$ or $Y_2$ is C(O); and the $\overline{---}$ between $Y_2$ and $Y_3$ is a single bond; or $Y_2$ and $Y_3$ are CH and the $\overline{---}$ between $Y_2$ and $Y_3$ is a double bond;

Z is $CH_2$, O, S or NH;

$R_a$ in each instance is independently H, $C_1$-$C_4$ alkyl or $C_3$-$C_6$ cycloalkyl;

$R_b$ is H, halogen, hydroxyl, cyano, —C(O)$NH_2$, —C(O)$N(R_a)_2$, —C(O)O($R_a$), —C(O)$R_a$, —$N(R_a)_2$, —O($R_a$), $C_3$-$C_6$ cycloalkyl, $C_3$-$C_7$ heterocyclyl, optionally substituted $C_1$-$C_4$ alkyl or optionally substituted $C_2$-$C_6$ alkenyl;

m is 0, 1, 2 or 3; and n is 1 or 2.

In other embodiments, $R_1$ and $R_2$ are each independently H, F, Cl, Br or $N(R_a)_2$; Z is $CH_2$, O or NH; $R_a$ in each instance is independently H or methyl; $R_b$ is H, $N(R_a)_2$, F, Cl or Br; and m is 0 or 1.

In particular embodiments, the compounds of Formula II have the structure of Formula IIa:

(Formula IIa)

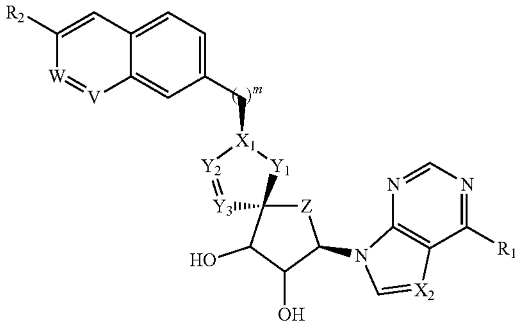

or a pharmaceutically acceptable salt thereof. Alternatively, the compounds of Formula II have the structure of Formula IIb:

(Formula IIb)

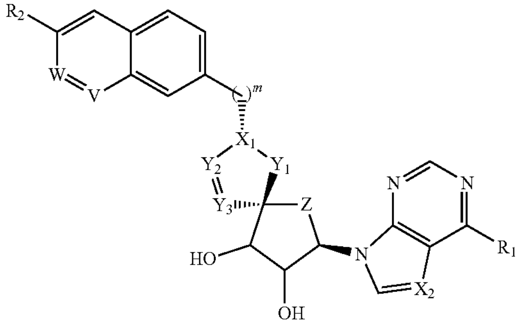

or a pharmaceutically acceptable salt thereof.

In certain embodiments, the compound of Formula I has the structure of Formula III:

(Formula III)

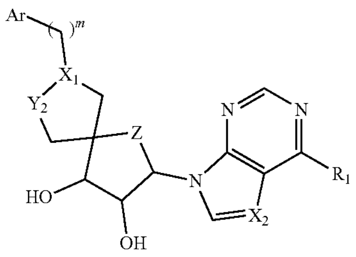

or a pharmaceutically acceptable salt thereof, wherein:

Ar is an optionally substituted aryl or heteroaryl, wherein one, two, or three optional substituents are independently selected from halogen, hydroxyl, cyano, —C(O)$NH_2$, —C(O)$N(R_a)_2$, —C(O)O($R_a$), —C(O)$R_a$, —$N(R_a)_2$, —O($R_a$), $C_3$-$C_6$ cycloalkyl, $C_3$-$C_7$ heterocyclyl, optionally substituted $C_1$-$C_4$ alkyl and optionally substituted $C_2$-$C_6$ alkenyl;

$R_1$ is H, halogen, $C_1$-$C_4$ alkyl, $C_2$-$C_4$ alkenyl, —O($R_a$), $C_3$-$C_6$ cycloalkyl, $C_3$-$C_7$ heterocyclyl or $N(R_a)_2$;

$X_1$ and $X_2$ are each independently CH or N;

$Y_2$ is $CH_2$, S, O or N($R_a$);

Z is $CH_2$, O, S or NH;

$R_a$ in each instance is independently H, $C_1$-$C_4$ alkyl or $C_3$-$C_6$ cycloalkyl; and m is 0, 1, 2 or 3.

In particular embodiments, the compounds of Formula III have the structure of Formula IIIa:

(Formula IIIa)

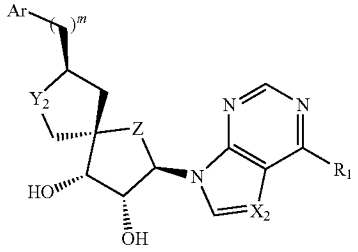

or a pharmaceutically acceptable salt thereof. In certain embodiments of compounds of Formula IIIa, m is 0. Alternatively, the compounds of Formula III have the structure of Formula IIIb:

(Formula IIIb)

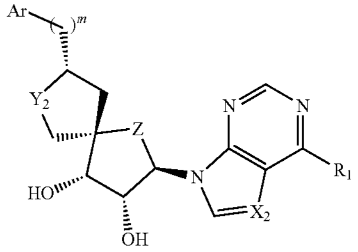

or a pharmaceutically acceptable salt thereof. In certain embodiments of compounds of Formula IIIb, m is 0.

In certain embodiments, the compound of Formula I has the structure of Formula IV:

(Formula IV)

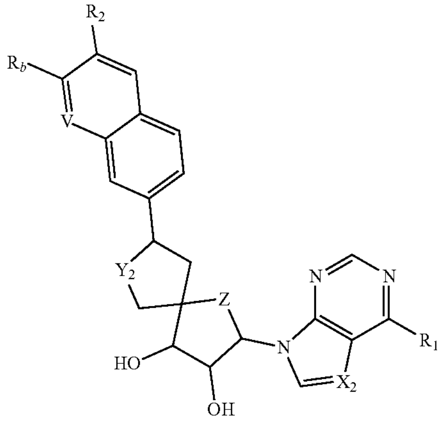

or a pharmaceutically acceptable salt thereof, wherein:

$R_1$ is H, halogen, $C_1$-$C_4$ alkyl, $C_2$-$C_4$ alkenyl, —O($R_a$), $C_3$-$C_6$ cycloalkyl, $C_3$-$C_7$ heterocyclyl or $N(R_a)_2$;

$R_2$ is H, halogen, hydroxyl, cyano, —C(O)$NH_2$, —C(O)N$(R_a)_2$, —C(O)O($R_a$), —C(O)$R_a$, —N$(R_a)_2$, —O($R_a$), $C_3$-$C_6$ cycloalkyl, $C_3$-$C_7$ heterocyclyl, optionally substituted $C_1$-$C_4$ alkyl or optionally substituted $C_2$-$C_6$ alkenyl;

$X_1$ and $X_2$ are each independently CH or N;

V is CH or N;

$Y_2$ is $CH_2$, S, O or N($R_a$);

Z is $CH_2$, O, S or NH;

$R_a$ in each instance is independently H, $C_1$-$C_4$ alkyl or $C_3$-$C_6$ cycloalkyl; and $R_b$ is H, halogen, hydroxyl, cyano, —C(O)$NH_2$, —C(O)N$(R_a)_2$, —C(O)O($R_a$), —C(O)$R_a$, —N$(R_a)_2$, —O($R_a$), $C_3$-$C_6$ cycloalkyl, $C_3$-$C_7$ heterocyclyl, optionally substituted $C_1$-$C_4$ alkyl or optionally substituted $C_2$-$C_6$ alkenyl.

In other embodiments, $R_1$ and $R_2$ are each independently H, F, Cl, Br or N$(R_a)_2$; Z is $CH_2$, O or NH; $R_a$ in each instance is independently H or methyl; and $R_b$ is H, N$(R_a)_2$, F, Cl or Br.

In particular embodiments, the compounds of Formula IV have the structure of Formula IVa:

(Formula IVa)

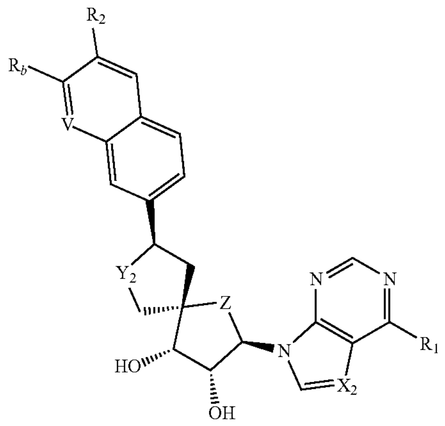

or a pharmaceutically acceptable salt thereof. Alternatively, the compounds of Formula IV have the structure of Formula IVb:

(Formula IVb)

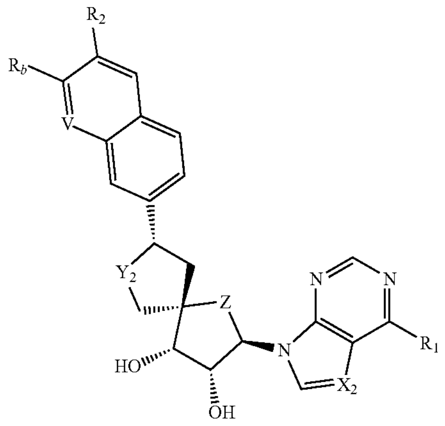

or a pharmaceutically acceptable salt thereof.

In certain embodiments, the compound of Formula I has the structure of Formula V:

(Formula V)

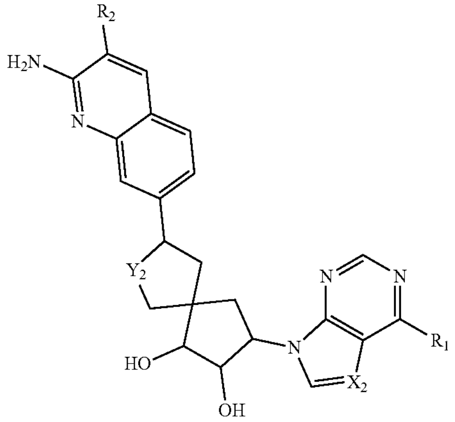

or a pharmaceutically acceptable salt thereof, wherein:

$R_1$ is H, halogen, $C_1$-$C_4$ alkyl, $C_2$-$C_4$ alkenyl, —O($R_a$), $C_3$-$C_6$ cycloalkyl, $C_3$-$C_7$ heterocyclyl or N$(R_a)_2$;

$R_2$ is H, halogen, hydroxyl, cyano, —C(O)$NH_2$, —C(O)N$(R_a)_2$, —C(O)O($R_a$), —C(O)$R_a$, —N$(R_a)_2$, —O($R_a$), $C_3$-$C_6$ cycloalkyl, $C_3$-$C_7$ heterocyclyl, optionally substituted $C_1$-$C_4$ alkyl or optionally substituted $C_2$-$C_6$ alkenyl;

$X_2$ is CH or N;

$Y_2$ is $CH_2$, S, O or N($R_a$); and $R_a$ in each instance is independently H, $C_1$-$C_4$ alkyl or $C_3$-$C_6$ cycloalkyl.

In particular embodiments, the compounds of Formula V have the structure of Formula Va:

(Formula Va)

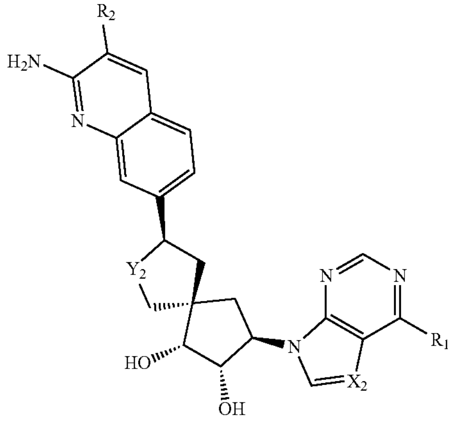

or a pharmaceutically acceptable salt thereof. Alternatively, the compounds of Formula V have the structure of Formula Vb:

(Formula Vb)

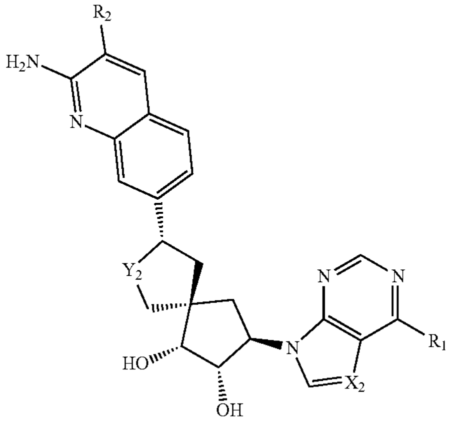

or a pharmaceutically acceptable salt thereof.

In some embodiments, the invention relates to a compound having the structure of Formula V, Va or Vb, wherein the compound has a PRMT5 $IC_{50}$ of about 100 nM or lower.

In further embodiments, the compound of Formula V, Va or Vb has an average percent of maximum effect of about 60% or lower for the drug-resistant cell lines of Table 4.

In yet further embodiments, the compound of Formula V, Va or Vb has an average percent of maximum effect of about 60% or greater for the drug-sensitive cell lines of Table 4.

In some embodiments, the invention relates to any compound described herein, wherein $C_1$-$C_4$ alkyl in each instance is independently methyl, ethyl, n-propyl, iso-propyl, n-butyl, sec-butyl, tert-butyl, pentyl or hexyl. In preferred embodiments, $C_1$-$C_4$ alkyl is methyl, ethyl, n-propyl or iso-propyl.

In some embodiments, the invention relates to any compound described herein, wherein $C_3$-$C_6$ cycloalkyl in each instance is independently cyclopropyl, cyclobutyl or cyclopentyl.

In some embodiments, the invention relates to any compound described herein, wherein $C_3$-$C_7$ heterocyclyl in each instance is independently aziridinyl, azetidinyl, diazetidinyl, oxetanyl, thietanyl, pyrrolidinyl, imidazolidinyl, tetrahydrofuranyl, piperidinyl, piperazinyl, tetrahydropyranyl, morpholinyl, 2-oxa-6-azaspiro[3.3]heptanyl, 2,6-diazaspiro[3.3]heptanyl or azaspiro[3.3]heptanyl.

In some embodiments, the invention relates to any compound described herein, wherein $X_1$ is CH.

In some embodiments, the invention relates to any compound described herein, wherein $X_2$ is CH. Sometimes, $X_2$ is N.

In some embodiments, the invention relates to any compound described herein, wherein V is N.

In some embodiments, the invention relates to any compound described herein, wherein $R_b$ is Cl or $NH_2$. Sometimes, $R_b$ is $NH_2$.

In some embodiments, the invention relates to any compound described herein, wherein Z is $CH_2$.

In some embodiments, the invention relates to any compound described herein, wherein $Y_2$ is N(H). Sometimes, $Y_2$ is O.

In some embodiments, the invention relates to any compound described herein, wherein $R_1$ is Cl or $NH_2$. Sometimes, $R_1$ is Cl. Sometimes, $R_1$ is $NH_2$.

In some embodiments, the invention relates to any compound described herein, wherein $R_2$ is Cl or Br. Sometimes, $R_2$ is Br.

In some embodiments, the invention relates to any compound described herein, wherein $X_1$ is CH, $X_2$ is CH, V is N, $R_b$ is $NH_2$, Z is $CH_2$, $Y_2$ is N(H), $R_1$ is Cl or $NH_2$, and $R_2$ is Br.

In some embodiments, the invention relates to a compound having the structure of Formula I, Ia, Ib, II, IIa, IIb, III, IIIa or IIIb, wherein m is 0, 1 or 2, and more preferably, m is 0 or 1.

In preferred embodiments, the invention relates to a compound having the structure of Formula I, Ia, Ib, II, IIa, IIb, III, IIIa, IIIb, IV, IVa, IVb, V, Va or Vb, wherein $R_1$ is $N(R_a)_2$, one instance of $R_a$ is H and the other instance of $R_a$ is $C_1$-$C_4$ alkyl, preferably methyl.

In some aspects, the invention relates to a compound of Formula I having a structure selected from:

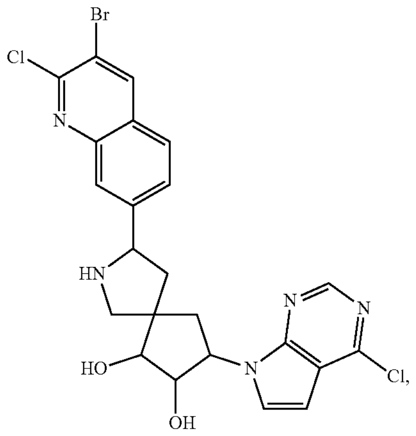

,

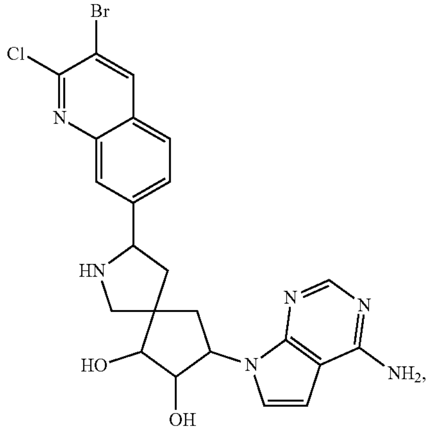

,

-continued
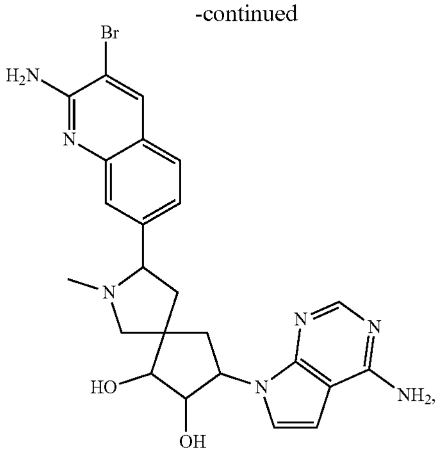
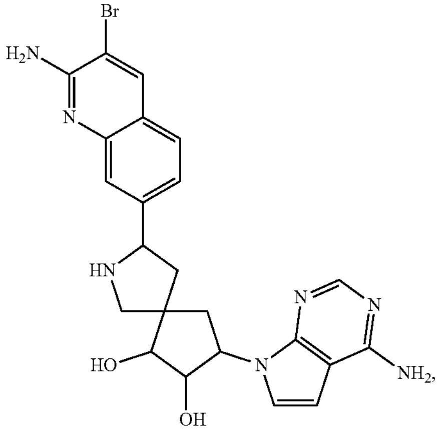
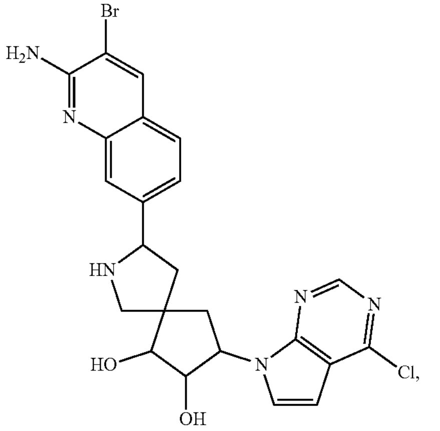
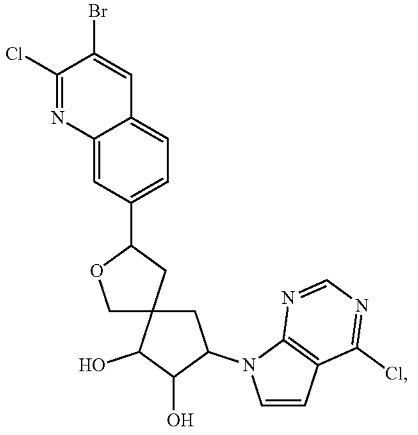
-continued
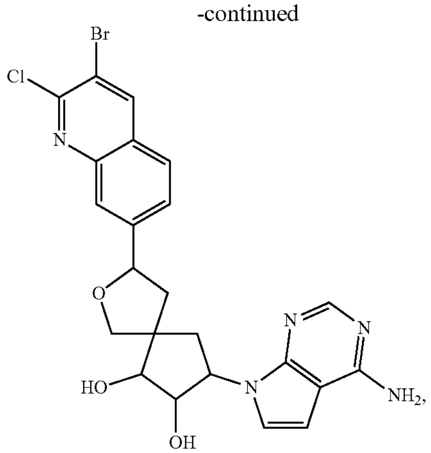
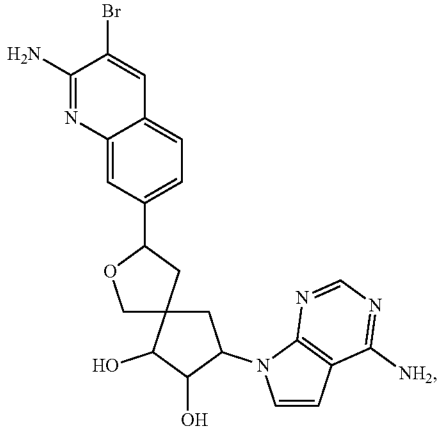
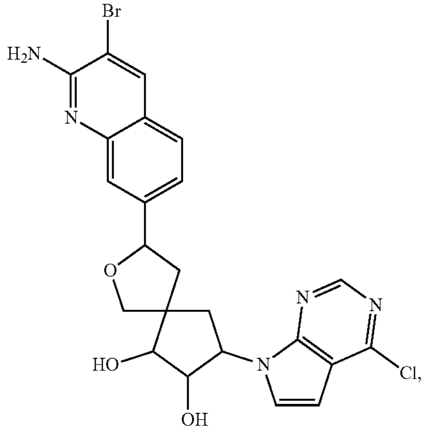
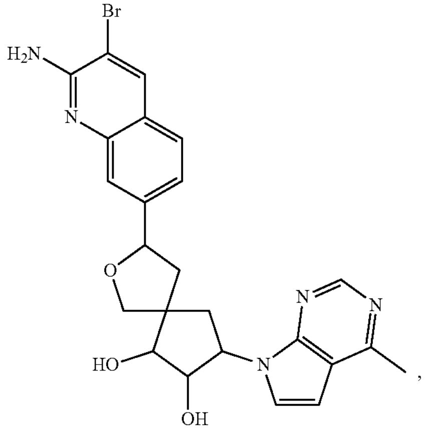

-continued
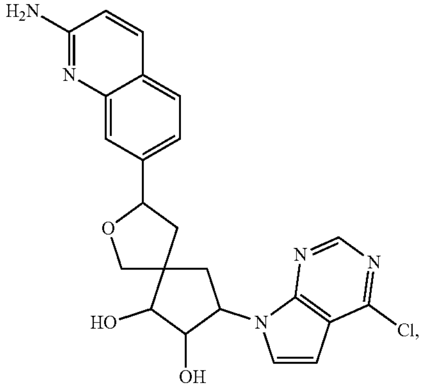
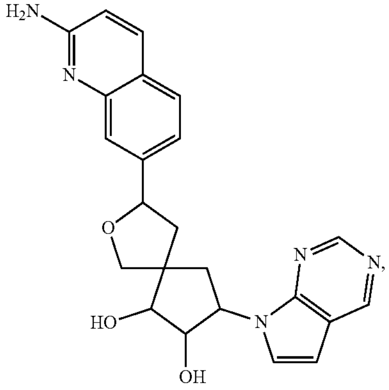
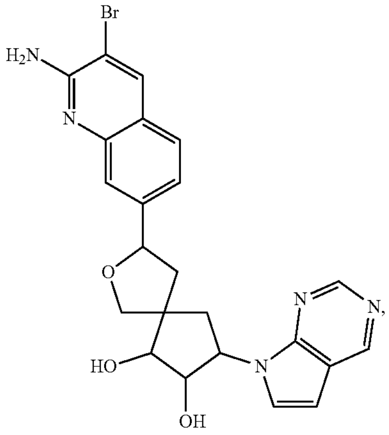
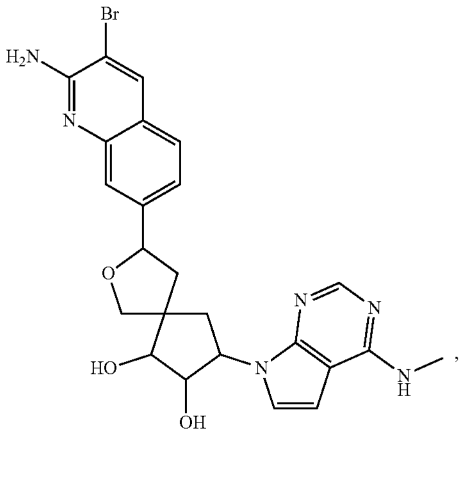
-continued
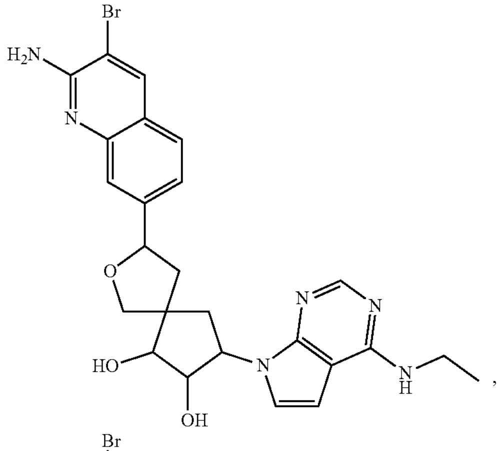
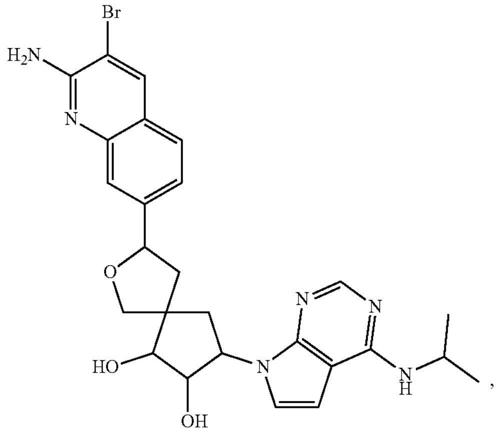
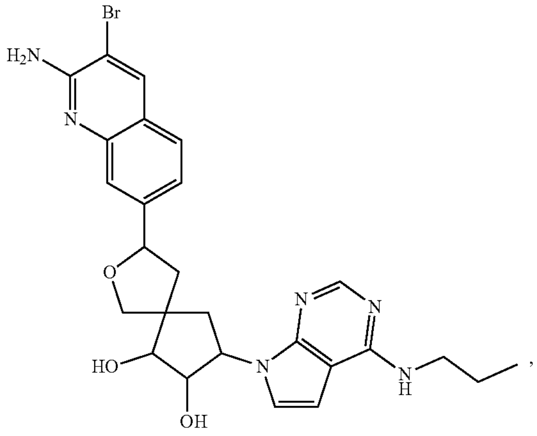
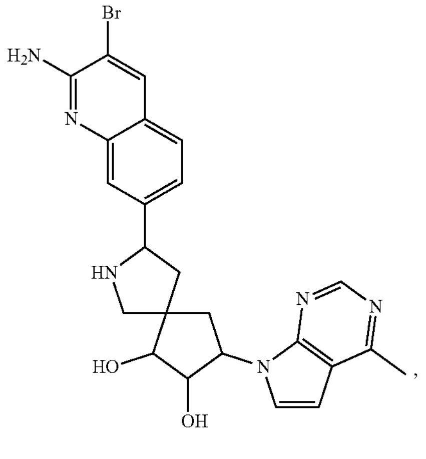

-continued
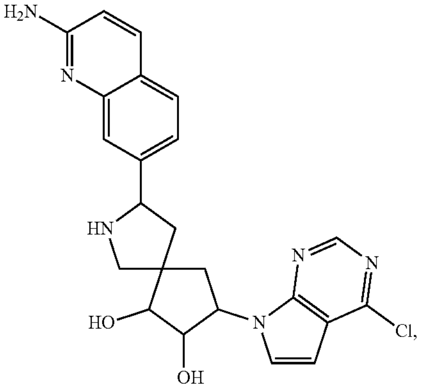
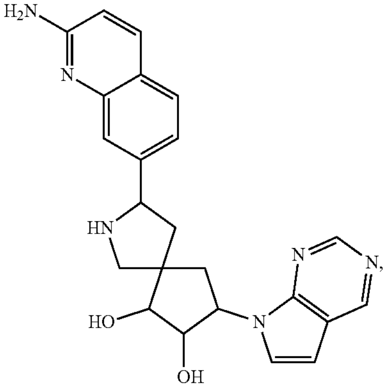
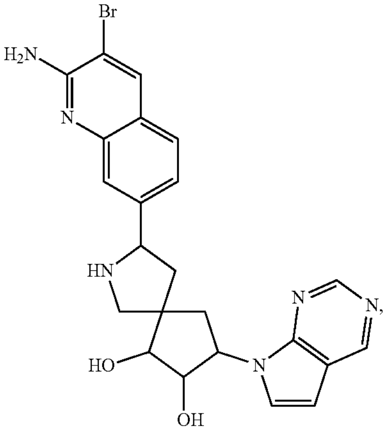
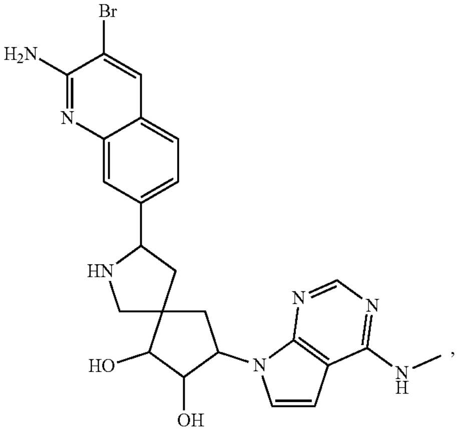
-continued
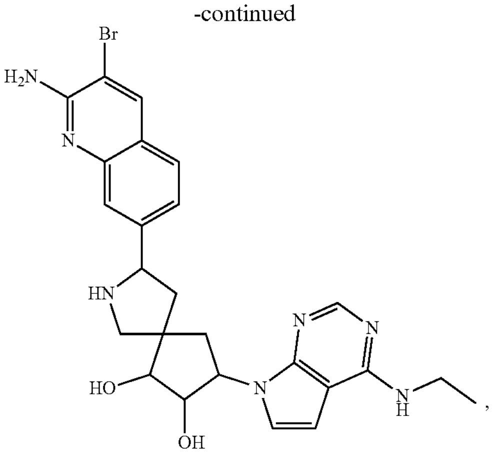
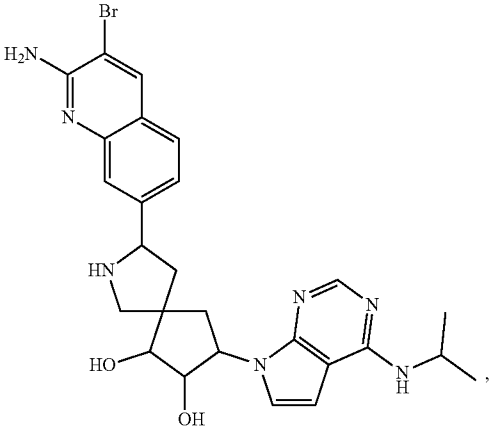
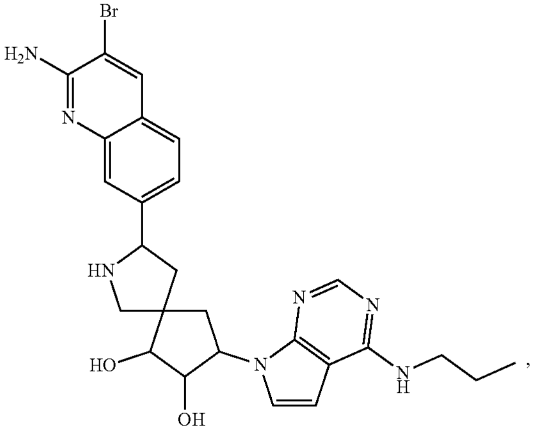
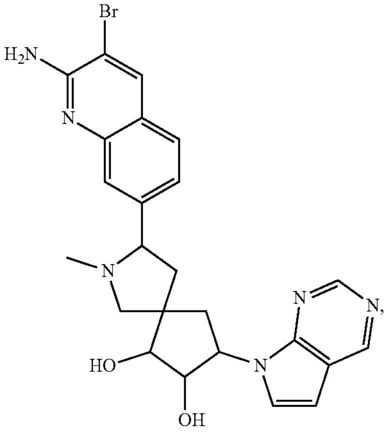

-continued
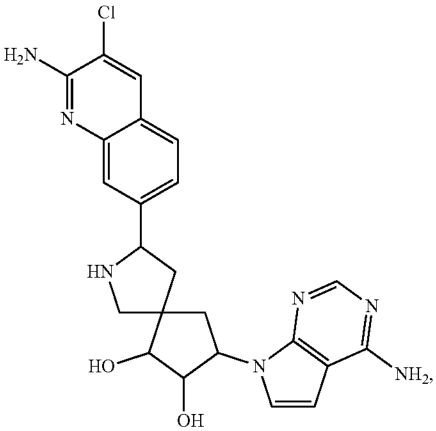
,
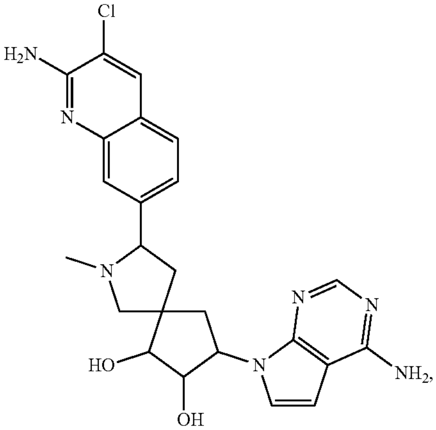
,
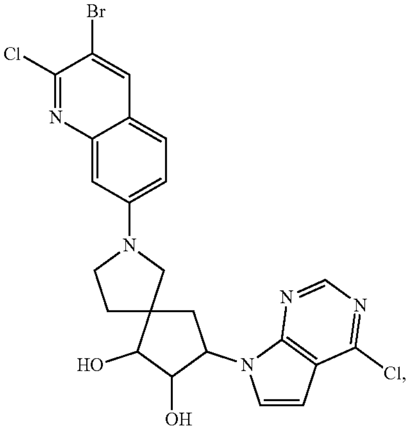
,
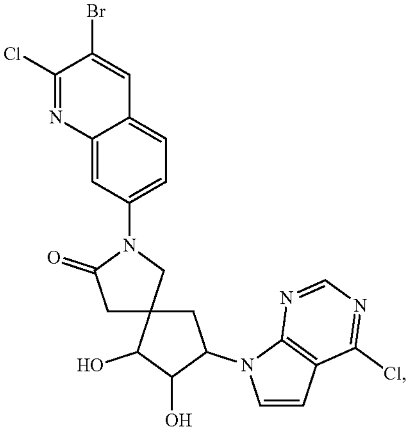
,
-continued
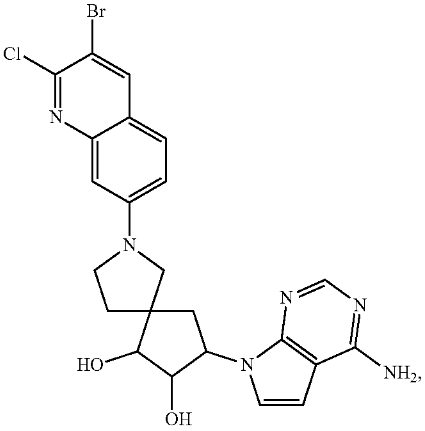
,
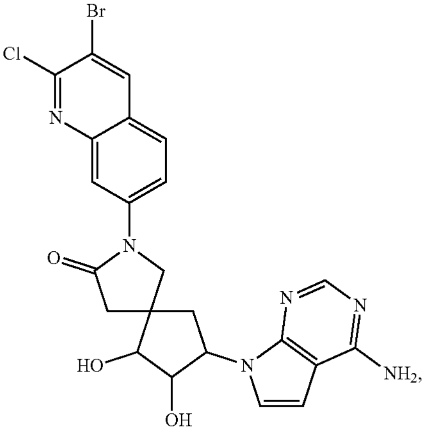
,
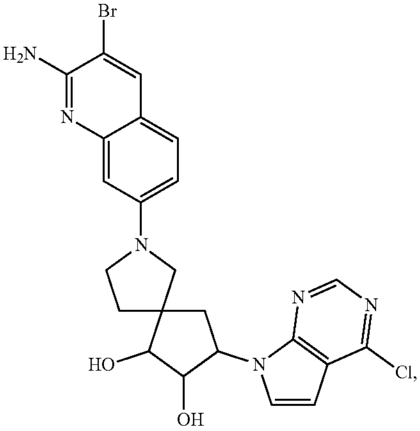
,
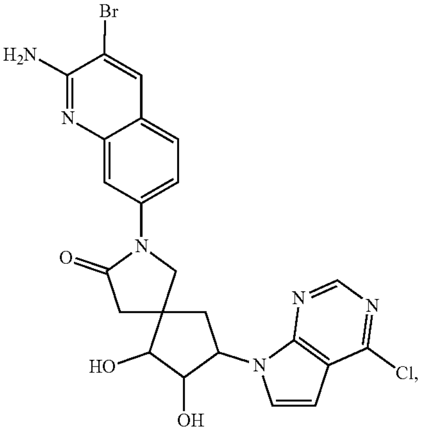
, -continued
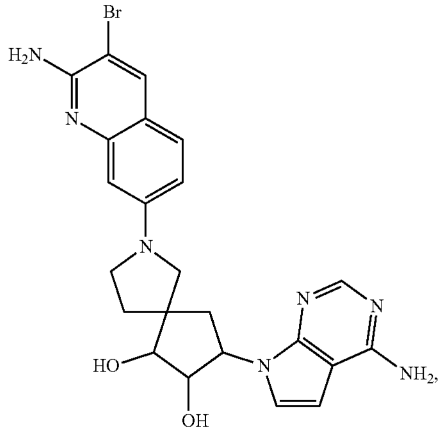
,
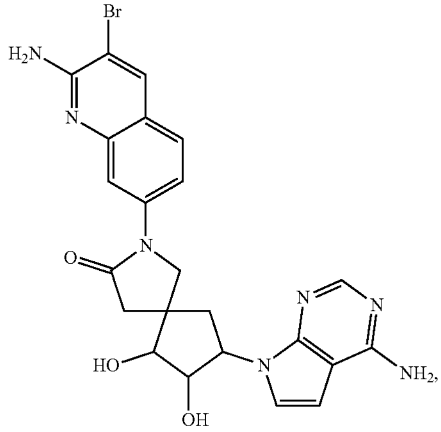
,
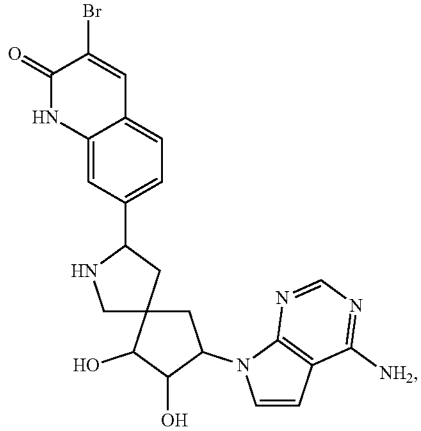
,
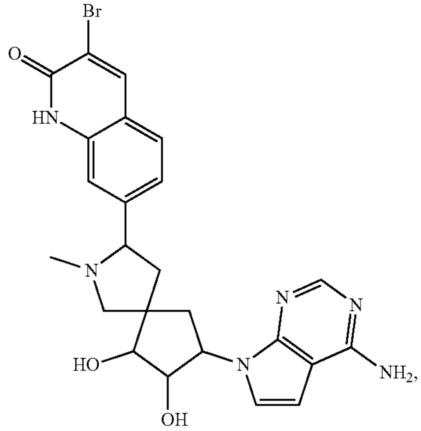
,
-continued
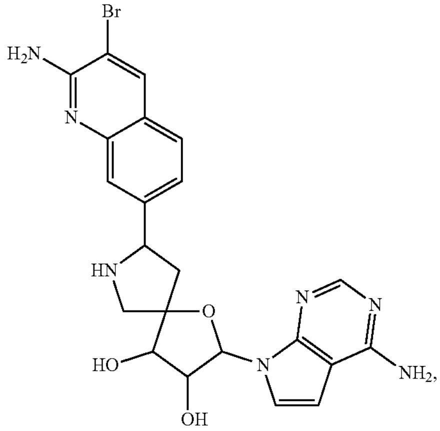
,
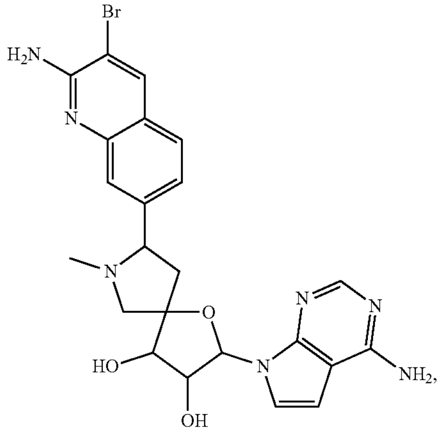
,
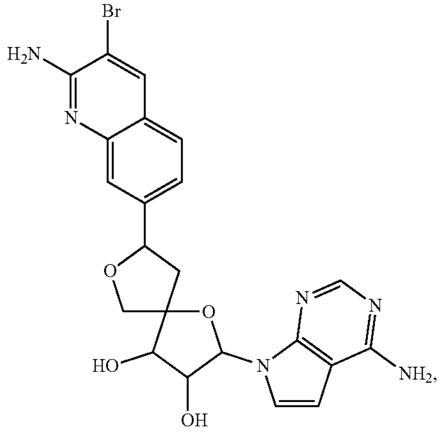
,
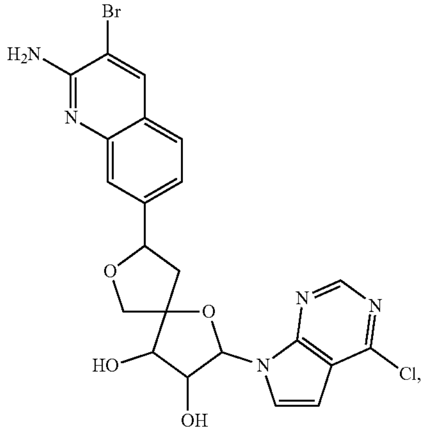
, -continued
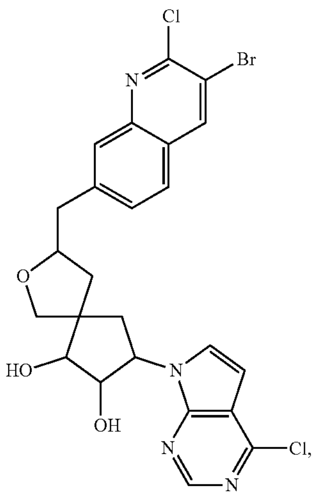
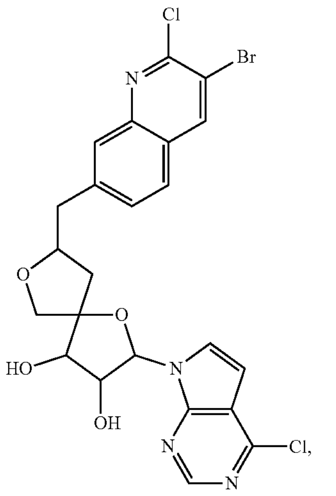
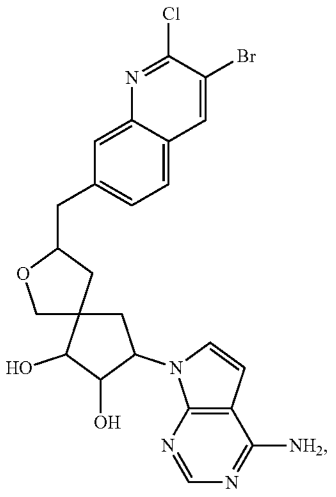
-continued
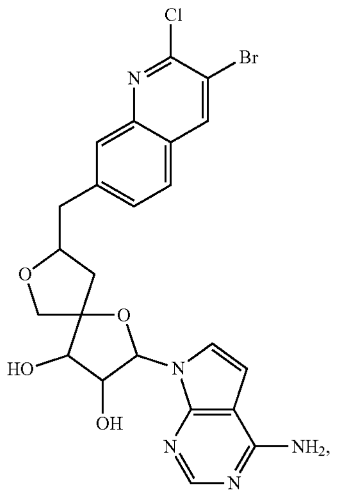
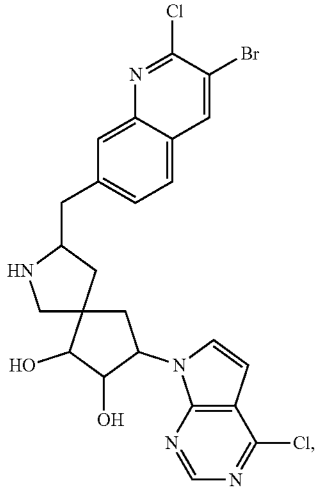
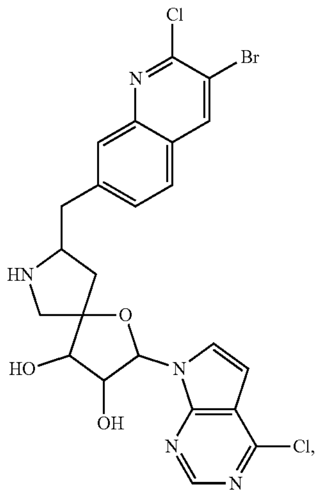

-continued
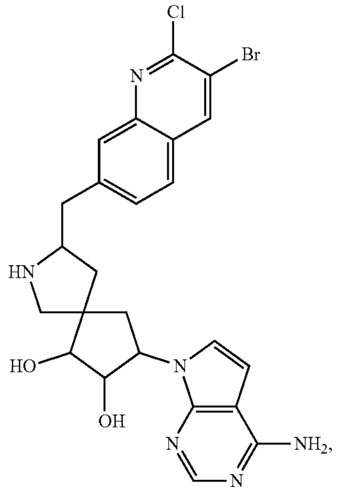
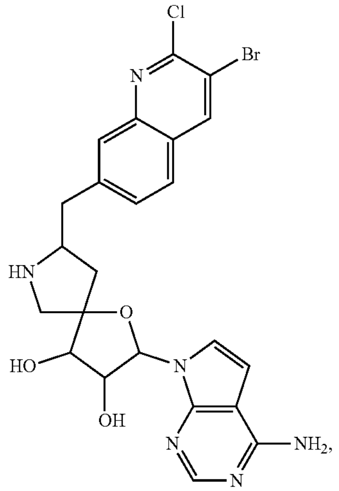
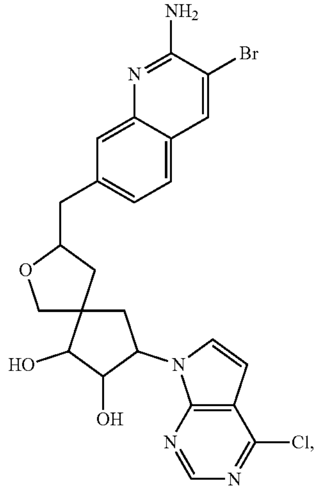
-continued
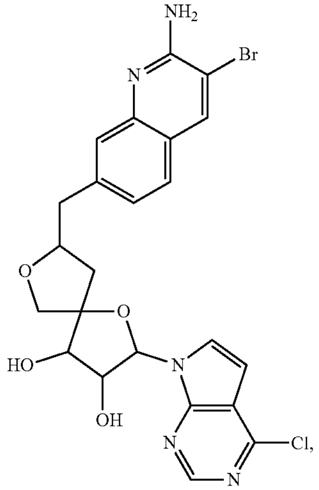
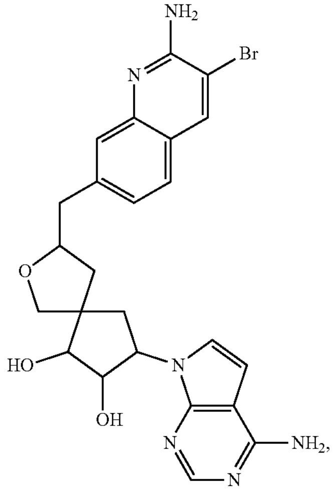
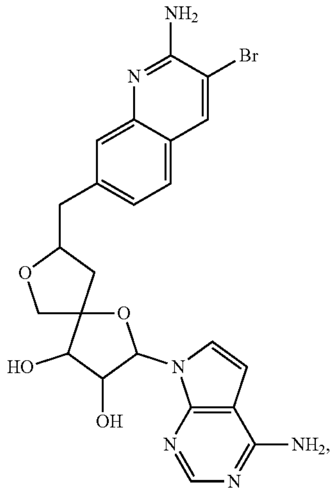

-continued
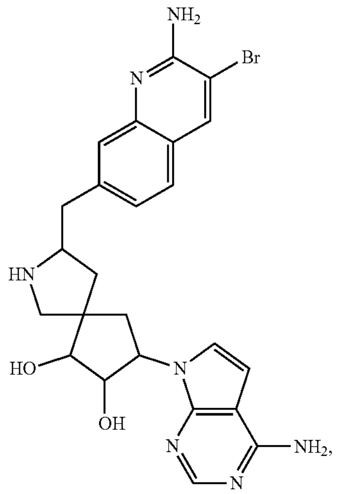
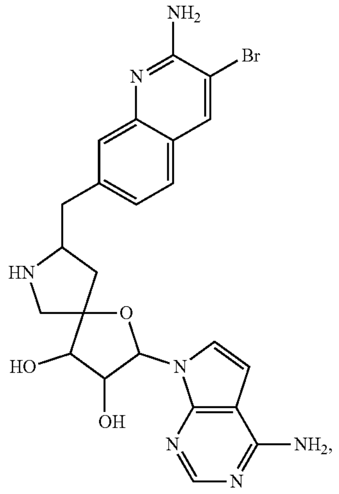
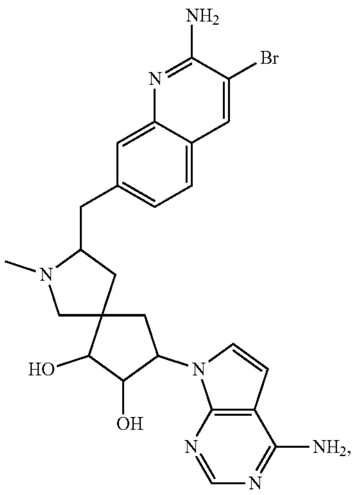
-continued
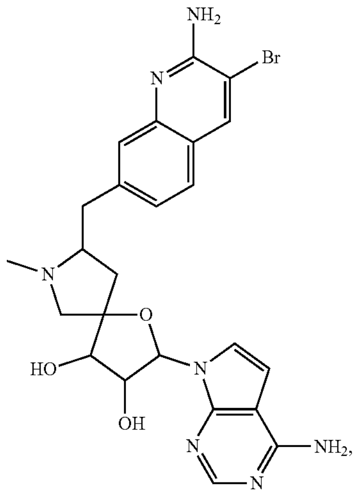
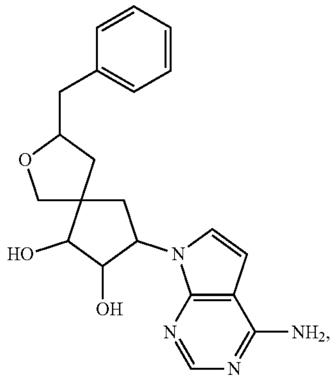
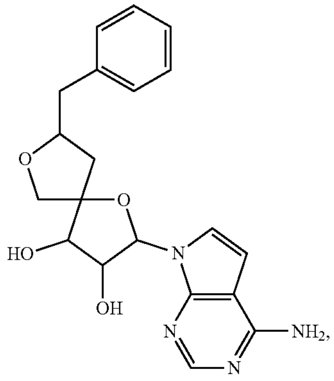
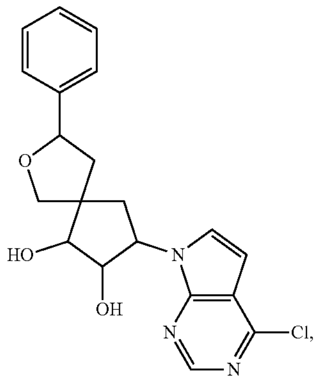

-continued
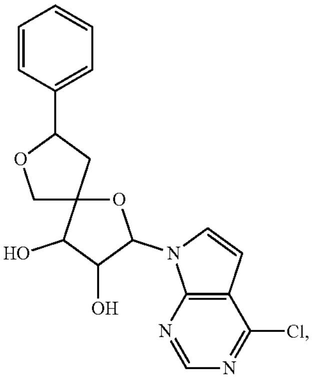
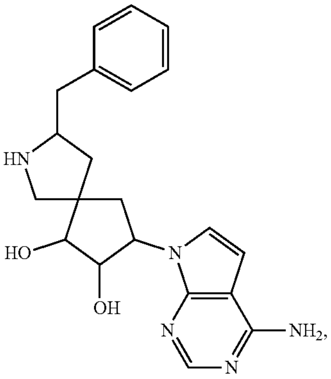
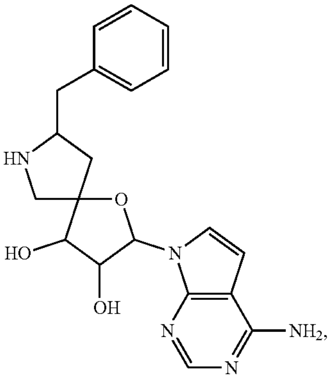
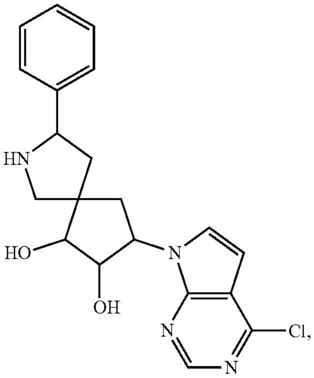
-continued
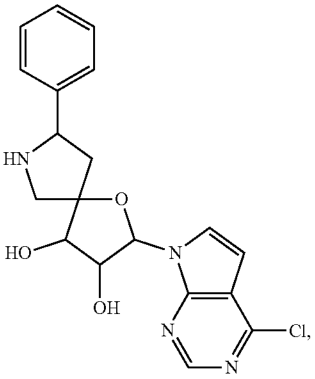
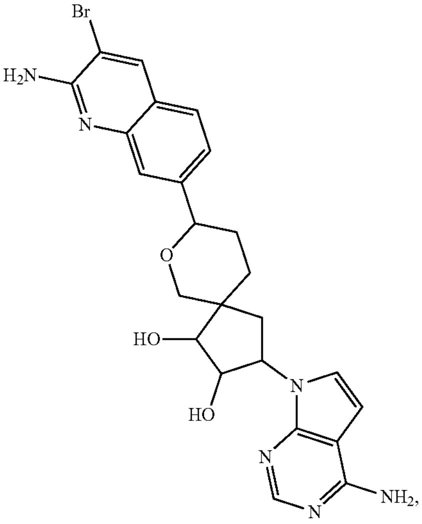
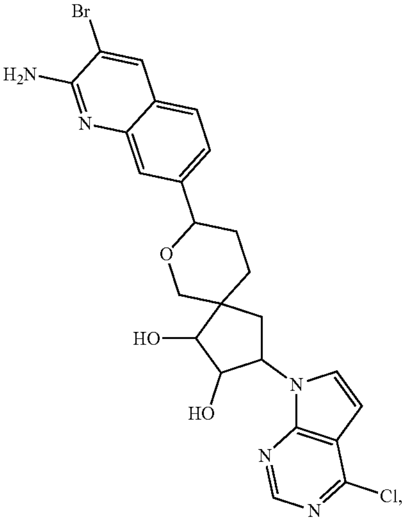

-continued
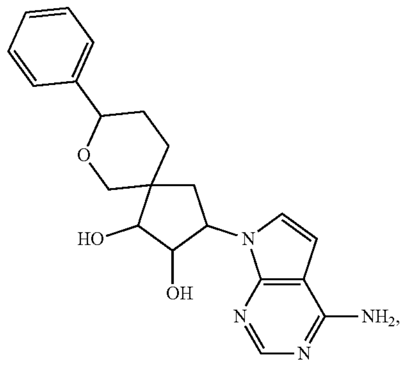
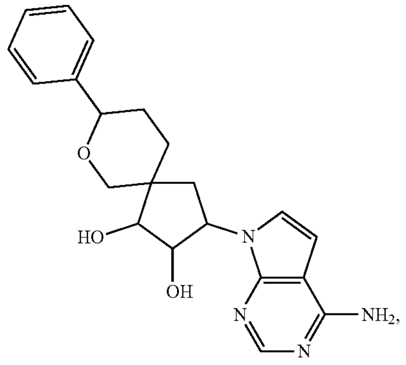
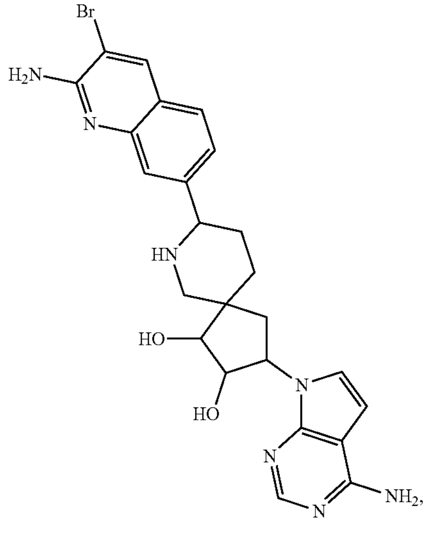
-continued
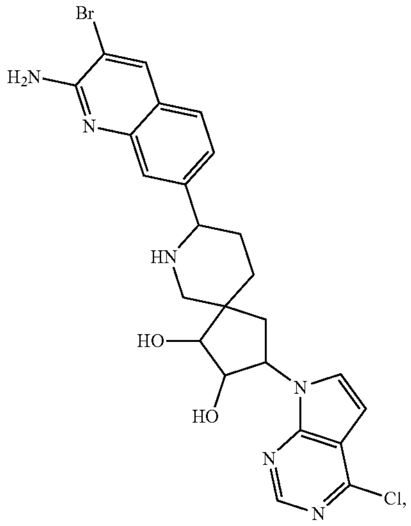
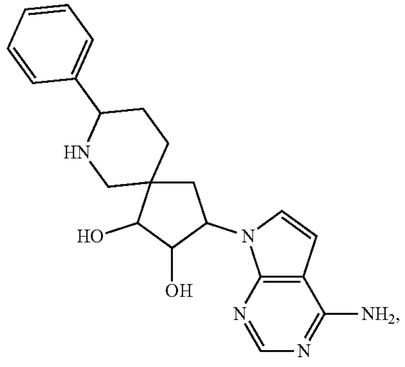
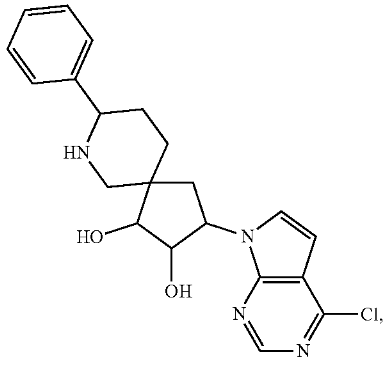
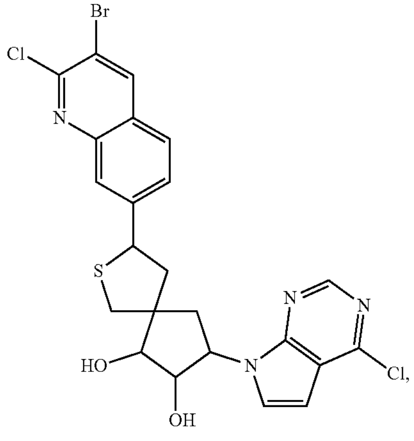

-continued
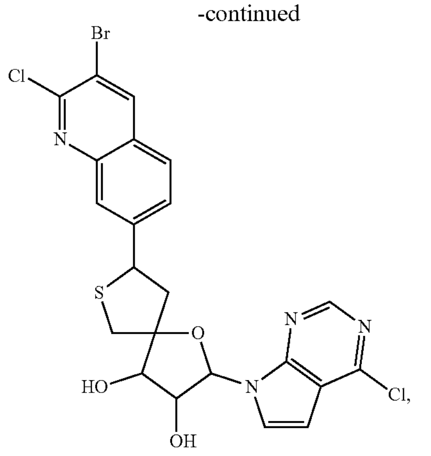
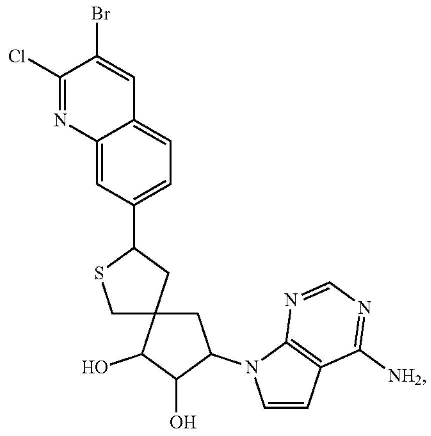
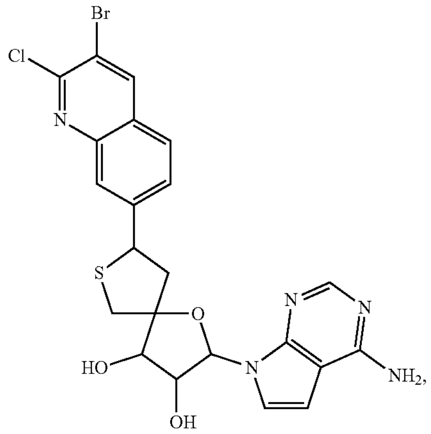
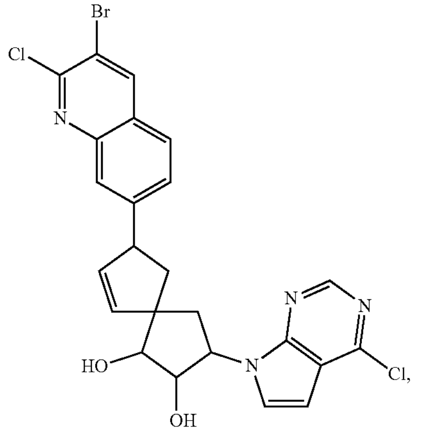
-continued
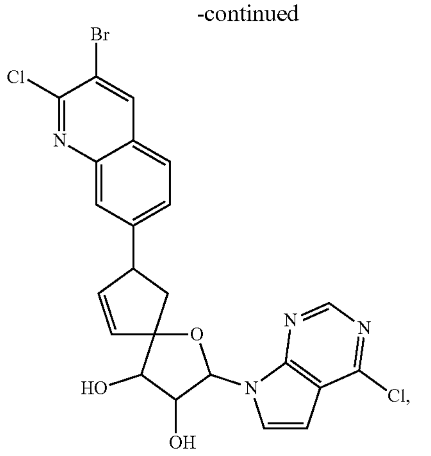
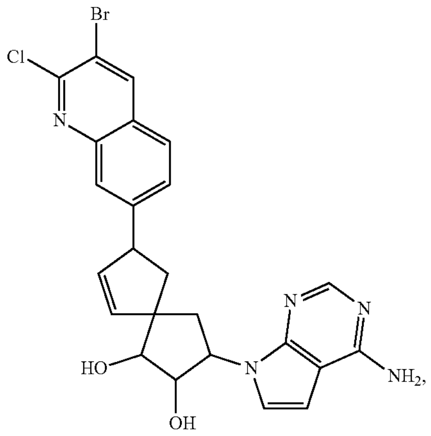
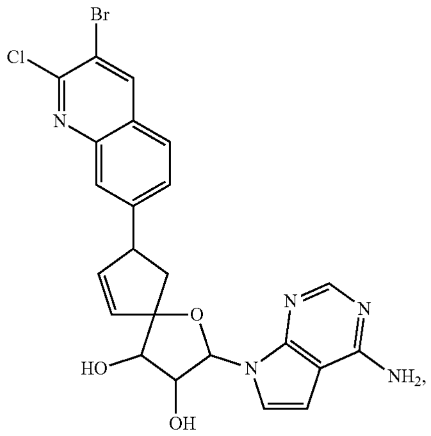
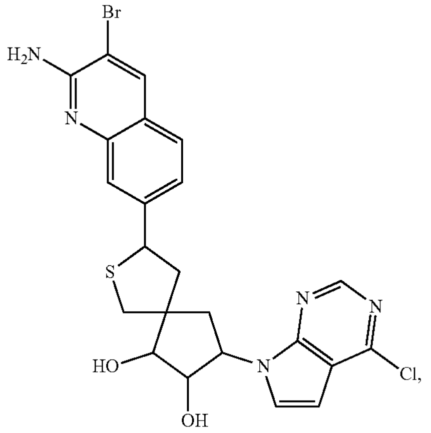

-continued
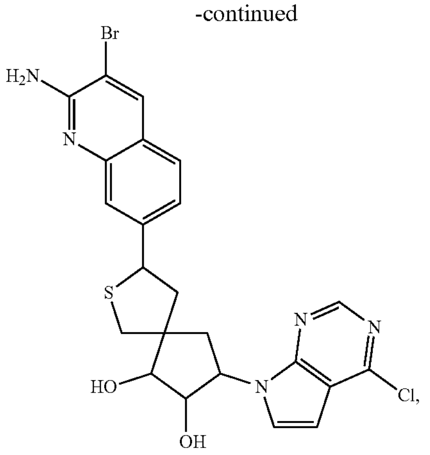
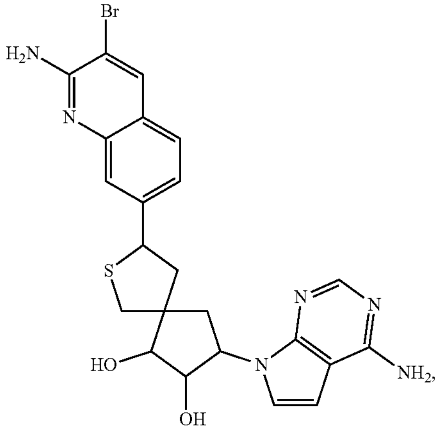
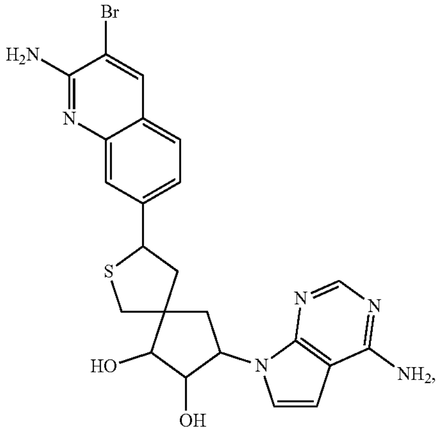
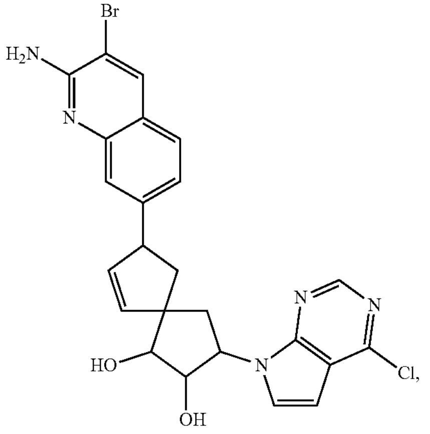
-continued
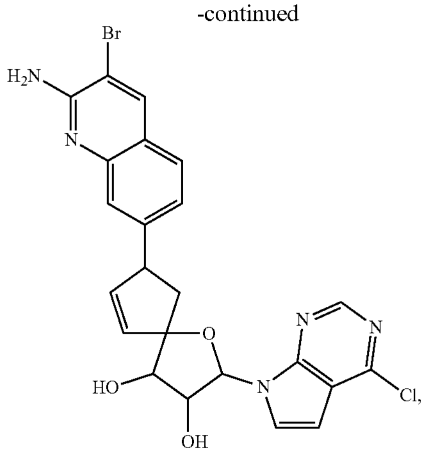
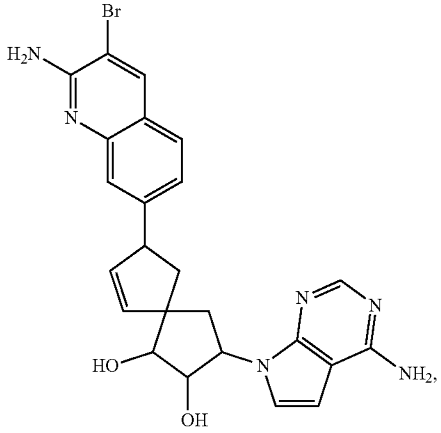
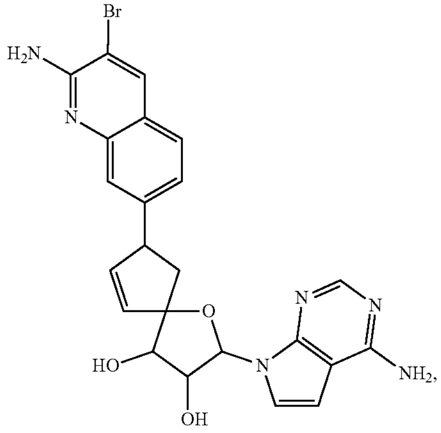
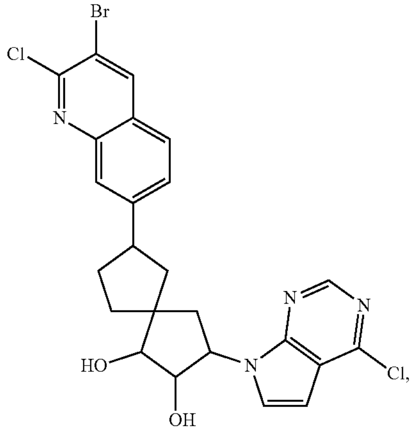

-continued
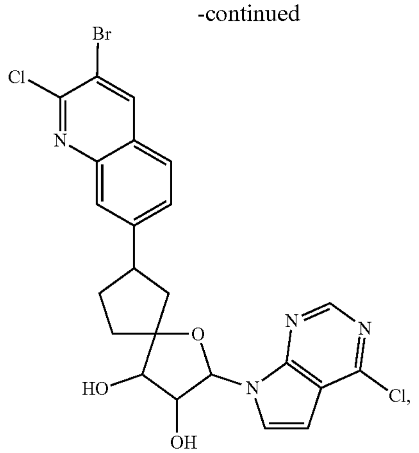
,
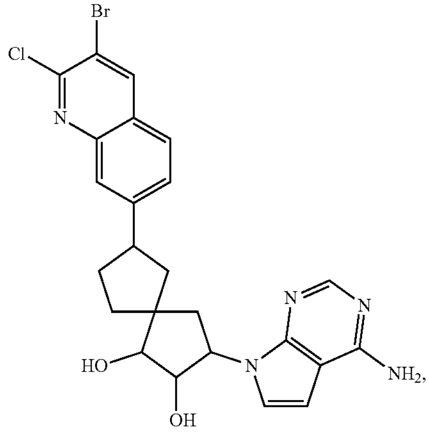
,
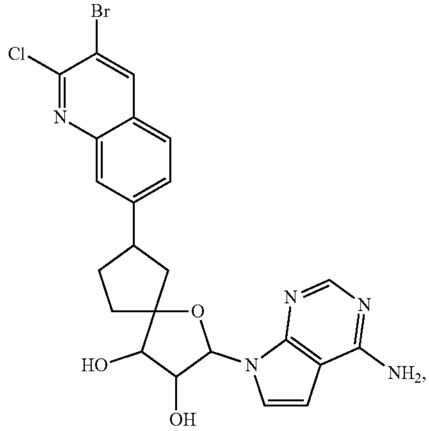
,
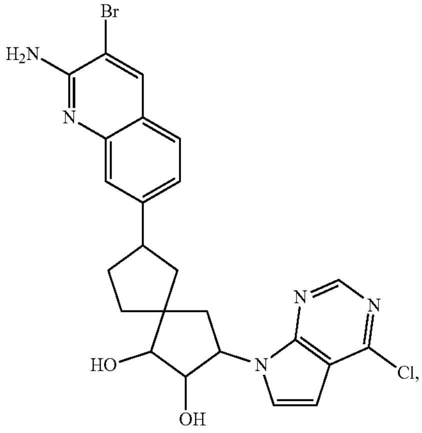
,
-continued
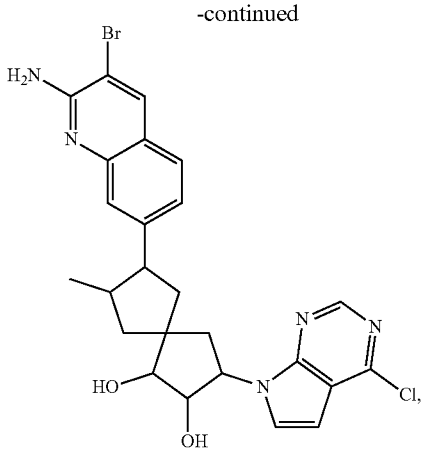
,
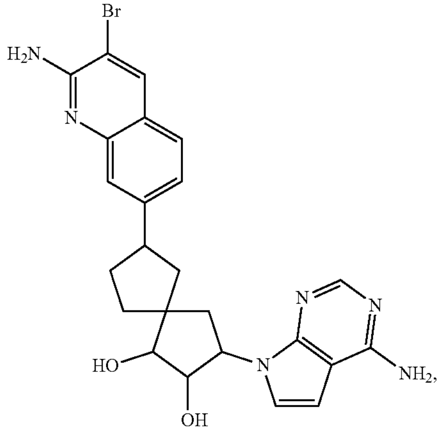
,
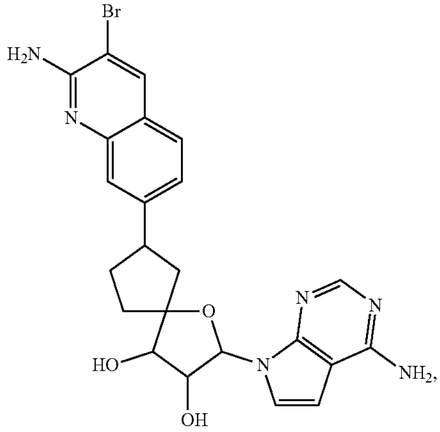
,
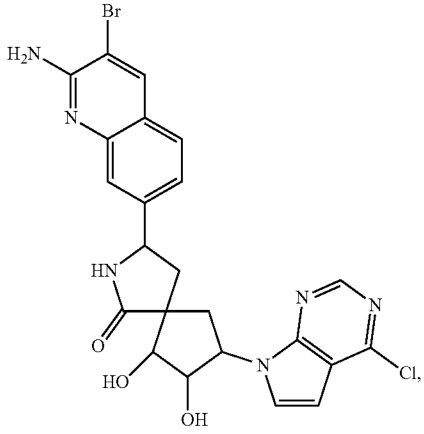
, -continued
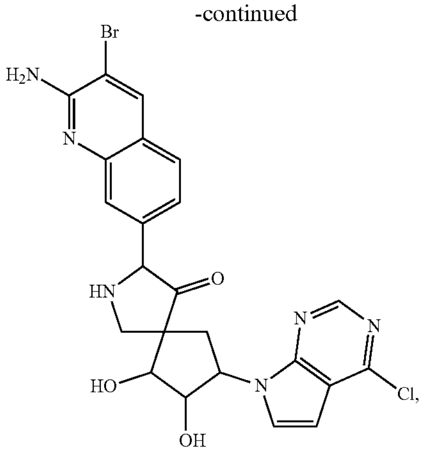
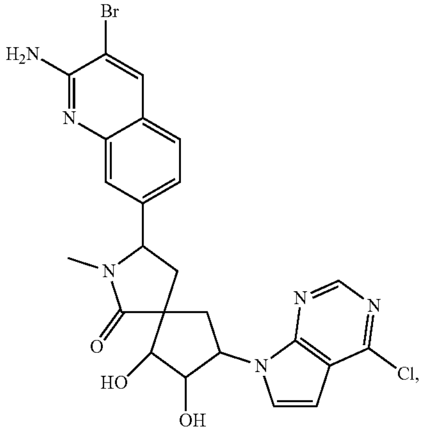
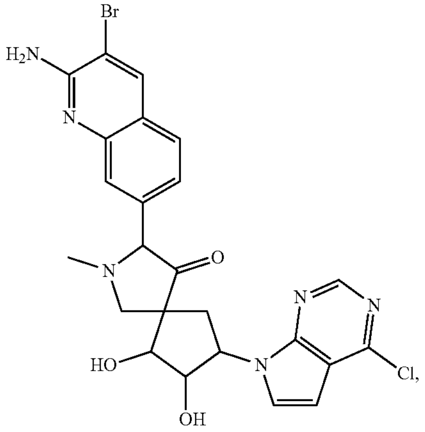
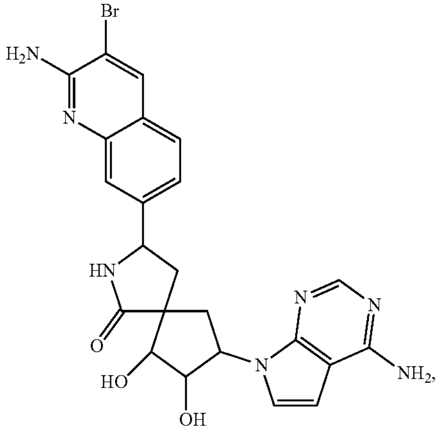
-continued
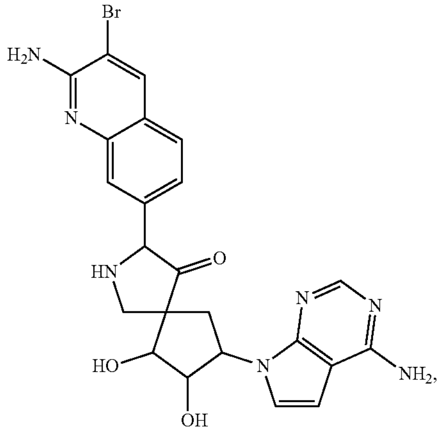
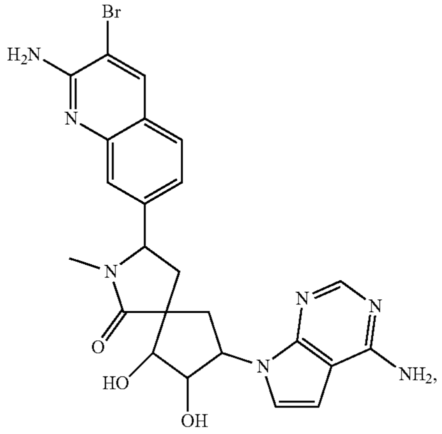
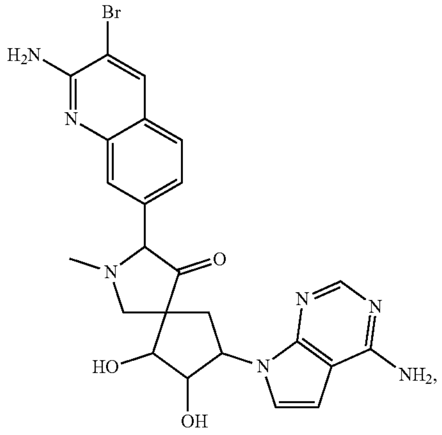
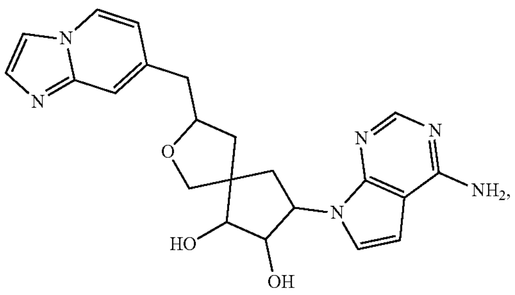

-continued
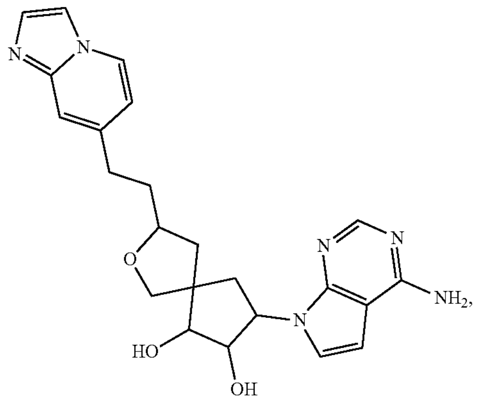
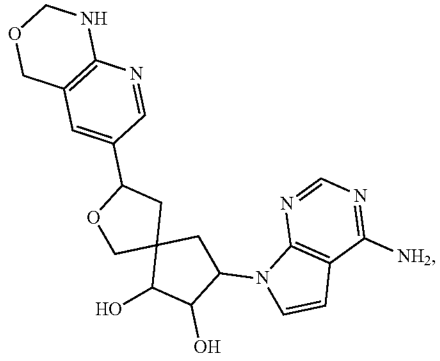
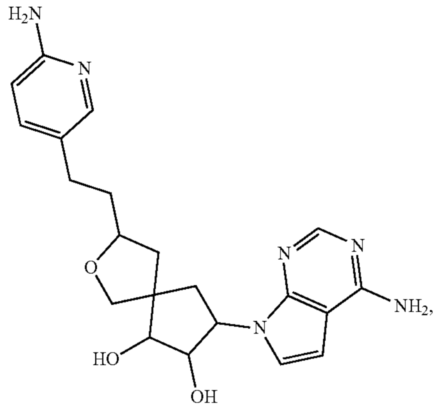
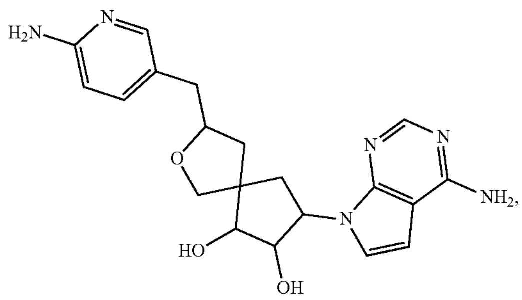
-continued
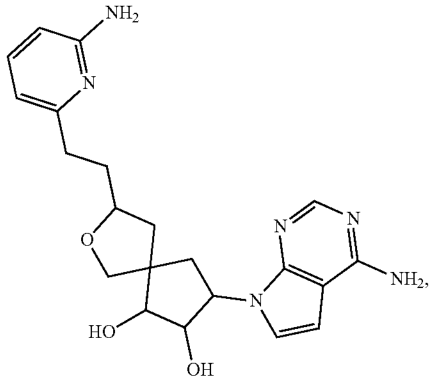
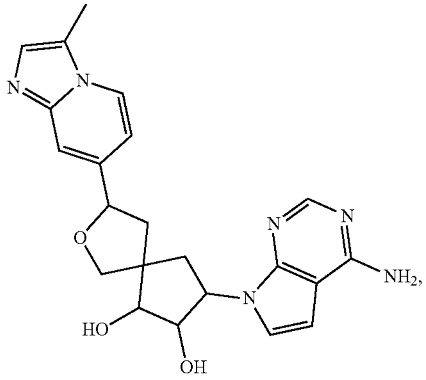
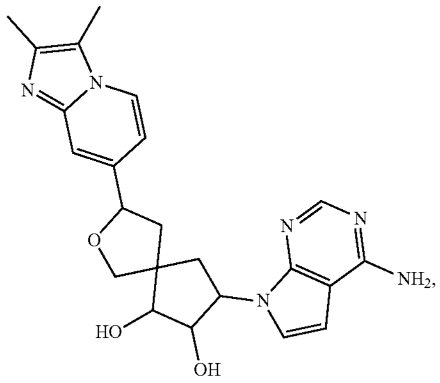
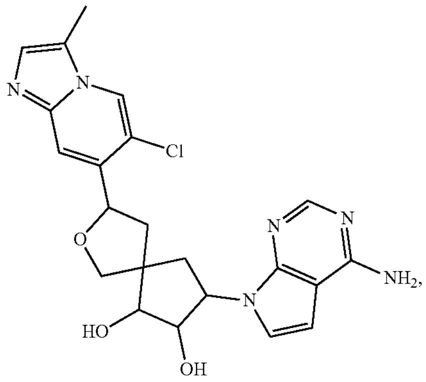

-continued
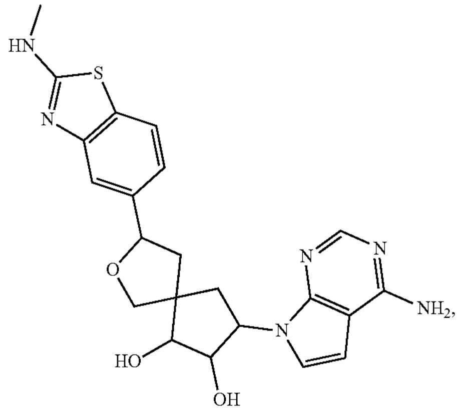
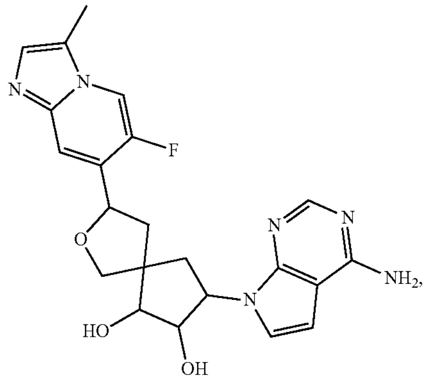
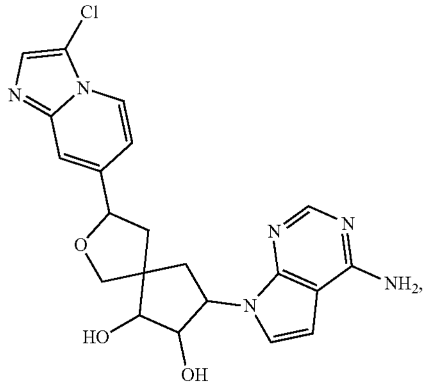
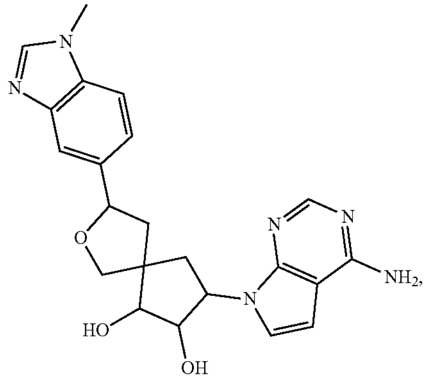
-continued
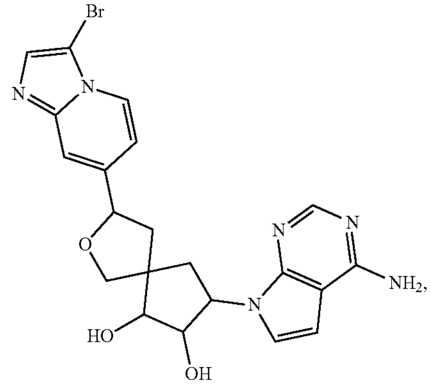
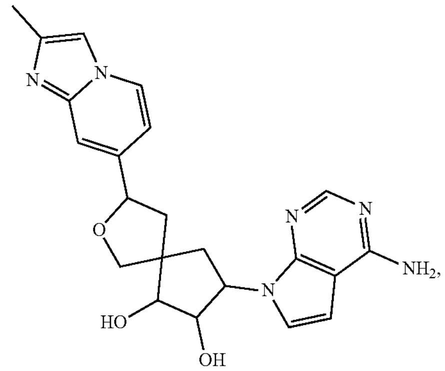
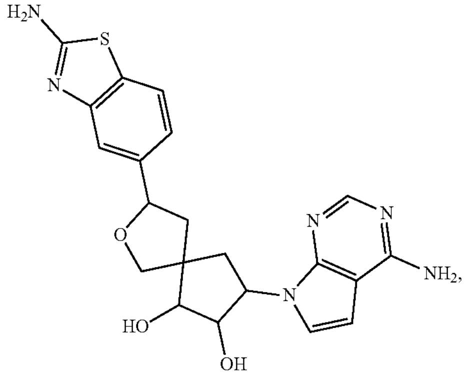
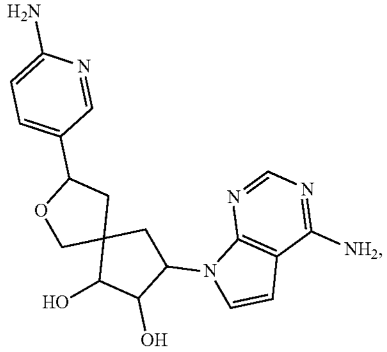

-continued
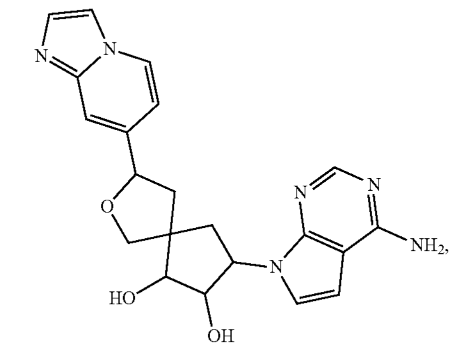
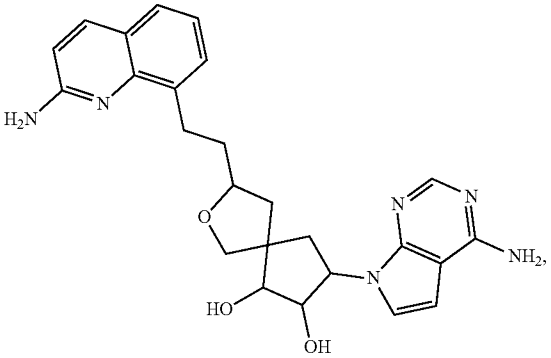
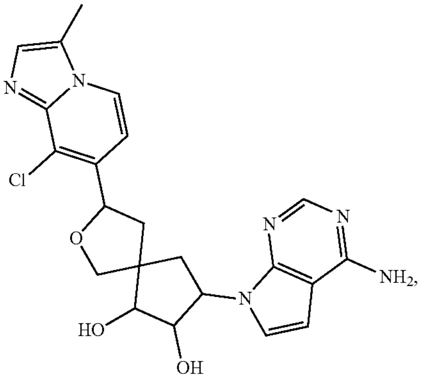
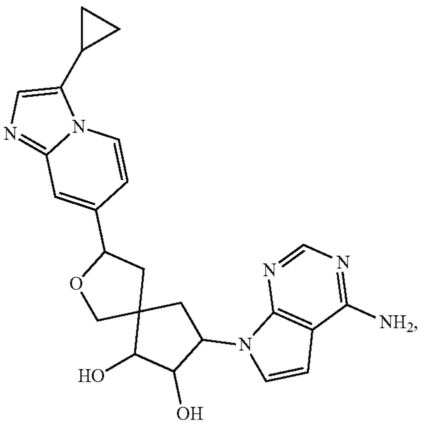
-continued
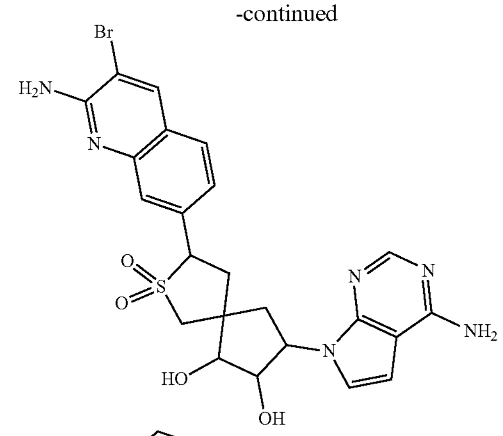
and
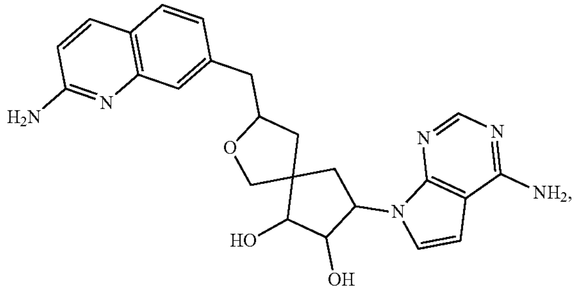
or a pharmaceutically salt thereof.
In some aspects, the invention relates to a compound of Formula I having a structure selected from:
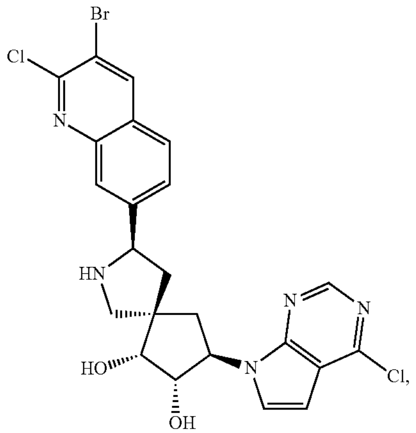
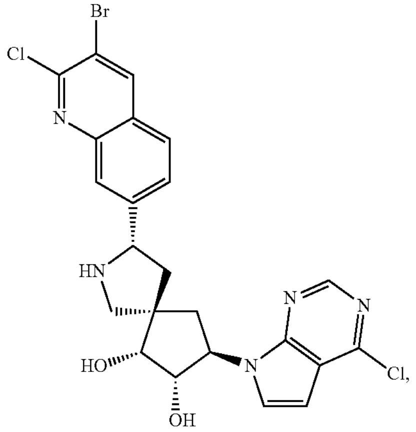

-continued
-continued
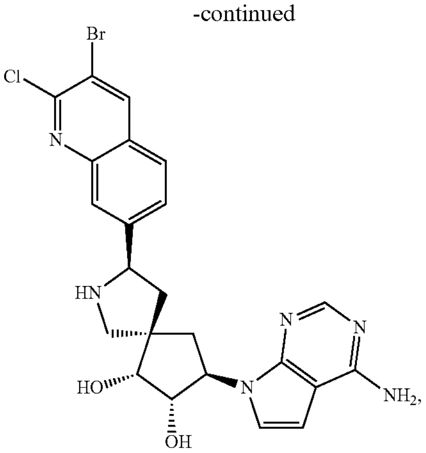
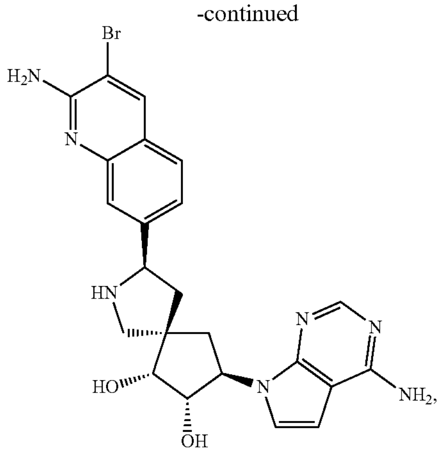
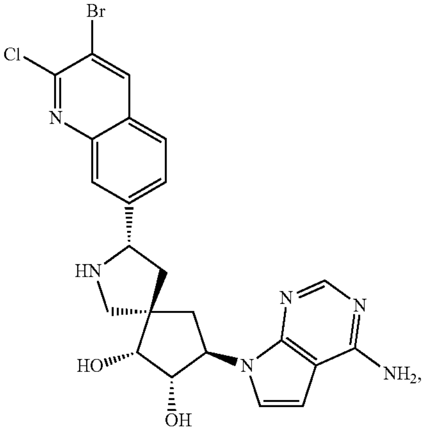
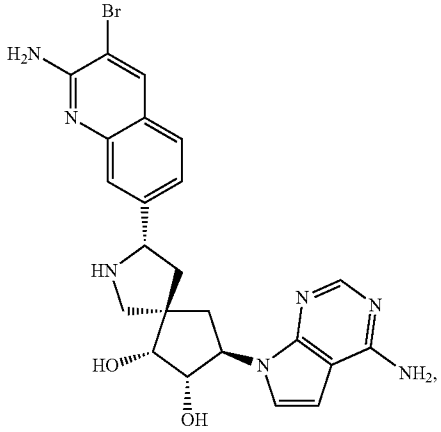
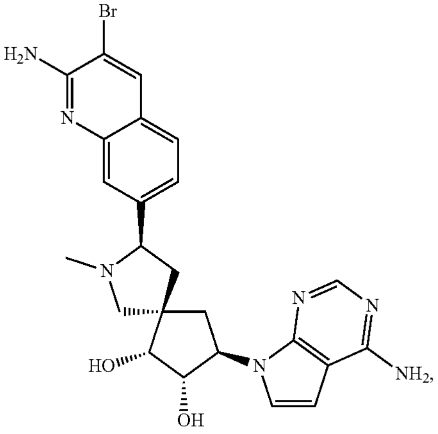
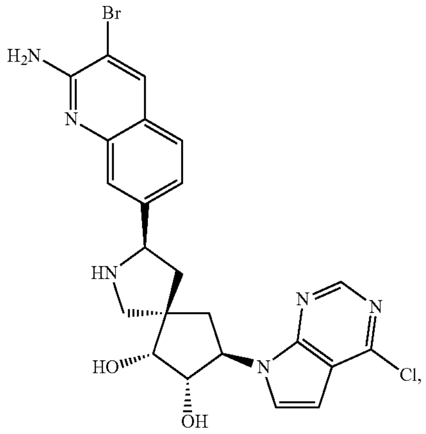
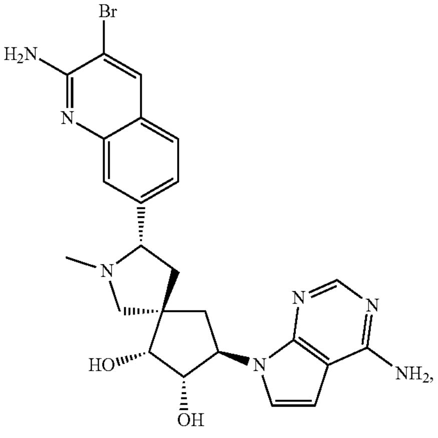
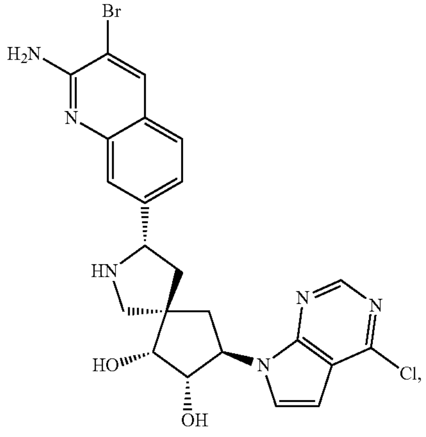

-continued
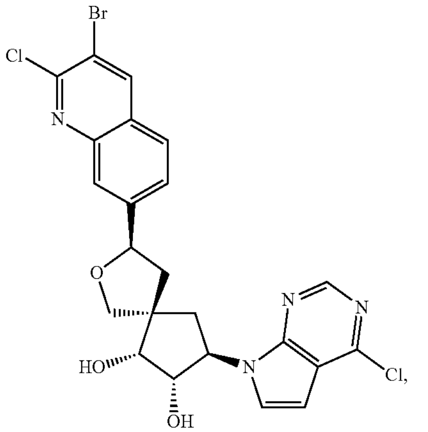
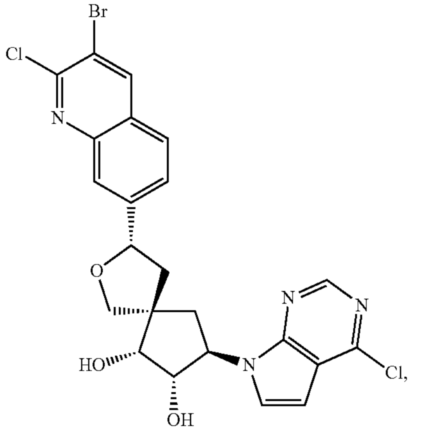
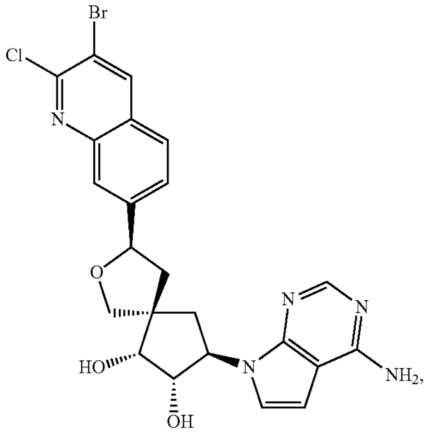
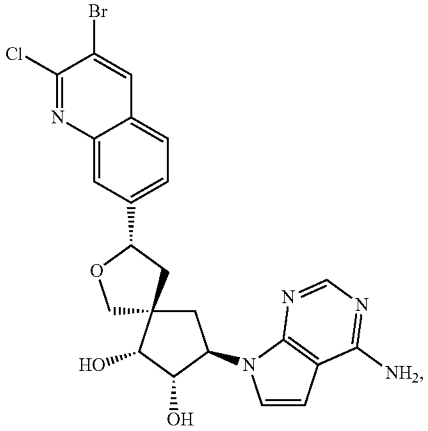
-continued
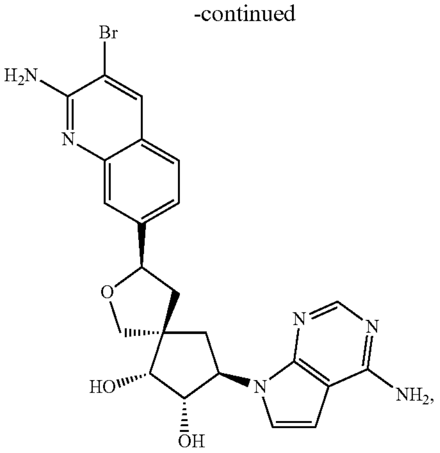
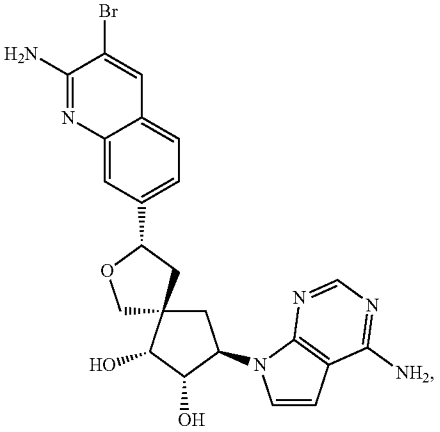
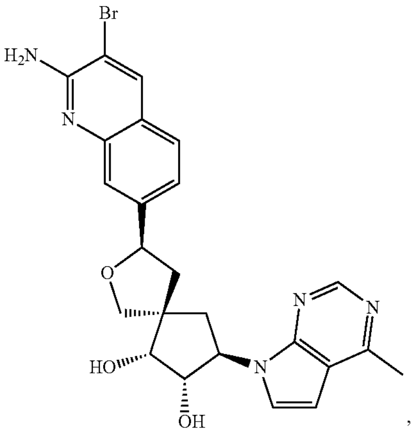
,
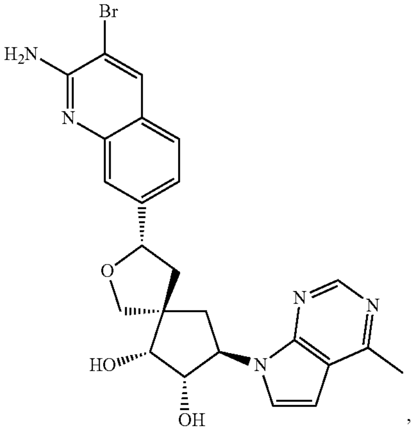
, -continued
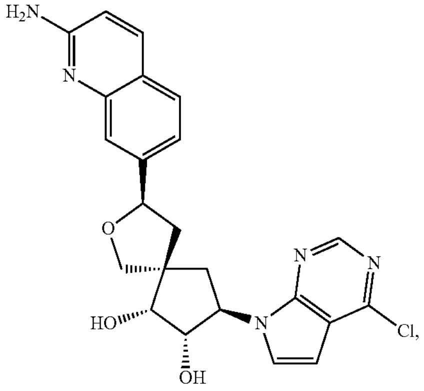
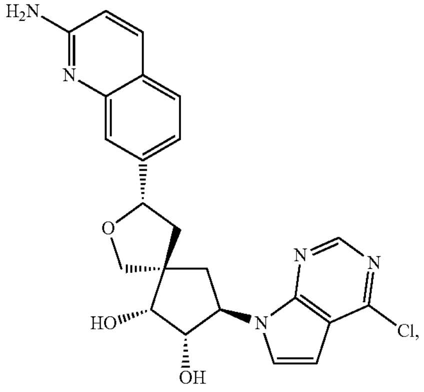
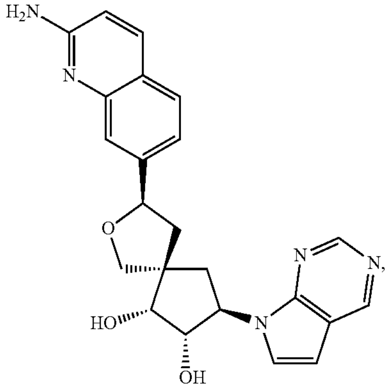
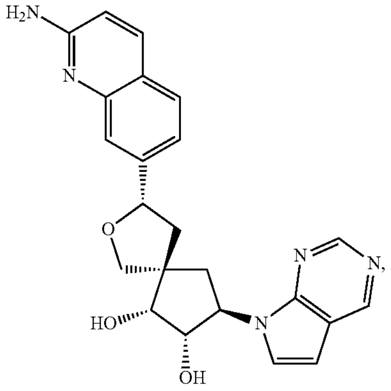
-continued
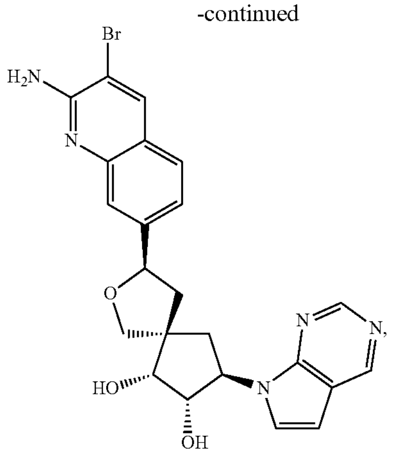
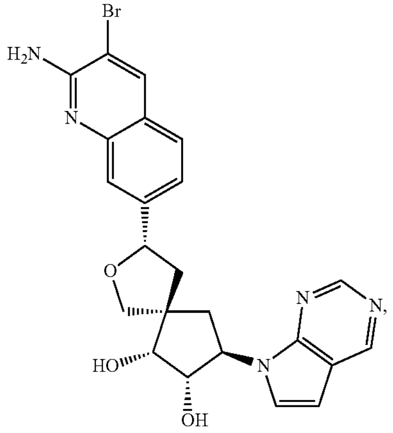
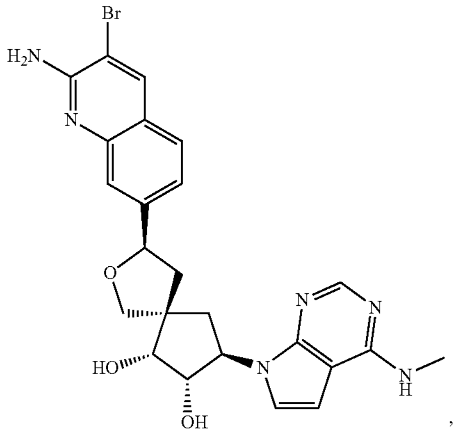
,
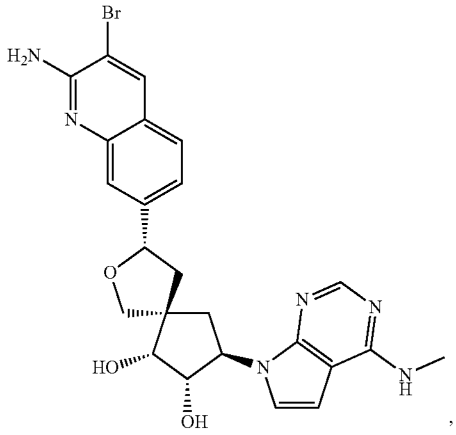
, -continued
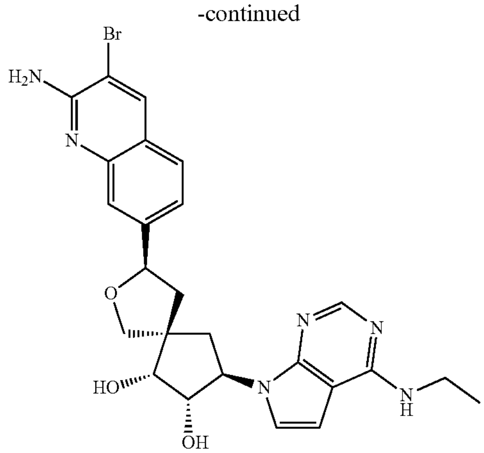
,
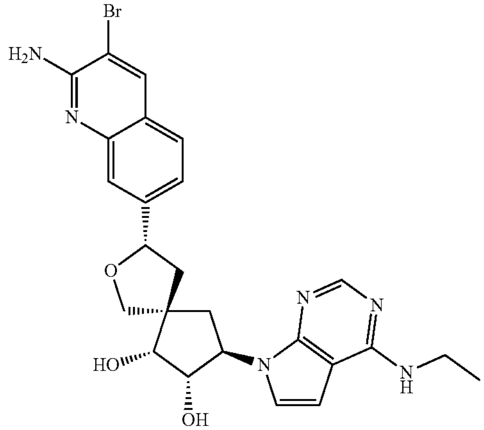
,
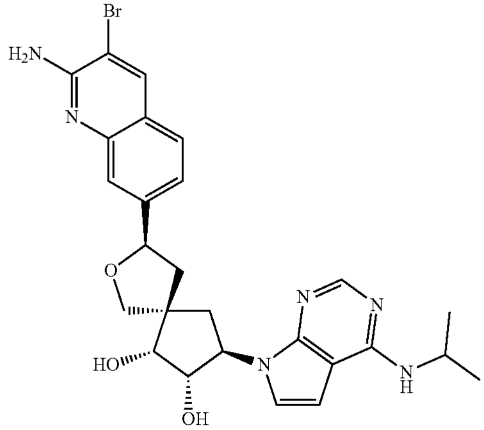
,
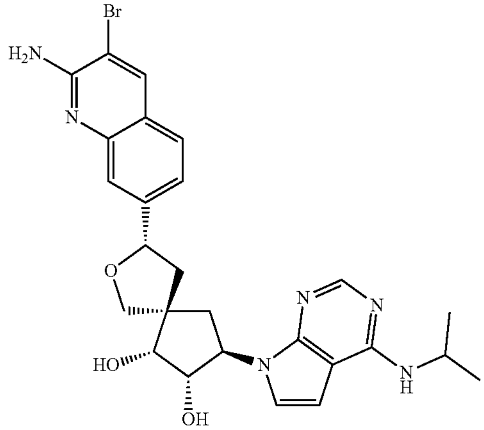
,
-continued
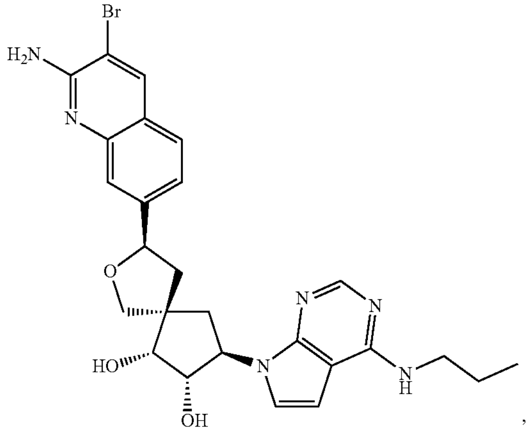
,
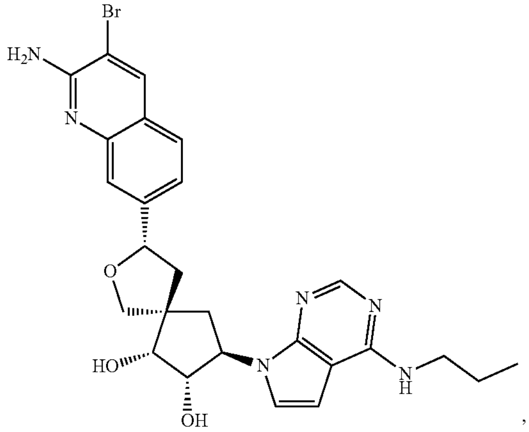
,
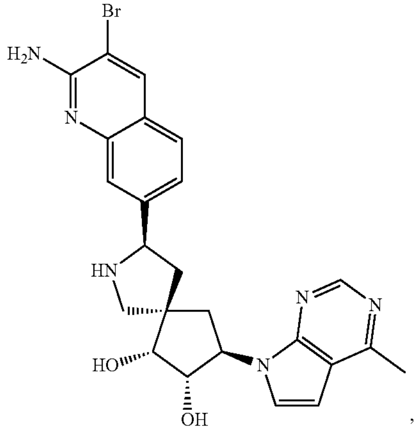
,
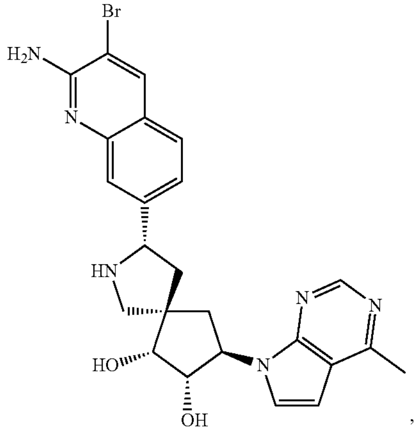
, -continued
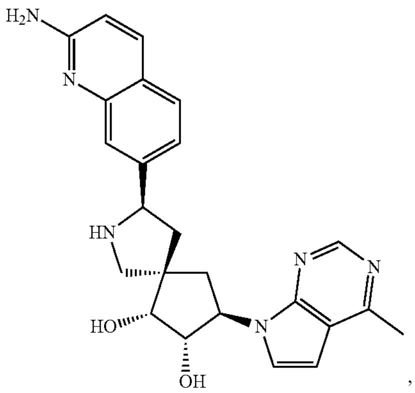
,
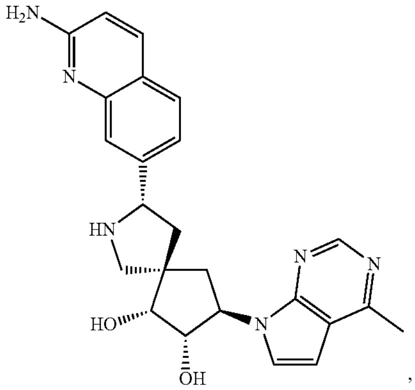
,
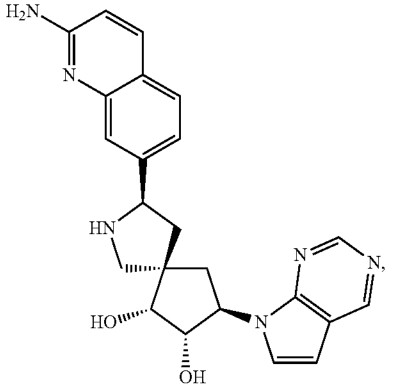
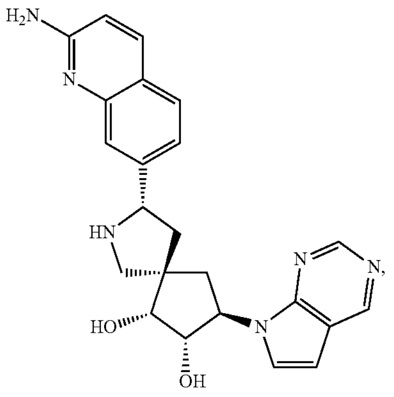
-continued
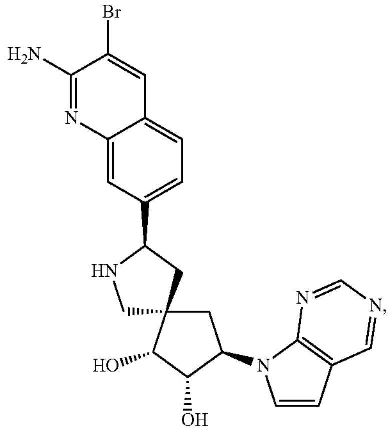
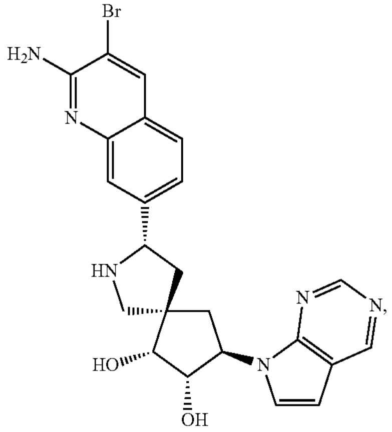
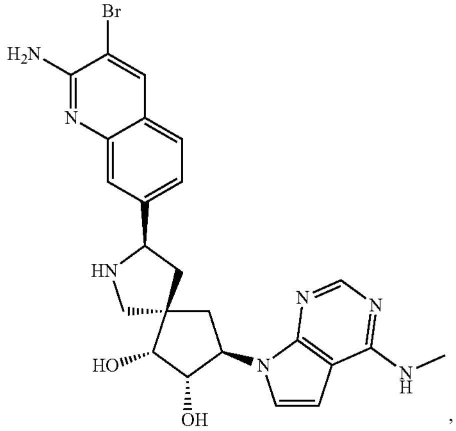
,
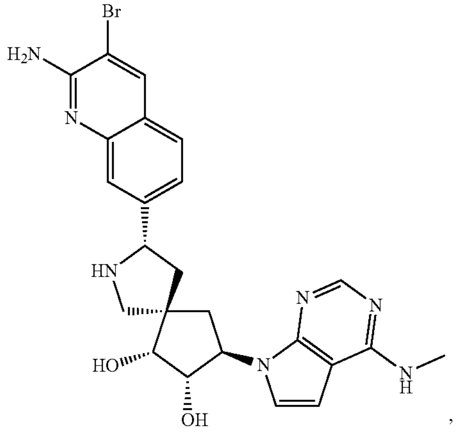
, -continued
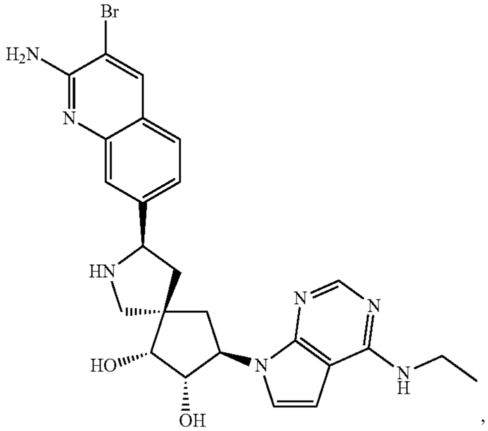
,
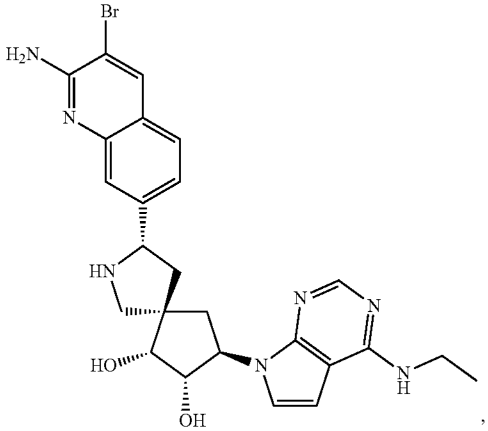
,
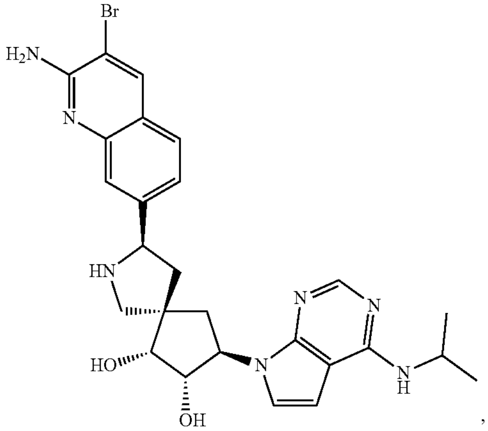
,
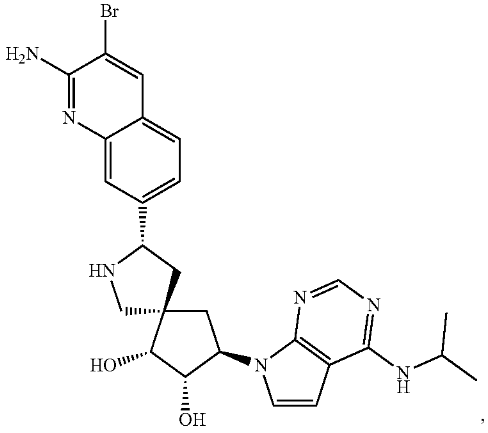
,
-continued
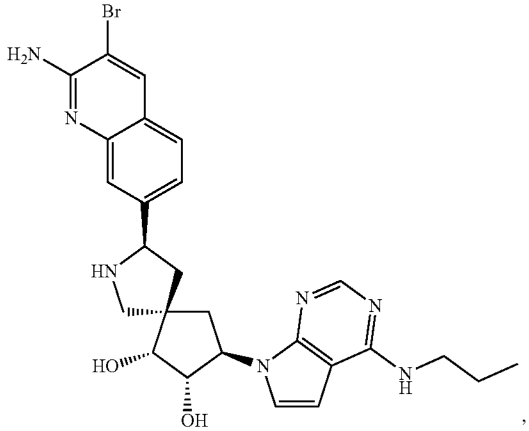
,
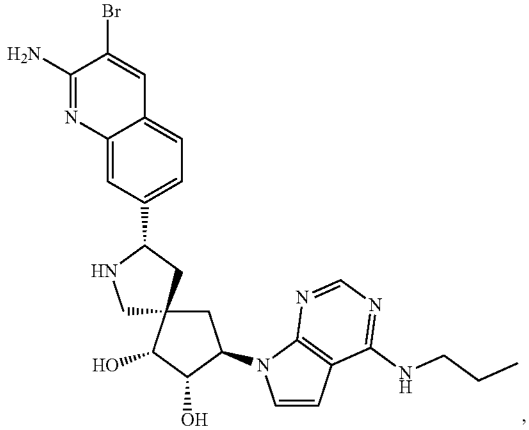
,
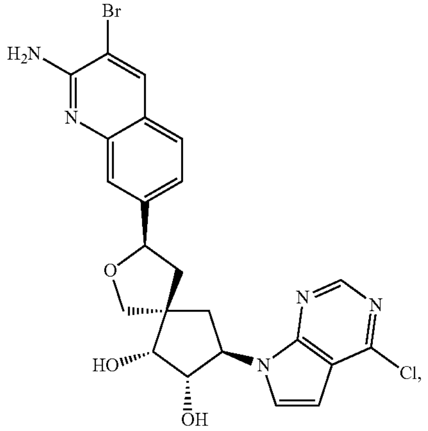
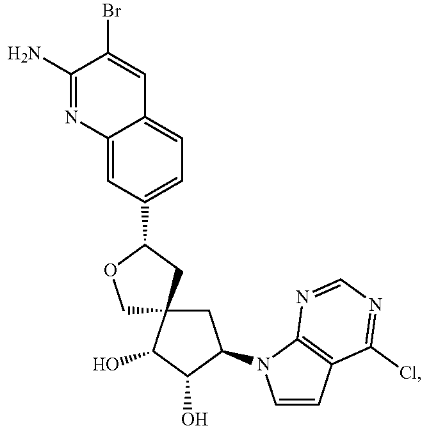

-continued
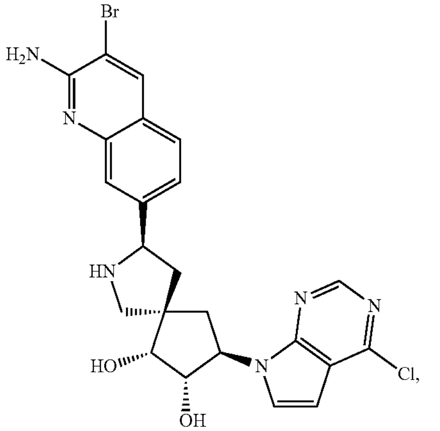
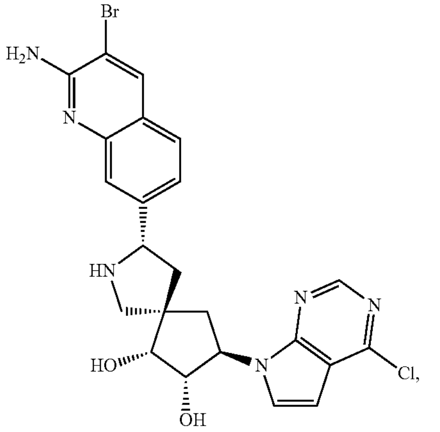
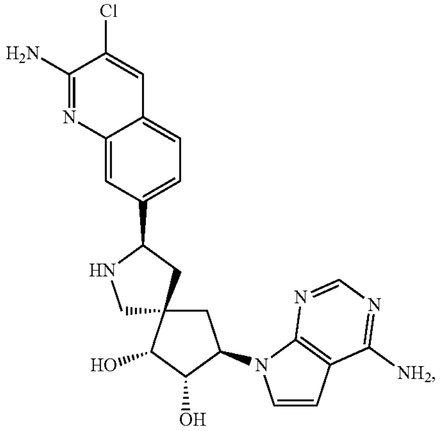
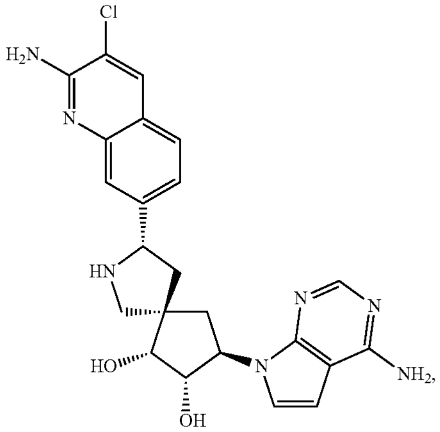
-continued
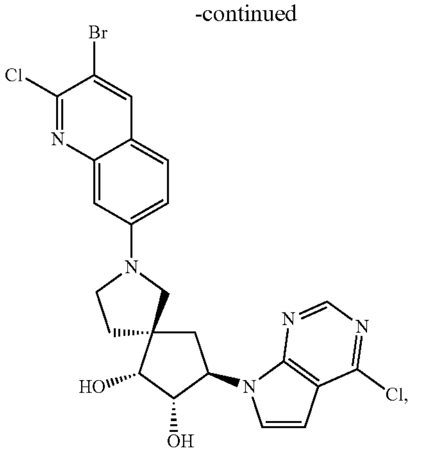
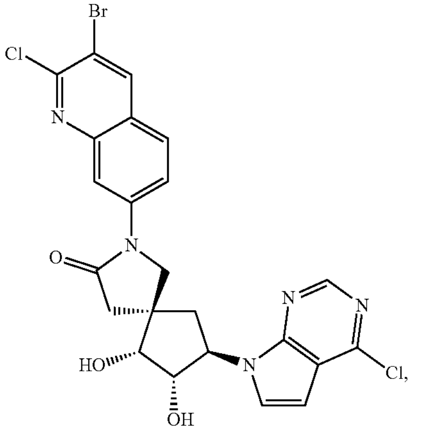
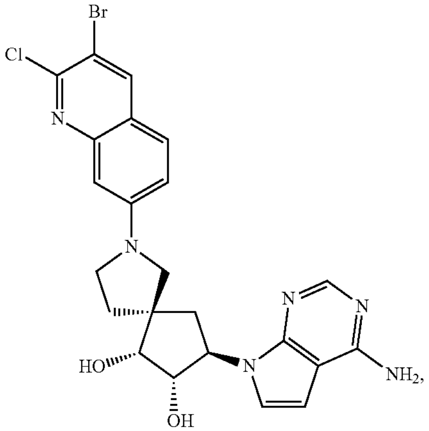
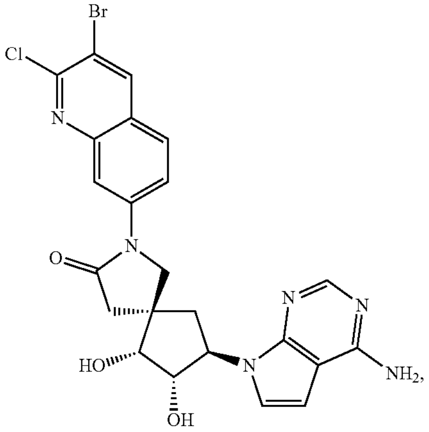

-continued
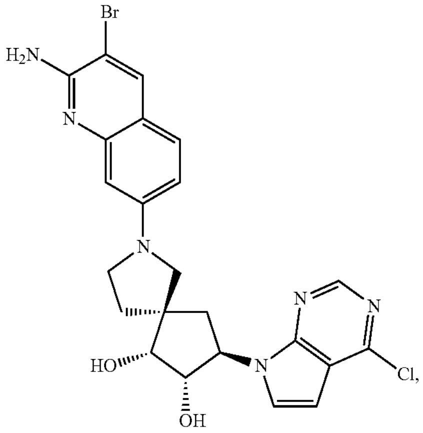
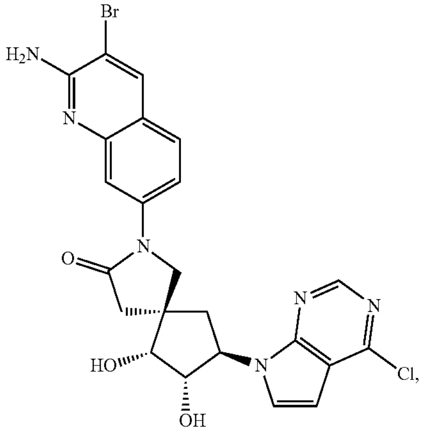
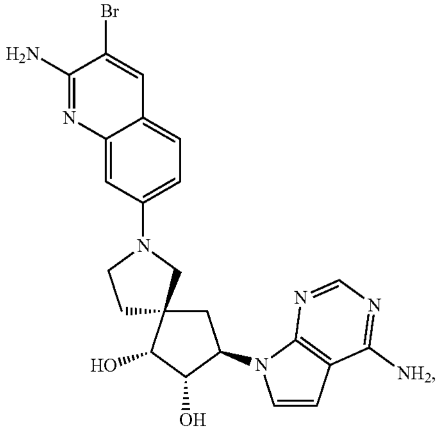
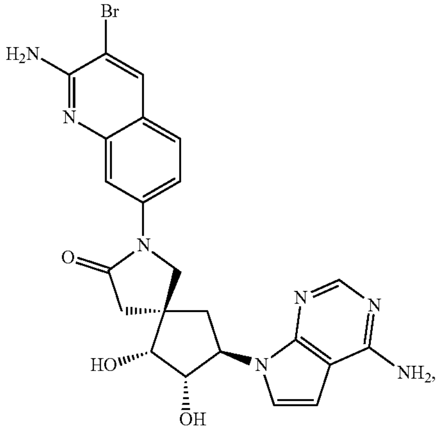
-continued
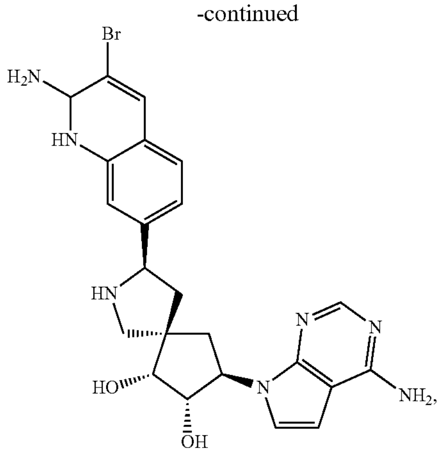
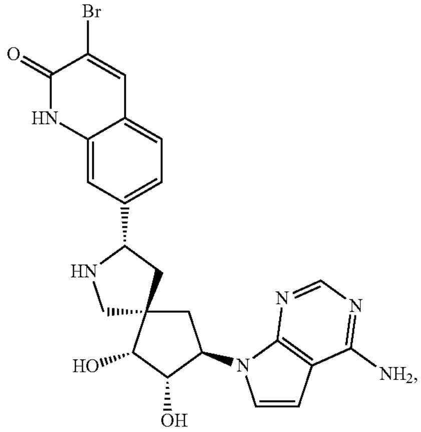
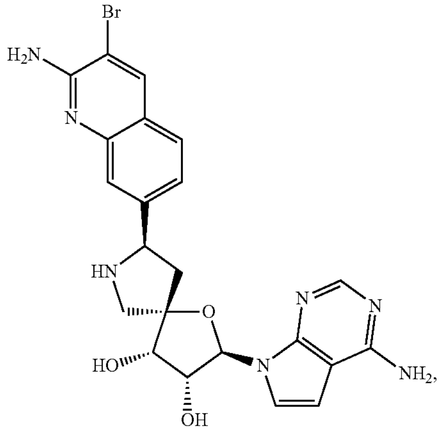
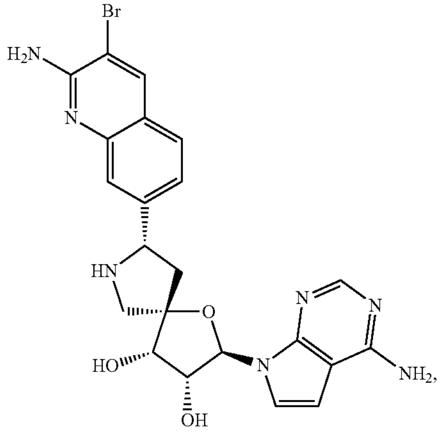

-continued
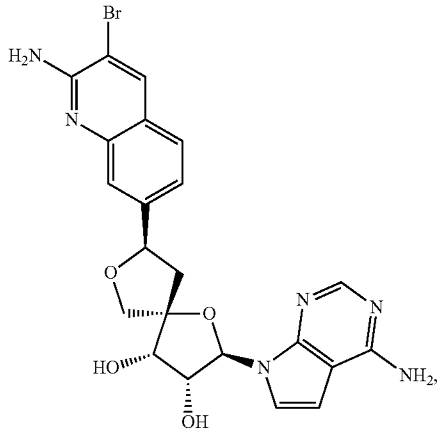
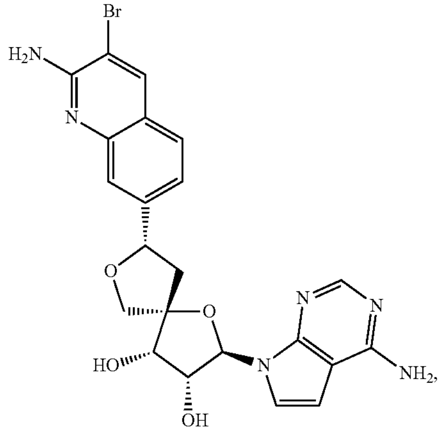
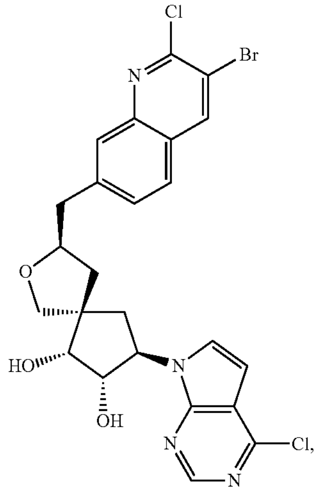
-continued
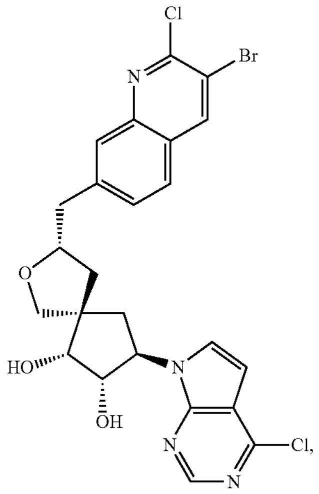
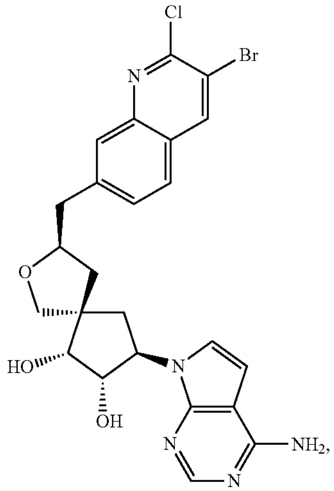
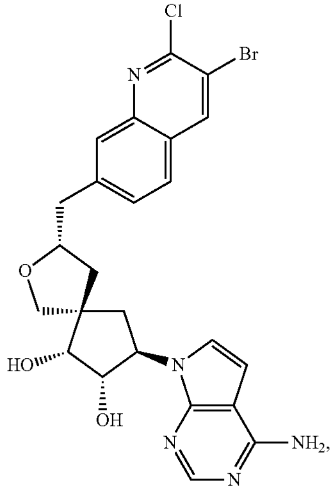

-continued
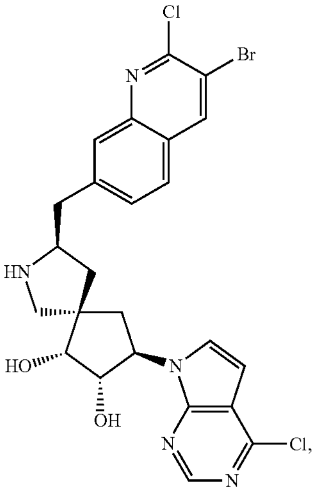
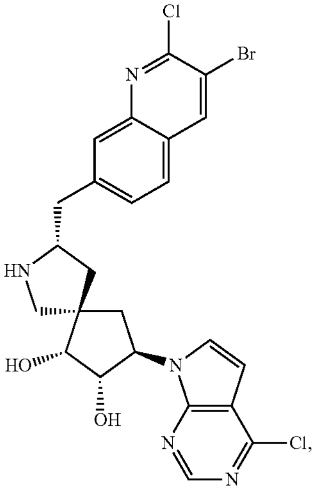
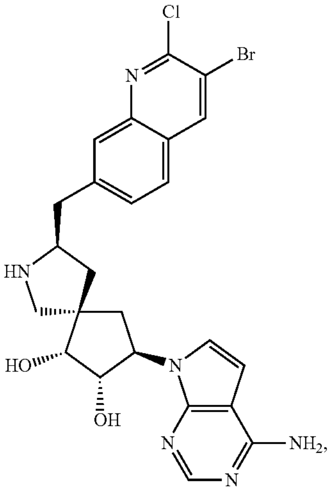
-continued
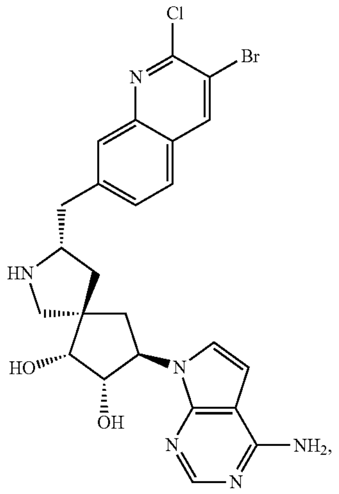
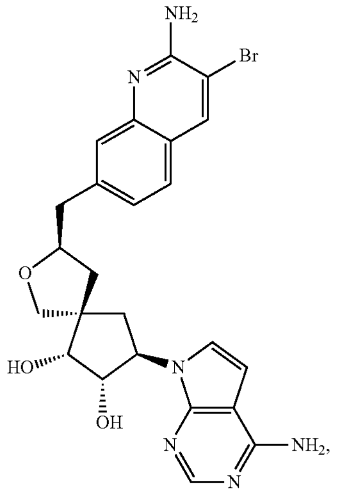
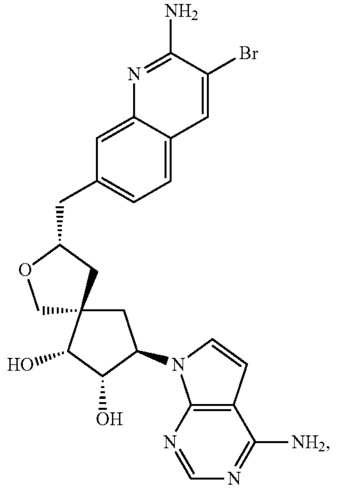

-continued
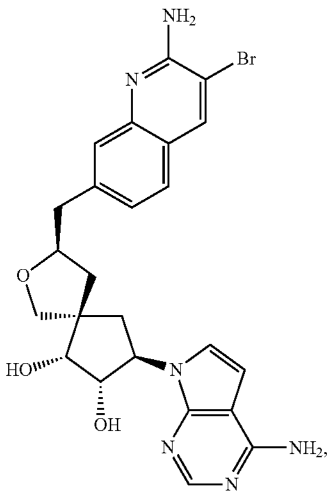
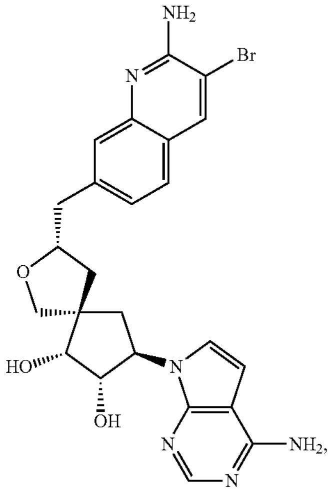
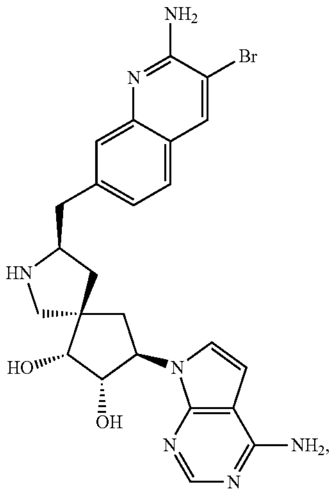
-continued
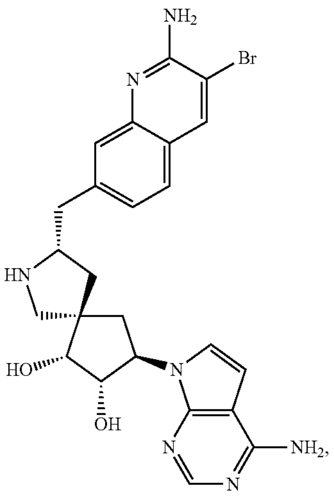
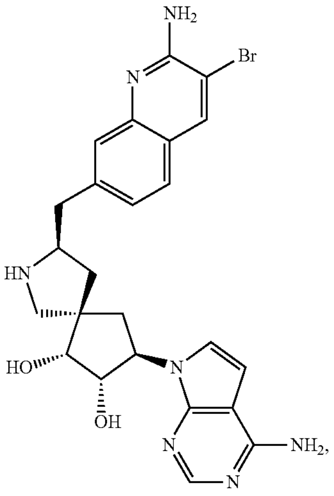
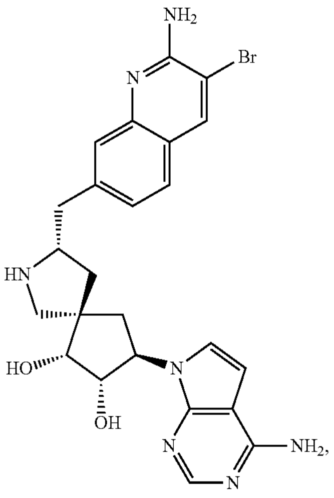

-continued
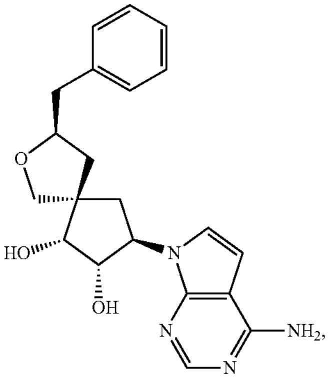
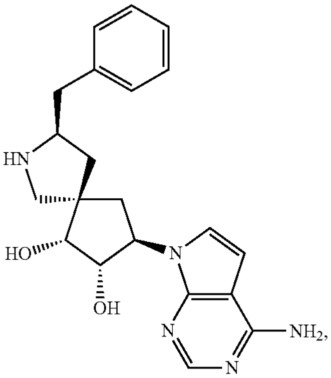
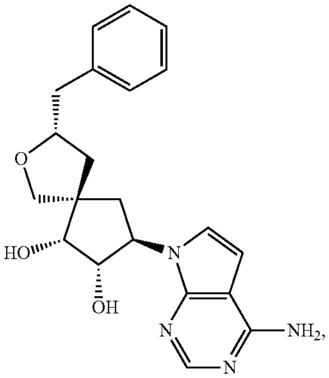
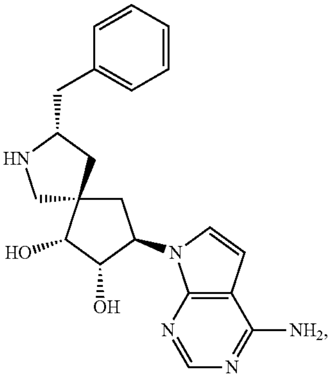
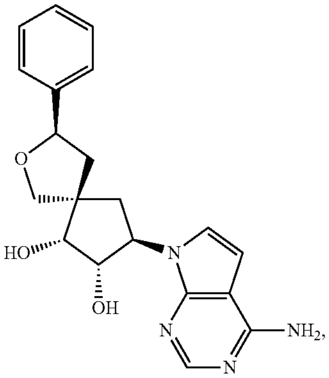
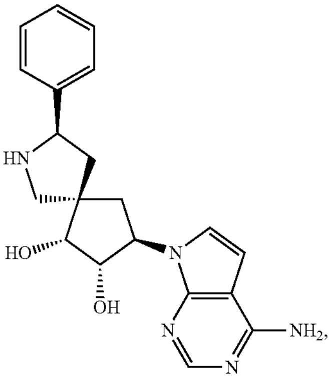
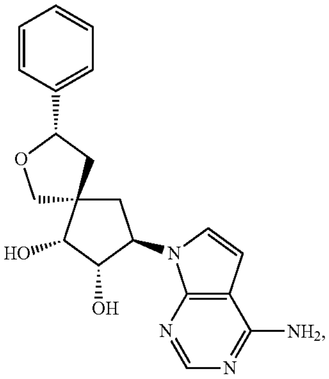
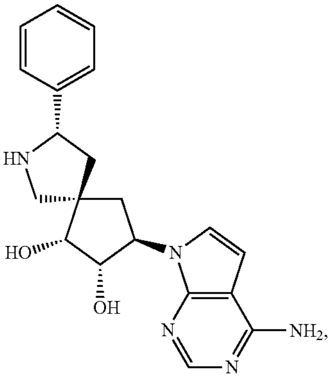
-continued -continued
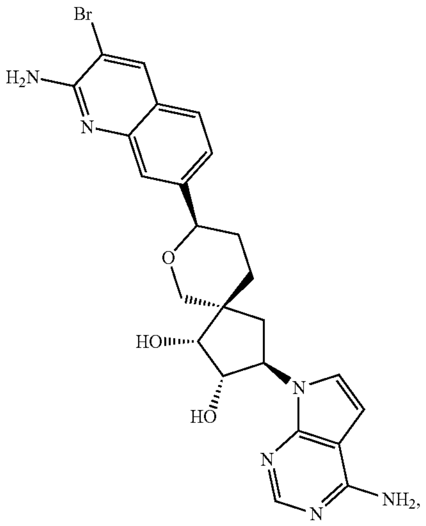
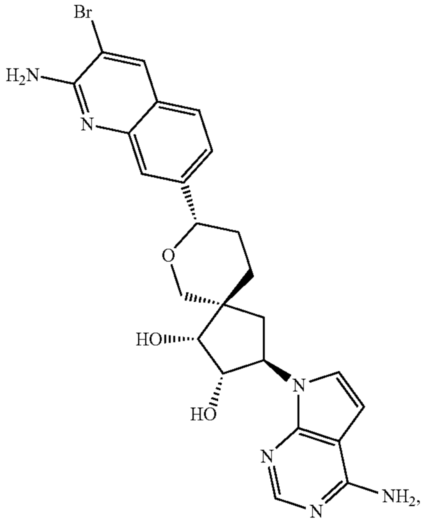
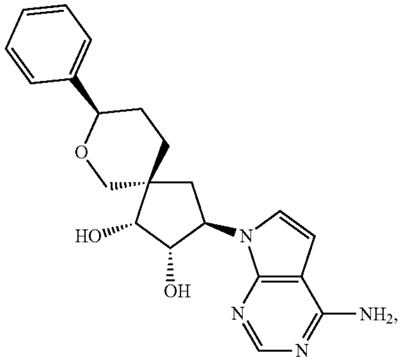
-continued
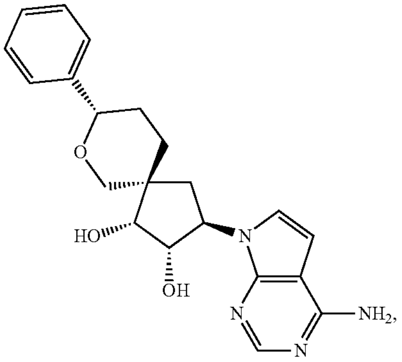
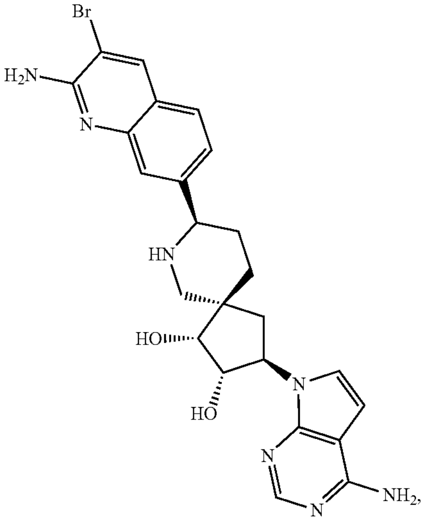
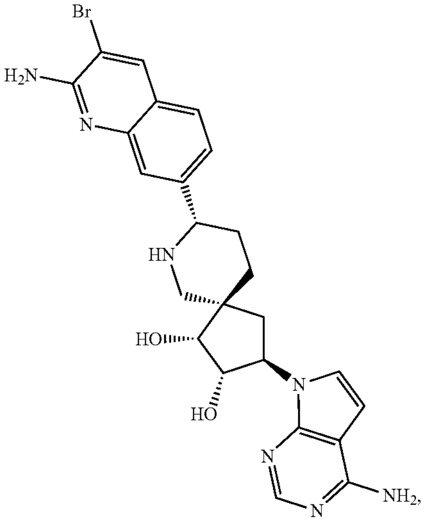

-continued
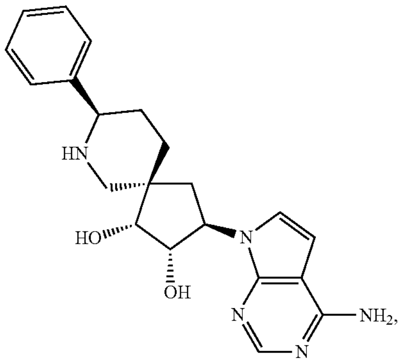
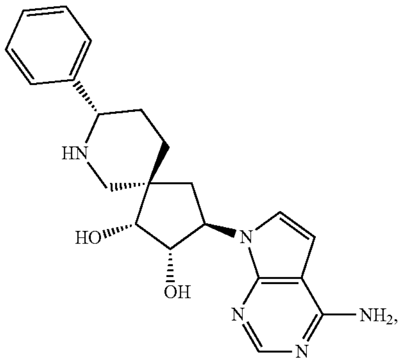
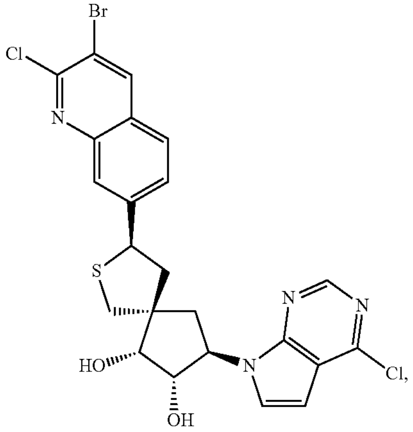
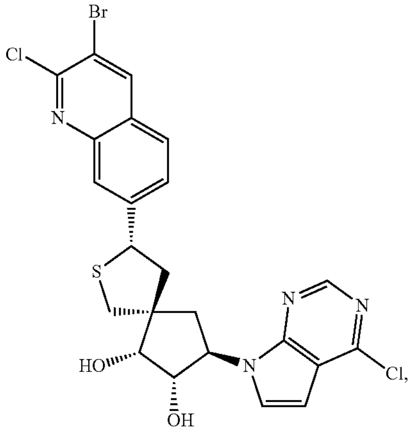
-continued
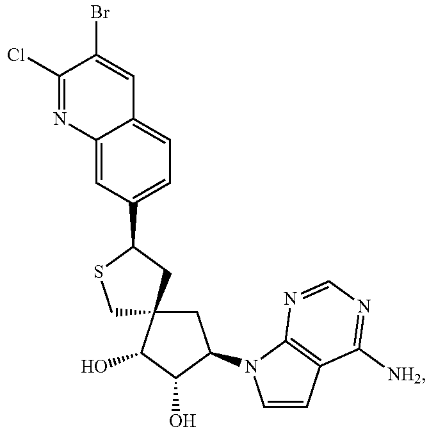
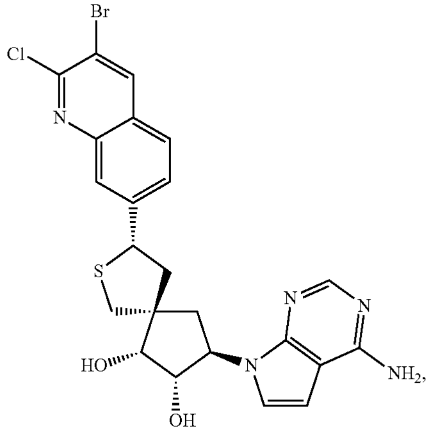
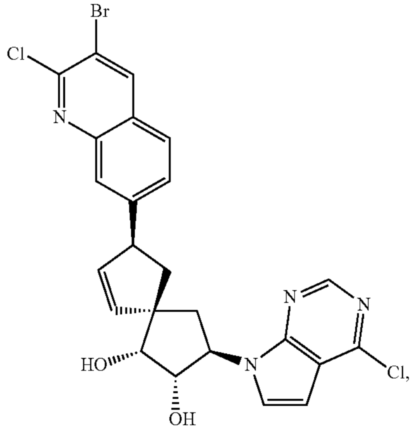
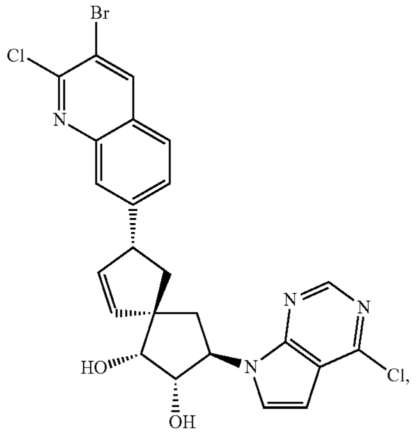

-continued
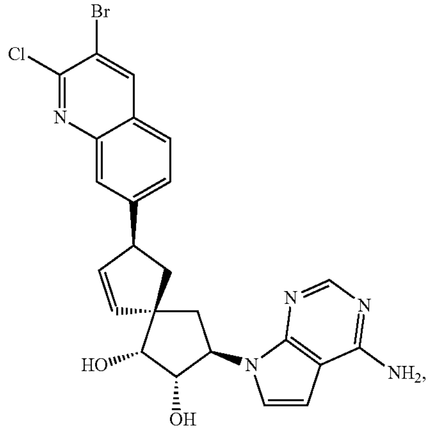,
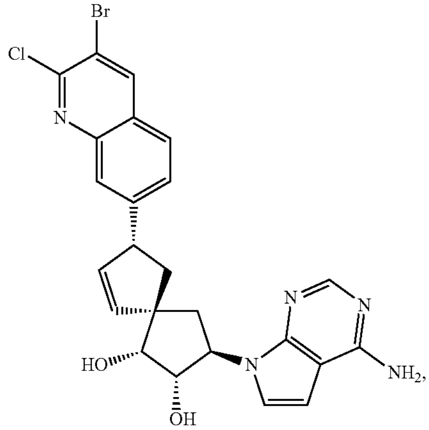,
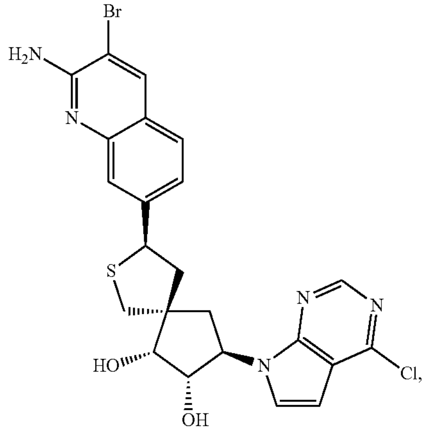,
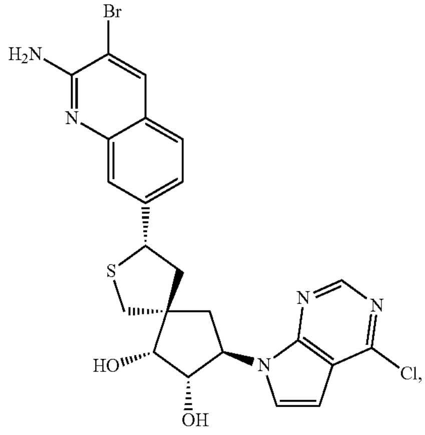,
-continued
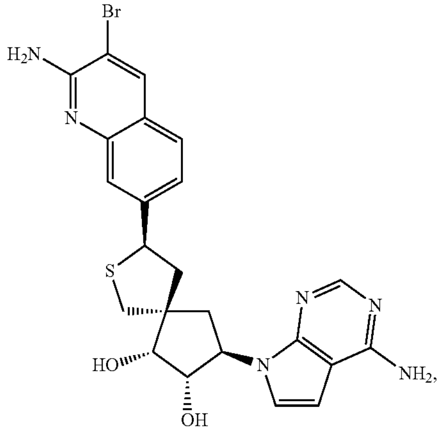,
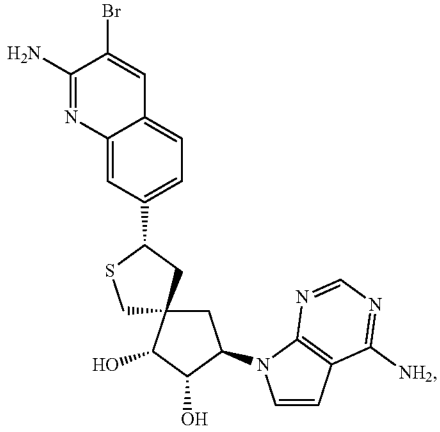,
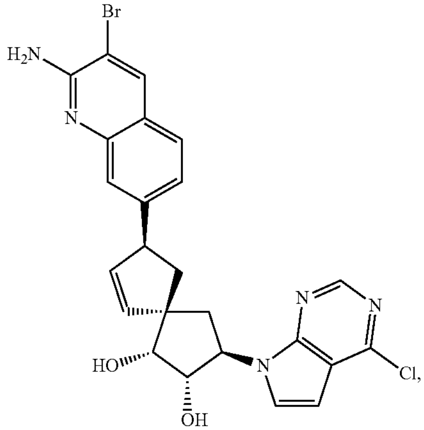,
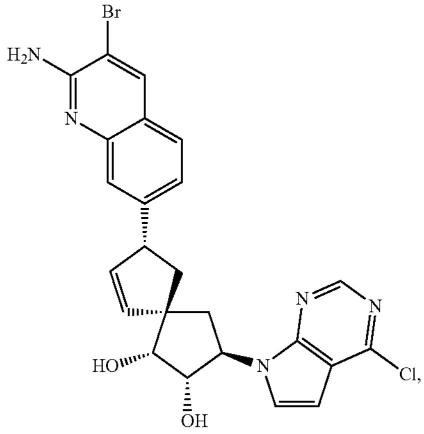, -continued
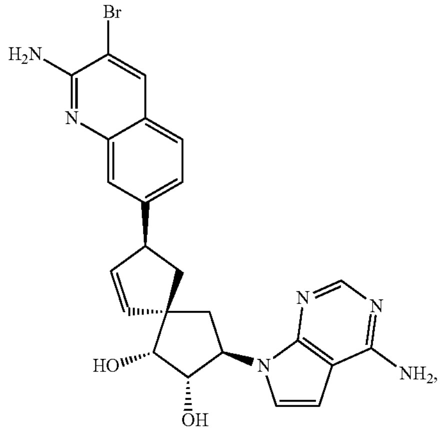
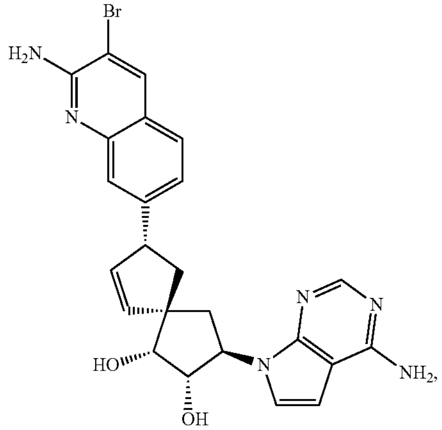
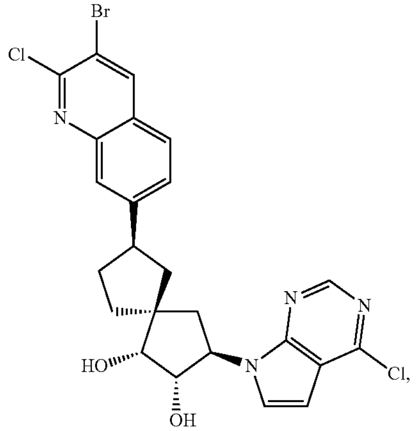
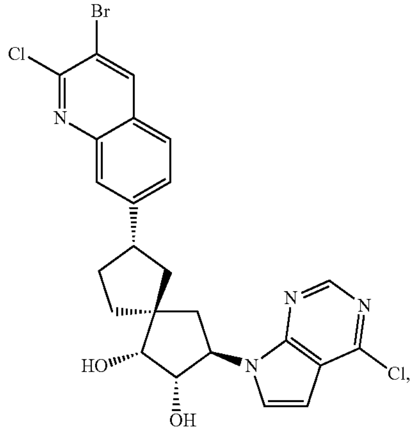
-continued
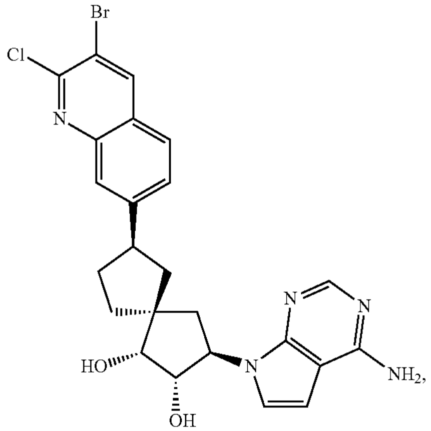
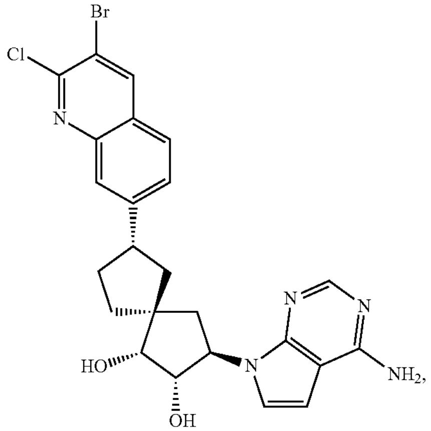
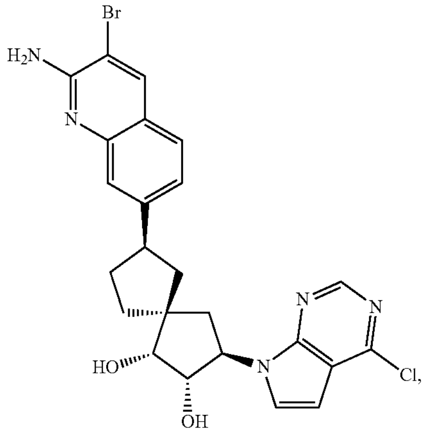
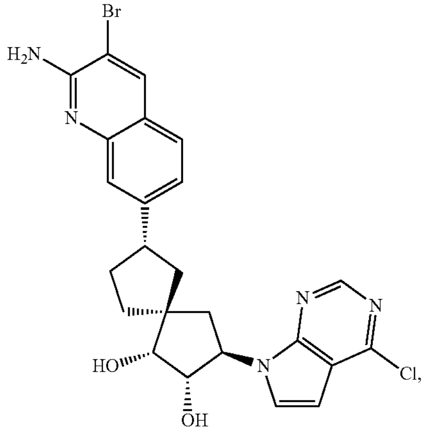

-continued
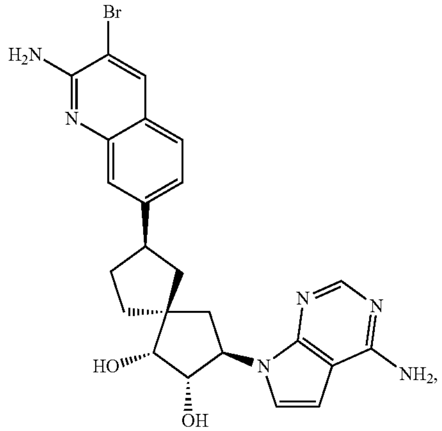
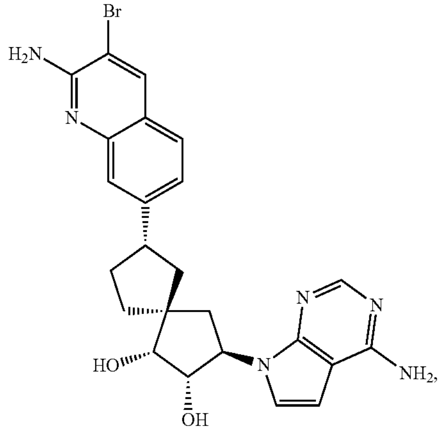
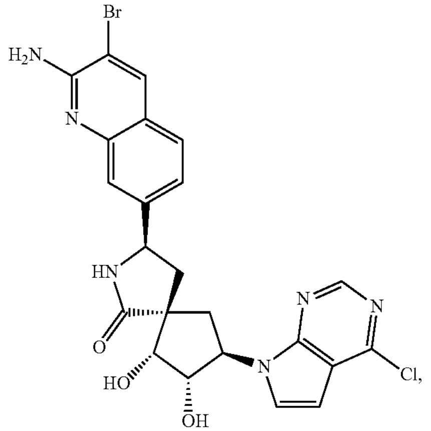
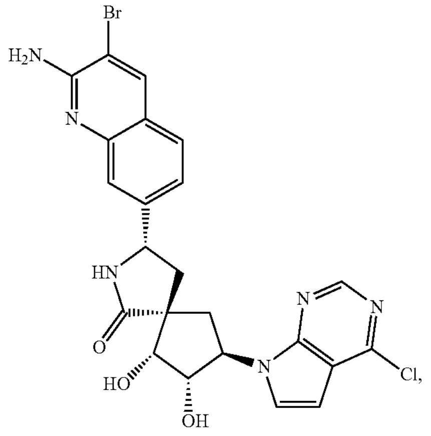
-continued
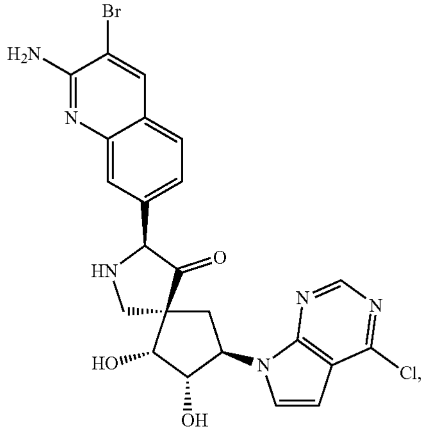
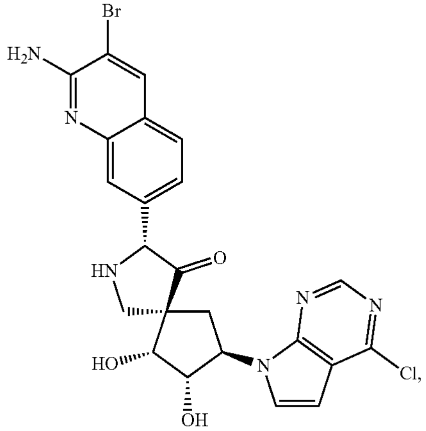
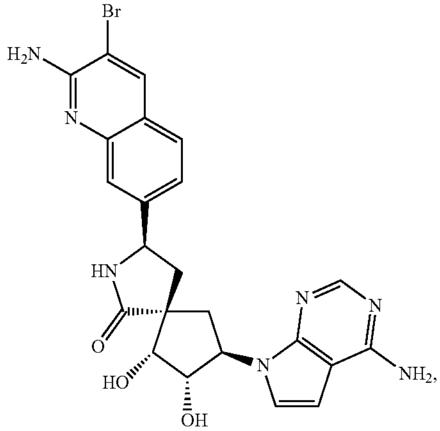
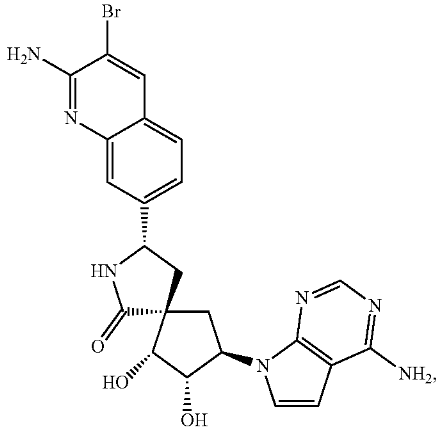

-continued
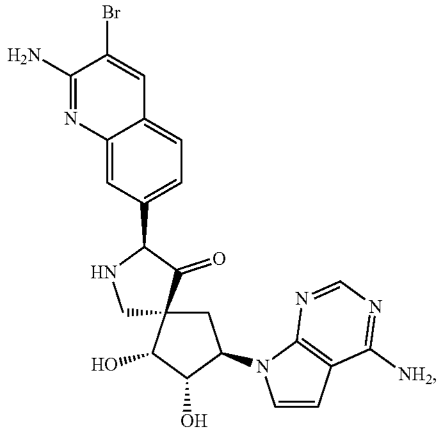
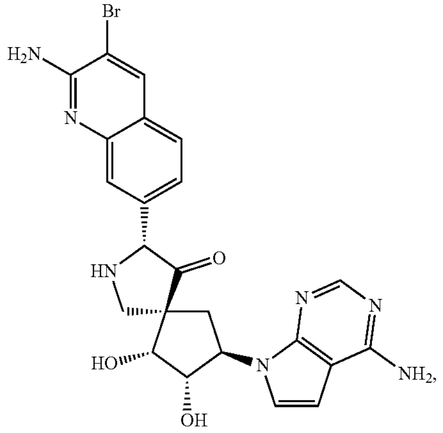
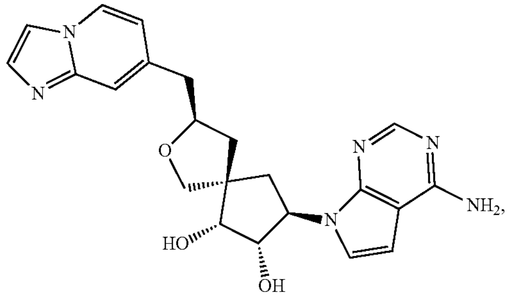
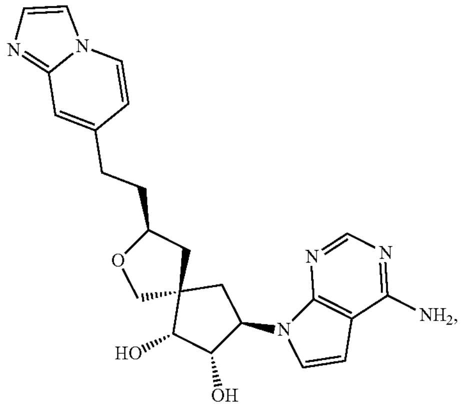
-continued
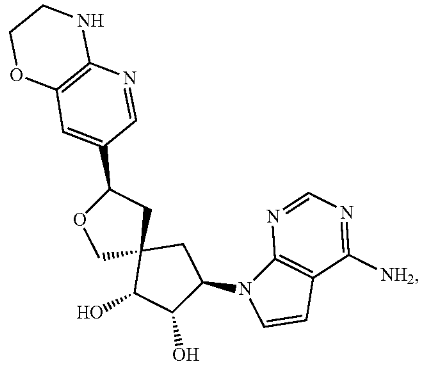
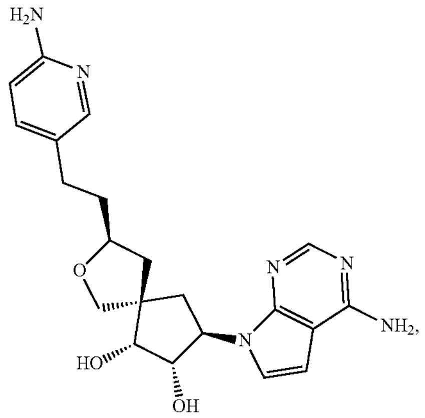
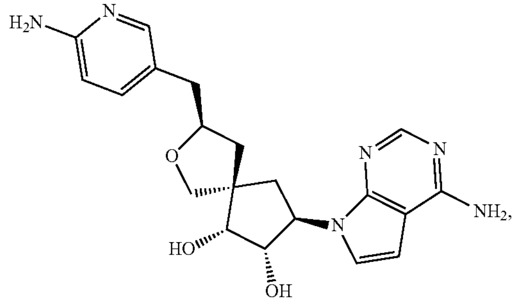
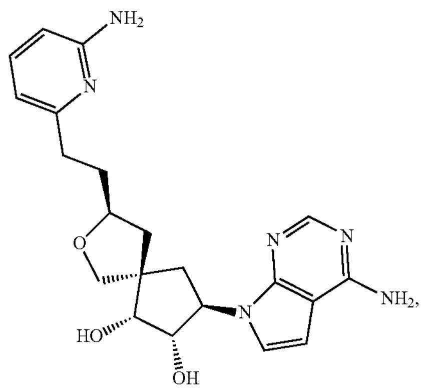

-continued
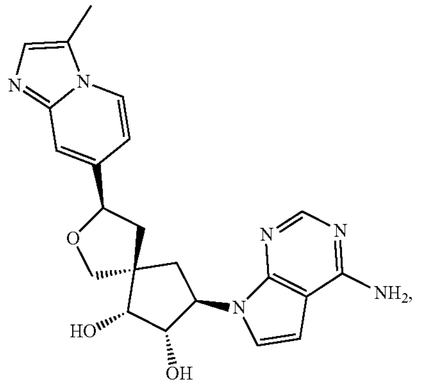,
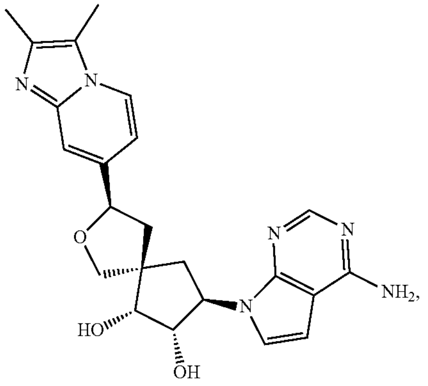,
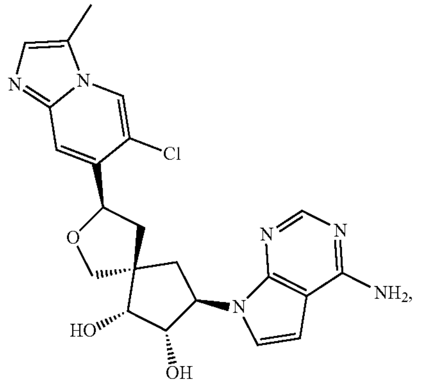,
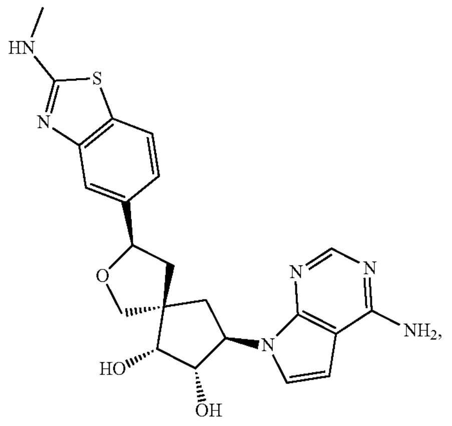,
-continued
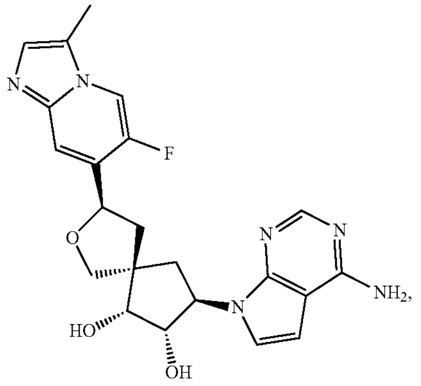,
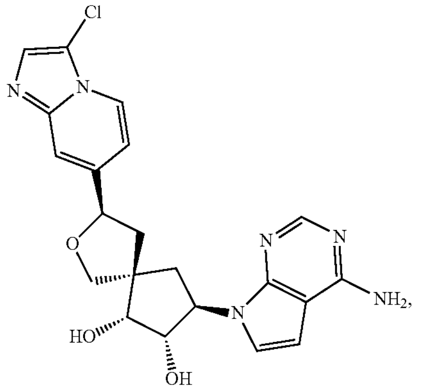,
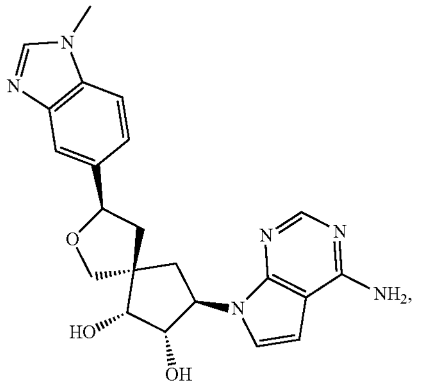,
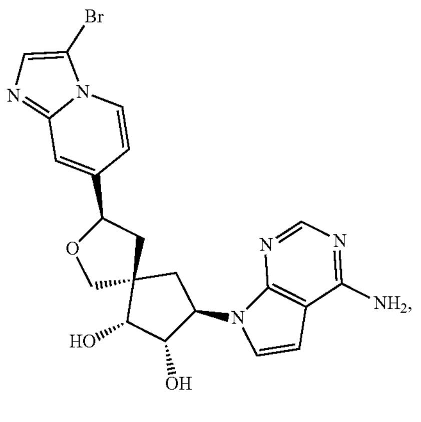, -continued
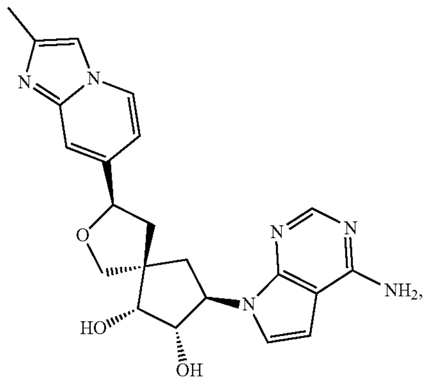
,
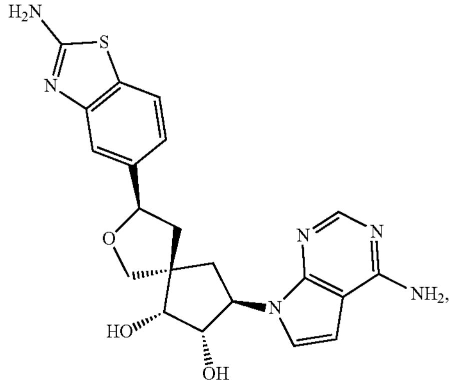
,
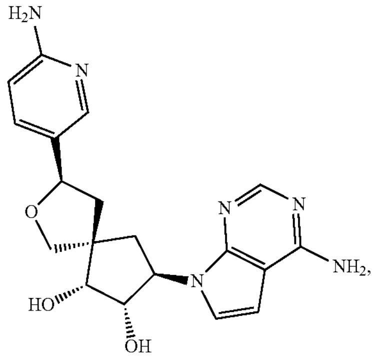
,
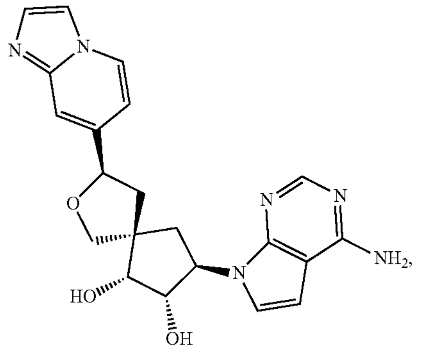
,
-continued
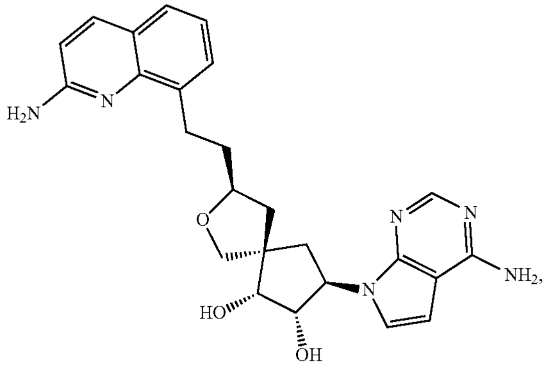
,
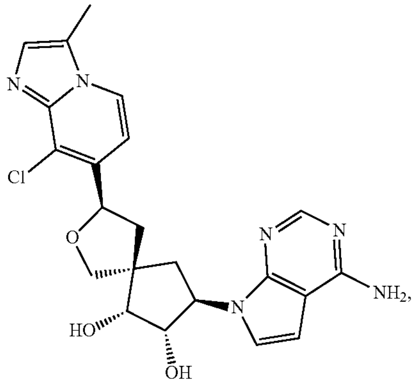
,
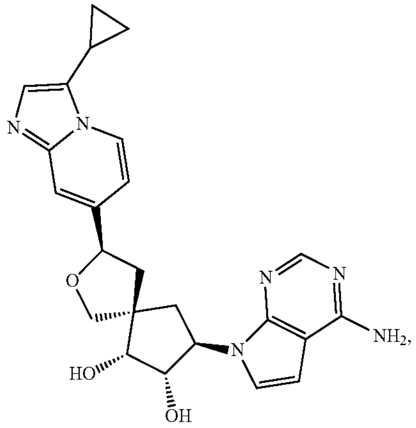
,
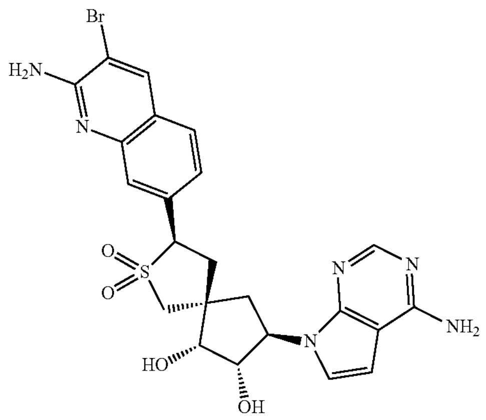
and -continued
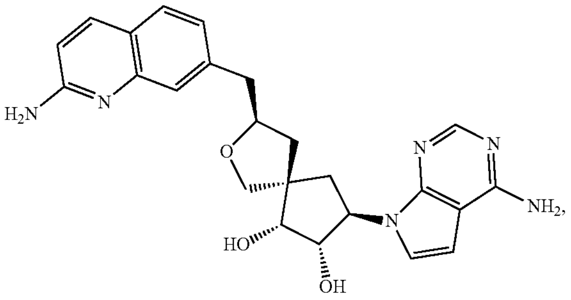 [SMILES: Nc1ccc2ccc(C[C@H]3C[C@@]4(CO3)C[C@@H](n3ccc5c(N)ncnc53)[C@H](O)[C@@H]4O)cc2n1]
or a pharmaceutically salt thereof.
In some aspects, the invention relates to a compound of Formula I having a structure selected from:
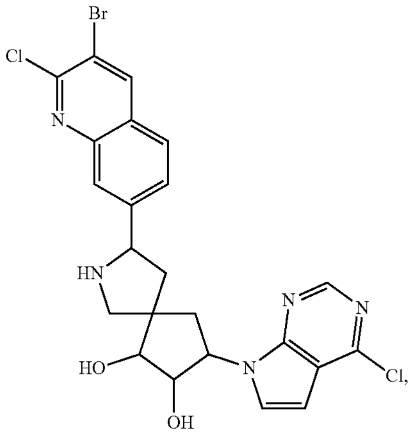
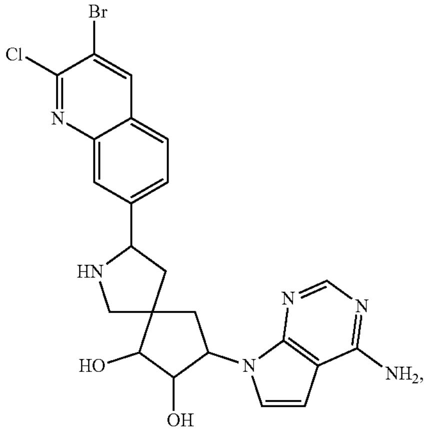
-continued
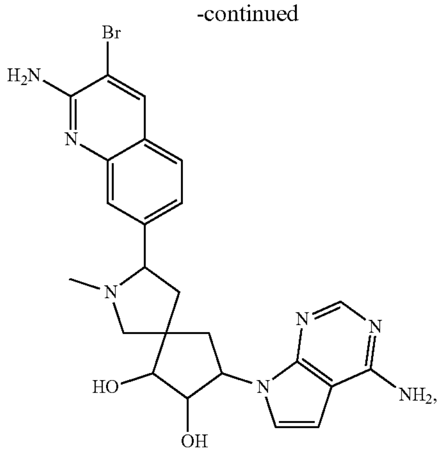
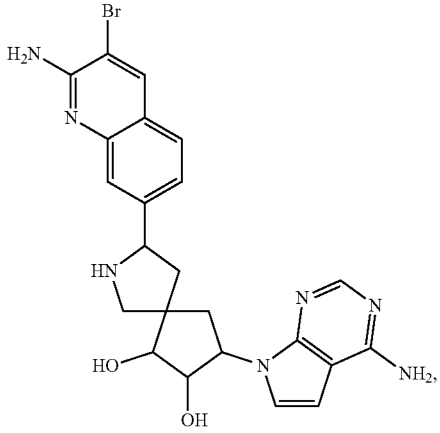
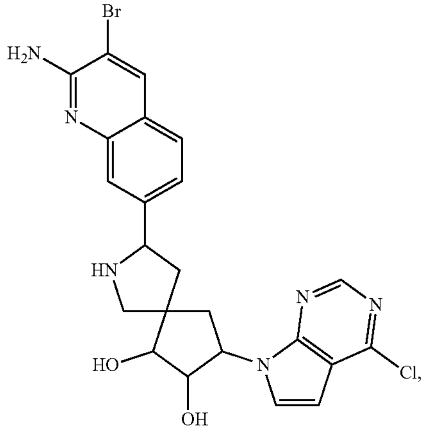
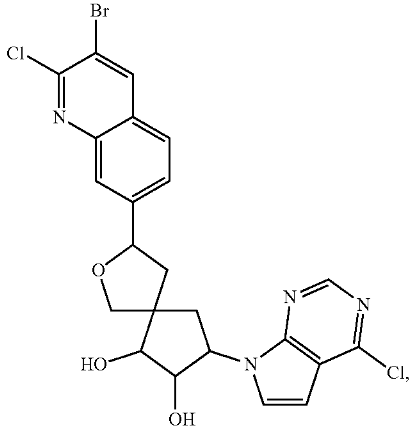

-continued
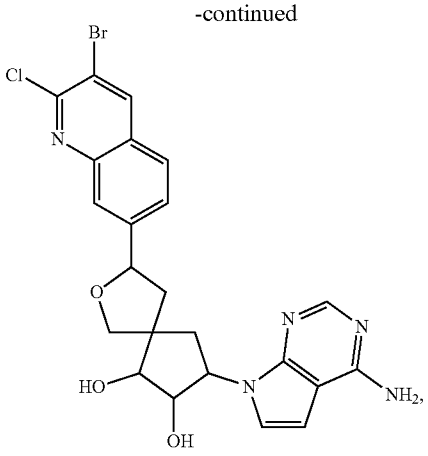
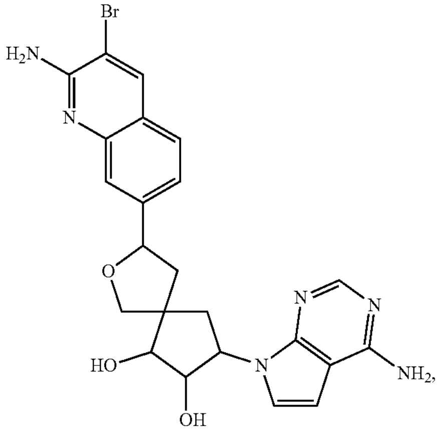
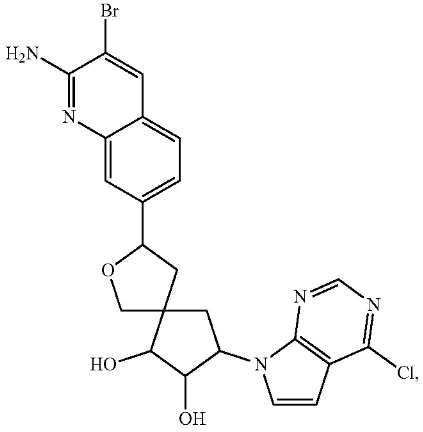
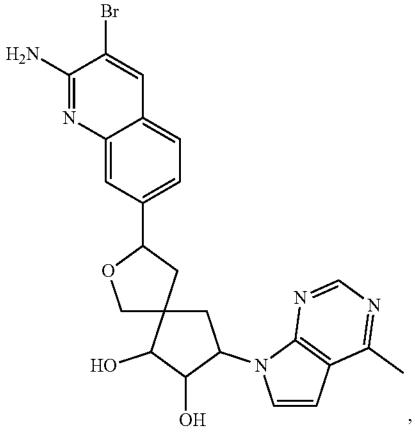
,
-continued
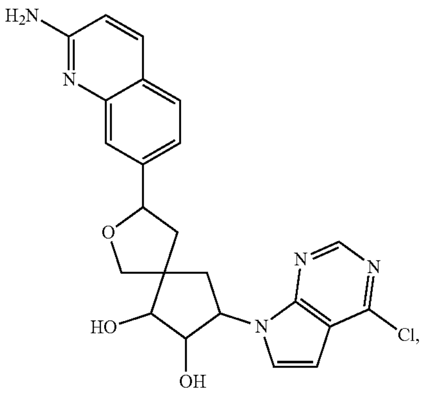
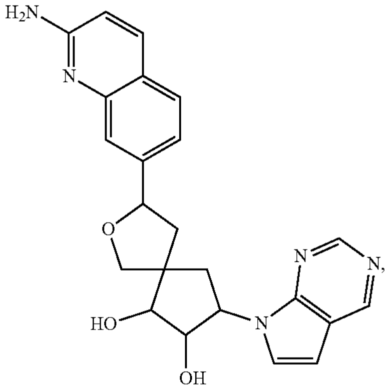
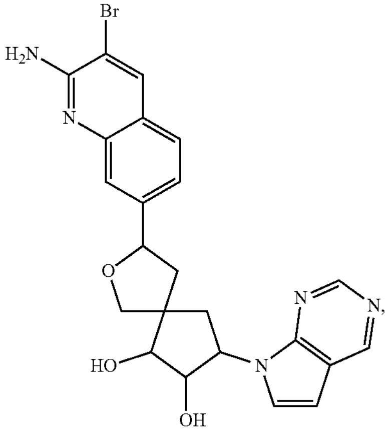
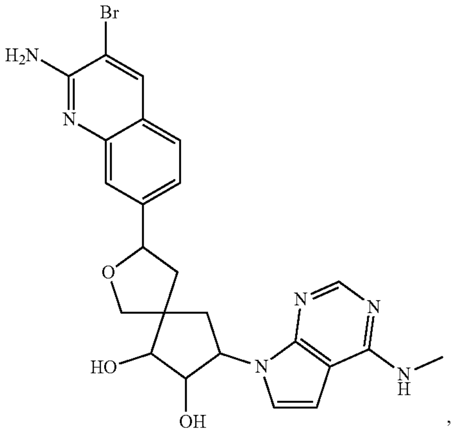
, -continued
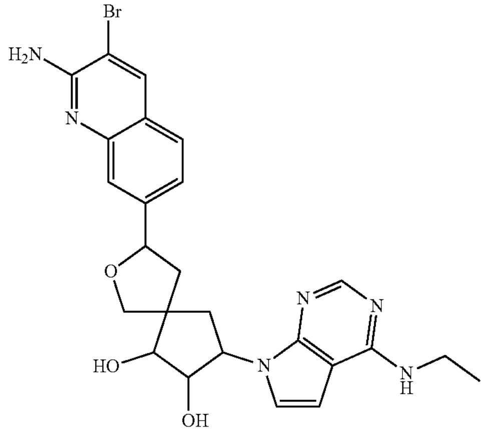
,
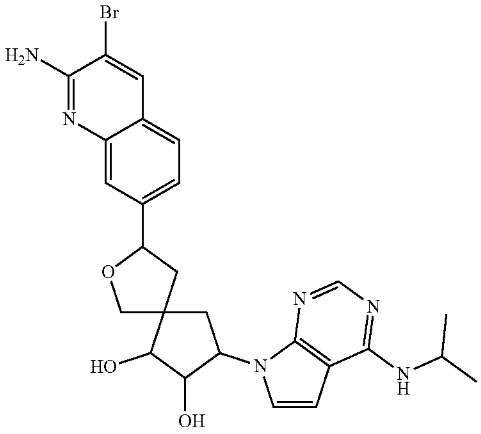
and
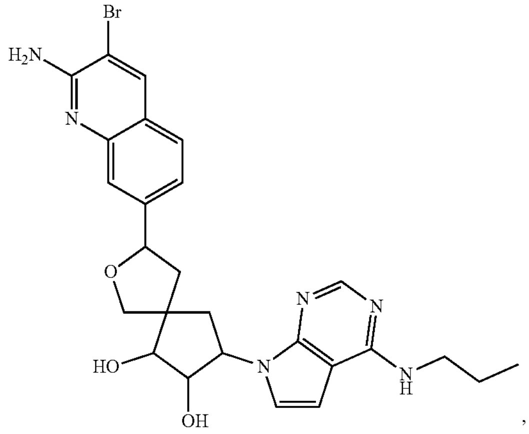 [SMILES: CCCNc1ncnc2c1ccn2C1CC2(COC(c3ccc4cc(Br)c(N)nc4c3)C2)C(O)C1O]
,
or a pharmaceutically salt thereof.
In some aspects, the invention relates to a compound of Formula I having a structure selected from:
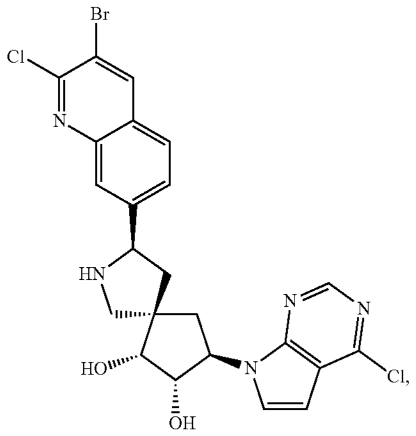
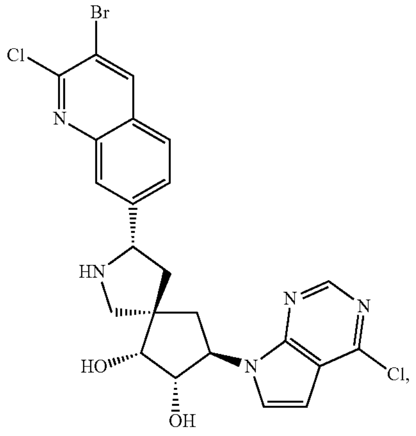
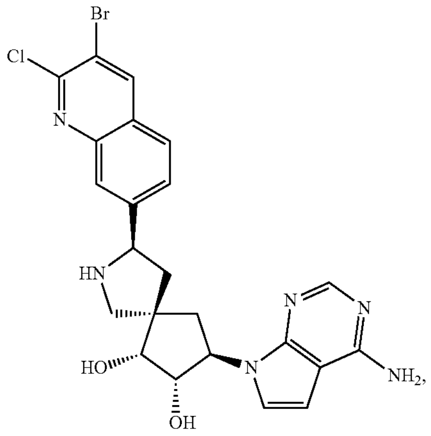

-continued
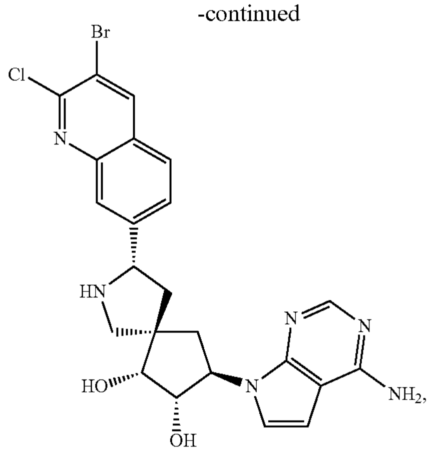
,
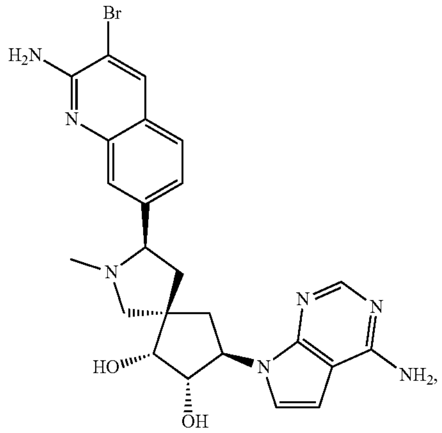
,
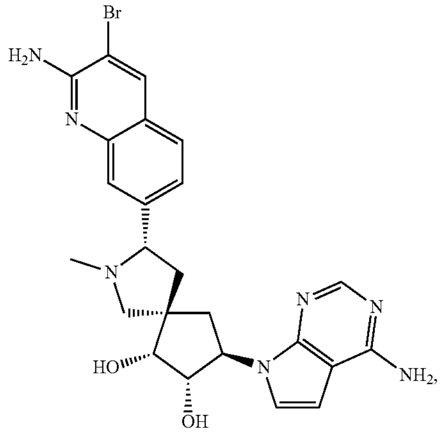
,
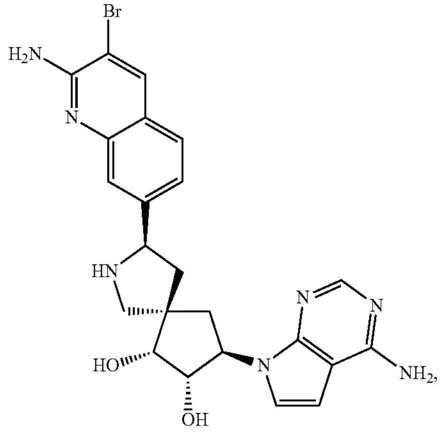
,
-continued
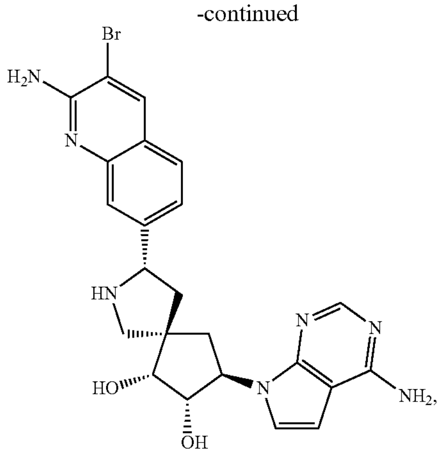
,
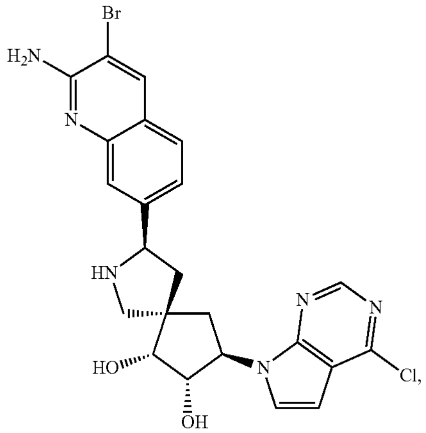
,
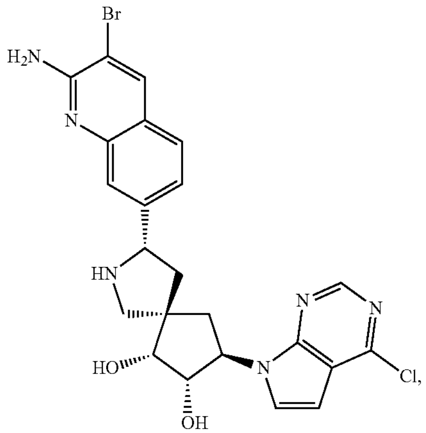
,
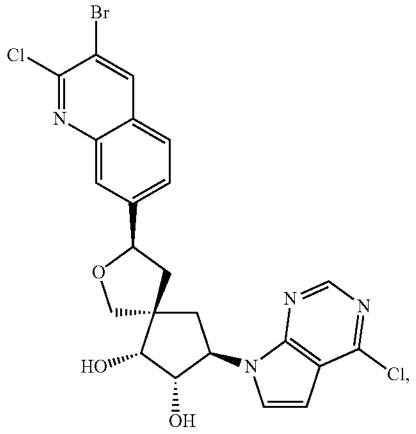
, -continued
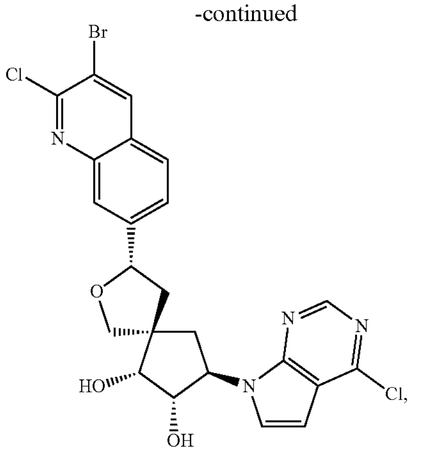
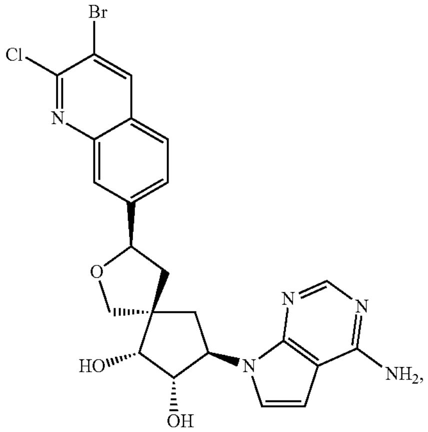
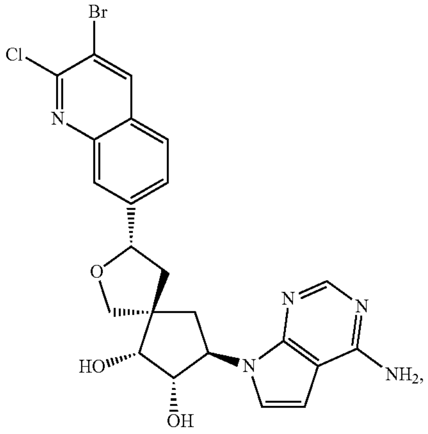
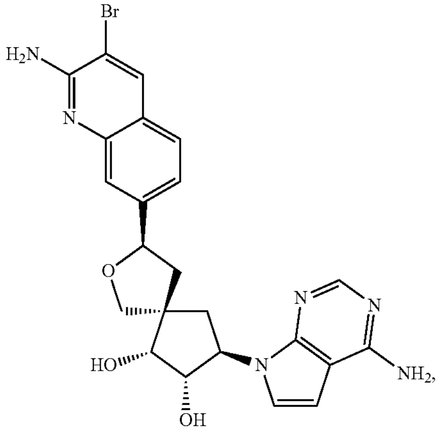
-continued
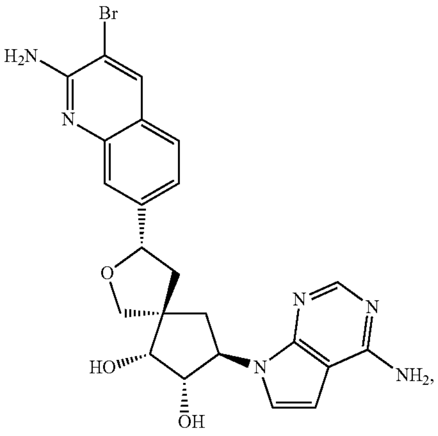
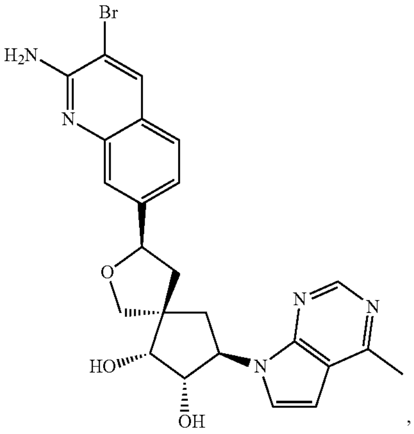
,
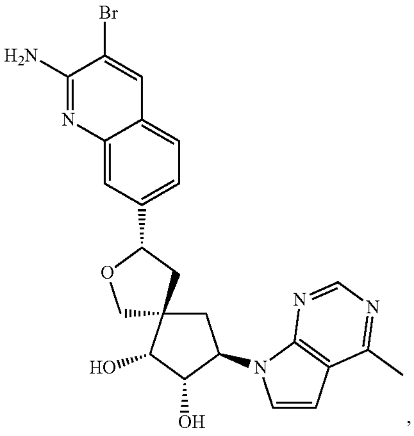
,
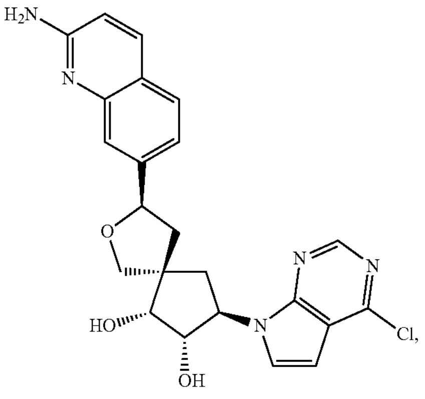

-continued
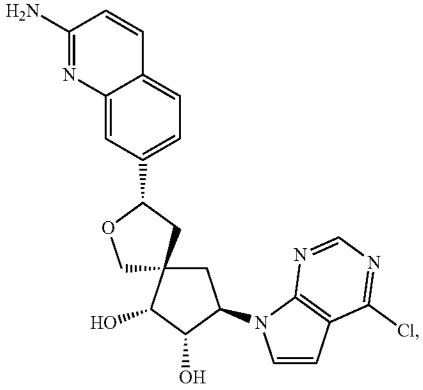
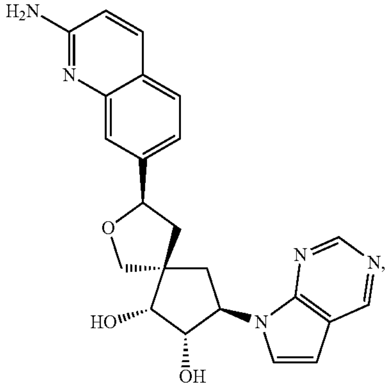
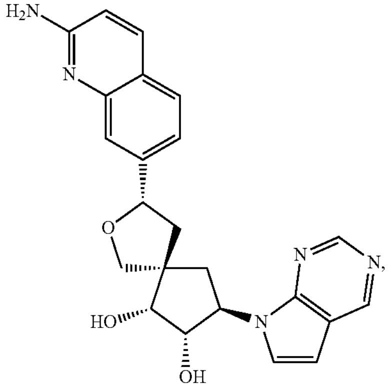
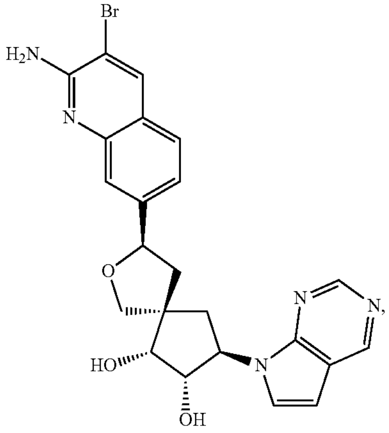
-continued
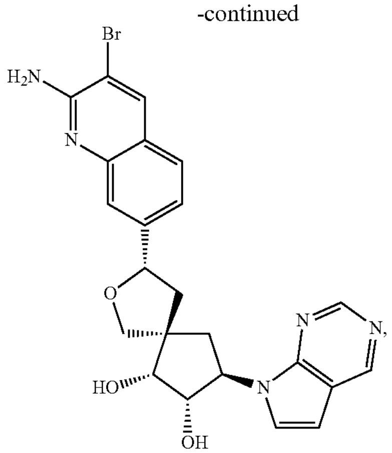
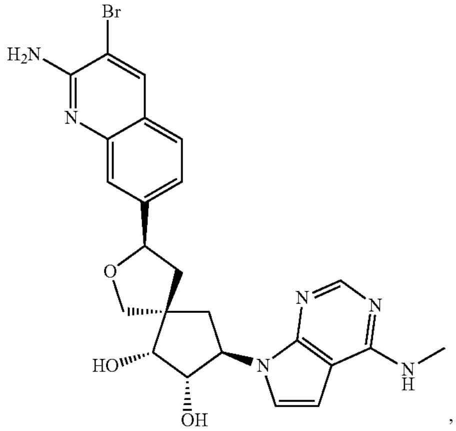
,
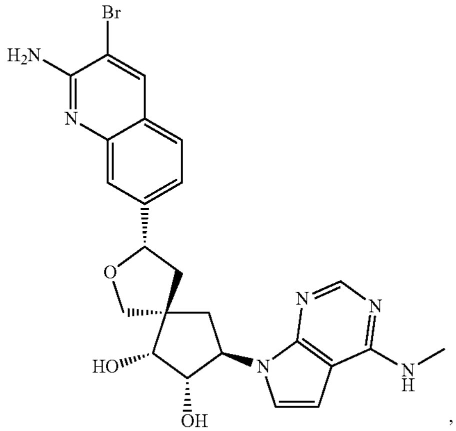
,
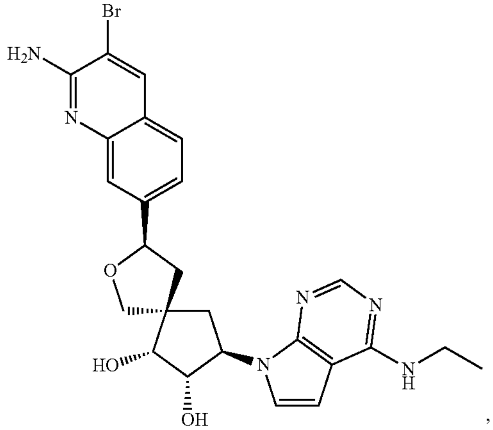
, -continued
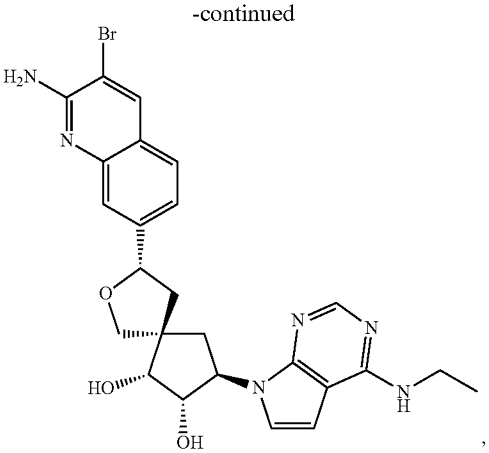
,
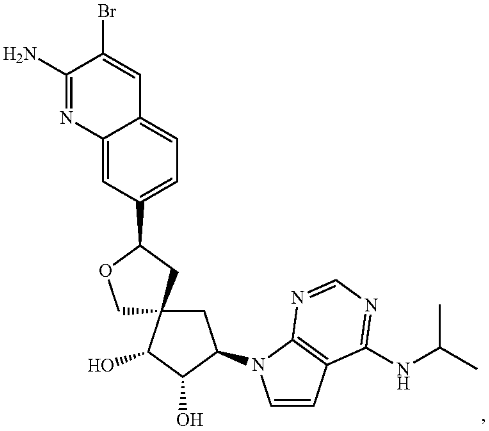
,
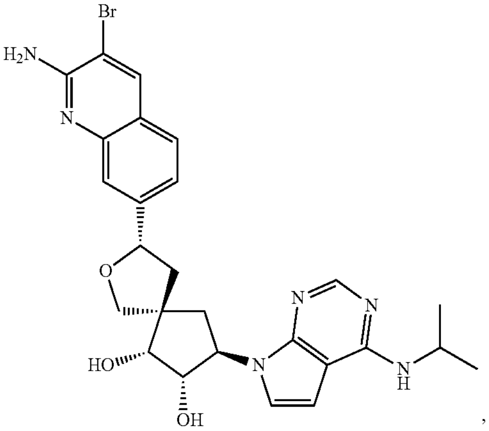
,
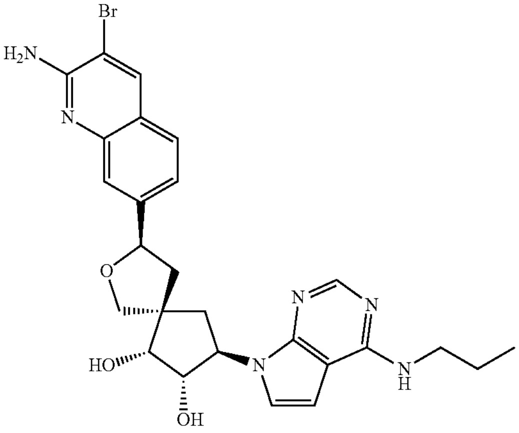
and
-continued
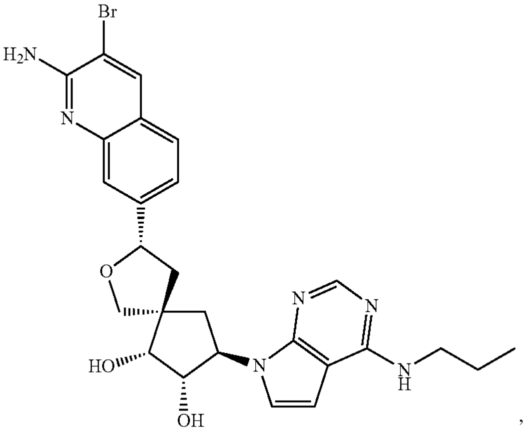
,
or a pharmaceutically salt thereof.
In some aspects, the invention relates to a compound of Formula V having a structure selected from:
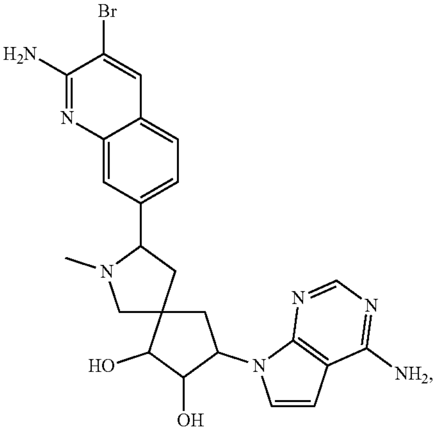
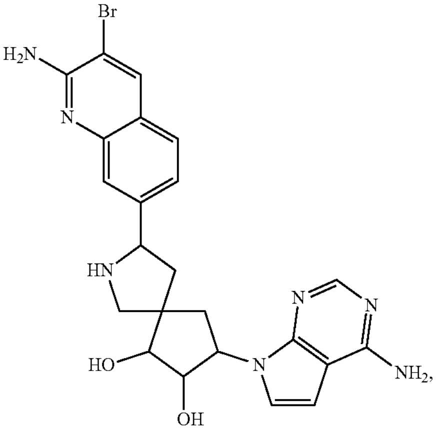

-continued
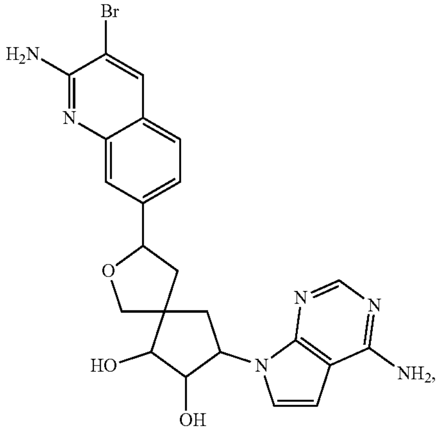
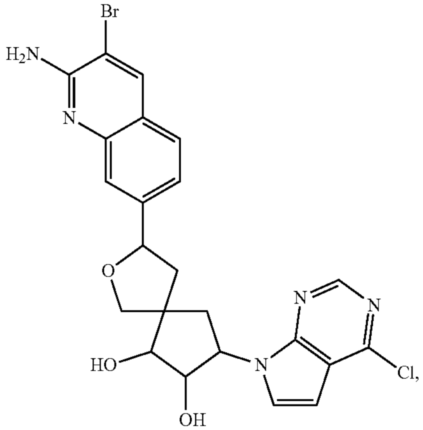
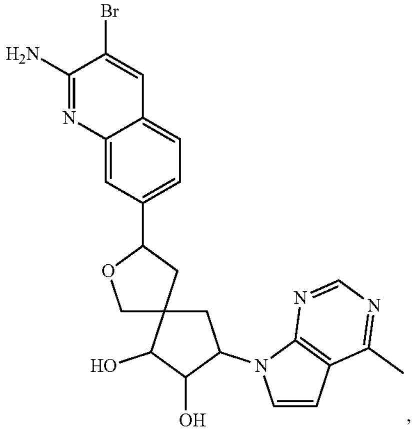
,
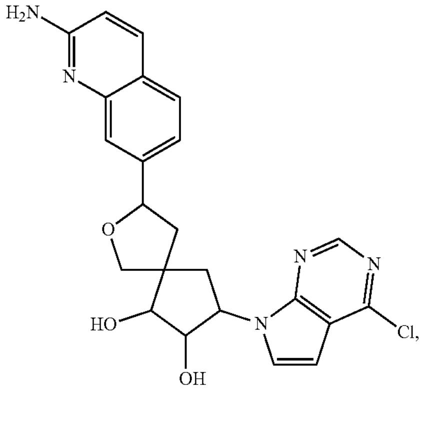
-continued
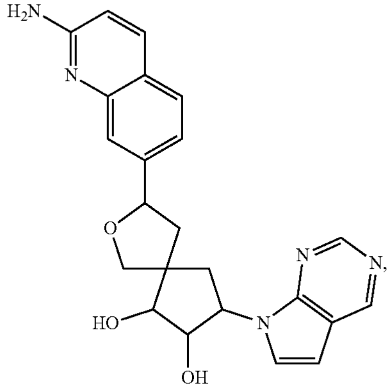
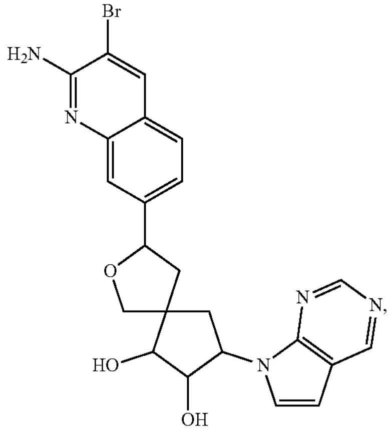
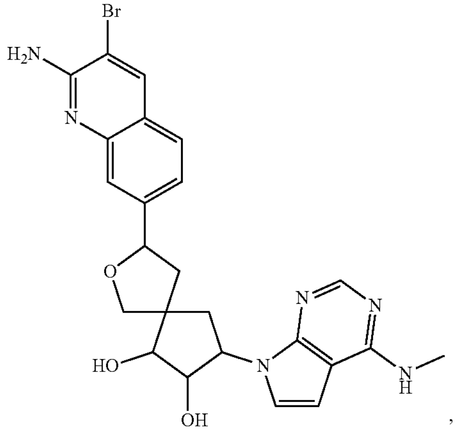
,
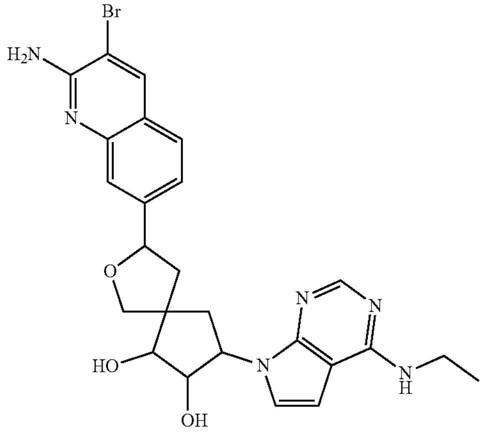
, -continued
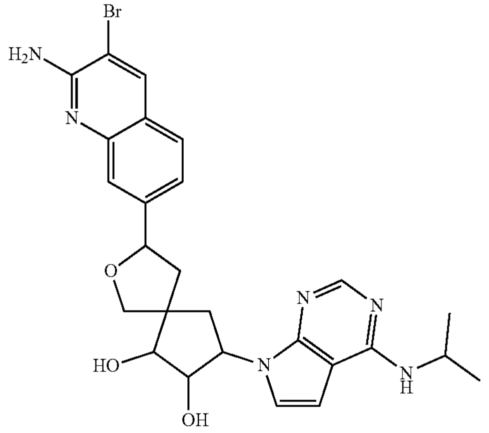
and
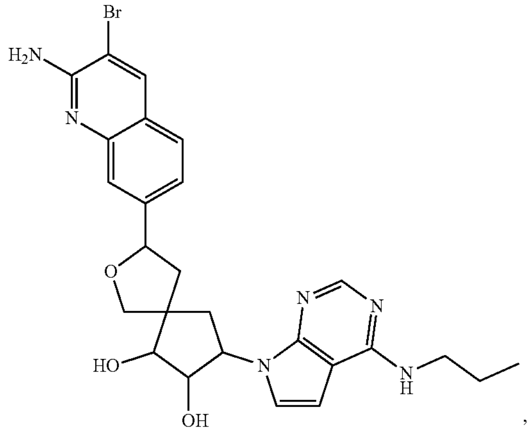
,
or a pharmaceutically salt thereof.
In some aspects, the invention relates to a compound of Formula V having a structure selected from:
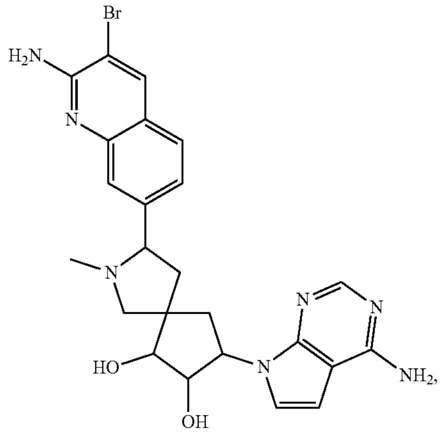
-continued
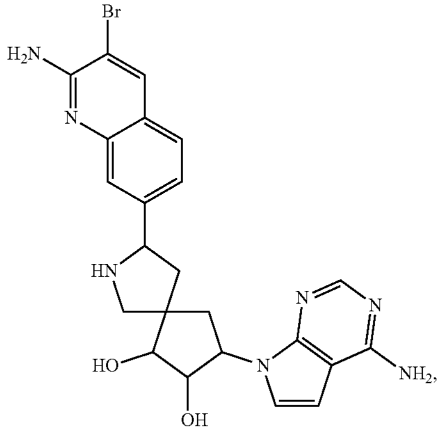
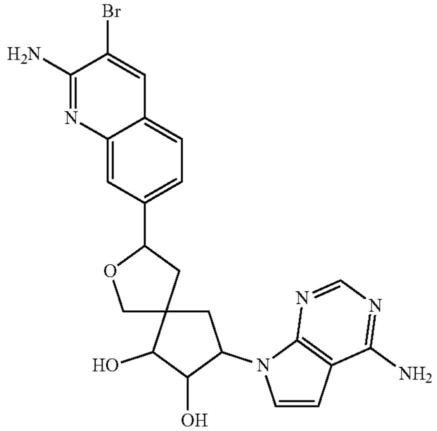
and
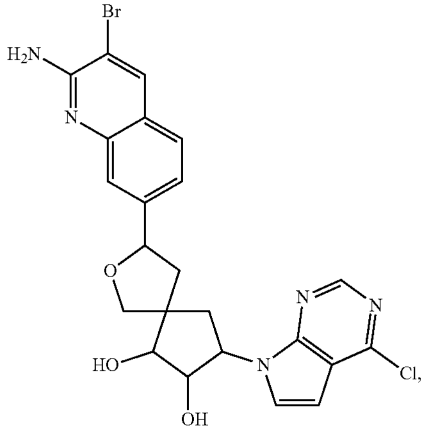
or a pharmaceutically salt thereof.

In further aspects, the invention relates to a compound of Formula V having a structure selected from:
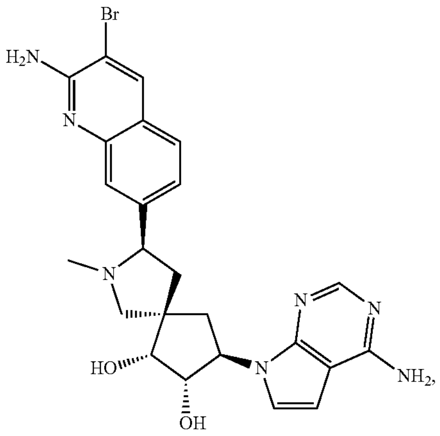
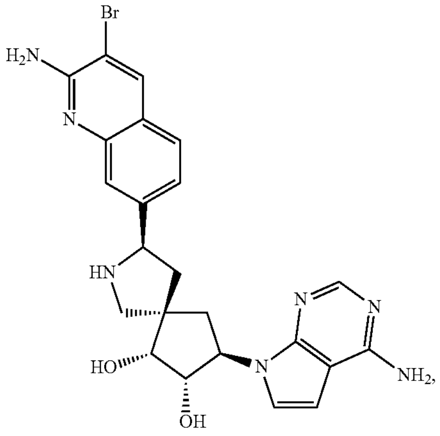
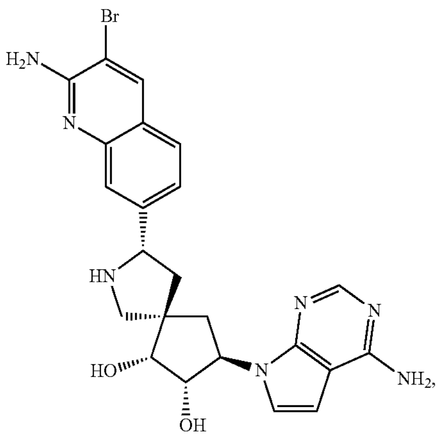
-continued
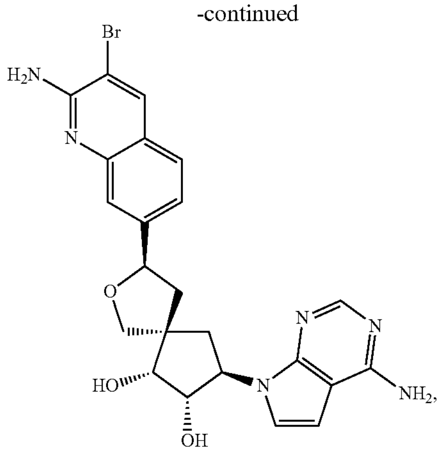
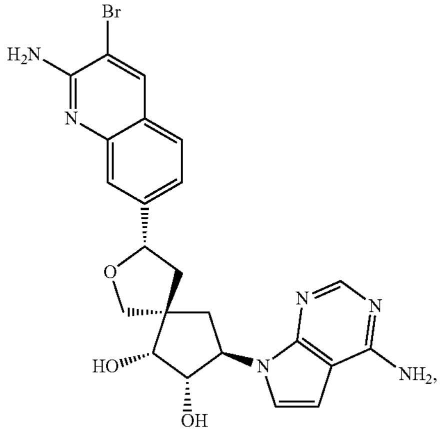
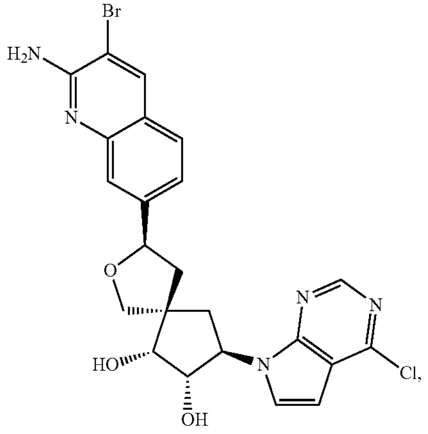
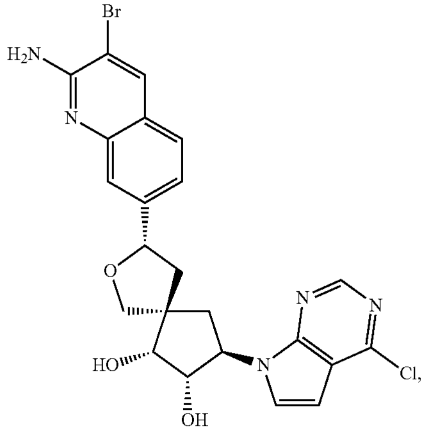

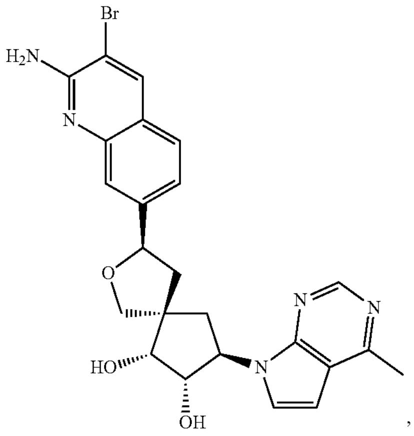
,
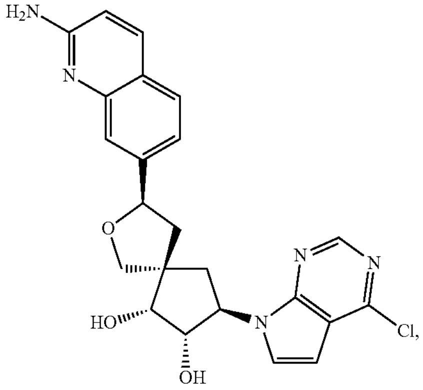
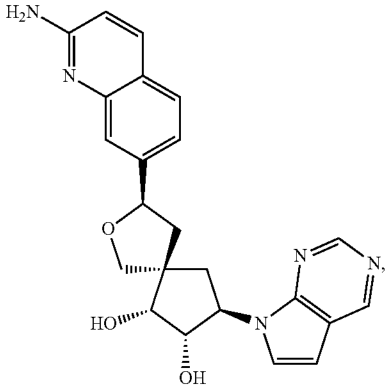
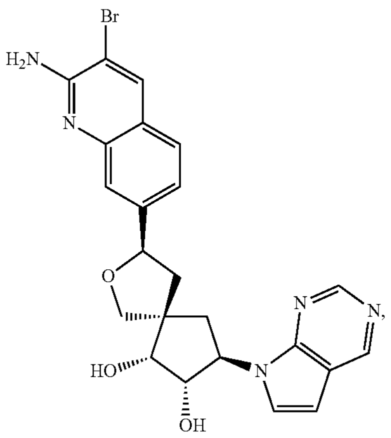
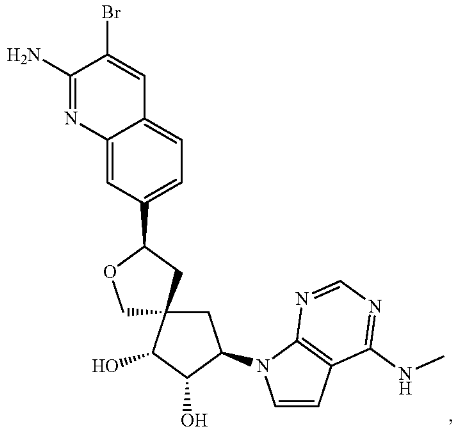
,
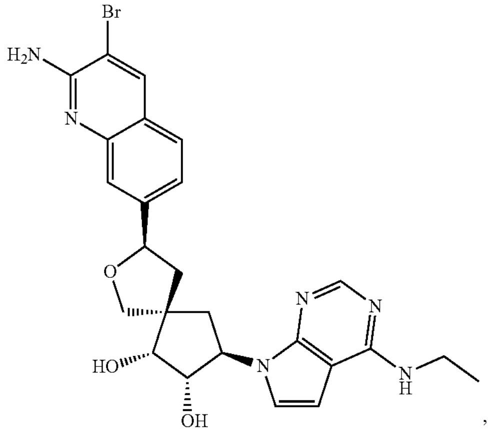
,
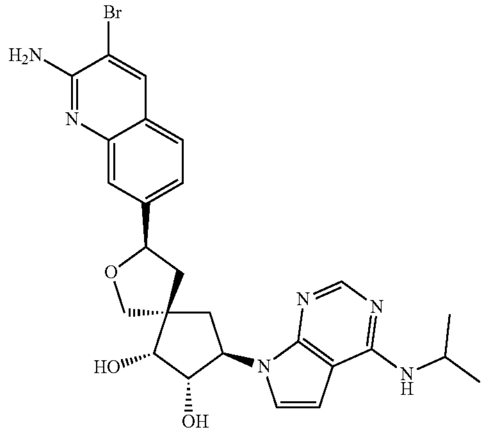
and -continued
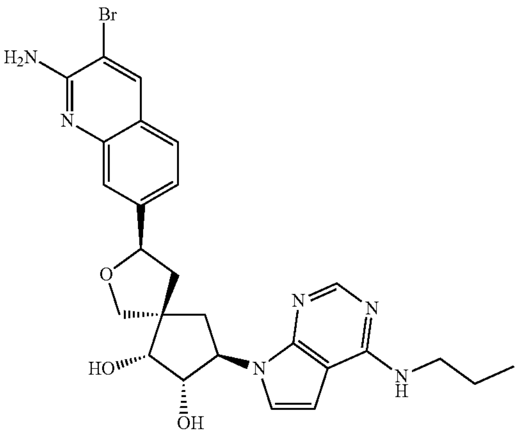
,
or a pharmaceutically salt thereof.
In some aspects, the invention relates to a compound of Formula I having a structure selected from:
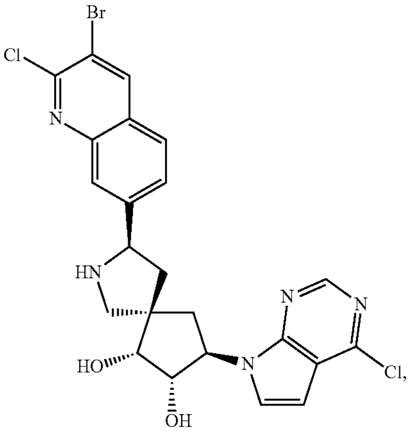
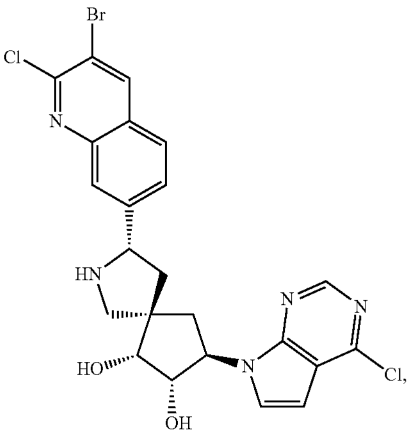
-continued
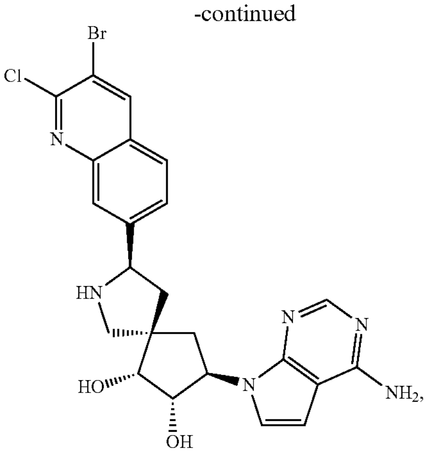
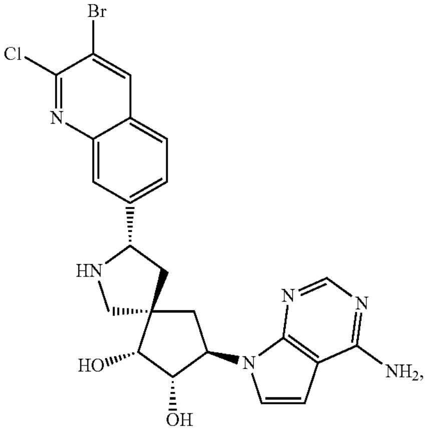
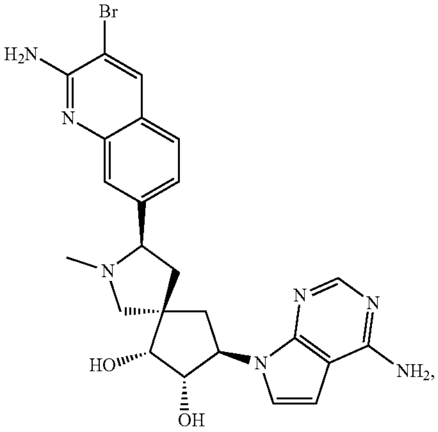
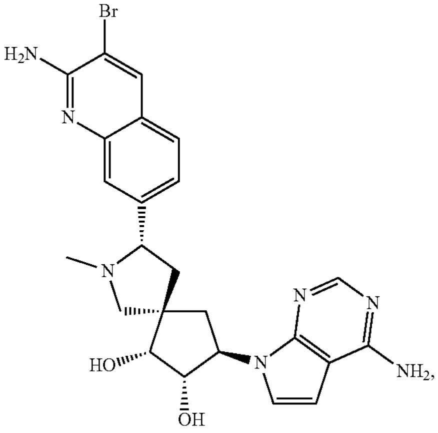

-continued
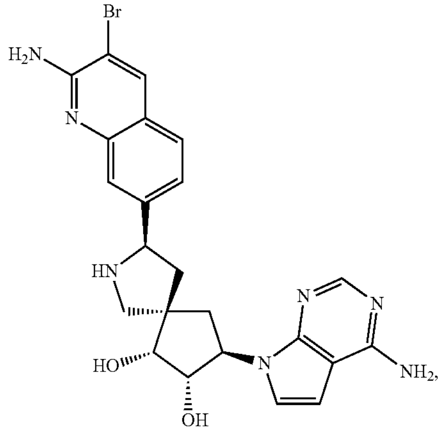
,
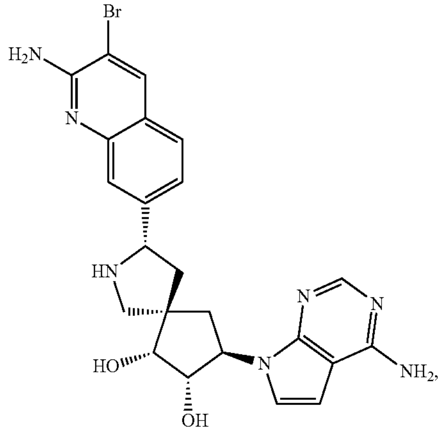
,
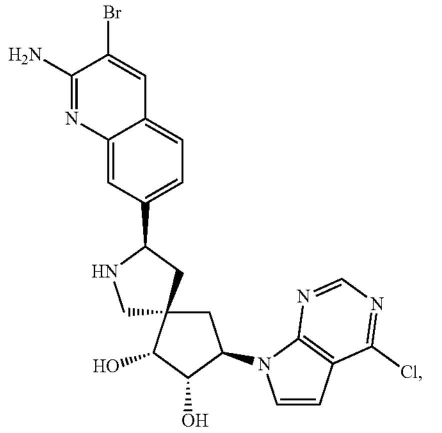
,
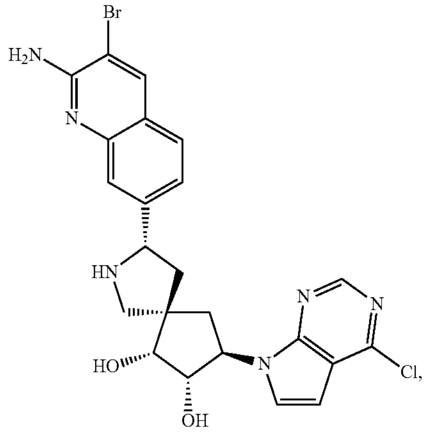
,
-continued
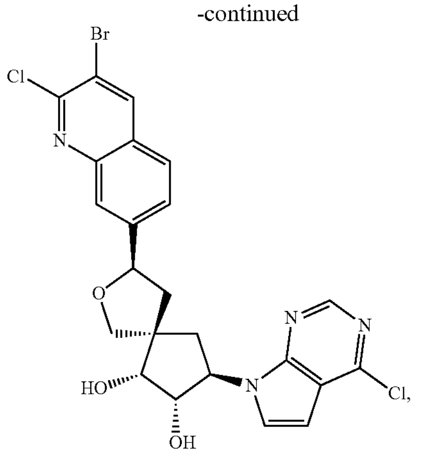
,
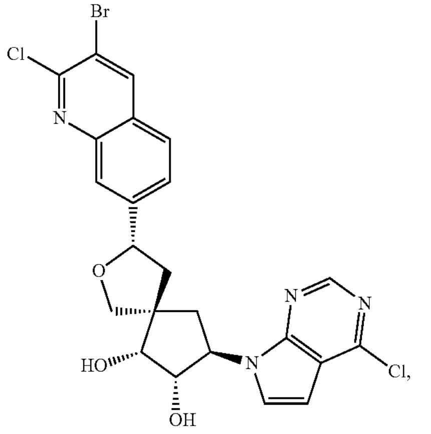
,
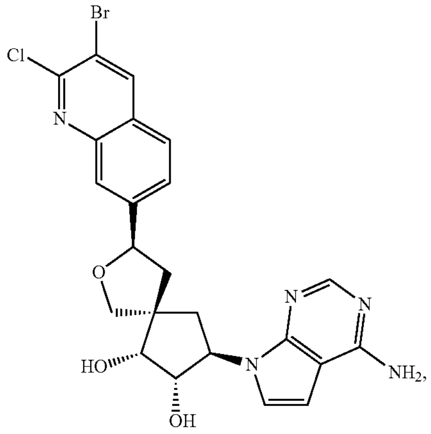
,
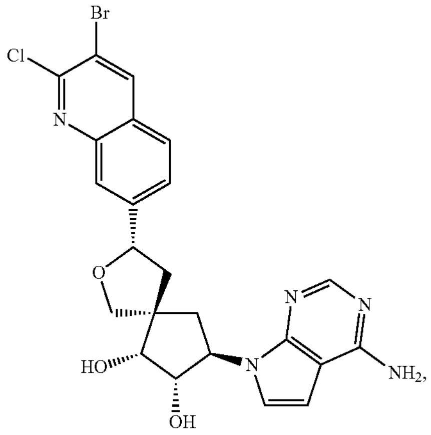
, -continued
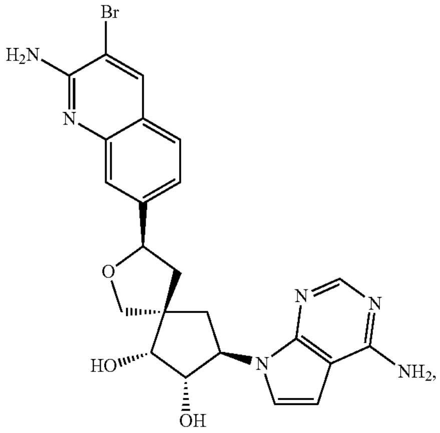
,
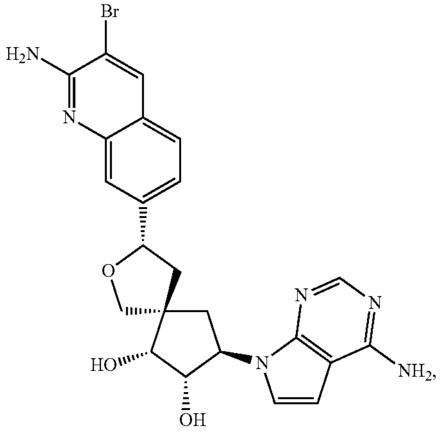
,
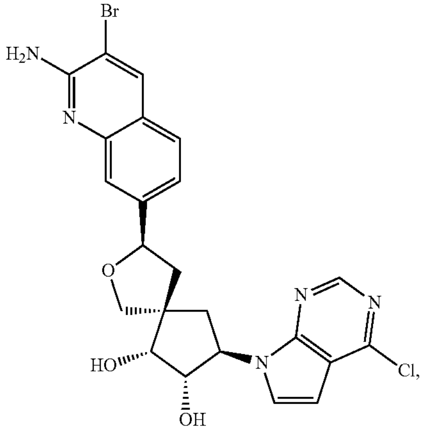
,
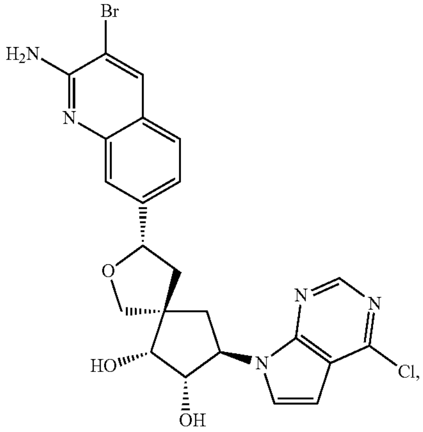
,
-continued
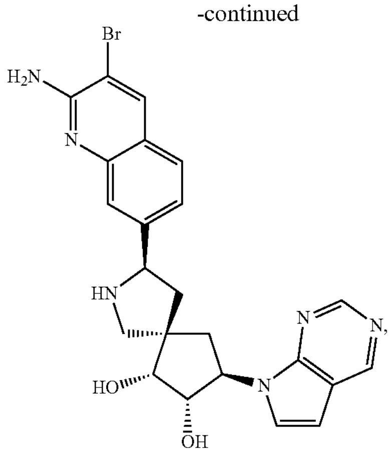
,
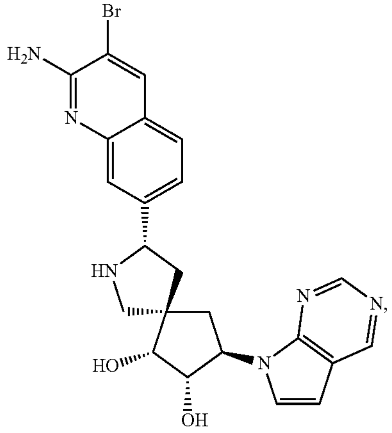
,
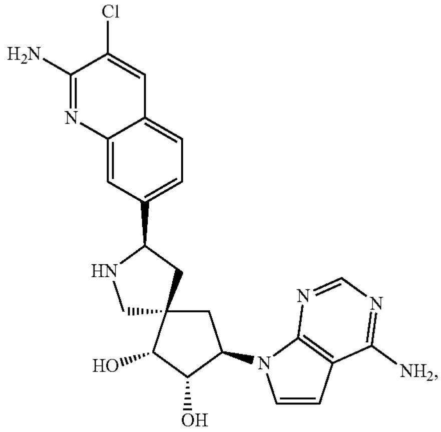
,
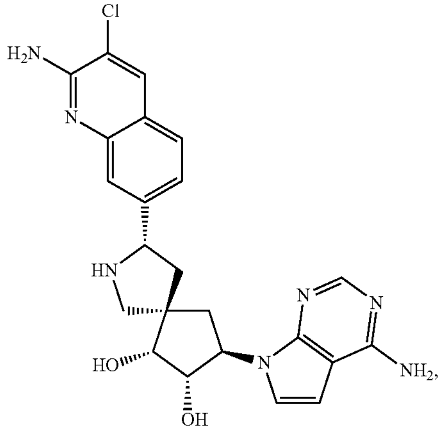
, -continued
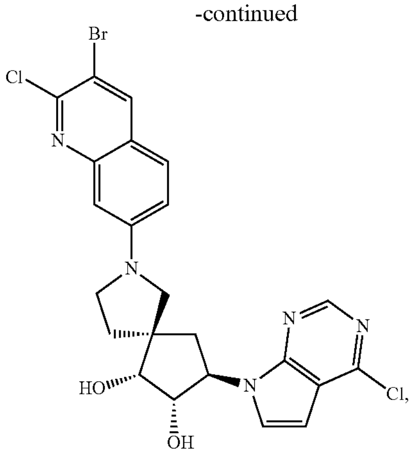
Cl,
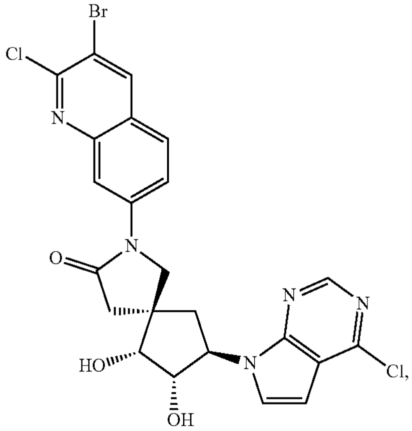
Cl,
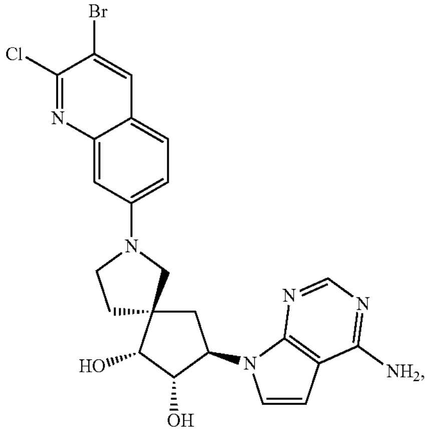
$NH_2$,
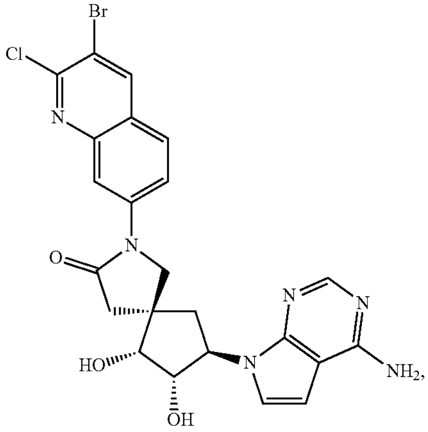
$NH_2$,
-continued
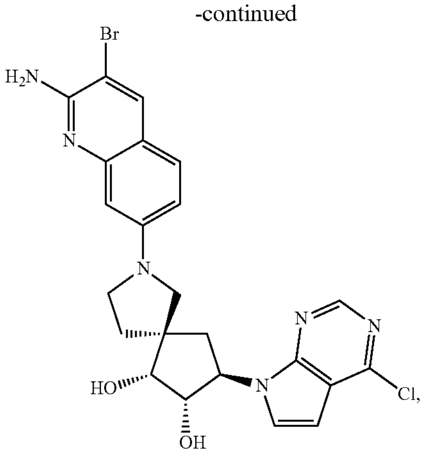
Cl,
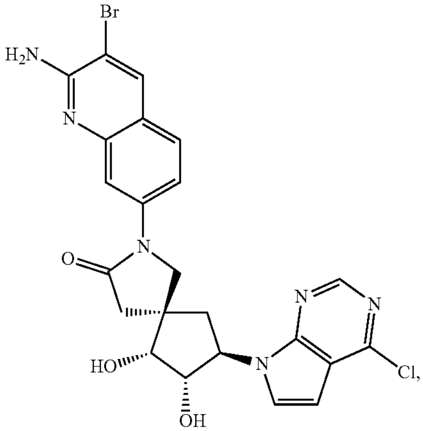
Cl,
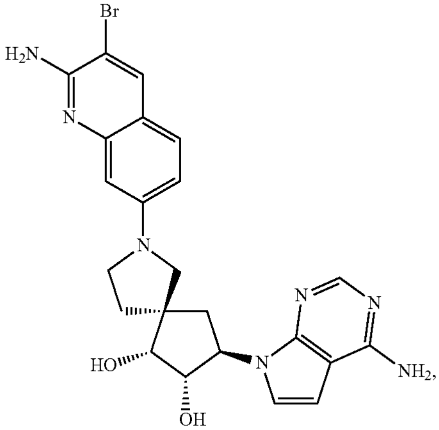
$NH_2$,
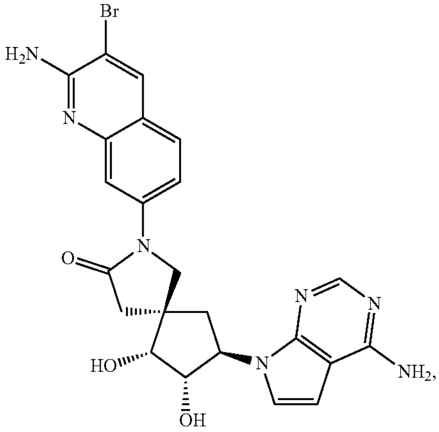
$NH_2$, -continued
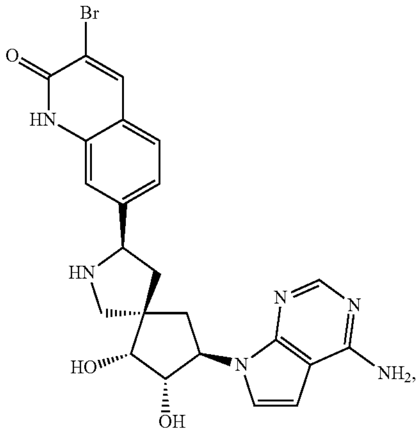
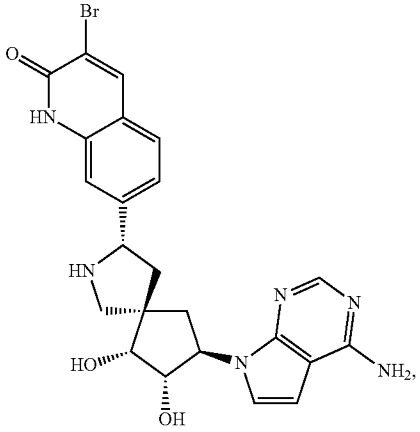
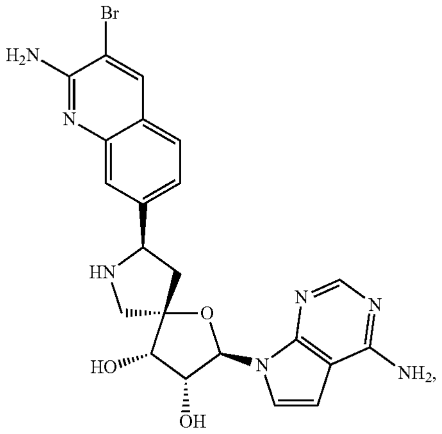
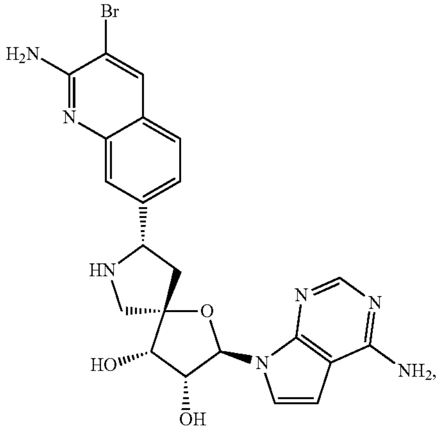
-continued
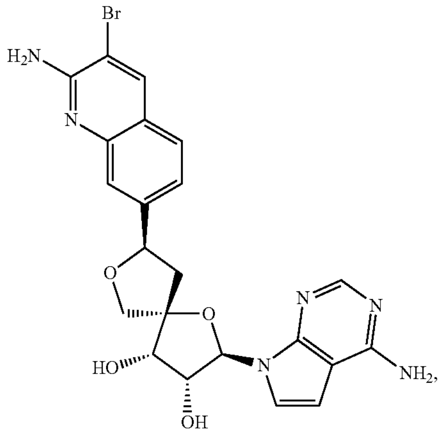
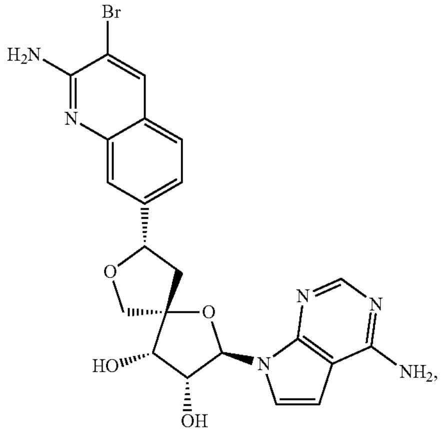
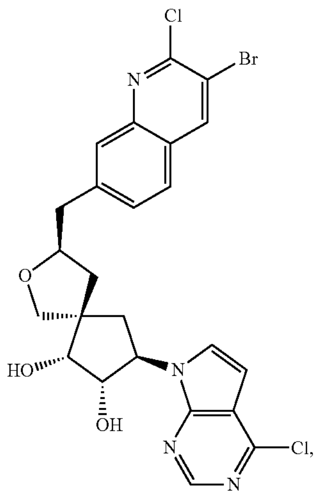

-continued
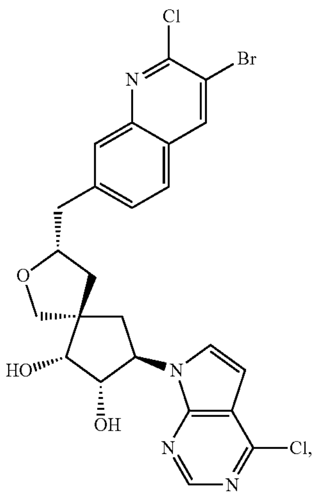
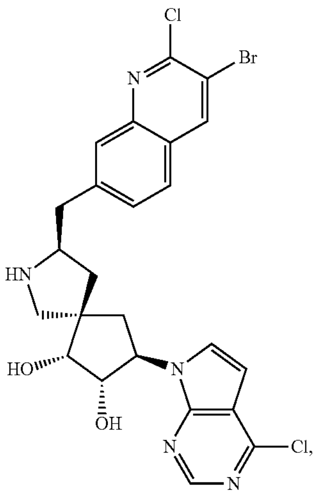
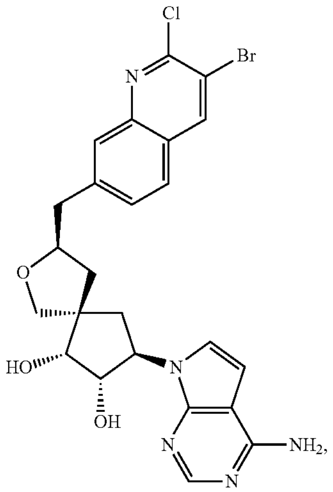
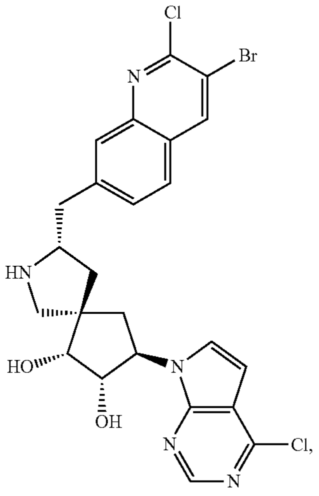
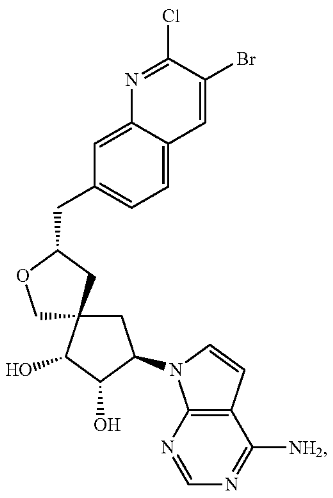
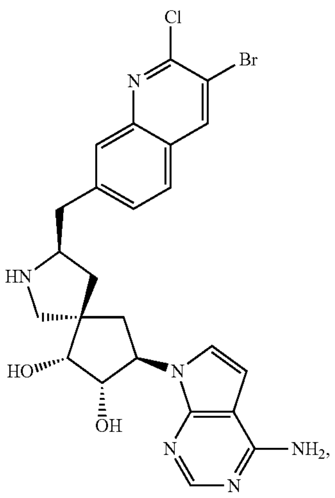
-continued -continued
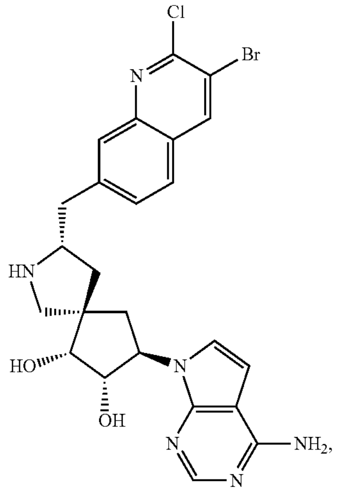
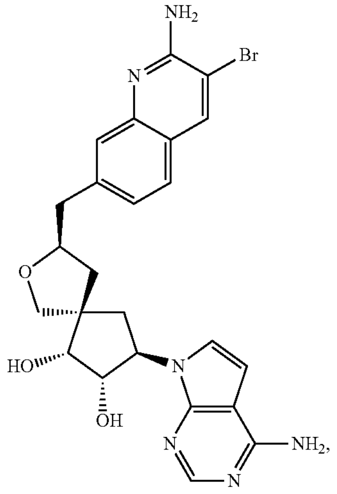
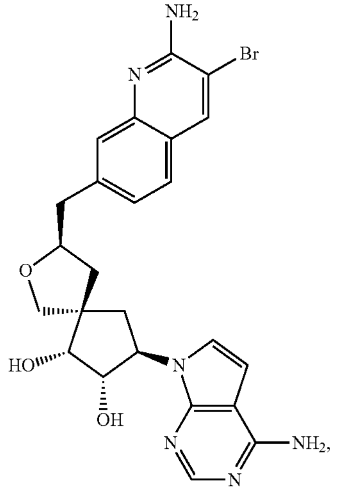
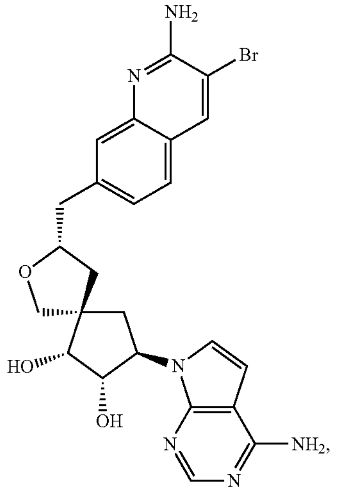
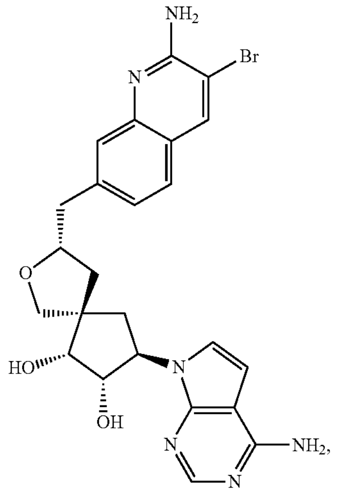
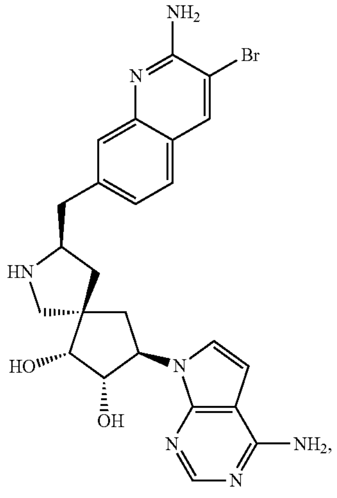

-continued
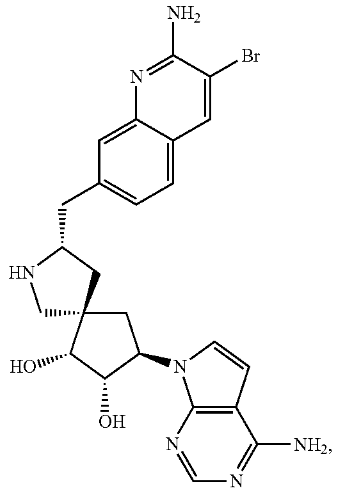
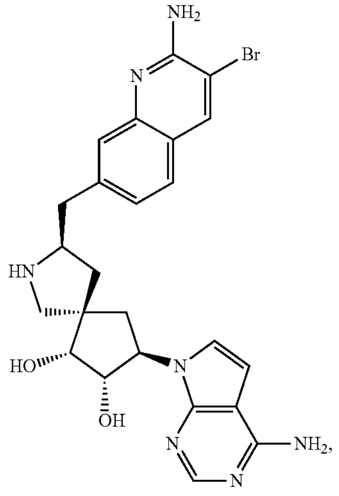
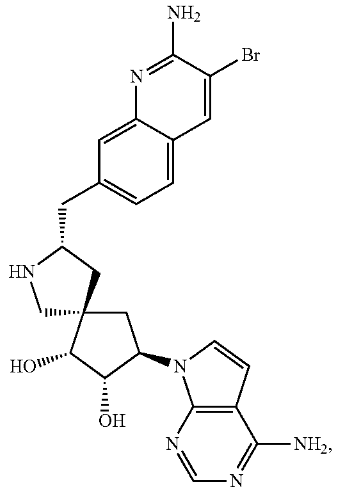
-continued
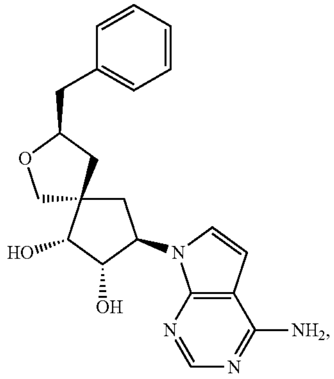
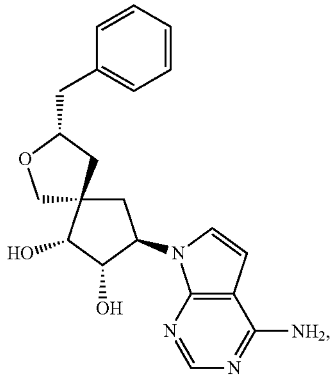
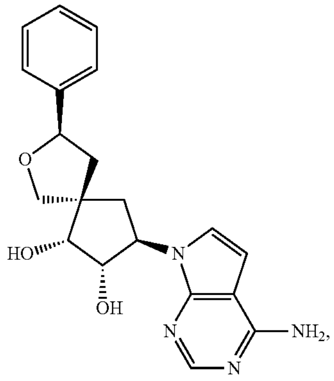
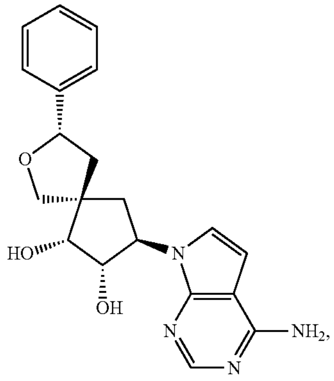

-continued
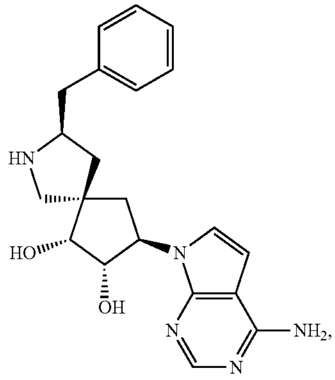
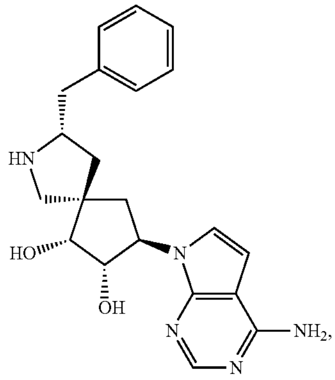
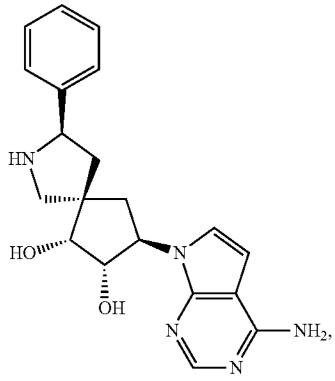
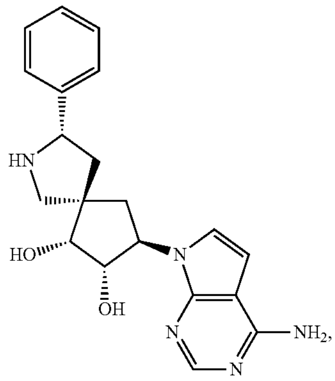
-continued
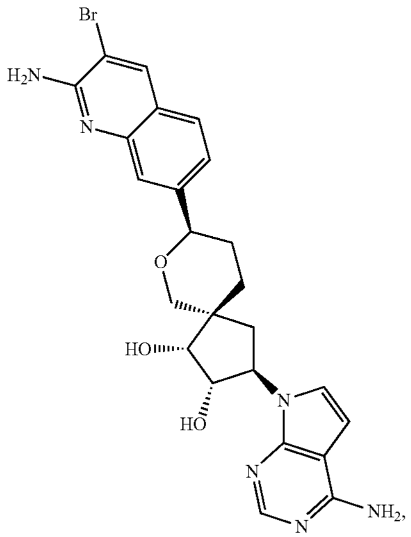
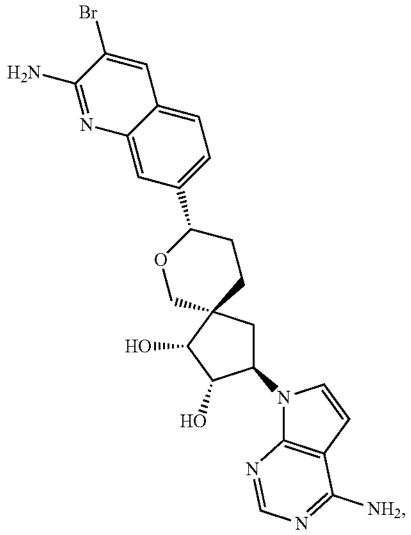
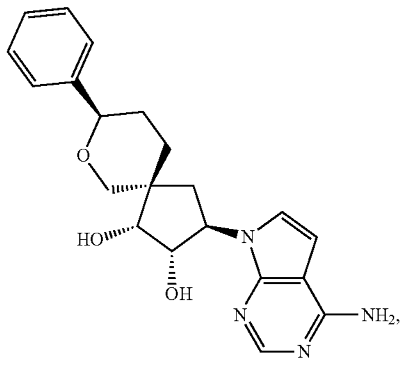

-continued
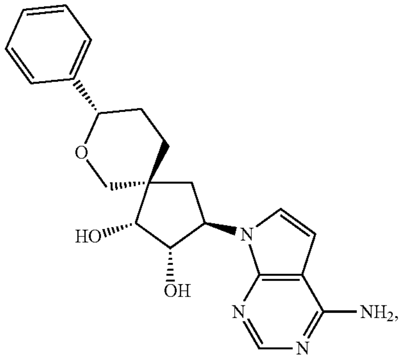
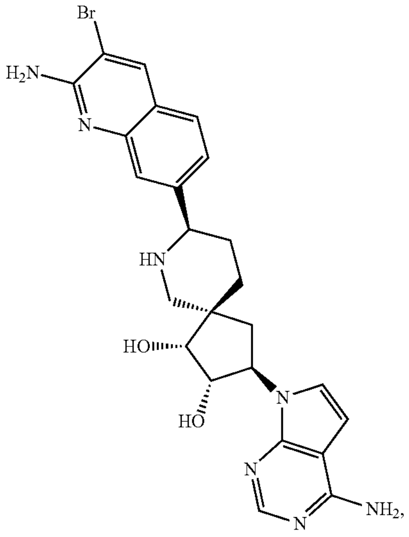
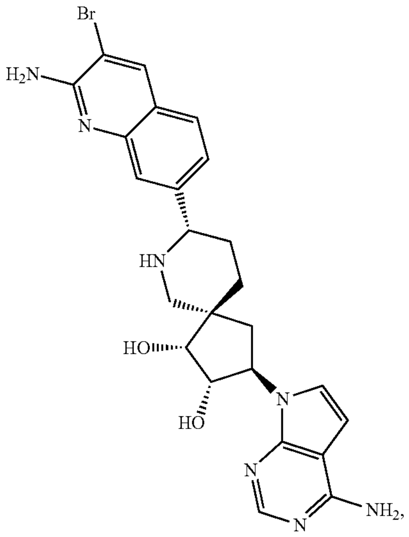
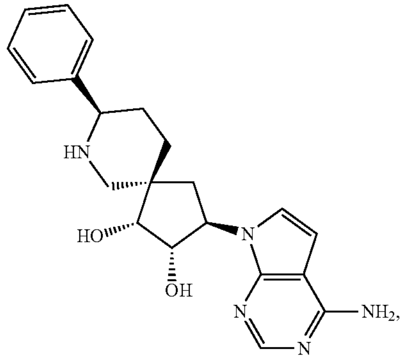
-continued
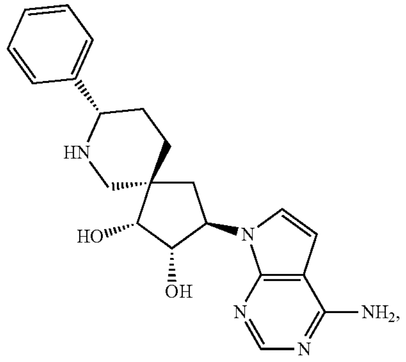
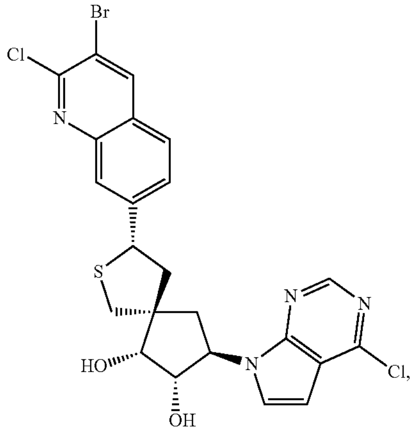
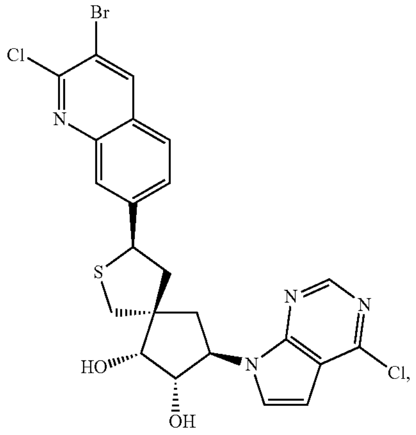

-continued
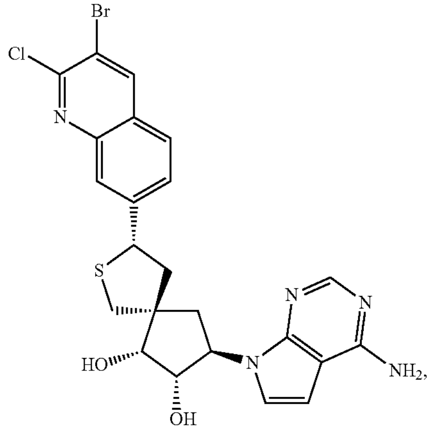
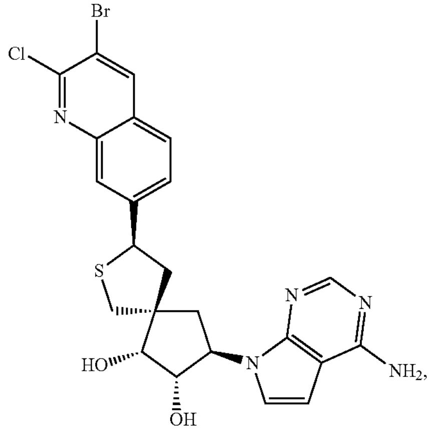
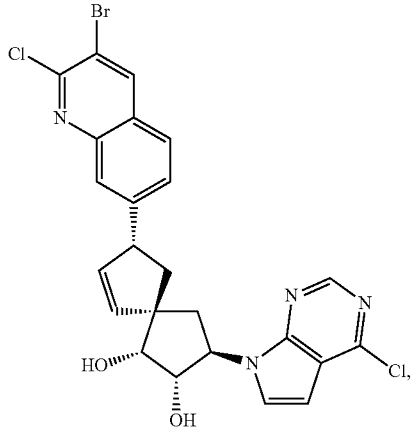
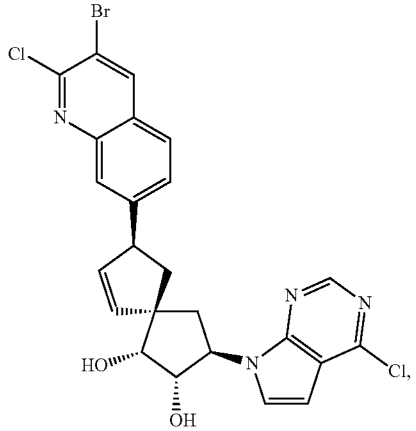
-continued
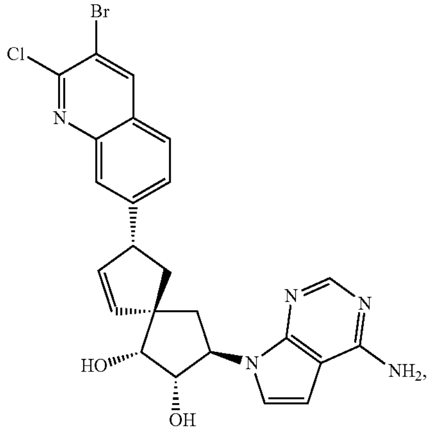
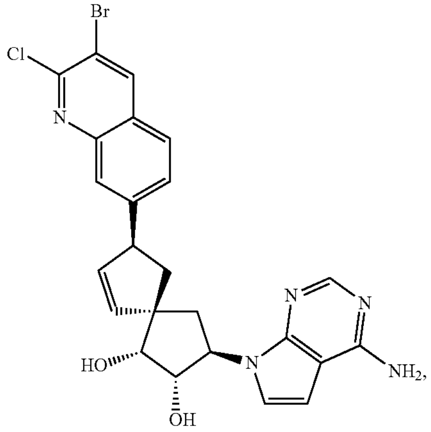
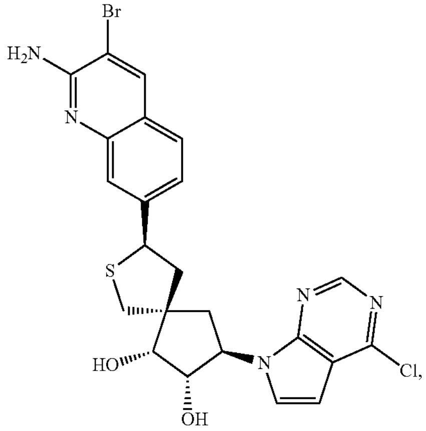
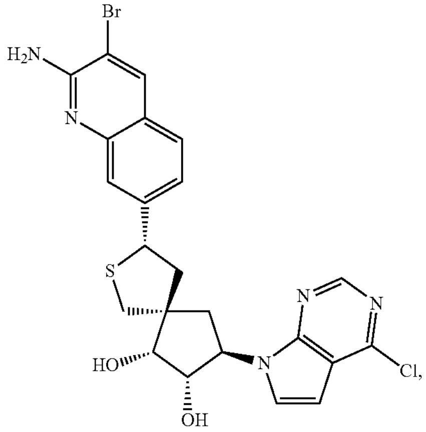

-continued
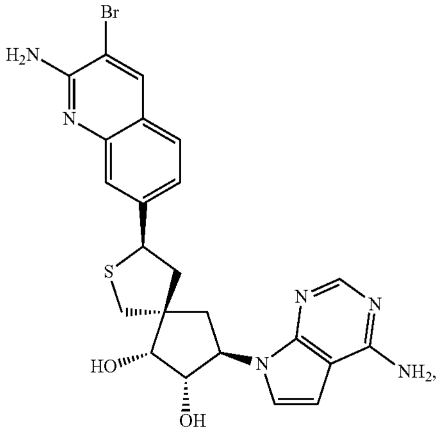
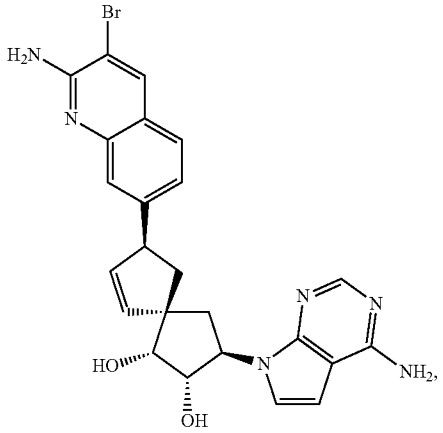
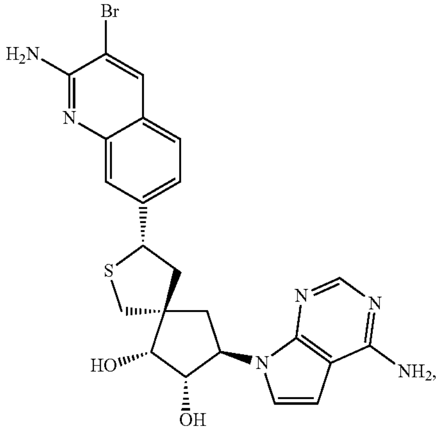
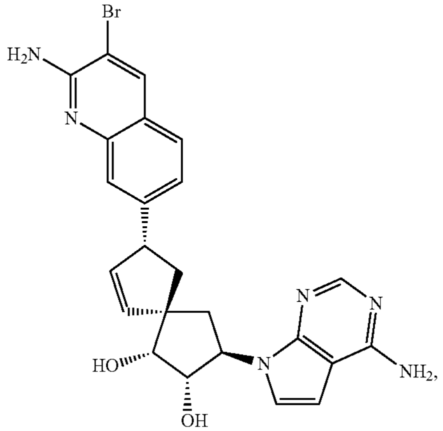
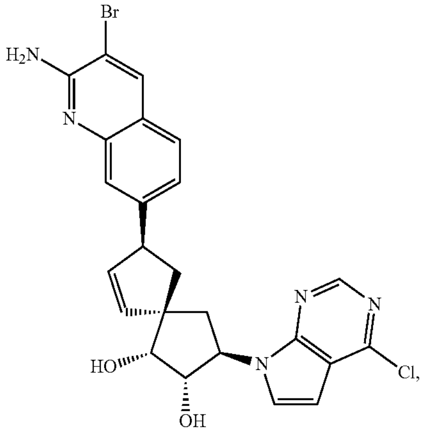
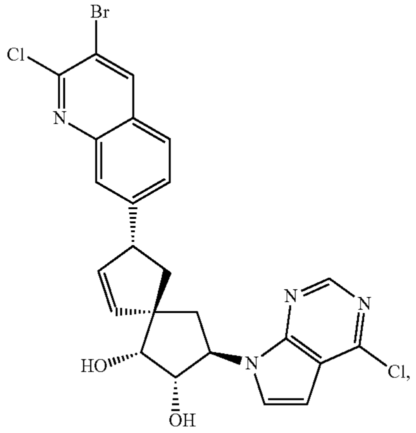
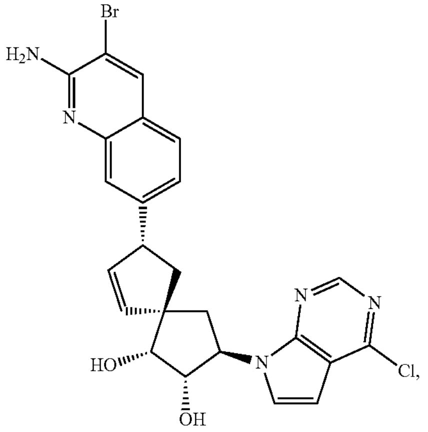
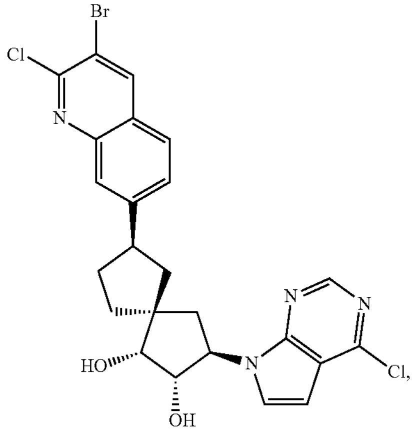
-continued -continued
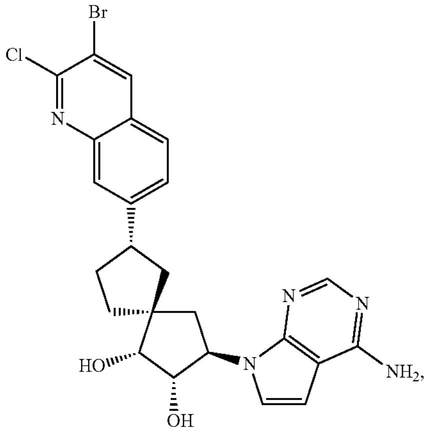
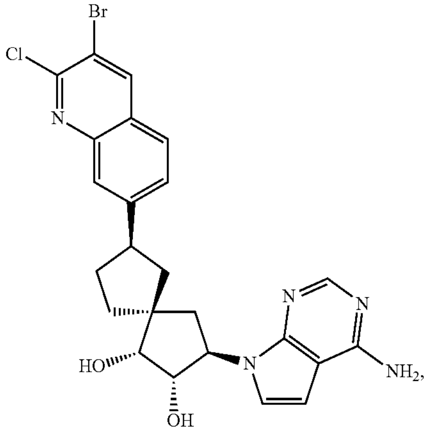
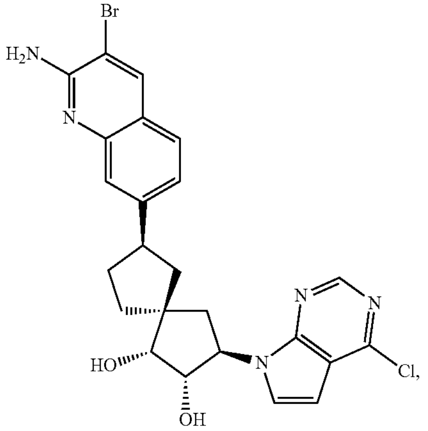
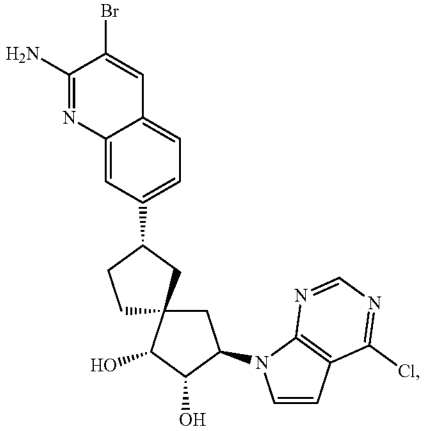
-continued
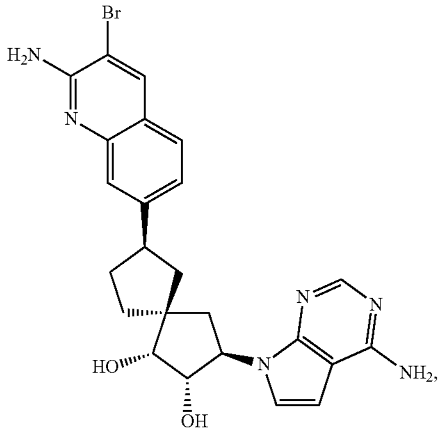
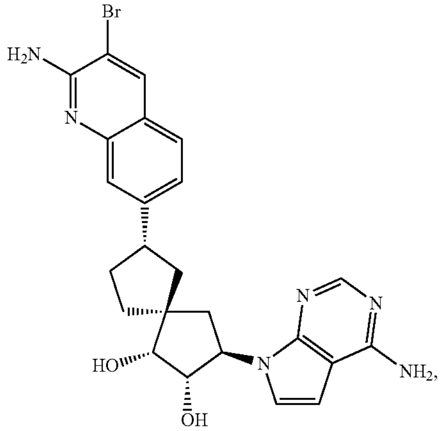
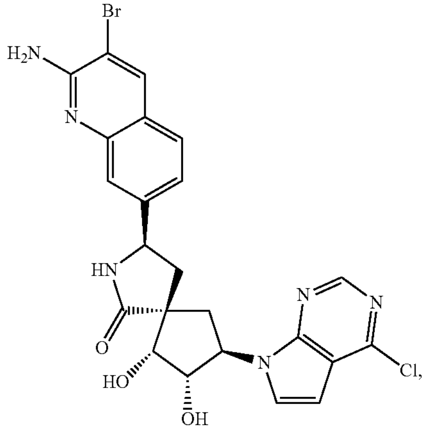
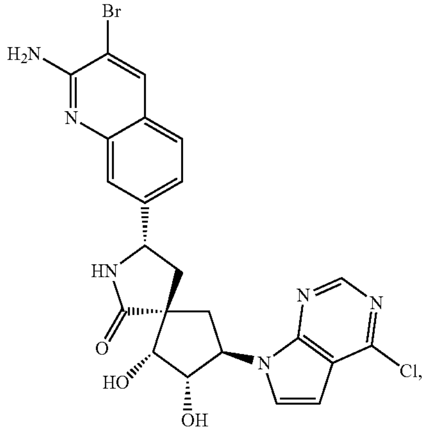

-continued
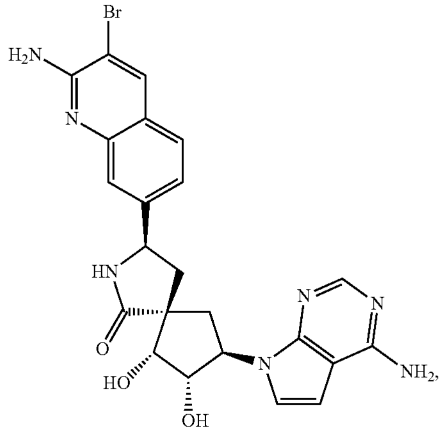
,
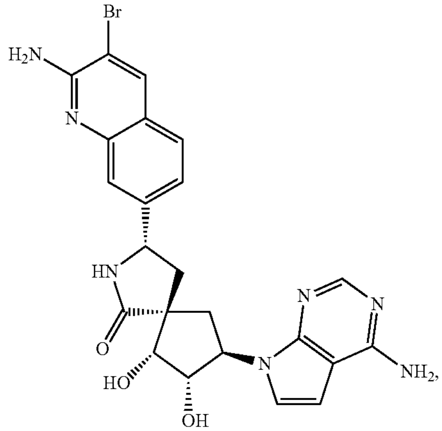
,
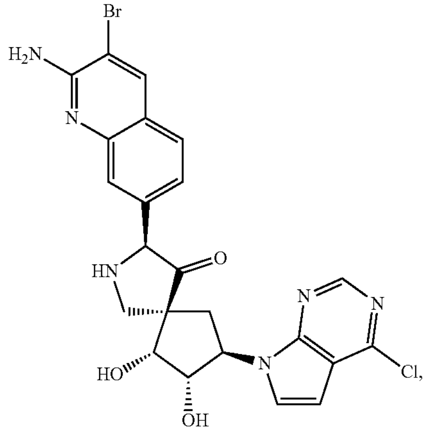
,
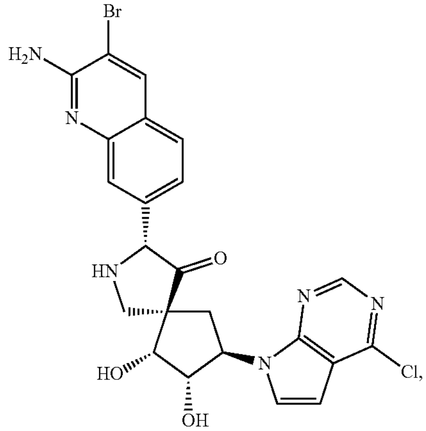
,
-continued
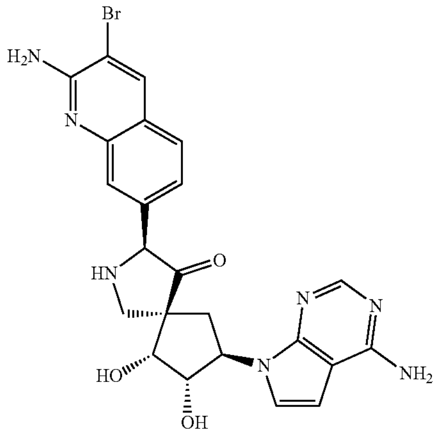
and
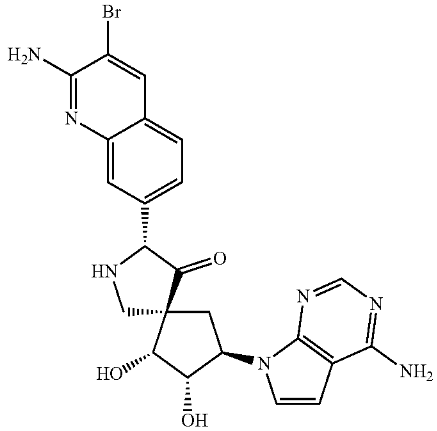
or a pharmaceutically acceptable salt thereof.
In particular aspects, the compound is selected from:
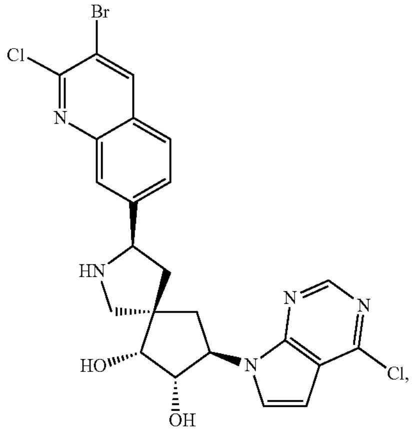
, -continued
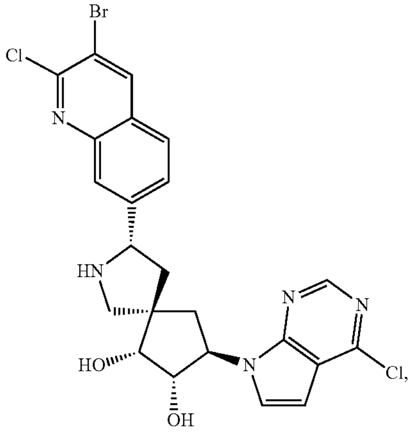
,
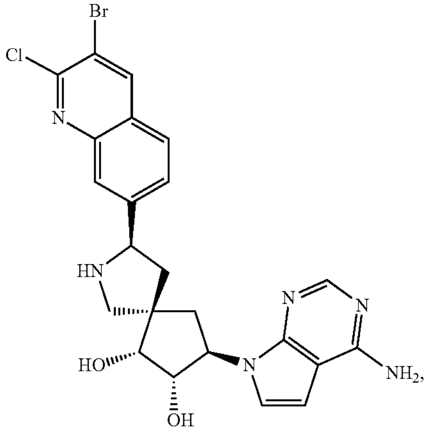
,
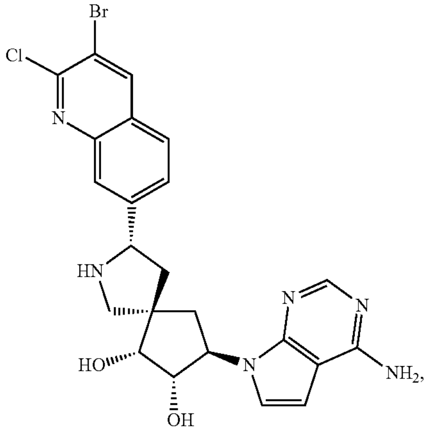
,
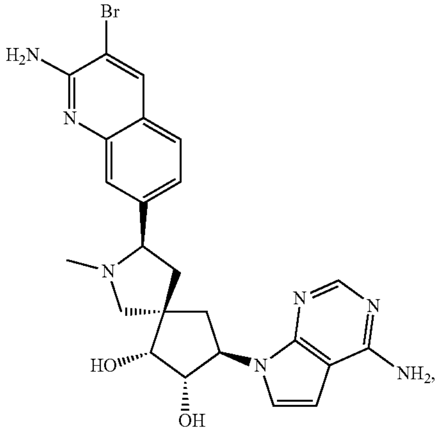
,
-continued
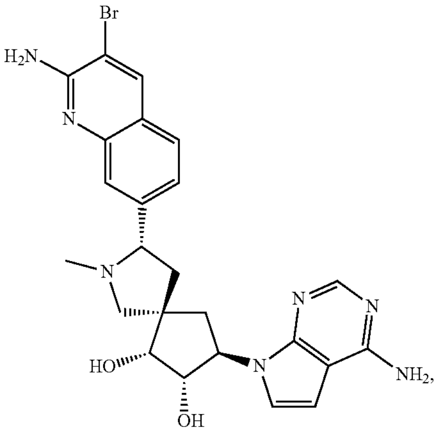
,
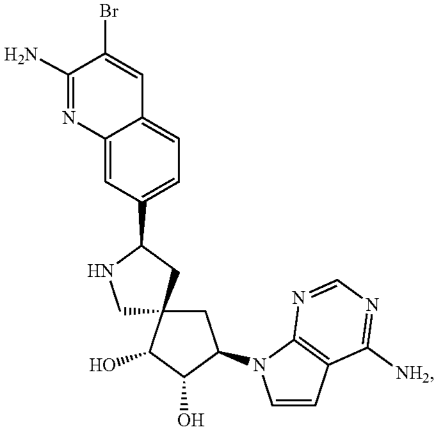
,
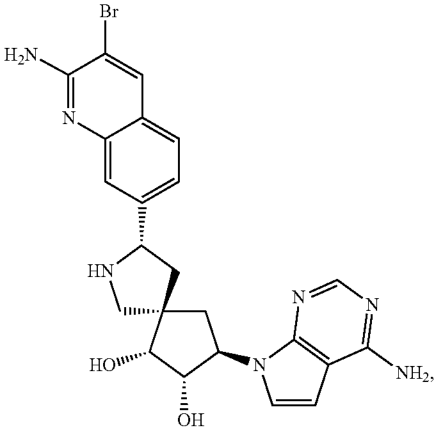
,
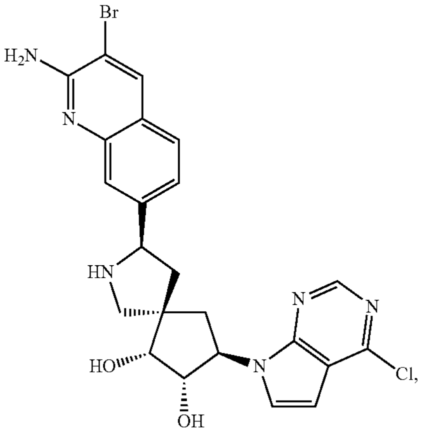
, -continued
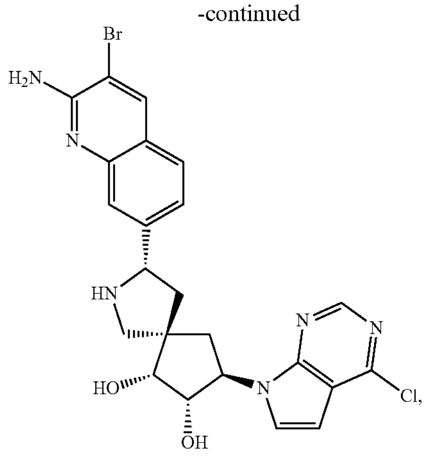,
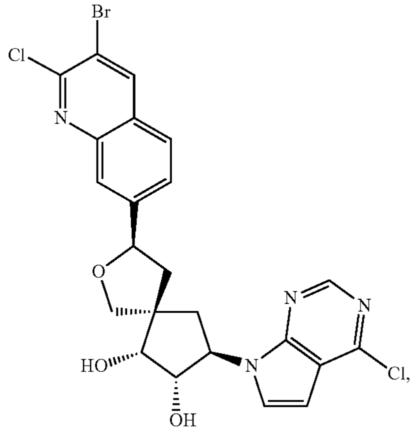,
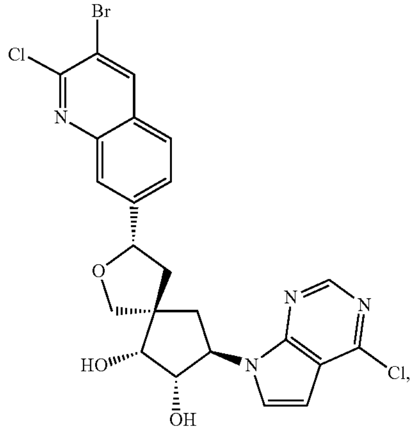,
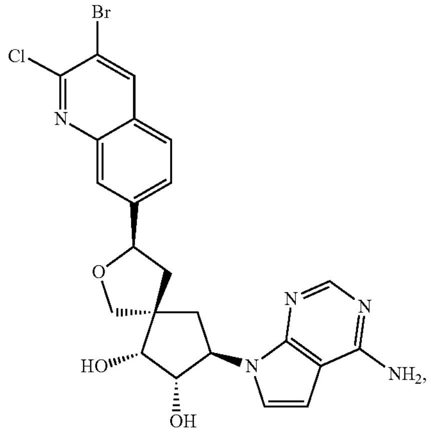,
-continued
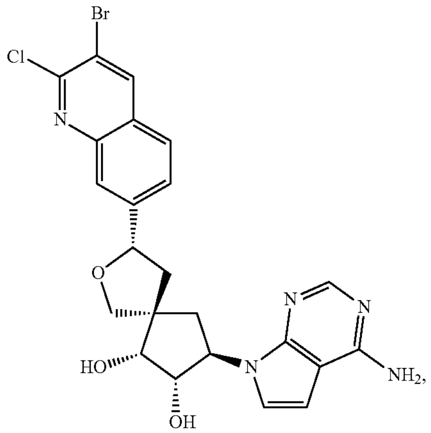,
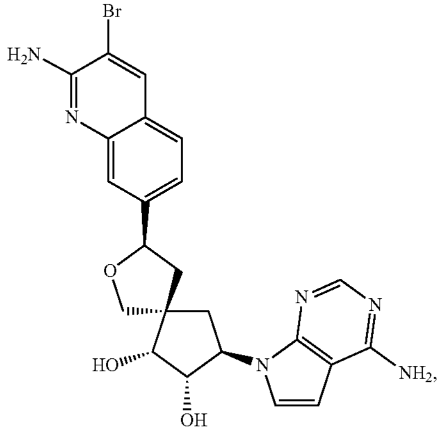,
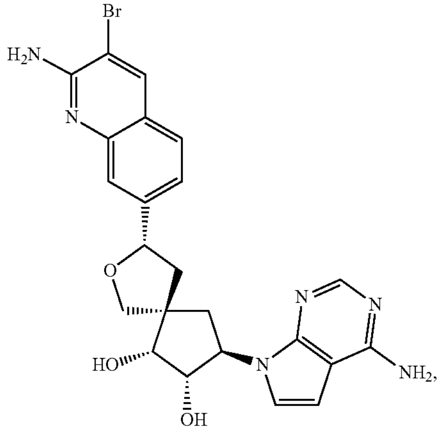,
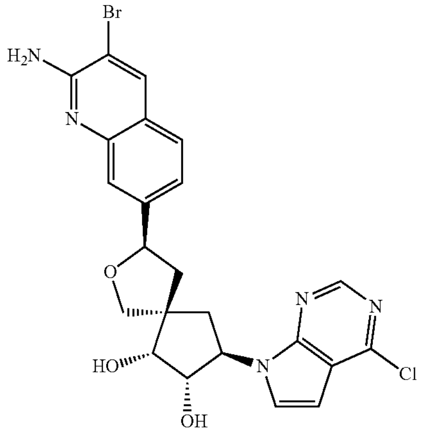 and -continued
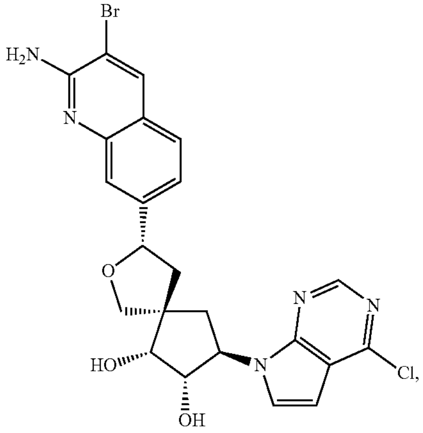
or a pharmaceutically acceptable salt thereof.
In other particular aspects, the compound is selected from:
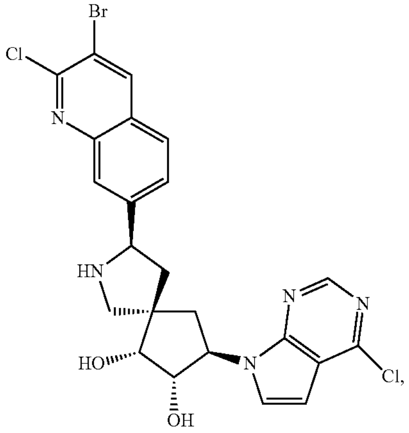
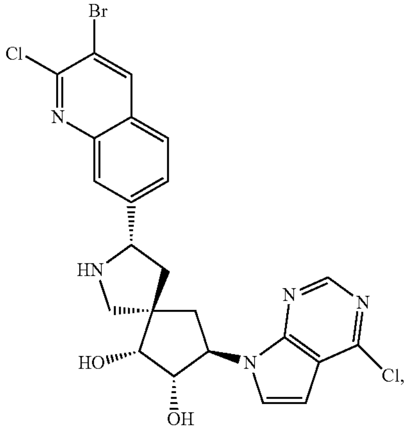
-continued
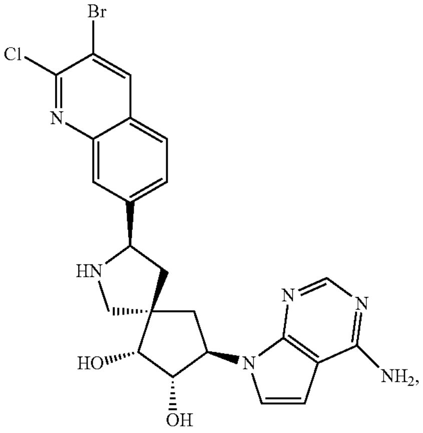
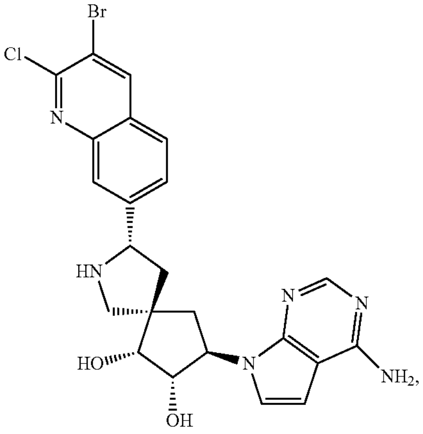
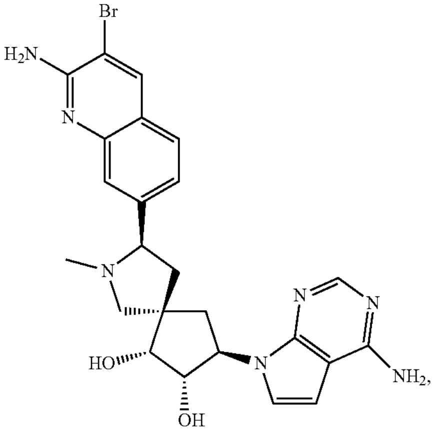
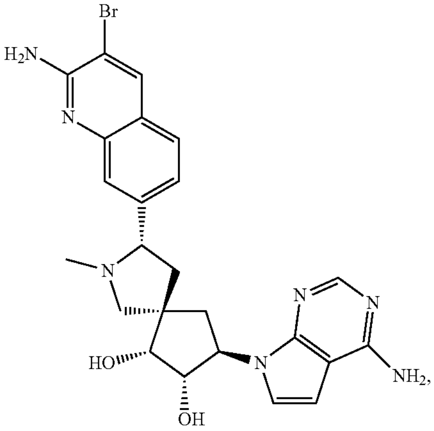

-continued
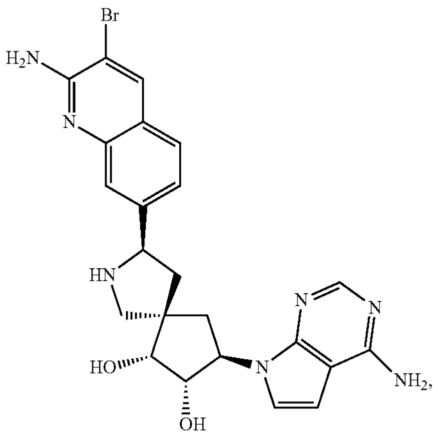
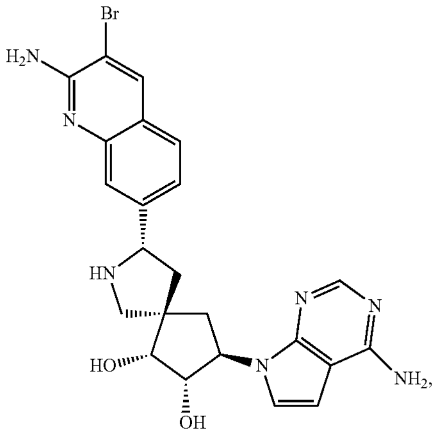
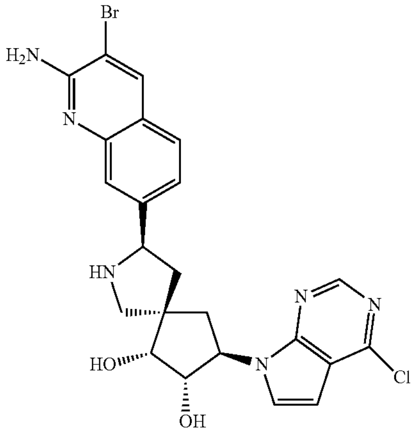
and
-continued
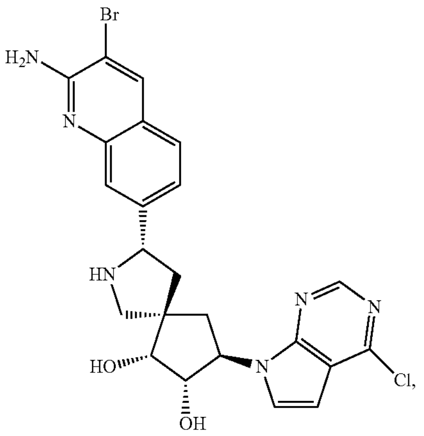
or a pharmaceutically acceptable salt thereof.
In other particular aspects, the compound is selected from:
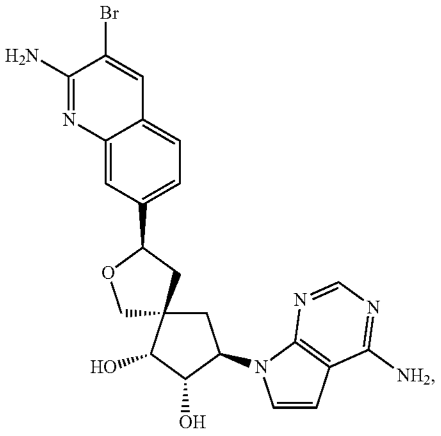
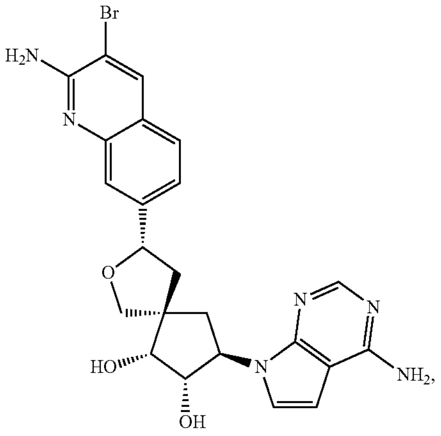

-continued
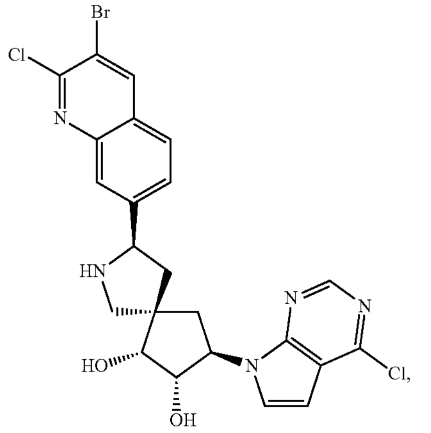
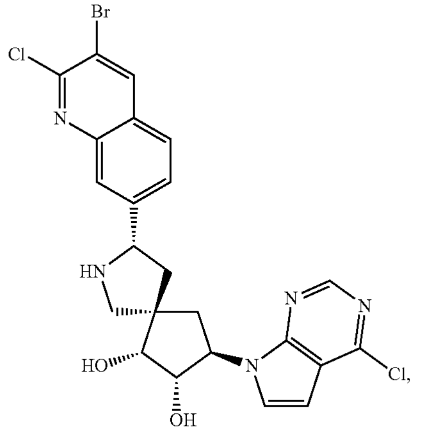
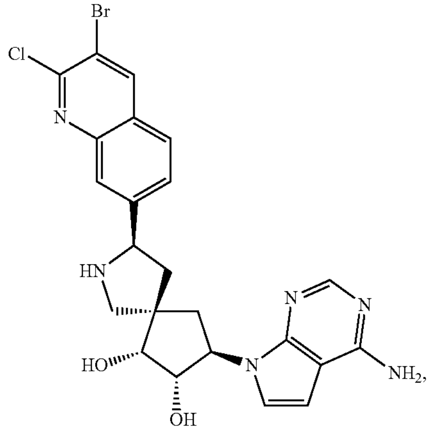
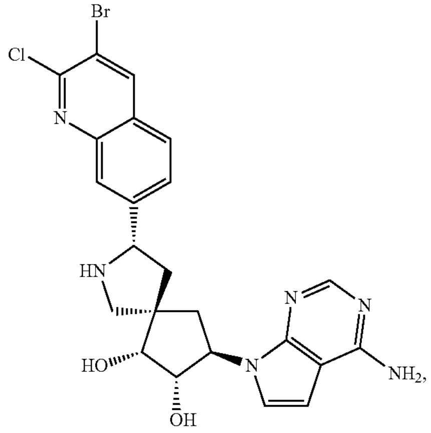
-continued
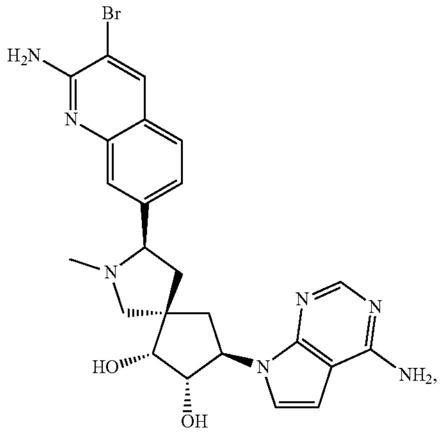
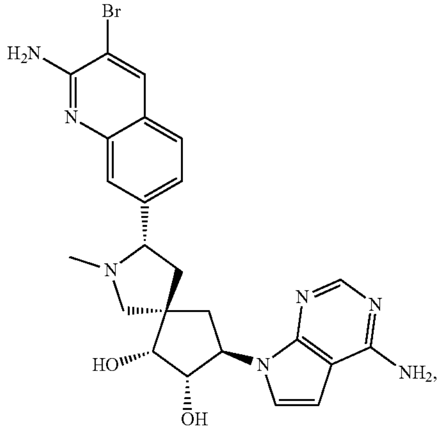
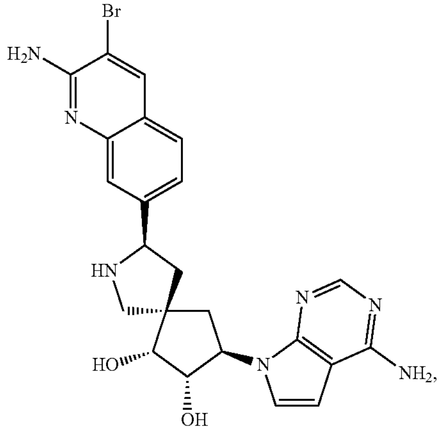
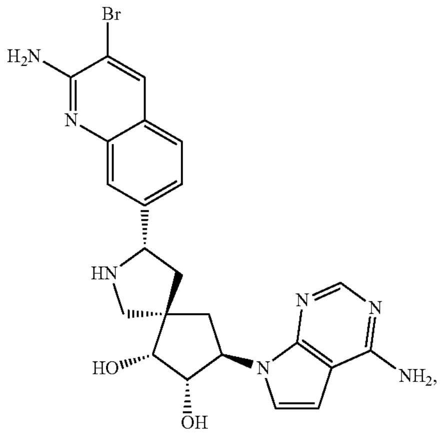

-continued
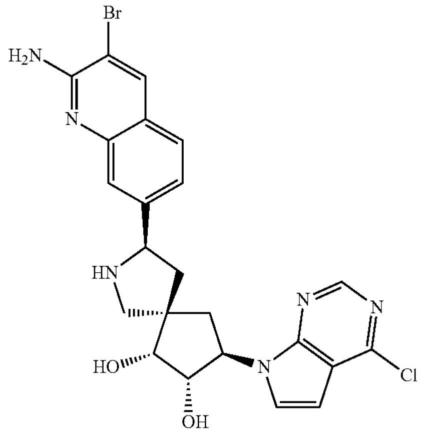
and
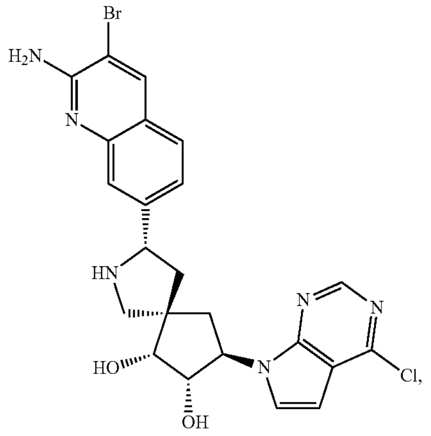
or a pharmaceutically acceptable salt thereof.
In yet other particular aspects, the compound is selected from:
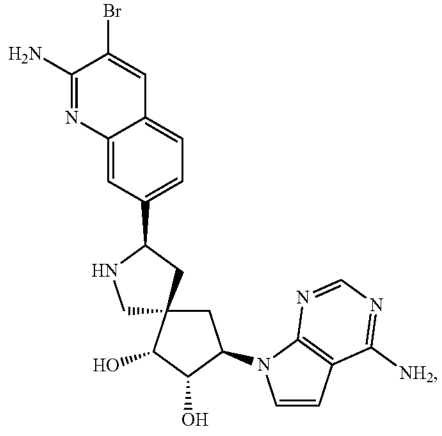
-continued
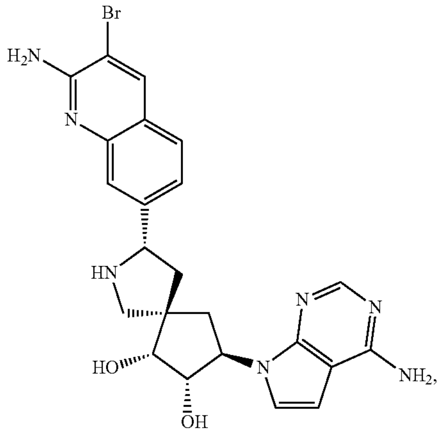
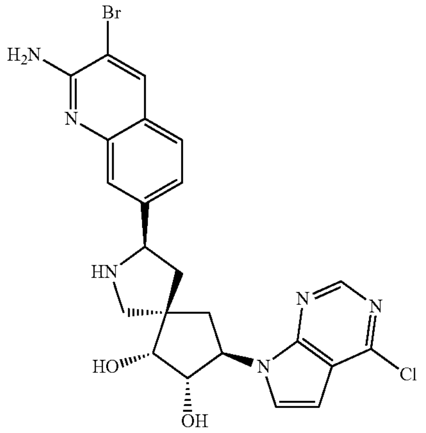
and
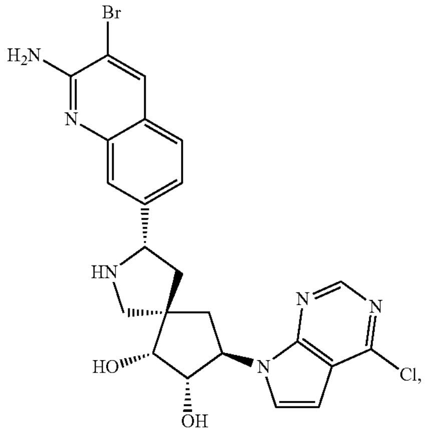
or a pharmaceutically acceptable salt thereof.

In yet other particular aspects, the compound is selected from:
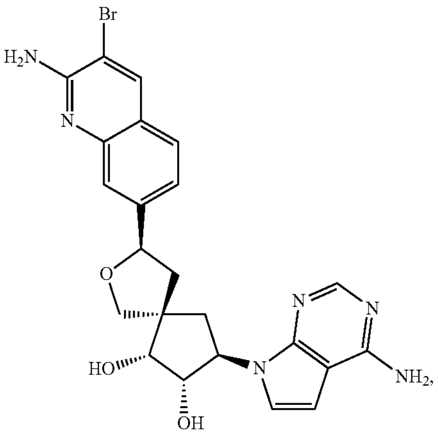
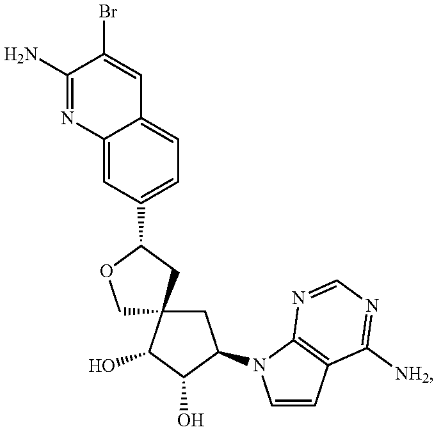
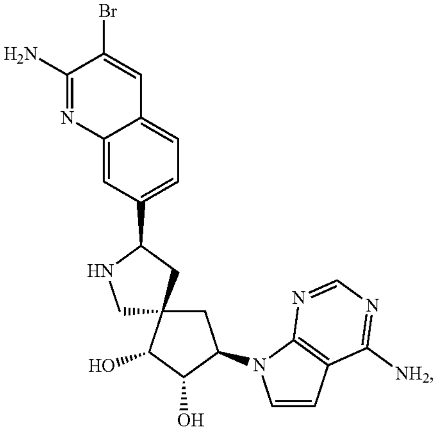
-continued
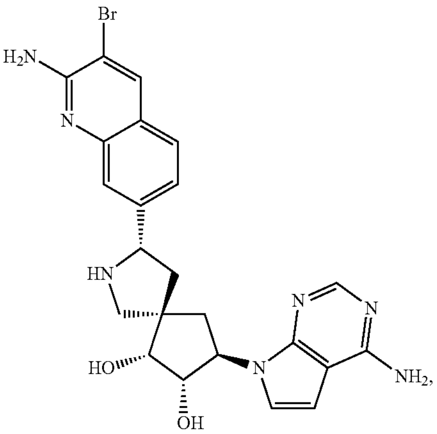
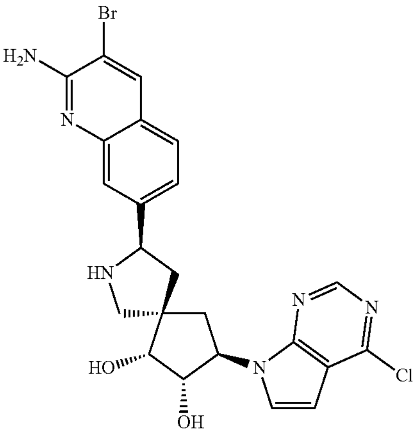
and
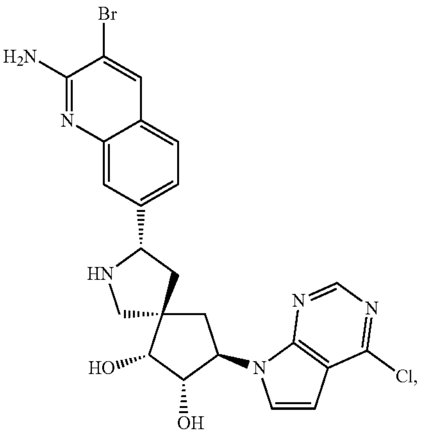
or a pharmaceutically acceptable salt thereof.

In yet other particular aspects, the compound is selected from:
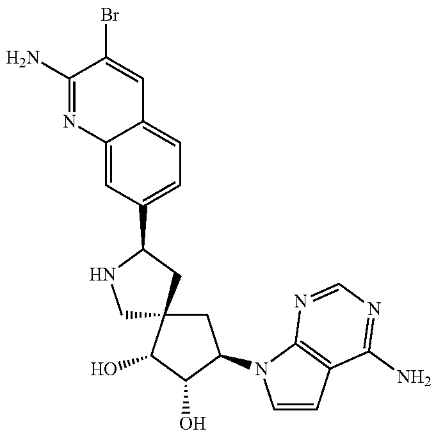
and
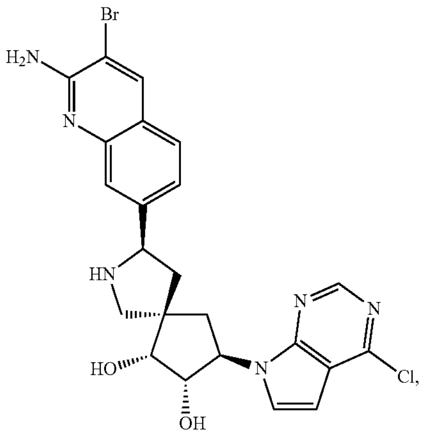
or a pharmaceutically acceptable salt thereof.
In yet other particular aspects, the compound is selected from:
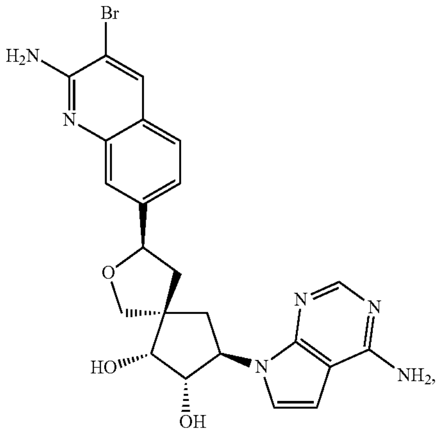
-continued
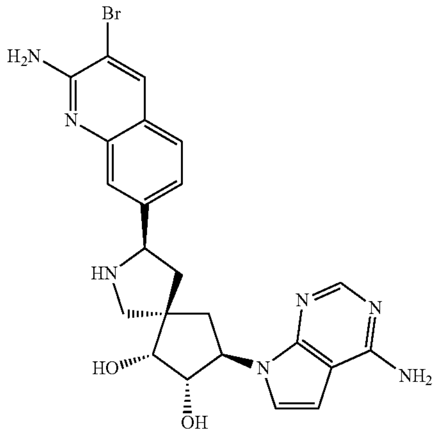
and
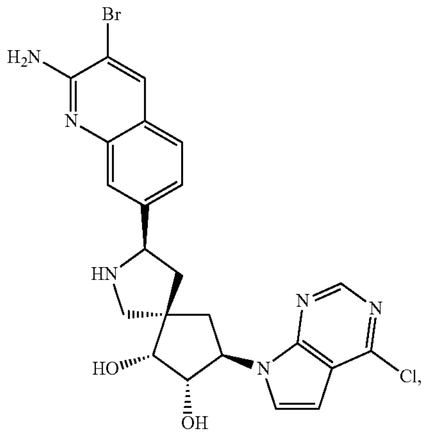
or a pharmaceutically acceptable salt thereof.
In yet other particular aspects, the compound is selected from:
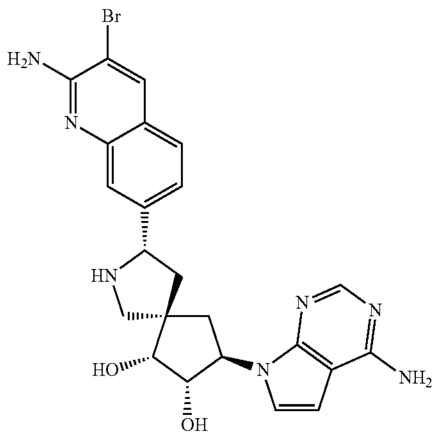
and -continued

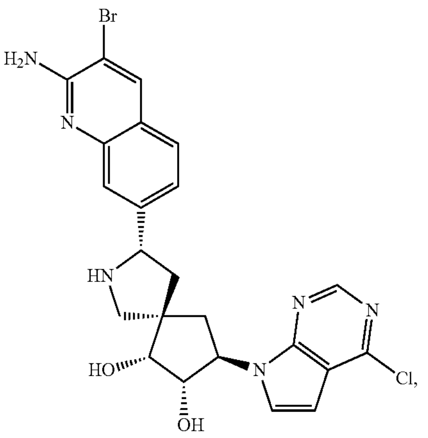

or a pharmaceutically acceptable salt thereof.

In yet other particular aspects, the compound is selected from:

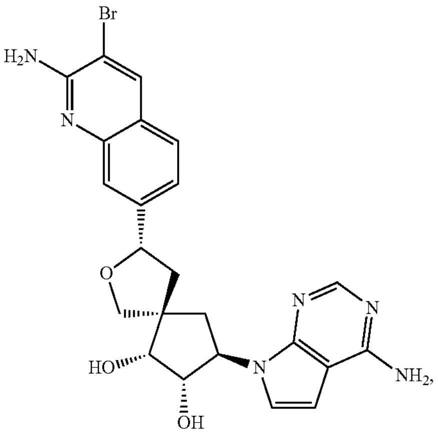

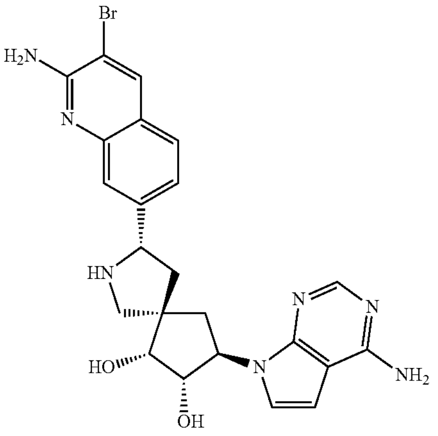

and

-continued

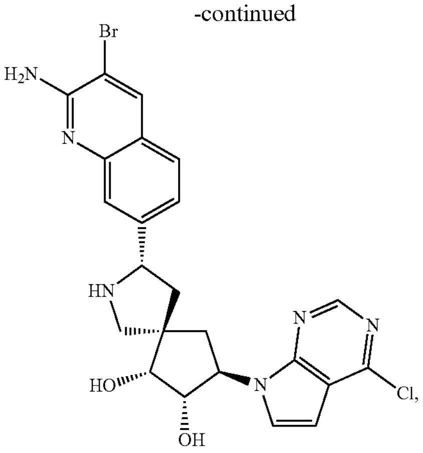

or a pharmaceutically acceptable salt thereof.

In yet other aspects, the compound is selected from:

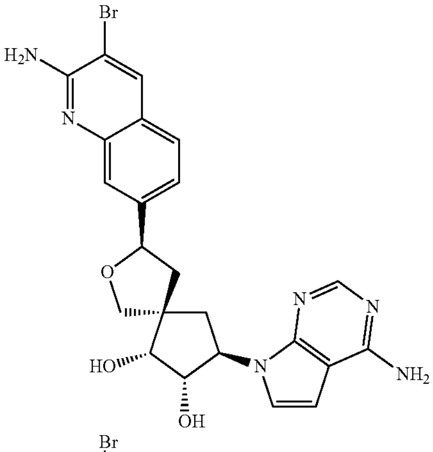

and

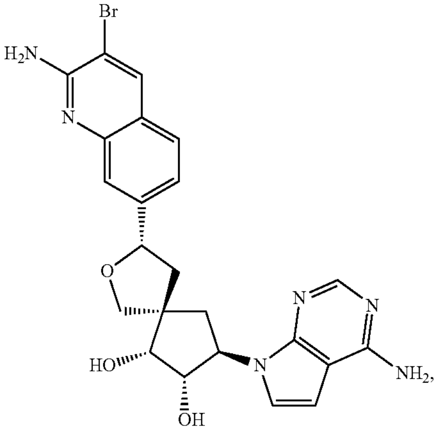

or a pharmaceutically acceptable salt thereof.

In particular aspects, the compound is selected from Table 2.

In certain embodiments, the invention relates to a pharmaceutical composition comprising any of the compounds described herein and a pharmaceutically acceptable diluent or excipient.

Example Methods of Treatment/Use

The compounds described herein are inhibitors of PRMT5 and therefore may be useful for treating diseases wherein the underlying pathology is (at least in part) mediated by PRMT5 or the dysregulation of its normal activity. Such diseases include cancer and other diseases in which there is a disorder of transcription, cell proliferation, apoptosis, or differentiation.

In certain embodiments, the method of treating cancer in a subject in need thereof comprises administering to the subject an effective amount of any of the compounds described herein, or a pharmaceutically acceptable salt thereof. For example, the cancer may be selected from carcinoma (e.g., a carcinoma of the endometrium, bladder, breast, colon (e.g., colorectal carcinomas such as colon adenocarcinoma and colon adenoma)), sarcoma (e.g., a sarcoma such as Kaposi's, osteosarcoma, tumor of mesenchymal origin, for example fibrosarcoma or habdomyosarcoma), kidney, epidermis, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, nose, head and neck, prostate, and skin (e.g., squamous cell carcinoma), human breast cancers (e.g., primary breast tumors, node-negative breast cancer, invasive duct adenocarcinomas of the breast, non-endometrioid breast cancers), familial melanoma, and melanoma. Other examples of cancers that may be treated with a compound of the invention include hematopoietic tumors of lymphoid lineage (e.g. leukemia, acute lymphocytic leukemia, mantle cell lymphoma, chronic lymphocytic leukaemia, B-cell lymphoma (such as diffuse large B cell lymphoma), T-cell lymphoma, multiple myeloma, Hodgkin's lymphoma, non-Hodgkin's lymphoma, hairy cell lymphoma, and Burkett's lymphoma), and hematopoietic tumors of myeloid lineage, for example acute and chronic myelogenous leukemias, myelodysplastic syndrome, and promyelocytic leukemia. Other cancers include a tumor of the central or peripheral nervous system, for example astrocytoma, neuroblastoma, glioma or schwannoma; seminoma; teratocarcinoma; xeroderma pigmentosum; retinoblastoma; keratoctanthoma; and thyroid follicular cancer.

In particular embodiments, the treated cancer is selected from colorectal cancer, head and neck cancer, pancreatic cancer, sarcoma, melanoma, myeloma, lymphoma, lung cancer (including non-small cell lung cancer and small cell lung cancer), breast cancer, ovarian cancer, liver cancer, gastric cancer, endometrial cancer, kidney cancer, bladder cancer, and acute myelogenous leukemia.

In more particular embodiments, the treated cancer is selected from colorectal cancer, head and neck cancer, pancreatic cancer, sarcoma, melanoma, myeloma, lymphoma, non-small cell lung cancer, breast cancer, ovarian cancer, liver cancer, gastric cancer, bladder cancer, and acute myelogenous leukemia.

In some aspects, the subject is a mammal, for example, a human.

Further disclosed herein are methods of inhibiting PRMT5 in a cell comprising contacting said cell with any of the compounds described herein, or a pharmaceutically acceptable salt thereof, such that PRMT5 enzyme is inhibited in said cell. For example, the cell is a cancer cell. In preferred embodiments, proliferation of the cell is inhibited or cell death is induced.

Further disclosed herein is a method of treating a disease treatable by inhibition of PRMT5 (e.g., a disease characterized by increased expression of PRMT5) in a subject, comprising administering to the subject in recognized need of such treatment, an effective amount of any of the compounds described herein and/or a pharmaceutically acceptable salt thereof. Diseases treatable by inhibition of PRMT5 (e.g., diseases characterized by increased expression of PRMT5) include, for example, cancers, metabolic diseases, and blood diseases. Further exemplary diseases include colorectal cancer, head and neck cancer, pancreatic cancer, sarcoma, melanoma, myeloma, lymphoma, lung cancer (including non-small cell lung cancer and small cell lung cancer), breast cancer, ovarian cancer, liver cancer, gastric cancer, endometrial cancer, kidney cancer, bladder cancer, and acute myelogenous leukemia.

The methods of treatment comprise administering a compound of the invention, or a pharmaceutically acceptable salt thereof, to a subject in need thereof. Individual embodiments include methods of treating any one of the above-mentioned disorders or diseases by administering an effective amount of a compound of the invention, or a pharmaceutically acceptable salt thereof, to a subject in need thereof.

Certain embodiments include a method of modulating PRMT5 activity in a subject comprising administering to the subject a compound of the invention, or a pharmaceutically acceptable salt thereof. Additional embodiments provide a method for the treatment of a disorder or a disease mediated by PRMT5 in a subject in need thereof, comprising administering to the subject an effective amount of the compound of Formula I, Ia, Ib, II, IIa, IIb, III, IIIa, IIIb, IV, IVa, IVb, V, Va or Vb, or a pharmaceutically acceptable salt thereof. Other embodiments of the invention provide a method of treating a disorder or a disease mediated by PRMT5, in a subject in need of treatment thereof comprising administering an effective amount of a compound of the invention, or a pharmaceutically acceptable salt thereof, wherein the disorder or the disease is selected from carcinomas with genetic aberrations that activate PRMT5 activity. These include, but are not limited to, cancers.

The present method also provides the use of a compound of invention, or a pharmaceutically acceptable salt thereof, for the treatment of a disorder or disease mediated by PRMT5.

In some embodiments, a compound of the invention, or a pharmaceutically acceptable salt thereof, is used for the treatment of a disorder or a disease mediated by PRMT5.

Yet other embodiments of the present method provide a compound according to Formula I, Ia, Ib, II, IIa, IIb, III, IIIa, IIIb, IV, IVa, IVb, V, Va or Vb, or a pharmaceutically acceptable salt thereof, for use as a medicament.

Still other embodiments of the present method encompass the use of a compound of Formula I, Ia, Ib, II, IIa, IIb, III, IIIa, IIIb, IV, IVa, IVb, V, Va or Vb, or a pharmaceutically acceptable salt thereof, in the manufacture of a medicament for the treatment of a disorder or disease mediated by PRMT5.

Specific embodiments of the invention include those compounds listed in Table 1. The identifying number ("Cmpd"), the chemical structure ("Structure"), the example method used to synthesize the compound ("Method"), and the order of elution in a chromatographic separation process, if determined and as compared to the diastereomer of that compound, ("Elution") are disclosed in Table 1 for each compound.

Specific embodiments of the invention include compounds of Formula IV, wherein V, $X_1$, $X_2$, $Y_2$, Z, $R_1$, $R_2$, and $R_b$ are defined as listed in Table 2 for each compound.

TABLE 1
| Cmpd | Structure | Method | Elution |
| --- | --- | --- | --- |
| 1 | 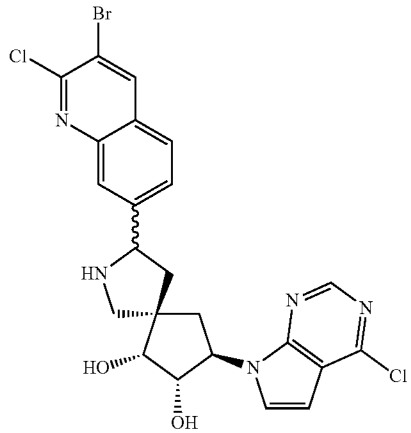 | 1 | 2 |
| 2 | 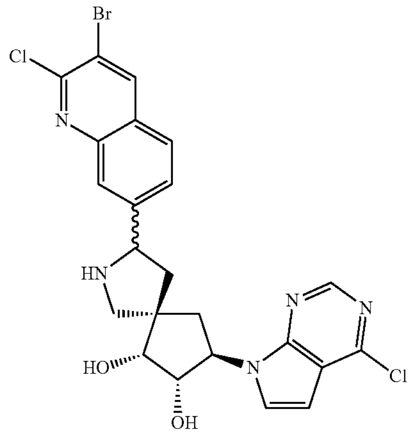 | 1 | 1 |
| 3 | 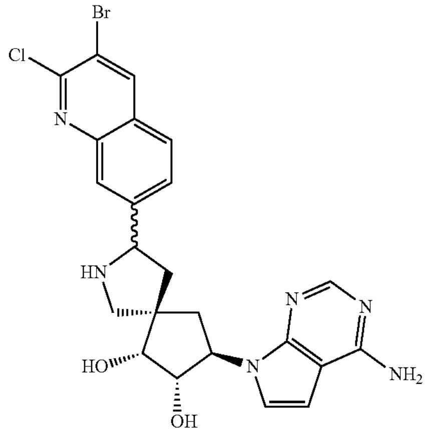 | 1 | 2 |

TABLE 1-continued
| Cmpd | Structure | Method | Elution |
|---|---|---|---|
| 4 | 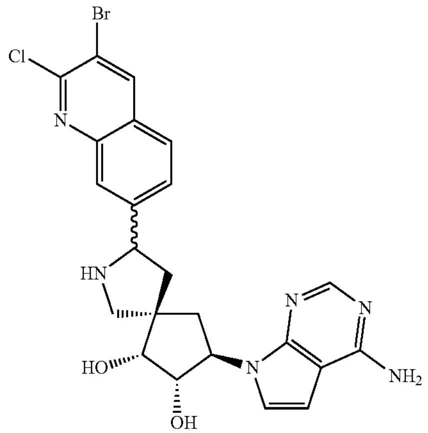 | 1 | 1 |
| 5 | 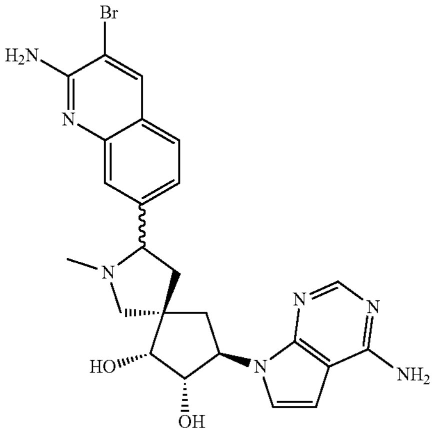 | 1 | 1 |
| 6 | 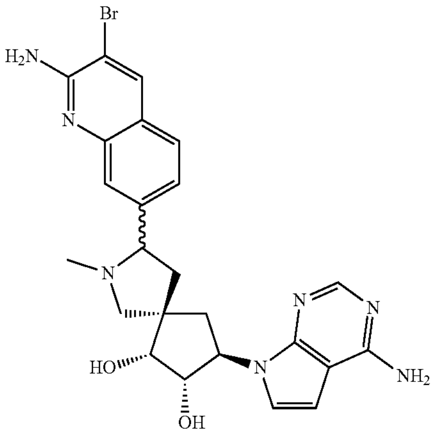 | 1 | 2 |

TABLE 1-continued
| Cmpd | Structure | Method | Elution |
|---|---|---|---|
| 7 | 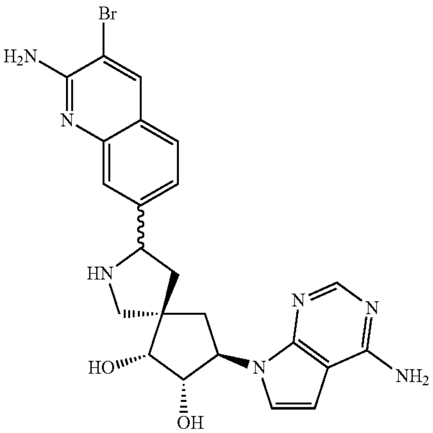 | 1 | 1 |
| 8 | 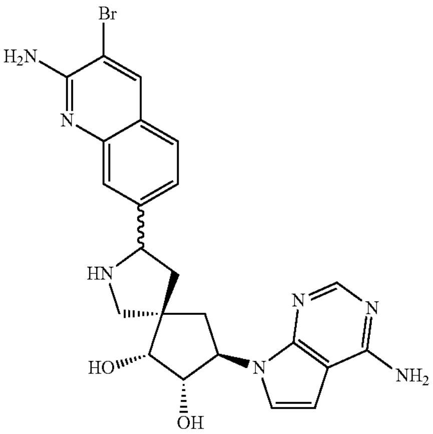 | 1 | 2 |
| 9 | 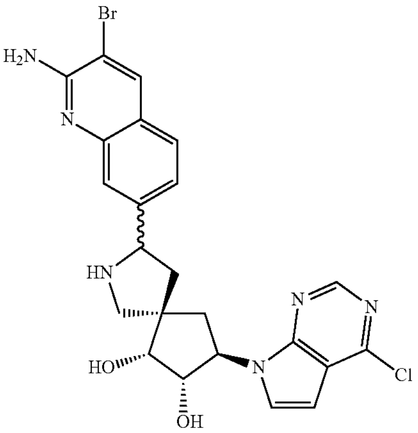 | 1 | 1 |

TABLE 1-continued
| Cmpd | Structure | Method | Elution |
|---|---|---|---|
| 10 | 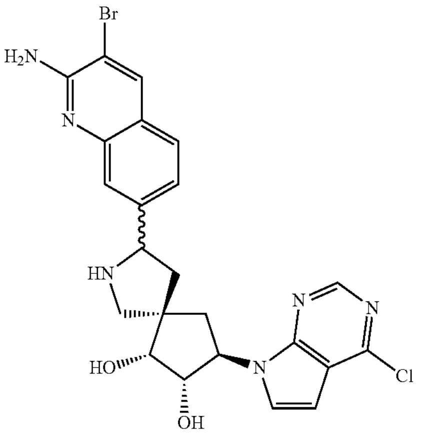 | 1 | 2 |
| 11 | 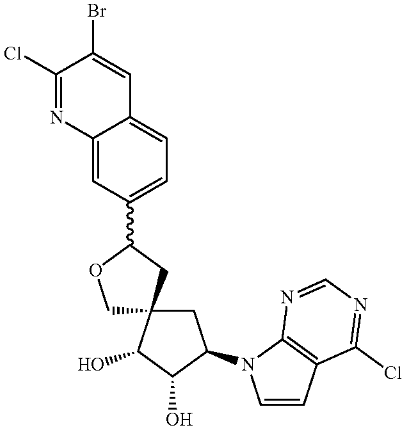 | 2 | |
| 12 | 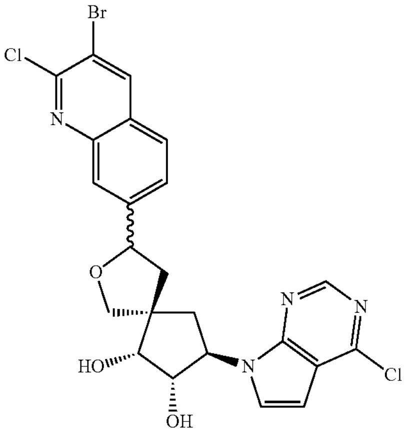 | 2 | |

TABLE 1-continued
| Cmpd | Structure | Method | Elution |
|---|---|---|---|
| | Epimer of Cmpd 11 | | |
| 13 | 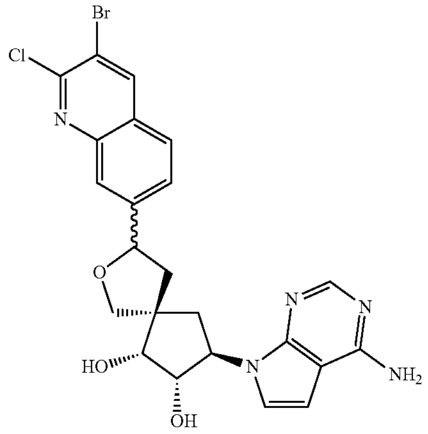 | 2 | |
| 14 | 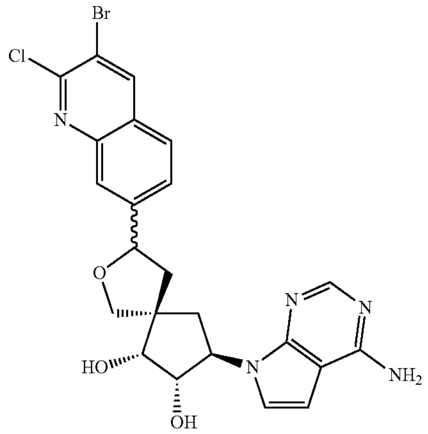 Epimer of Cmpd 13 | 2 | |
| 15 | 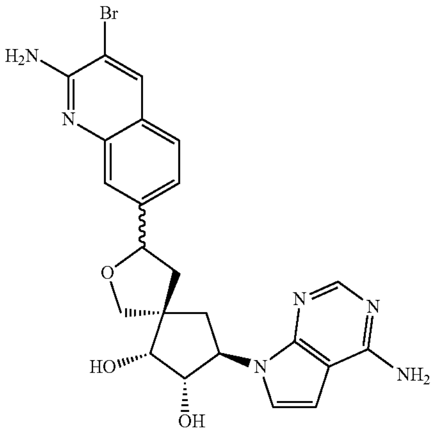 | 2 | 1 |

TABLE 1-continued
| Cmpd | Structure | Method | Elution |
| --- | --- | --- | --- |
| 16 | 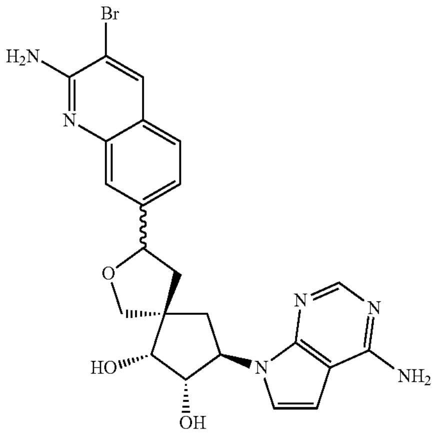 | 2 | 2 |
| 17 | 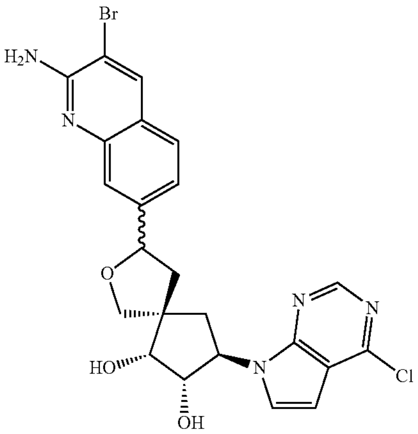 | 2 | |
| 18 | 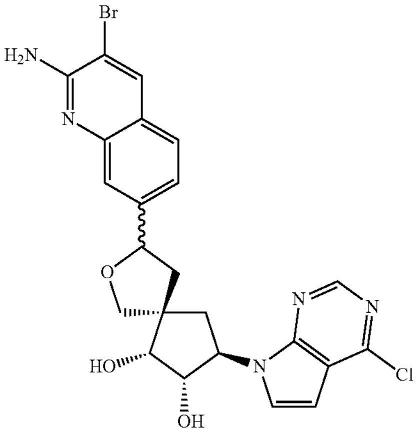 | 2 | |

TABLE 1-continued
| Cmpd | Structure | Method | Elution |
|---|---|---|---|
| | Epimer of Cmpd 17 | | |
| 19 | 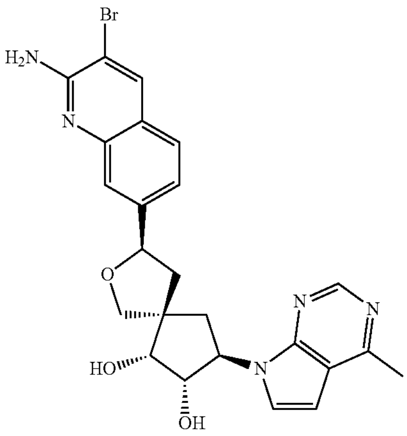 [SMILES: Cc1ncnc2c1ccn2[C@@H]1C[C@@]2(CO[C@@H](c3ccc4cc(Br)c(N)nc4c3)C2)[C@@H](O)[C@H]1O] | 2 | |
| 20 | 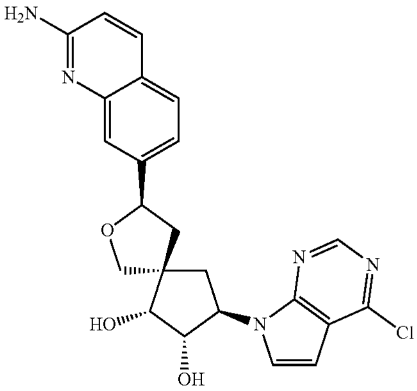 [SMILES: Nc1ccc2ccc([C@H]3C[C@@]4(CO3)C[C@@H](n3ccc5c(Cl)ncnc53)[C@H](O)[C@@H]4O)cc2n1] | 2 | |
| 21 | 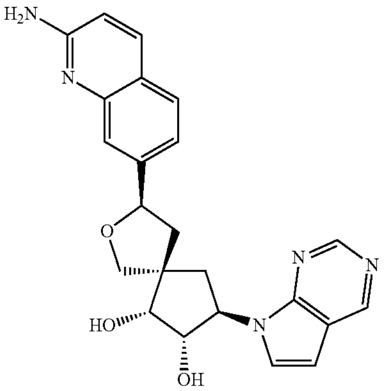 [SMILES: Nc1ccc2ccc([C@H]3C[C@@]4(CO3)C[C@@H](n3ccc5cncnc53)[C@H](O)[C@@H]4O)cc2n1] | 2 | |

TABLE 1-continued
| Cmpd | Structure | Method | Elution |
|---|---|---|---|
| 22 | 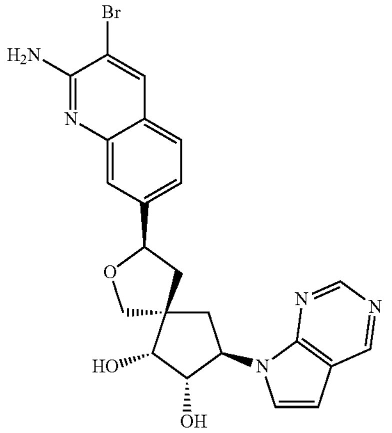 [SMILES: Nc1nc2cc([C@H]3C[C@@]4(CO3)C[C@@H](n3ccc5cncnc53)[C@H](O)[C@@H]4O)ccc2cc1Br] | 2 | |
| 23 | 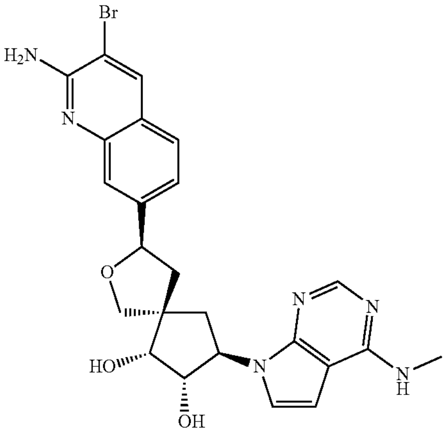 [SMILES: CNc1ncnc2c1ccn2[C@@H]1C[C@@]2(CO[C@@H](c3ccc4cc(Br)c(N)nc4c3)C2)[C@@H](O)[C@H]1O] | 2 | |
| 24 | 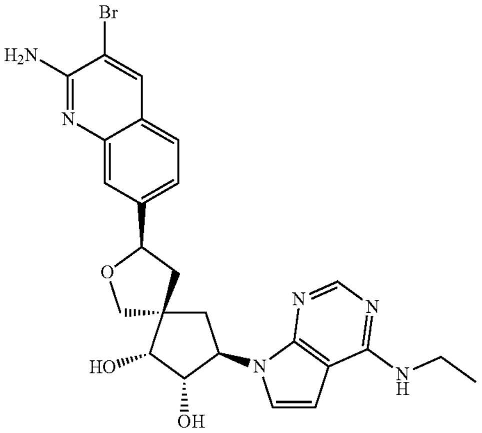 [SMILES: CCNc1ncnc2c1ccn2[C@@H]1C[C@@]2(CO[C@@H](c3ccc4cc(Br)c(N)nc4c3)C2)[C@@H](O)[C@H]1O] | 2 | |

TABLE 1-continued

| Cmpd | Structure | Method | Elution |
|---|---|---|---|
| 25 | 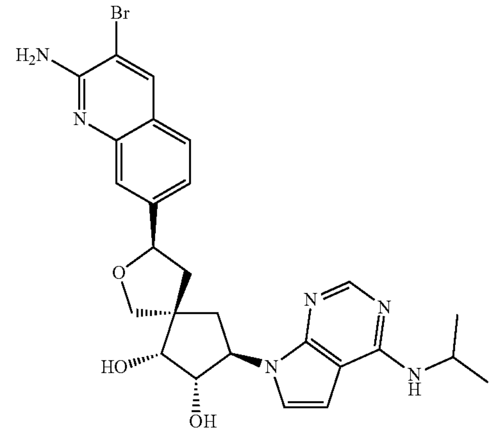 [SMILES: CC(C)Nc1ncnc2c1ccn2[C@@H]1C[C@@]2(CO[C@@H](c3ccc4cc(Br)c(N)nc4c3)C2)[C@@H](O)[C@H]1O] | 2 | |
| 26 | 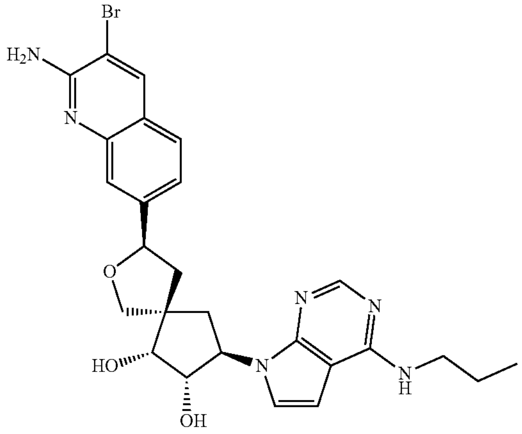 [SMILES: CCCNc1ncnc2c1ccn2[C@@H]1C[C@@]2(CO[C@@H](c3ccc4cc(Br)c(N)nc4c3)C2)[C@@H](O)[C@H]1O] | 2 | |

TABLE 2

| V | $X_1$ | $X_2$ | $Y_2$ | Z | $R_1$ | $R_2$ | $R_b$ |
|---|---|---|---|---|---|---|---|
| CH | CH | CH | CH2 | CH2 | H | H | F |
| CH | CH | N | CH2 | CH2 | NH2 | Br | NH2 |
| CH | CH | N | CH2 | O | Br | Cl | Cl |
| CH | N | CH | NH | N(H) | N(CH3)2 | NH2 | H |
| N | CH | CH | CH2 | CH2 | F | Cl | N(CH3)2 |
| CH | CH | CH | O | O | H | H | NH2 |
| CH | N | N | O | CH2 | NH2 | Cl | N(H)CH3 |
| N | CH | N | O | O | NH2 | Cl | N(H)CH3 |
| N | N | CH | S | N(H) | N(H)CH3 | H | F |
| N | CH | N | NH | CH2 | F | Br | F |
| N | N | N | CH2 | O | Br | F | N(CH3)2 |
| CH | CH | N | NH | CH2 | Br | N(H)CH3 | N(CH3)2 |
| N | N | N | S | CH2 | Cl | N(H)CH3 | N(H)CH3 |
| N | N | CH | N(CH3) | O | N(H)CH3 | N(CH3)2 | N(H)CH3 |
| CH | CH | CH | S | O | Cl | H | Cl |
| N | CH | N | CH2 | N(H) | F | F | N(CH3)2 |
| CH | CH | CH | O | O | NH2 | NH2 | N(CH3)2 |
| CH | CH | N | S | CH2 | H | NH2 | N(H)CH3 |
| CH | CH | N | NH | O | F | N(H)CH3 | Br |
| CH | N | CH | S | CH2 | Br | H | H |
| CH | N | CH | NH | CH2 | H | NH2 | N(H)CH3 |
| CH | CH | N | CH2 | N(H) | Cl | H | H |
| N | N | CH | O | N(H) | Cl | H | N(CH3)2 |
| N | CH | N | CH2 | N(H) | H | NH2 | Cl |
| CH | N | N | O | O | Cl | NH2 | Br |
| N | CH | CH | O | O | NH2 | Br | NH2 |
| N | CH | CH | O | CH2 | Br | H | Br |
| N | N | CH | CH2 | N(H) | NH2 | H | N(H)CH3 |
| CH | N | CH | S | CH2 | NH2 | N(CH3)2 | Br |

TABLE 2-continued

| V | $X_1$ | $X_2$ | $Y_2$ | Z | $R_1$ | $R_2$ | $R_b$ |
|---|---|---|---|---|---|---|---|
| N | CH | N | S | N(H) | NH2 | NH2 | Cl |
| N | CH | N | N(CH3) | N(H) | H | H | N(H)CH3 |
| N | N | CH | O | CH2 | Br | H | Br |
| CH | CH | N | N(CH3) | CH2 | F | NH2 | N(H)CH3 |
| N | CH | N | S | O | H | F | F |
| CH | CH | CH | S | N(H) | H | H | F |
| CH | CH | N | N(CH3) | CH2 | NH2 | Cl | N(CH3)2 |
| N | CH | CH | S | O | Br | NH2 | N(CH3)2 |
| CH | CH | CH | O | N(H) | N(H)CH3 | Cl | NH2 |
| N | N | N | S | CH2 | Br | Cl | Br |
| CH | N | CH | N(CH3) | N(H) | Cl | N(H)CH3 | NH2 |
| N | N | CH | NH | O | N(CH3)2 | H | Cl |
| N | N | CH | O | CH2 | N(CH3)2 | N(H)CH3 | N(H)CH3 |
| CH | CH | N | N(CH3) | N(H) | H | N(H)CH3 | F |
| CH | N | N | NH | O | NH2 | Cl | NH2 |
| N | CH | CH | O | N(H) | N(H)CH3 | N(H)CH3 | N(H)CH3 |
| N | CH | N | N(CH3) | N(H) | NH2 | NH2 | Br |
| CH | CH | N | S | N(H) | H | N(CH3)2 | N(H)CH3 |
| N | CH | N | S | CH2 | NH2 | Br | Cl |
| CH | CH | CH | S | N(H) | Br | N(H)CH3 | H |
| CH | N | N | S | O | NH2 | Br | NH2 |
| N | CH | CH | O | CH2 | Br | NH2 | H |
| CH | N | N | NH | N(H) | N(CH3)2 | Br | H |
| CH | CH | CH | S | CH2 | N(H)CH3 | H | F |
| CH | N | CH | S | O | N(H)CH3 | NH2 | F |
| N | N | CH | S | O | N(CH3)2 | N(CH3)2 | NH2 |
| CH | N | CH | O | O | Br | F | Cl |
| N | CH | CH | N(CH3) | O | N(CH3)2 | H | N(CH3)2 |
| CH | CH | N | CH2 | O | N(H)CH3 | H | Br |

TABLE 2-continued

| V | $X_1$ | $X_2$ | $Y_2$ | Z | $R_1$ | $R_2$ | $R_b$ |
|---|---|---|---|---|---|---|---|
| CH | N | CH | NH | N(H) | Br | NH2 | Br |
| CH | N | N | N(CH3) | O | NH2 | Cl | H |
| N | N | N | CH2 | N(H) | N(H)CH3 | Br | N(H)CH3 |
| CH | N | N | N(CH3) | N(H) | H | Br | NH2 |
| N | CH | CH | CH2 | CH2 | H | N(CH3)2 | NH2 |
| N | CH | N | S | N(H) | F | Br | H |
| N | CH | CH | O | CH2 | NH2 | H | Br |
| CH | CH | CH | NH | N(H) | H | NH2 | Br |
| CH | CH | N | S | CH2 | H | Cl | F |
| CH | CH | N | CH2 | N(H) | H | NH2 | N(H)CH3 |
| CH | CH | CH | O | N(H) | Br | H | Cl |
| CH | CH | CH | O | N(H) | NH2 | H | N(CH3)2 |
| CH | N | CH | CH2 | N(H) | F | N(H)CH3 | N(CH3)2 |
| CH | CH | N | O | N(H) | Cl | F | F |
| N | N | N | O | N(H) | F | N(CH3)2 | F |
| CH | CH | CH | S | N(H) | H | N(H)CH3 | F |
| CH | CH | N | NH | N(H) | NH2 | N(CH3)2 | N(H)CH3 |
| N | N | CH | NH | O | F | N(CH3)2 | N(H)CH3 |
| N | N | N | NH | CH2 | NH2 | N(CH3)2 | N(H)CH3 |
| CH | N | N | S | N(H) | F | Cl | F |
| CH | N | CH | S | O | Br | N(CH3)2 | N(H)CH3 |
| CH | CH | N | O | O | N(CH3)2 | Br | N(CH3)2 |
| N | N | CH | S | N(H) | Cl | N(CH3)2 | N(H)CH3 |
| N | N | CH | O | N(H) | Br | Cl | N(H)CH3 |
| N | CH | N | NH | CH2 | Cl | Br | Cl |
| N | CH | N | N(CH3) | O | F | F | F |
| CH | CH | N | NH | N(H) | Cl | NH2 | Cl |
| CH | CH | CH | S | CH2 | H | NH2 | F |
| N | CH | CH | NH | N(H) | N(CH3)2 | F | Br |
| N | CH | N | NH | O | N(CH3)2 | Br | N(H)CH3 |
| CH | CH | N | NH | O | Cl | NH2 | N(H)CH3 |
| CH | CH | CH | N(CH3) | CH2 | NH2 | Cl | F |
| CH | N | N | CH2 | O | H | Cl | NH2 |
| CH | N | N | O | CH2 | H | F | N(CH3)2 |
| CH | CH | N | NH | O | Cl | Br | Cl |
| CH | N | CH | N(CH3) | N(H) | NH2 | N(CH3)2 | H |
| CH | N | N | CH2 | CH2 | F | N(H)CH3 | F |
| CH | N | CH | CH2 | O | Br | H | H |
| N | N | CH | O | O | NH2 | Br | H |
| N | CH | N | NH | N(H) | Br | F | Br |
| CH | CH | CH | N(CH3) | CH2 | N(H)CH3 | Cl | N(CH3)2 |
| N | N | N | CH2 | O | Cl | N(H)CH3 | NH2 |
| CH | CH | CH | NH | CH2 | N(H)CH3 | Cl | H |
| CH | N | N | N(CH3) | CH2 | N(H)CH3 | H | NH2 |
| CH | N | CH | CH2 | O | N(H)CH3 | F | H |
| N | N | CH | S | O | N(H)CH3 | NH2 | F |
| N | CH | CH | NH | O | Cl | N(CH3)2 | NH2 |
| CH | CH | N | S | O | H | NH2 | N(CH3)2 |
| CH | N | N | S | O | H | F | Br |
| N | N | N | CH2 | N(H) | NH2 | H | Cl |
| CH | N | CH | CH2 | N(H) | H | N(CH3)2 | Cl |
| N | CH | N | S | O | Cl | F | H |
| N | CH | N | CH2 | N(H) | Br | NH2 | N(CH3)2 |
| N | CH | N | NH | O | NH2 | Br | N(CH3)2 |
| N | CH | CH | CH2 | O | N(CH3)2 | F | N(H)CH3 |
| N | N | N | O | N(H) | Br | F | Br |
| CH | CH | CH | S | CH2 | NH2 | NH2 | N(CH3)2 |
| CH | CH | N | NH | O | N(H)CH3 | N(CH3)2 | Cl |
| N | N | N | N(CH3) | N(H) | H | NH2 | Br |
| CH | CH | CH | S | CH2 | H | NH2 | N(CH3)2 |
| CH | N | CH | S | CH2 | Br | Cl | N(H)CH3 |
| N | N | CH | O | O | H | F | Br |
| N | N | N | NH | O | Br | H | N(H)CH3 |
| CH | CH | CH | S | CH2 | N(H)CH3 | Br | NH2 |
| CH | CH | N | N(CH3) | N(H) | Cl | N(CH3)2 | N(H)CH3 |
| N | CH | CH | O | CH2 | H | Br | NH2 |
| N | N | CH | NH | CH2 | NH2 | F | N(H)CH3 |
| N | N | N | NH | N(H) | F | F | N(H)CH3 |
| N | N | N | NH | CH2 | N(CH3)2 | F | F |
| CH | CH | CH | NH | O | H | N(H)CH3 | N(CH3)2 |
| CH | CH | N | N(CH3) | CH2 | Br | NH2 | F |
| N | N | CH | S | CH2 | F | Br | N(CH3)2 |
| CH | CH | N | NH | N(H) | F | N(CH3)2 | N(H)CH3 |
| CH | CH | CH | N(CH3) | CH2 | N(H)CH3 | F | NH2 |
| N | CH | N | N(CH3) | O | F | H | H |
| CH | CH | CH | S | N(H) | N(CH3)2 | N(CH3)2 | N(H)CH3 |
| CH | N | CH | S | O | Br | F | Cl |
| N | CH | CH | S | N(H) | N(CH3)2 | H | H |

TABLE 2-continued

| V | $X_1$ | $X_2$ | $Y_2$ | Z | $R_1$ | $R_2$ | $R_b$ |
|---|---|---|---|---|---|---|---|
| N | N | CH | O | CH2 | Br | N(CH3)2 | NH2 |
| N | N | N | S | N(H) | H | Cl | Cl |
| N | N | CH | S | N(H) | H | NH2 | NH2 |
| N | N | N | S | O | NH2 | N(H)CH3 | N(H)CH3 |
| CH | N | CH | S | N(H) | N(H)CH3 | Cl | N(H)CH3 |
| N | CH | N | NH | N(H) | Cl | Cl | Br |
| N | CH | CH | CH2 | O | Cl | F | H |
| N | N | N | CH2 | N(H) | NH2 | F | NH2 |
| CH | CH | CH | S | CH2 | H | Cl | N(CH3)2 |
| N | N | N | S | CH2 | Br | N(H)CH3 | N(CH3)2 |
| CH | CH | N | CH2 | N(H) | Cl | Cl | N(H)CH3 |
| N | N | N | O | N(H) | NH2 | NH2 | Cl |
| CH | N | CH | NH | O | H | Cl | N(CH3)2 |
| N | CH | CH | N(CH3) | CH2 | F | Cl | N(H)CH3 |
| N | N | CH | S | CH2 | Cl | F | N(H)CH3 |
| CH | N | CH | N(CH3) | O | Br | F | NH2 |
| CH | CH | N | O | CH2 | Br | N(H)CH3 | NH2 |
| N | N | N | O | O | N(H)CH3 | Br | F |
| CH | CH | CH | N(CH3) | O | Cl | Br | N(CH3)2 |
| CH | CH | N | O | N(H) | N(CH3)2 | H |  |
| CH | CH | N | NH | N(H) | Cl | Br | N(H)CH3 |
| CH | N | CH | O | O | H | N(H)CH3 | N(H)CH3 |
| CH | N | CH | O | O | N(H)CH3 | F | N(CH3)2 |
| CH | N | N | N(CH3) | O | Br | H | Cl |
| N | CH | CH | NH | O | NH2 | Cl | NH2 |
| N | CH | N | N(CH3) | O | H | N(CH3)2 | F |
| N | N | N | CH2 | O | N(CH3)2 | NH2 | N(CH3)2 |
| CH | CH | CH | N(CH3) | O | NH2 | NH2 | Br |
| CH | CH | N | NH | CH2 | Br | F | N(CH3)2 |
| N | CH | CH | NH | O | Br | Br | H |
| N | CH | N | NH | N(H) | F | Br | H |
| N | N | N | N(CH3) | N(H) | F | Cl | N(H)CH3 |
| N | N | CH | S | CH2 | F | Cl | NH2 |
| N | N | N | NH | O | Br | N(CH3)2 | N(CH3)2 |
| N | N | CH | CH2 | O | N(CH3)2 | H | H |
| CH | CH | CH | NH | N(H) | N(CH3)2 | NH2 | N(CH3)2 |
| N | N | CH | S | N(H) | Cl | F | Cl |
| N | N | CH | CH2 | O | H | F | NH2 |
| N | N | N | S | O | N(H)CH3 | N(H)CH3 | N(H)CH3 |
| N | CH | N | NH | O | N(H)CH3 | Br | F |
| CH | N | N | S | N(H) | N(H)CH3 | NH2 | H |
| N | CH | N | O | O | Cl | H | H |
| CH | N | CH | N(CH3) | O | N(H)CH3 | F | Br |
| N | N | CH | O | O | N(CH3)2 | F | N(CH3)2 |
| N | N | CH | N(CH3) | O | NH2 | F | N(CH3)2 |
| CH | N | CH | S | N(H) | H | N(CH3)2 | H |
| N | CH | CH | S | O | H | H | NH2 |
| N | N | CH | O | O | Br | Cl | F |
| CH | CH | CH | S | O | Br | N(CH3)2 | H |
| N | CH | CH | N(CH3) | N(H) | N(CH3)2 | N(H)CH3 | Br |
| N | N | CH | S | O | H | N(CH3)2 | N(CH3)2 |
| N | N | N | S | CH2 | F | N(CH3)2 | N(H)CH3 |
| N | CH | N | NH | CH2 | Br | NH2 | N(H)CH3 |
| CH | N | N | N(CH3) | N(H) | Br | F | Cl |
| CH | CH | N | S | N(H) | NH2 | N(H)CH3 | NH2 |
| CH | CH | CH | O | CH2 | NH2 | H | Br |
| CH | CH | CH | NH | CH2 | N(H)CH3 | H | Cl |
| CH | N | CH | S | O | Br | N(CH3)2 | NH2 |
| CH | N | N | S | CH2 | Cl | N(H)CH3 | N(H)CH3 |
| CH | CH | CH | NH | CH2 | Cl | H | NH2 |
| CH | CH | N | NH | N(H) | Cl | F | Cl |
| CH | N | N | CH2 | CH2 | N(CH3)2 | H | Br |
| CH | CH | CH | NH | O | N(H)CH3 | NH2 | NH2 |
| CH | CH | N | O | N(H) | Br | N(CH3)2 | Br |
| CH | CH | N | CH2 | CH2 | Cl | NH2 | H |
| CH | N | CH | N(CH3) | CH2 | NH2 | Cl | Br |
| N | CH | CH | CH2 | O | F | N(H)CH3 | Br |
| N | CH | CH | S | N(H) | F | N(H)CH3 | F |
| N | CH | CH | O | CH2 | N(CH3)2 | F | Cl |
| N | N | CH | N(CH3) | N(H) | N(CH3)2 | Cl | H |
| N | CH | N | S | CH2 | F | N(CH3)2 | F |
| CH | N | CH | N(CH3) | CH2 | NH2 | Cl | F |
| CH | N | CH | CH2 | CH2 | F | NH2 | NH2 |
| N | CH | N | CH2 | N(H) | Cl | N(H)CH3 | NH2 |
| N | CH | CH | N(CH3) | CH2 | Br | N(CH3)2 | N(CH3)2 |
| CH | CH | N | O | CH2 | F | F | N(CH3)2 |
| CH | N | CH | S | N(H) | Cl | Br | Cl |
| N | N | N | CH2 | CH2 | H | F | N(CH3)2 |

TABLE 2-continued

| V | $X_1$ | $X_2$ | $Y_2$ | Z | $R_1$ | $R_2$ | $R_b$ |
|---|---|---|---|---|---|---|---|
| N | CH | N | NH | O | Br | H | NH2 |
| CH | N | N | S | CH2 | H | Br | H |
| CH | CH | N | O | N(H) | NH2 | Cl | F |
| N | N | CH | N(CH3) | O | Br | H | F |
| N | N | N | S | N(H) | N(CH3)2 | H | N(CH3)2 |
| N | CH | CH | NH | CH2 | N(H)CH3 | F | Cl |
| N | CH | N | O | N(H) | N(H)CH3 | NH2 | NH2 |
| N | CH | N | O | N(H) | N(H)CH3 | Br | N(H)CH3 |
| N | N | CH | S | N(H) | N(CH3)2 | N(CH3)2 | Cl |
| CH | N | N | O | O | N(CH3)2 | H | F |
| N | N | CH | NH | N(H) | Cl | NH2 | N(H)CH3 |
| CH | N | CH | O | O | N(CH3)2 | Br | Br |
| N | CH | CH | N(CH3) | CH2 | Cl | H | NH2 |
| CH | N | CH | NH | CH2 | Br | N(H)CH3 | Br |
| N | N | CH | CH2 | O | Cl | F | H |
| CH | CH | CH | S | O | Br | N(H)CH3 | NH2 |
| N | N | CH | S | O | NH2 | Br | Cl |
| N | N | N | S | O | NH2 | H | Cl |
| CH | N | CH | CH2 | N(H) | Cl | NH2 | N(H)CH3 |
| CH | N | CH | N(CH3) | CH2 | NH2 | N(CH3)2 | N(H)CH3 |
| CH | CH | N | NH | N(H) | NH2 | Br | NH2 |
| CH | CH | N | CH2 | N(H) | Cl | NH2 | Br |
| N | CH | N | S | CH2 | N(H)CH3 | Cl | F |
| N | CH | N | NH | CH2 | NH2 | N(CH3)2 | NH2 |
| N | CH | N | NH | CH2 | N(CH3)2 | NH2 | N(CH3)2 |
| N | CH | CH | CH2 | CH2 | Br | N(H)CH3 | H |
| CH | CH | N | N(CH3) | N(H) | N(H)CH3 | H | H |
| CH | N | CH | CH2 | O | N(CH3)2 | Br | Br |
| N | CH | CH | O | CH2 | Cl | H | N(CH3)2 |
| N | CH | CH | CH2 | CH2 | F | Cl | Cl |
| CH | N | N | S | CH2 | H | Br | NH2 |
| N | N | CH | O | N(H) | H | Cl | Cl |
| CH | CH | N | O | O | Br | N(CH3)2 | N(CH3)2 |
| N | N | CH | N(CH3) | CH2 | H | Cl | N(H)CH3 |
| N | CH | CH | N(CH3) | CH2 | F | N(H)CH3 | NH2 |
| CH | N | CH | N(CH3) | O | N(CH3)2 | N(CH3)2 | Br |
| N | CH | CH | N(CH3) | N(H) | F | Cl | N(H)CH3 |
| CH | N | CH | CH2 | CH2 | H | NH2 | Cl |
| N | CH | CH | NH | CH2 | Br | NH2 | Br |
| CH | CH | N | O | N(H) | N(CH3)2 | N(H)CH3 | Br |
| N | N | CH | NH | N(H) | Br | N(H)CH3 | N(H)CH3 |
| N | CH | N | CH2 | N(H) | N(H)CH3 | N(H)CH3 | Cl |
| N | CH | N | O | N(H) | N(H)CH3 | N(CH3)2 | F |
| N | N | CH | CH2 | N(H) | F | N(H)CH3 | N(H)CH3 |
| N | CH | CH | N(CH3) | N(H) | F | N(CH3)2 | H |
| N | CH | CH | N(CH3) | O | NH2 | N(CH3)2 | F |
| N | N | CH | NH | N(H) | Br | N(H)CH3 | F |
| CH | N | N | CH2 | CH2 | N(CH3)2 | H | F |
| N | N | N | S | N(H) | H | N(CH3)2 | N(CH3)2 |
| CH | CH | CH | S | O | H | H | H |
| N | CH | CH | O | N(H) | H | N(CH3)2 | F |
| CH | CH | CH | S | CH2 | NH2 | H | Cl |
| N | N | N | CH2 | CH2 | N(H)CH3 | H | H |
| N | CH | CH | O | O | NH2 | N(H)CH3 | NH2 |
| N | N | CH | O | N(H) | N(CH3)2 | H | Cl |
| CH | N | N | S | CH2 | F | F | N(CH3)2 |
| CH | CH | CH | O | N(H) | Br | F | F |
| CH | N | N | NH | O | N(H)CH3 | F | Cl |
| N | CH | N | CH2 | N(H) | Br | Cl | F |
| CH | N | CH | NH | CH2 | H | H | Br |
| CH | CH | N | CH2 | CH2 | N(H)CH3 | N(H)CH3 | F |
| N | N | CH | NH | O | Br | Br | Br |
| CH | N | CH | N(CH3) | CH2 | H | N(H)CH3 | NH2 |
| CH | CH | CH | CH2 | CH2 | F | N(H)CH3 | Br |
| CH | N | CH | NH | CH2 | N(H)CH3 | F | N(CH3)2 |
| N | CH | N | CH2 | N(H) | N(H)CH3 | Br | H |
| CH | CH | CH | CH2 | N(H) | N(CH3)2 | F | N(H)CH3 |
| CH | N | N | O | CH2 | N(CH3)2 | NH2 | H |
| N | CH | N | S | N(H) | N(CH3)2 | F | Cl |
| N | N | N | O | O | O | NH2 | N(H)CH3 |
| CH | CH | CH | N(CH3) | CH2 | N(CH3)2 | H | N(CH3)2 |
| CH | CH | N | S | N(H) | NH2 | N(H)CH3 | |
| N | N | CH | N(CH3) | O | Br | Cl | NH2 |
| N | N | N | CH2 | CH2 | N(CH3)2 | N(H)CH3 | N(H)CH3 |
| CH | N | CH | CH2 | CH2 | N(H)CH3 | N(H)CH3 | N(H)CH3 |
| N | CH | N | N(CH3) | N(H) | NH2 | Cl | F |
| N | CH | N | S | O | N(H)CH3 | H | Br |
| N | N | N | CH2 | N(H) | Br | N(H)CH3 | N(CH3)2 |

TABLE 2-continued

| V | $X_1$ | $X_2$ | $Y_2$ | Z | $R_1$ | $R_2$ | $R_b$ |
|---|---|---|---|---|---|---|---|
| CH | N | N | S | O | N(CH3)2 | Cl | H |
| CH | CH | N | NH | N(H) | Br | H | Br |
| CH | CH | N | N(CH3) | N(H) | Cl | F | N(CH3)2 |
| N | CH | CH | O | CH2 | N(H)CH3 | H | N(H)CH3 |
| N | N | N | CH2 | CH2 | Br | Br | F |
| N | N | N | CH2 | N(H) | H | F | H |
| N | CH | CH | CH2 | O | Br | Cl | NH2 |
| N | N | CH | N(CH3) | O | N(CH3)2 | F | Cl |
| N | N | CH | S | N(H) | H | Cl | N(CH3)2 |
| CH | N | N | NH | CH2 | N(H)CH3 | N(CH3)2 | N(H)CH3 |
| N | CH | N | S | N(H) | N(H)CH3 | NH2 | N(CH3)2 |
| CH | CH | N | N(CH3) | CH2 | NH2 | Cl | H |
| CH | CH | CH | NH | CH2 | F | Cl | N(H)CH3 |
| CH | CH | N | O | O | NH2 | H | N(CH3)2 |
| CH | CH | N | NH | CH2 | N(H)CH3 | H | Cl |
| CH | CH | N | S | CH2 | Cl | N(CH3)2 | Br |
| N | CH | CH | S | CH2 | NH2 | F | Cl |
| N | N | N | S | CH2 | Br | N(CH3)2 | N(H)CH3 |
| N | N | CH | S | N(H) | Br | Cl | F |
| N | N | N | N(CH3) | CH2 | N(CH3)2 | H | F |
| CH | N | CH | S | N(H) | F | F | H |
| CH | N | CH | N(CH3) | N(H) | N(CH3)2 | Br | Br |
| CH | N | CH | CH2 | O | NH2 | H | Br |
| CH | N | N | NH | CH2 | N(CH3)2 | NH2 | F |
| N | N | CH | S | CH2 | F | H | F |
| N | CH | CH | O | CH2 | NH2 | NH2 | NH2 |
| N | N | N | N(CH3) | O | NH2 | N(H)CH3 | N(CH3)2 |
| N | CH | CH | N(CH3) | O | Br | H | Br |
| N | N | CH | CH2 | N(H) | N(H)CH3 | N(CH3)2 | N(H)CH3 |
| CH | N | N | N(CH3) | N(H) | Br | N(CH3)2 | N(H)CH3 |
| N | CH | CH | CH2 | O | N(CH3)2 | H | NH2 |
| N | CH | N | N(CH3) | O | N(H)CH3 | N(H)CH3 | F |
| N | N | CH | NH | O | Cl | N(H)CH3 | N(CH3)2 |
| CH | CH | N | S | O | N(H)CH3 | N(CH3)2 | N(H)CH3 |
| N | CH | N | CH2 | N(H) | N(H)CH3 | H | Cl |
| N | N | N | S | O | Br | F | F |
| N | CH | N | NH | N(H) | Cl | N(CH3)2 | H |
| N | N | CH | S | O | Br | N(H)CH3 | H |
| CH | N | CH | S | N(H) | NH2 | NH2 | N(CH3)2 |
| CH | N | N | CH2 | CH2 | H | Cl | H |
| N | N | N | NH | O | Cl | NH2 | Br |
| N | N | N | N(CH3) | O | Br | N(CH3)2 | F |
| CH | CH | N | NH | N(H) | Br | F | F |
| CH | N | N | CH2 | O | Cl | N(H)CH3 | NH2 |
| N | CH | N | S | CH2 | Br | Br | Br |
| CH | CH | CH | NH | N(H) | Br | N(CH3)2 | H |
| CH | CH | N | S | CH2 | NH2 | H | NH2 |
| CH | N | CH | CH2 | N(H) | Cl | Br | Br |
| N | N | CH | CH2 | O | NH2 | Cl | N(CH3)2 |
| CH | CH | N | NH | N(H) | H | Br | F |
| N | N | CH | N(CH3) | CH2 | N(H)CH3 | NH2 | Cl |
| CH | CH | N | O | N(H) | N(CH3)2 | N(H)CH3 | Cl |
| CH | CH | CH | NH | O | NH2 | N(H)CH3 | F |
| CH | CH | CH | O | N(H) | N(CH3)2 | NH2 | Cl |
| N | CH | CH | S | CH2 | Br | Br | Cl |
| N | N | CH | CH2 | N(H) | NH2 | N(CH3)2 | Cl |
| CH | CH | CH | NH | O | H | H | N(H)CH3 |
| CH | N | N | CH2 | N(H) | F | N(CH3)2 | N(H)CH3 |
| CH | CH | N | S | N(H) | F | N(H)CH3 | H |
| CH | CH | N | O | CH2 | N(H)CH3 | N(H)CH3 | N(H)CH3 |
| CH | N | N | S | CH2 | N(H)CH3 | F | NH2 |
| N | N | CH | CH2 | N(H) | Br | F | Cl |
| N | N | N | O | N(H) | Cl | NH2 | F |
| N | CH | N | NH | O | N(H)CH3 | Br | NH2 |
| CH | N | N | N(CH3) | N(H) | N(H)CH3 | N(H)CH3 | N(CH3)2 |
| CH | N | N | N(CH3) | O | Br | Br | Br |
| CH | N | N | S | N(H) | NH2 | NH2 | Br |
| CH | N | CH | NH | O | N(H)CH3 | H | H |
| CH | CH | CH | NH | N(H) | H | F | N(H)CH3 |
| CH | CH | N | S | O | NH2 | H | Br |
| CH | N | N | N(CH3) | O | N(CH3)2 | Cl | NH2 |
| N | N | N | N(CH3) | CH2 | N(H)CH3 | H | H |
| CH | N | N | NH | CH2 | Cl | F | H |
| N | N | CH | NH | N(H) | H | Br | NH2 |
| N | N | N | NH | CH2 | H | N(CH3)2 | F |
| CH | CH | N | N(CH3) | O | Cl | Br | F |
| CH | CH | CH | N(CH3) | O | Cl | H | N(CH3)2 |
| CH | CH | N | CH2 | CH2 | Cl | H | N(CH3)2 |

TABLE 2-continued

| V | $X_1$ | $X_2$ | $Y_2$ | Z | $R_1$ | $R_2$ | $R_b$ |
|---|---|---|---|---|---|---|---|
| CH | CH | N | S | CH2 | N(H)CH3 | H | N(CH3)2 |
| N | N | N | N(CH3) | N(H) | N(CH3)2 | N(H)CH3 | Cl |
| N | N | N | S | CH2 | F | Br | Cl |
| CH | CH | N | NH | O | Cl | Cl | F |
| CH | N | N | N(CH3) | N(H) | N(H)CH3 | N(CH3)2 | NH2 |
| CH | N | N | S | N(H) | Cl | H | Br |
| CH | N | CH | N(CH3) | N(H) | H | Cl | F |
| N | N | CH | O | CH2 | NH2 | F | Br |
| CH | N | CH | CH2 | O | F | F | F |
| N | CH | N | CH2 | O | NH2 | N(H)CH3 | Br |
| CH | N | CH | NH | CH2 | Cl | NH2 | N(CH3)2 |
| N | CH | CH | CH2 | CH2 | N(CH3)2 | Cl | H |
| N | N | CH | O | CH2 | F | Cl | H |
| CH | CH | N | S | CH2 | Cl | H | Cl |
| CH | CH | N | O | O | N(CH3)2 | F | Br |
| N | CH | CH | NH | CH2 | H | F | Br |
| CH | CH | N | O | CH2 | H | Cl | NH2 |
| CH | CH | N | NH | O | N(H)CH3 | F | N(CH3)2 |
| N | CH | N | CH2 | N(H) | NH2 | Br | Br |
| N | N | N | O | N(H) | Cl | Cl | N(CH3)2 |
| N | N | N | NH | N(H) | N(CH3)2 | F | N(CH3)2 |
| CH | CH | CH | CH2 | N(H) | Br | N(H)CH3 | Cl |
| CH | N | N | N(CH3) | N(H) | Br | N(H)CH3 | H |
| N | N | N | CH2 | O | Cl | F | NH2 |
| CH | N | CH | N(CH3) | O | H | Cl | F |
| N | CH | CH | NH | CH2 | N(CH3)2 | Cl | H |
| CH | CH | N | O | N(H) | NH2 | F | F |
| N | CH | CH | N(CH3) | O | N(CH3)2 | Br | Br |
| CH | CH | CH | S | N(H) | H | F | F |
| CH | CH | CH | CH2 | N(H) | Br | Cl | Cl |
| CH | CH | N | CH2 | CH2 | N(H)CH3 | Cl | N(H)CH3 |
| CH | CH | N | NH | N(H) | Br | Cl | N(H)CH3 |
| N | N | CH | NH | CH2 | Br | Br | F |
| CH | N | N | O | N(H) | N(CH3)2 | NH2 | Cl |
| N | N | N | NH | N(H) | F | F | Br |
| CH | CH | CH | S | O | N(H)CH3 | Br | Br |
| CH | N | CH | CH2 | CH2 | Cl | Br | N(CH3)2 |
| N | N | N | O | O | F | F | N(H)CH3 |
| CH | N | CH | N(CH3) | CH2 | N(CH3)2 | N(CH3)2 | NH2 |
| CH | N | N | S | O | H | Cl | N(H)CH3 |
| CH | N | N | NH | O | N(CH3)2 | Br | Cl |
| CH | N | CH | O | CH2 | Br | Cl | NH2 |
| N | N | CH | NH | CH2 | N(CH3)2 | H | NH2 |
| N | CH | CH | N(CH3) | N(H) | Cl | Cl | Cl |
| N | N | N | N(CH3) | O | NH2 | N(H)CH3 | F |
| N | CH | CH | S | O | H | H | H |
| N | CH | N | NH | CH2 | Br | Cl | NH2 |
| N | CH | N | NH | CH2 | NH2 | H | Cl |
| N | CH | CH | N(CH3) | CH2 | Br | H | H |
| CH | N | CH | NH | N(H) | H | Cl | H |
| CH | CH | N | N(CH3) | N(H) | N(CH3)2 | F | NH2 |
| N | CH | CH | NH | O | H | H | Br |
| N | N | N | O | N(H) | NH2 | N(H)CH3 | Br |
| N | N | N | N(CH3) | CH2 | F | Cl | Cl |
| CH | CH | CH | O | O | N(CH3)2 | F | F |
| CH | N | CH | N(CH3) | N(H) | Cl | N(H)CH3 | Br |
| CH | CH | N | N(CH3) | N(H) | NH2 | H | NH2 |
| N | CH | CH | CH2 | CH2 | NH2 | Cl | Br |
| N | CH | N | S | N(H) | NH2 | N(H)CH3 | N(CH3)2 |
| N | N | N | CH2 | N(H) | NH2 | N(CH3)2 | N(H)CH3 |
| CH | N | CH | NH | N(H) | Cl | N(H)CH3 | Cl |
| CH | CH | N | NH | O | Cl | H | NH2 |
| N | CH | CH | S | O | H | Cl | Cl |
| N | CH | CH | N(CH3) | CH2 | H | NH2 | N(H)CH3 |
| N | CH | CH | S | N(H) | F | N(CH3)2 | F |
| CH | CH | CH | CH2 | O | NH2 | N(H)CH3 | F |
| CH | N | N | N(CH3) | N(H) | F | NH2 | N(CH3)2 |
| N | N | CH | NH | N(H) | Cl | Cl | Cl |
| N | CH | N | CH2 | O | Cl | Cl | N(CH3)2 |
| N | CH | CH | N(CH3) | N(H) | N(CH3)2 | H | Br |
| CH | CH | CH | NH | O | N(CH3)2 | H | N(H)CH3 |
| CH | CH | CH | CH2 | O | N(H)CH3 | F | N(H)CH3 |
| CH | N | CH | CH2 | O | F | NH2 | NH2 |
| N | N | N | O | O | Cl | F | H |
| CH | N | CH | CH2 | CH2 | F | N(H)CH3 | NH2 |
| N | N | N | S | N(H) | H | F | Cl |
| N | CH | CH | N(CH3) | O | F | F | N(H)CH3 |
| N | CH | CH | S | CH2 | NH2 | Cl | Br |
| CH | CH | CH | O | N(H) | Br | F | N(H)CH3 |
| N | CH | N | O | O | Cl | NH2 | Cl |
| N | N | N | CH2 | O | F | H | Cl |
| N | CH | N | N(CH3) | O | N(H)CH3 | N(CH3)2 | Br |
| N | N | N | O | CH2 | NH2 | Br | F |
| CH | N | N | S | CH2 | N(CH3)2 | N(H)CH3 | N(H)CH3 |
| CH | CH | N | S | O | N(H)CH3 | NH2 | N(CH3)2 |
| N | N | N | O | CH2 | Cl | N(H)CH3 | NH2 |
| CH | CH | N | O | CH2 | N(CH3)2 | Cl | H |
| CH | CH | N | NH | O | Cl | N(H)CH3 | H |
| N | CH | CH | S | N(H) | F | Cl | Br |
| N | N | CH | O | CH2 | Br | Br | N(H)CH3 |
| CH | CH | N | NH | CH2 | Br | Br | F |
| N | N | N | NH | N(H) | N(CH3)2 | N(CH3)2 | N(CH3)2 |
| CH | CH | CH | CH2 | O | F | NH2 | N(H)CH3 |
| CH | N | N | CH2 | N(H) | F | H | Cl |
| N | N | N | O | N(H) | Cl | F | Cl |
| N | CH | N | N(CH3) | O | Br | N(CH3)2 | N(CH3)2 |
| CH | CH | N | N(CH3) | O | N(CH3)2 | NH2 | Cl |
| N | N | N | N(CH3) | CH2 | H | F | H |
| CH | CH | N | S | CH2 | NH2 | F | N(CH3)2 |
| CH | N | CH | CH2 | CH2 | N(CH3)2 | F | N(CH3)2 |
| N | CH | CH | NH | O | Cl | N(CH3)2 | N(H)CH3 |
| N | N | CH | O | O | N(H)CH3 | NH2 | Br |
| CH | N | CH | O | N(H) | Cl | Cl | Br |
| N | CH | CH | CH2 | CH2 | F | N(CH3)2 | N(CH3)2 |
| N | N | CH | CH2 | CH2 | NH2 | N(H)CH3 | Br |
| CH | CH | CH | CH2 | N(H) | H | F | F |
| CH | CH | N | CH2 | O | Br | N(CH3)2 | N(CH3)2 |
| N | N | N | S | N(H) | Cl | F | N(H)CH3 |
| N | N | N | NH | N(H) | N(CH3)2 | NH2 | Cl |
| CH | N | CH | O | CH2 | Br | F | F |
| CH | CH | CH | NH | O | F | Br | Cl |
| N | N | N | O | N(H) | Cl | H | H |
| CH | N | CH | CH2 | N(H) | N(CH3)2 | NH2 | Cl |
| CH | CH | CH | CH2 | O | F | N(CH3)2 | Cl |
| N | CH | CH | S | O | NH2 | Br | Cl |
| N | CH | N | S | O | H | H | F |
| N | N | N | CH2 | N(H) | N(H)CH3 | H | H |
| N | CH | CH | NH | CH2 | Cl | N(CH3)2 | N(CH3)2 |
| CH | CH | N | S | O | H | F | H |
| CH | N | CH | CH2 | CH2 | Br | F | Br |
| N | CH | N | NH | N(H) | Br | NH2 | H |
| CH | N | CH | CH2 | O | NH2 | Cl | F |
| CH | N | N | CH2 | CH2 | F | Br | Cl |
| CH | N | N | O | O | N(H)CH3 | N(CH3)2 | H |
| CH | CH | CH | O | CH2 | N(CH3)2 | N(CH3)2 | Cl |
| CH | CH | CH | CH2 | O | N(H)CH3 | NH2 | F |
| N | CH | CH | N(CH3) | CH2 | H | N(H)CH3 | H |
| N | N | N | CH2 | O | Cl | Cl | NH2 |
| CH | N | CH | N(CH3) | CH2 | Br | N(H)CH3 | N(H)CH3 |
| N | N | CH | CH2 | O | N(H)CH3 | H | Br |

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

EXEMPLIFICATION

Synthetic Protocols

Compounds as disclosed herein can be synthesized via a number of specific methods. The examples which outline specific synthetic routes, and the generic schemes below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

Example 1: Syntheses of Compounds 1 Through 10

Preparation of Intermediate 1-1

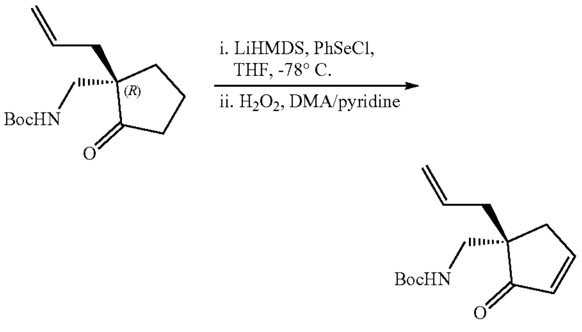

Intermediate 1-1

The starting material tert-butyl (R)-((1-allyl-2-oxocyclopentyl)methyl)carbamate was prepared according to the procedure of Y. Numajiri, B. P. Pritchett, K. Chiyoda, and B. M. Stoltz published in *J. Am. Chem. Soc.* in 2015, volume 137, on pages 1040-1043. A solution of tert-butyl (R)-((1-allyl-2-oxocyclopentyl)methyl)carbamate (16.19 g, 64.01 mmol) in tetrahydrofuran (25 mL) was added dropwise via cannula to a cold (−78° C.) solution of lithium hexamethyldisilazide (280 mL, 0.5 M solution in tetrahydrofuran, 140 mmol). After 15 minutes a solution of phenyl selenium chloride (14.61 g, 76.30 mmol) in tetrahydrofuran (25 mL) was added rapidly via cannula.

After 30 minutes at constant temperature, the reaction was quenched by the addition of saturated aqueous ammonium chloride (250 mL) and diluted with diethyl ether (500 mL). The mixture was transferred to a separatory funnel. The aqueous phase was separated and the organic phase was further washed with 0.5 N HCl, water and 3:1 brine/saturated sodium bicarbonate solution (400 mL portions). The organic phase was dried over sodium sulfate, filtered and concentrated to yield an orange oil (35.49 g crude) that was used without further purification.

The crude product from the previous step was dissolved in dimethylacetamide (200 mL) and eight reactions were run sequentially (25 mL each). To each solution behind a blast shield was added pyridine (1.93 mL, 24.0 mmol) followed (after cooling to 0° C.) by 35% aqueous hydrogen peroxide (2.69 mL, 32.0 mmol). As the reaction was allowed to warm to room temperature a strong exotherm occurred and the temperature of the reaction increased from room temperature to 85-90° C. After the reaction temperature had returned to room temperature, each reaction was poured into diethyl ether (150 mL) and saturated sodium sulfite (37.5 mL) and water (37.5 mL) were added. After stirring for 30 minutes, the mixture was transferred to a separatory funnel. The aqueous phase was separated and the organic phase was further washed with water and saturated sodium bicarbonate (75 mL portions). The organic washings from all eight reactions were combined, dried over sodium sulfate, filtered and concentrated to dryness.

Silica gel chromatography (10-80% EtOAc/Hexanes) was performed with refractive index detection. The product could also be detected by potassium permanganate stain on TLC. The product fractions were pooled and concentrated to yield tert-butyl (S)-((1-allyl-2-oxocyclopent-3-en-1-yl)methyl)carbamate (intermediate 1-1) as a yellow oil (6.870 g, 43% yield over 2 steps).

$^1H$ NMR (400 MHz, Chloroform-d) δ 7.71 (dt, J=5.6, 2.7 Hz, 1H), 6.15 (dt, J=5.8, 2.2 Hz, 1H), 5.60 (dddd, J=16.8, 10.1, 8.1, 6.7 Hz, 1H), 5.18-4.98 (m, 2H), 4.85 (s, 1H), 3.45-3.05 (m, 2H), 2.61 (t, J=2.4 Hz, 2H), 2.44-2.12 (m, 2H), 1.41 (s, 9H) ppm.

LCMS: $[M+H]^+$ m/z=252.2 amu.

Preparation of Intermediate 1-2

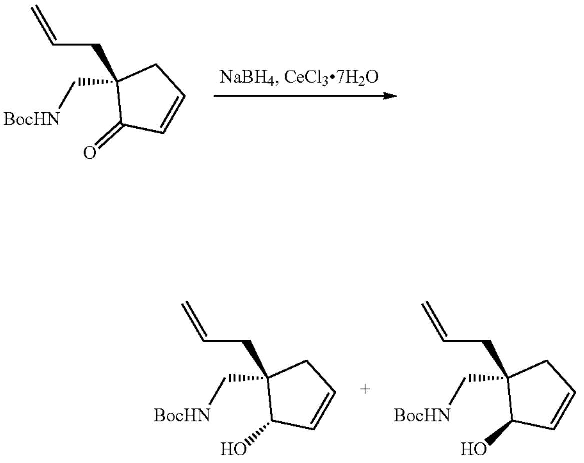

desired Intermediate 1-2 minor

To a cold (−78° C.) solution of intermediate 1-1 (6.870 g, 27.37 mmol) in methanol (150 mL) was added cerium trichloride heptahydrate (15.30 g, 41.06 mmol). The reaction was stirred for 15 minutes and sodium borohydride was added (1.040 g, 27.37 mmol). The reaction was kept in a cooling bath for 2 hours, then gradually allowed to rise to ambient temperature. Once the reaction was complete by TLC analysis, saturated ammonium chloride (200 mL) and water (200 mL) were added. The mixture was transferred to a separatory funnel and the aqueous phase was washed three times with dichloromethane (200 mL portions). The combined organic phase was dried over sodium sulfate, filtered and concentrated to give a yellow oil.

Silica gel chromatography (10-30% hexanes/acetone) was performed with refractive index detection. The product could also be detected by potassium permanganate stain on TLC. Intermediate 1-2, which is the major desired isomer, eluted first (3.10 g, 45% yield), followed by the minor isomer (2.05 g, 30% yield). The minor isomer could be recycled with pyridinium chlorochromate (PCC) oxidation (2 Eq. PCC, $CH_2Cl_2$, quantitative) and Luche reduction to yield additional tert-butyl (((1S,2S)-1-allyl-2-hydroxycyclopent-3-en-1-yl)methyl)carbamate (intermediate 1-2) (1.34 g, 19%, total: 4.44 g, 64% yield).

$^1H$ NMR (400 MHz, Chloroform-d) δ 5.97-5.68 (m, 3H), 5.20-4.90 (m, 2H), 4.33 (s, 1H), 3.45-3.09 (m, 2H), 2.30-2.00 (m, 4H), 1.44 (s, 9H) ppm.

LCMS: $[M+H]^+$ m/z=254.2 amu.

Preparation of Intermediate 1-3

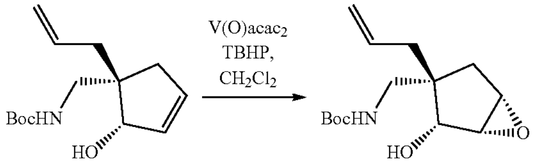

Intermediate 1-3

A solution of intermediate 1-2 (3.10 g, 12.25 mmol) in dichloromethane (120 mL) was cooled to 0° C. and treated with tert-butyl hydrogen peroxide (5.5 M in decane, 3.34 mL, 18.37 mmol). The reaction was stirred for five minutes and vandadyl acetylacetonate (390 mg, 1.47 mmol) was added in one portion as a solid. The reaction was removed from the cooling bath and stirred at ambient temperature for eight hours at which time TLC analysis showed complete conversion to the desired product.

The reaction was concentrated onto silica gel. Silica gel chromatography was performed with refractive index detection (10-50% hexanes/acetone). The product fractions were pooled and concentrated to yield intermediate 1-3 as a yellow oil (2.093 g, 65% yield).

$^1$H NMR (400 MHz, Chloroform-d) δ 5.80 (ddt, J=16.6, 10.5, 7.3 Hz, 1H), 5.27 (s, 1H), 5.17-5.05 (m, 2H), 4.04 (s, 1H), 3.59 (t, J=2.5 Hz, 1H), 3.47 (t, J=2.5 Hz, 1H), 3.23-3.06 (m, 2H), 2.25 (ddt, J=13.7, 7.2, 1.2 Hz, 1H), 2.13-2.05 (m, 1H), 1.93 (d, J=15.3 Hz, 1H), 1.80 (dd, J=15.2, 2.1 Hz, 1H), 1.44 (s, 9H) ppm.

LCMS: $[M+H]^+$ m/z=270.2 amu.

Preparation of Intermediate 1-4

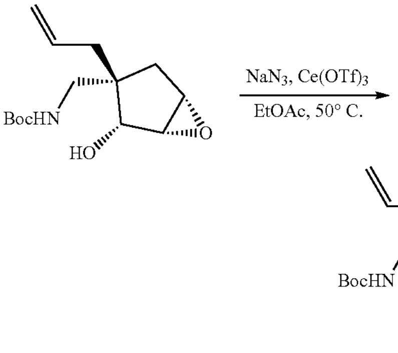

Intermediate 1-4

A round-bottomed flask was charged with intermediate 1-3 (1.857 g, 6.90 mmol), and ethyl acetate (70 mL) was added to yield a clear, yellow solution. The reaction was stirred vigorously under nitrogen and sodium azide was added (1.65 g, 20.7 mmol), followed after five minutes by cerium(III)triflate (2.35 g, 4.18 mmol). The reaction was warmed to 50° C. for two hours. TLC analysis indicated that the epoxide had been consumed.

The reaction was concentrated onto silica gel and dry-loaded. Silica gel chromatography was performed with refractive index detection (10-30% hexanes/acetone). The product fractions were pooled and concentrated to yield tert-butyl (((1S,2R,3S,4R)-1-allyl-4-azido-2,3-dihydroxy-cyclopentyl)methyl)carbamate (intermediate 1-4) as a clear oil (1.254 g, 58% yield).

$^1$H NMR (400 MHz, Chloroform-d) δ 5.80 (ddt, J=16.6, 10.5, 7.3 Hz, 1H), 5.27 (s, 1H), 5.19-5.05 (m, 2H), 4.04 (s, 1H), 3.59 (t, J=2.5 Hz, 1H), 3.47 (t, J=2.4 Hz, 1H), 3.19 (dd, J=14.2, 7.2 Hz, 1H), 3.13 (dd, J=14.2, 5.2 Hz, 1H), 2.81 (s, 1H), 2.29-2.20 (m, 1H), 2.13-2.04 (m, 1H), 1.93 (d, J=15.2 Hz, 1H), 1.80 (dd, J=15.2, 2.1 Hz, 1H), 1.44 (s, 9H) ppm.

LCMS: $[M+H]^+$ m/z=313.2 amu.

Preparation of Intermediate 1-5

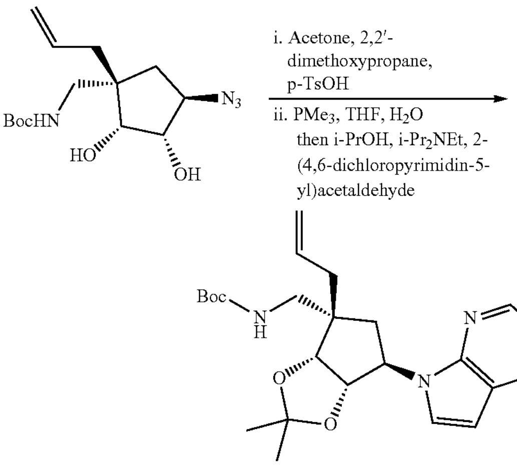

Intermediate 1-5

A flask containing intermediate 1-4 (1.254 g, 4.005 mmol) was charged with acetone (20 mL) and 2,2'-dimethoxypropane (20 mL), followed by p-toluenesulfonic acid monohydrate (38.1 mg, 0.20 mmol). The reaction was stirred at room temperature for two hours and quenched by addition of pyridine (0.020 mL).

Silica gel was added to the solution and volatiles were removed in vacuo. The residue was dry-loaded and purified by silica gel chromatography with refractive index detection (0-15% hexanes/diethyl ether). The product fractions were pooled and concentrated to yield a clear oil (1.253 g, 89% yield).

The clear oil product of the proceeding step (1.253 g, 3.53 mmol) was transferred to a round-bottomed flask and dissolved in tetrahydrofuran (9 mL) under an atmosphere of nitrogen. Water (0.64 mL, 35.3 mmol) was injected followed by trimethylphosphine (8.8 mL, 1 M solution in tetrahydrofuran, 8.8 mmol). The reaction was stirred for two hours and the volatiles were removed first under a stream of nitrogen and then in vacuo. To the resulting crude amine was added a mixture of Hünig's base (3.08 mL, 17.65 mmol) and iso-propyl alcohol (15 mL) under an atmosphere of nitrogen. To the resulting solution was added 2-(4,6-dichloropyrimidin-5-yl)acetaldehyde (1.011 g, 5.295 mmol). The reaction was sealed and warmed to 75° C. for 20 hours. At this time, the reaction was complete by TLC analysis, and was diluted with ethyl acetate (150 mL) and transferred to a separatory funnel. This organic phase was washed sequentially with water and saturated aqueous ammonium chloride (50 mL portions), dried over sodium sulfate, filtered and concentrated onto silica gel.

The residue was dry-loaded and purified by silica gel chromatography with refractive index detection (0-100% hexanes/EtOAc). The product fractions were pooled and concentrated to yield tert-butyl (((3aR,4S,6R,6aS)-4-allyl-6-(4-chloro-7H-pyrrolo[2,3-d]pyrimidin-7-yl)-2,2-dimethyltetrahydro-4H-cyclopenta[d][1,3]dioxol-4-yl)methyl)carbamate (intermediate 1-5) as a clear oil (841 mg, 52% yield).

$^1$H NMR (400 MHz, Chloroform-d) δ 8.64 (s, 1H), 7.30 (d, J=3.7 Hz, 1H), 6.62 (d, J=3.7 Hz, 1H), 6.08-5.76 (m, 1H), 5.22-5.02 (m, 4H), 4.57 (d, J=6.3 Hz, 1H), 3.53 (dd, J=14.0, 8.6 Hz, 1H), 3.29 (dd, J=14.1, 4.4 Hz, 1H), 2.51-2.33 (m, 2H), 2.27 (dd, J=14.0, 8.0 Hz, 1H), 2.17 (dd, J=13.8, 7.1 Hz, 1H), 1.61 (s, 3H), 1.46 (s, 9H), 1.32 (s, 3H) ppm.

LCMS: $[M+H]^+$ m/z=463.2 amu.

Preparation of Intermediates 1-6 R&S

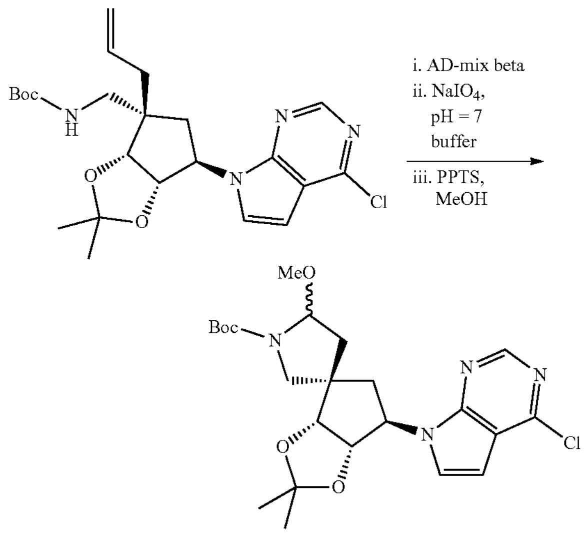

Intermediates 1-6 R&S

A flask containing intermediate 1-5 (841 mg, 1.81 mmol) was charged with tert-butanol and water to yield a biphasic solution (1:1; 20 mL). AD-mix-β was added (2.54 g, 1.4 g/mmol of substrate) followed by addition of hydroquinidine 1,4-phthalazinediyl diether ($DHQD_2PHAL$) (42.3 mg, 0.0543 mmol) and osmium tetroxide (0.345 mL, 4% w/w solution in water, 0.0543 mmol). The reaction was stirred for four hours and poured into a separatory funnel containing 1 N aqueous sodium sulfite (50 mL) and ethyl acetate (100 mL). The aqueous phase was separated and the organic was further washed with 0.2 N HCl, 0.2 N NaOH and brine (50 mL portions). The organic phase was concentrated in vacuo and used without further purification.

The resulting crude diol was dissolved in tert-butanol (30 mL) and pH 7 phosphate buffer (20 mL). Sodium periodate (675 mg, 1.81 mmol) was added in a single portion and the reaction was complete within 30 minutes as judged by TLC analysis. The reaction was poured into a separatory funnel containing ethyl acetate (100 mL) and saturated sodium bicarbonate (50 mL). The organic phase was dried over sodium sulfate, filtered and concentrated.

To the resulting oil was added methanol (20 mL) and pyridinium p-toluenesulfonate (PPTS) (45 mg, 0.18 mmol). The reaction was stirred for three hours and TLC indicated that the starting material had been consumed. Silica gel was added to the solution and volatiles were removed in vacuo. The residue was dry-loaded and purified by silica gel chromatography with refractive index detection (0-50% hexanes/EtOAc). The product fractions were pooled and concentrated to yield intermediates 1-6 R&S as a yellow oil mixture of stereoisomers (345 mg, 40% yield over 3 steps).

$^1$H NMR (400 MHz, Chloroform-d) δ 8.63-8.53 (m, 1H), 7.28 (m, 1H), 6.57 (m, 1H), 5.52-4.93 (m, 2H), 4.93-4.38 (m, 1H), 4.03-3.59 (m, 2H), 3.42 (s, 3H), 3.36-3.02 (m, 1H), 2.75-2.38 (m, 2H), 2.40-1.80 (m, 2H), 1.44 (m, 9H), 1.24-1.19 (m, 6H) ppm.

LCMS: $[M+H]^+$ m/z=479.2 amu.

Preparation of Compounds 1 and 2: Step 1

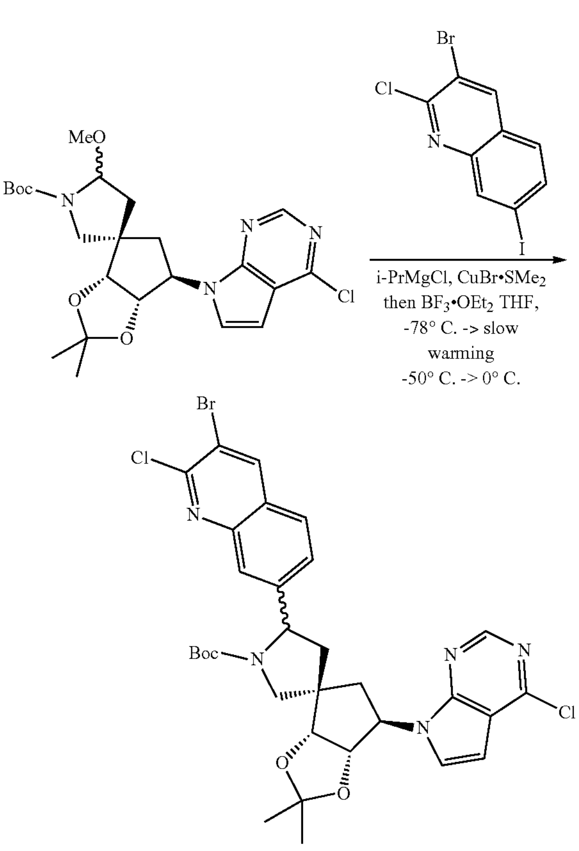

Intermediate 1-7 R&S

A flame-dried vial was charged with 3-bromo-2-chloro-7-iodoquinoline (129.2 mg, 0.351 mmol) and dry tetrahydrofuran was injected (1 mL) under an atmosphere of nitrogen. After cooling (−78° C.), a solution of iso-propyl magnesium chloride (0.18 mL, 2 M in tetrahydrofuran, 0.36 mmol) was injected. After 10 minutes, the resulting solution was transferred via syringe into a cold (−78° C.) slurry of copper(I)bromide dimethyl sulfide in tetrahydrofuran (1 mL). After 15 minutes, boron trifluoride diethyl etherate was injected (43 μL, 0.35 mmol), and after 15 additional minutes a solution of intermediates 1-6 R&S (42 mg, 0.087 mmol) in diethyl ether (6 mL) was injected.

The reaction was allowed to warm slowly over two hours at which time LC/MS analysis indicated consumption of the starting material. The reaction was quenched with saturated aqueous ammonium chloride and ammonium hydroxide (2 mL portions). The resulting mixture was poured into a separatory funnel containing ethyl acetate (50 mL) and the organic phase was washed with water and brine (50 mL portions). The organic phase was concentrated onto silica gel and the residue was purified by chromatography (5-20% hexane/acetone). Two fractions were collected with the minor diastereomer eluting first (12 mg, 15% yield), followed by the major diastereomer (36 mg, 45% yield).

Fraction 1 of intermediates 1-7 R&S (minor diastereomer): $^{1}H$ NMR (400 MHz, Chloroform-d) δ 8.61 (d, J=7.8 Hz, 1H), 8.42 (s, 1H), 7.83 (s, 1H), 7.74 (d, J=8.5 Hz, 1H), 7.52-7.46 (m, 2H), 7.29 (d, J=3.6 Hz, 1H), 6.62 (d, J=3.6 Hz, 1H), 5.21 (t, J=6.1 Hz, 1H), 4.91 (dt, J=11.7, 6.6 Hz, 1H), 4.82 (t, J=8.5 Hz, 1H), 4.71 (d, J=7.1 Hz, 1H), 3.96 (d, J=11.6 Hz, 1H), 3.79 (d, J=11.5 Hz, 1H), 2.68 (t, J=12.1 Hz, 1H), 2.47 (m, 2H), 1.27 (m, 6H), 1.06 (s, 9H) ppm.

LCMS: $[M+H]^+$ m/z=688.1 amu.

Fraction 2 of intermediates 1-7 R&S (major diastereomer): $^{1}H$ NMR (400 MHz, Chloroform-d) δ 8.53 (s, 1H), 8.31 (d, J=14.2 Hz, 1H), 7.80 (d, J=4.8 Hz, 1H), 7.63 (t, J=7.8 Hz, 1H), 7.41 (dd, J=13.7, 8.1 Hz, 1H), 7.20 (s, 1H), 6.52 (d, J=3.6 Hz, 1H), 5.18-4.70 (m, 3H), 4.59 (dd, J=16.7, 7.4 Hz, 1H), 4.35-4.17 (m, 1H), 3.33 (dd, J=10.8, 3.0 Hz, 1H), 2.71-1.82 (m, 2H). 1.40 (s, 3H), 1.27 (s, 3H), 1.05 (s, 9H) ppm.

LCMS: $[M+H]^+$ m/z=688.1 amu.

Preparation of Compounds 1 and 2: Step 2

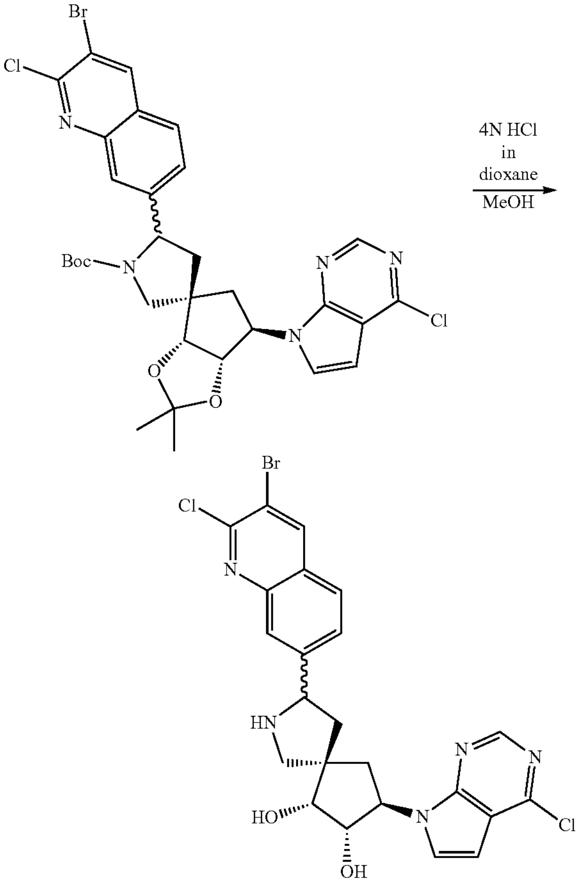

Both diastereomers prepared in step 1 were submitted to the following genera procedure. A vial containing the first fraction of intermediates 1-7 R&S (10.6 mg, 0.015 mmol) was dissolved in methanol (1 mL) to yield a clear solution, followed by 4 N hydrochloric acid in dioxane (50 μL, 0.15 mmol). The reaction was stirred at room temperature for 90 minutes, concentrated to dryness and the residue was dissolved in DMSO.

After filtration, reversed phase HPLC was performed (5-50% acetonitrile/water+0.25% acetic acid, 20 mm×250 mm C18 column, 40 mL/min gradient over 15 minutes, 242 nM detection wavelength, 3 total injections). The product fractions were pooled, frozen and concentrated on the lyophilzer to yield the product as a white solid (3.0 mg, 38% yield).

Fraction 1 (Compound 2): $^{1}H$ NMR (400 MHz, Acetonitrile-$d_3$) δ 8.52 (s, 1H), 8.50 (s, 1H), 7.86 (dd, J=1.7, 0.9 Hz, 1H), 7.77 (d, J=8.5 Hz, 1H), 7.66 (dd, J=8.5, 1.7 Hz, 1H), 7.55-7.44 (m, 1H), 6.59 (d, J=3.7 Hz, 1H), 5.11-4.91 (m, 1H), 4.49-4.32 (m, 2H), 3.83 (d, J=4.7 Hz, 1H), 3.46 (d, J=10.6 Hz, 1H), 2.80 (d, J=10.6 Hz, 1H), 2.48-2.33 (m, 2H), 1.75-1.64 (m, 2H) ppm.

LCMS: $[M+H]^+$ m/z=548.2 amu.

Fraction 2 (Compound 1): $^{1}H$ NMR (400 MHz, Acetonitrile-$d_3$) δ 8.61 (s, 1H), 8.49 (s, 1H), 8.01 (s, 1H), 7.91 (d, J=8.5 Hz, 1H), 7.67 (dd, J=8.5, 1.9 Hz, 1H), 7.50 (d, J=4.2 Hz, 1H), 6.58 (d, J=3.7 Hz, 1H), 4.91 (q, J=9.3 Hz, 1H), 4.55 (dd, J=8.7, 5.0 Hz, 1H), 4.07-3.95 (m, 2H), 3.46-3.21 (m, 1H), 2.70 (dd, J=13.6, 6.4 Hz, 1H), 2.55-2.38 (m, 2H), 2.05-2.00 (m, 2H) ppm.

LCMS: $[M+H]^+$ m/z=548.2 amu.

Preparation of Compounds 3 and 4

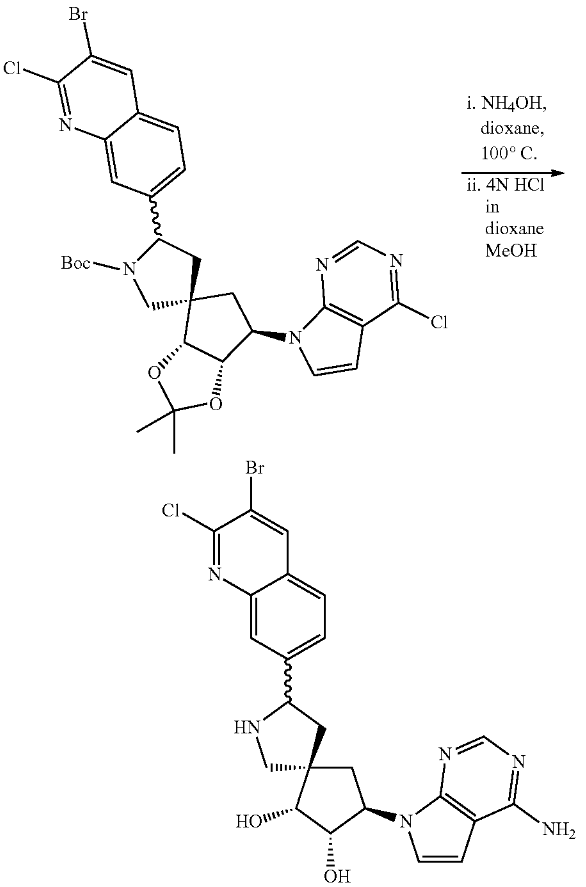

Both diastereomers prepared in step 1 of the preparation of compounds 1 and 2 were submitted to the following general procedure. A vial containing the first fraction of intermediates 1-7 R&S (3.9 mg, 0.0056 mmol) was treated with dioxane (100 μL) to yield a clear solution, followed by ammonium hydroxide (100 μL). The reaction was stirred at 100° C. for 18 hours, allowed to cool and the solvent was concentrated in vacuo.

The residue was taken up in benzene (2 mL) and concentrated again. To the crude oil was added methanol (0.9 mL) and 4 N hydrochloride acid in dioxane (0.1 mL). After 45 minutes the yellow solution was concentrated, dissolved in DMSO (1 mL) and purified by reversed phase HPLC (5-25% acetonitrile/water+0.25% acetic acid, 20 mm×250 mm C18 column, 40 mL/min gradient over 15 minutes, 242 nM detection wavelength, 5 total injections). The product fractions were pooled, frozen and concentrated on the lyophilzer to yield the product as a white solid (1.1 mg, 37% yield).

Fraction 1 (Compound 4): $^1$H NMR (400 MHz, Acetonitrile-$d_3$) δ 8.51 (s, 1H), 8.06 (s, 1H), 7.85 (dd, J=1.7, 0.8 Hz, 1H), 7.77 (d, J=8.5 Hz, 1H), 7.65 (dd, J=8.5, 1.6 Hz, 1H), 7.10 (d, J=3.6 Hz, 1H), 6.41 (d, J=3.6 Hz, 1H), 5.62 (s, 2H), 4.96-4.75 (m, 1H), 4.45-4.35 (m, 1H), 4.31 (dd, J=7.7, 4.8 Hz, 1H), 3.81 (d, J=4.8 Hz, 1H), 3.45 (d, J=10.6 Hz, 1H), 2.79 (d, J=10.7 Hz, 1H), 2.36 (ddd, J=13.7, 8.6, 4.8 Hz, 2H), 1.74-1.61 (m, 2H) ppm.

LCMS: $[M+H]^+$ m/z=529.1 amu.

Fraction 2 (Compound 3): $^1$H NMR (400 MHz, Acetonitrile-$d_3$) δ 8.51 (s, 1H), 8.02 (s, 1H), 7.87 (d, J=1.5 Hz, 1H), 7.77 (d, J=8.5 Hz, 1H), 7.65 (dd, J=8.6, 1.7 Hz, 1H), 6.99 (d, J=3.6 Hz, 1H), 6.36 (d, J=3.6 Hz, 1H), 5.61 (s, 2H), 4.75 (q, J=9.0 Hz, 1H), 4.53 (t, J=8.3 Hz, 1H), 4.37 (dd, J=8.0, 5.1 Hz, 1H), 3.88 (d, J=4.9 Hz, 1H), 3.53 (d, J=10.9 Hz, 1H), 2.86 (d, J=10.8 Hz, 1H), 2.44 (dd, J=12.8, 7.5 Hz, 1H), 2.32 (dd, J=13.6, 9.6 Hz, 1H), 2.05-2.00 (m, 2H) ppm.

LCMS: $[M+H]^+$ m/z=529.1 amu.

Preparation of Compounds 5 and 6: Step 1

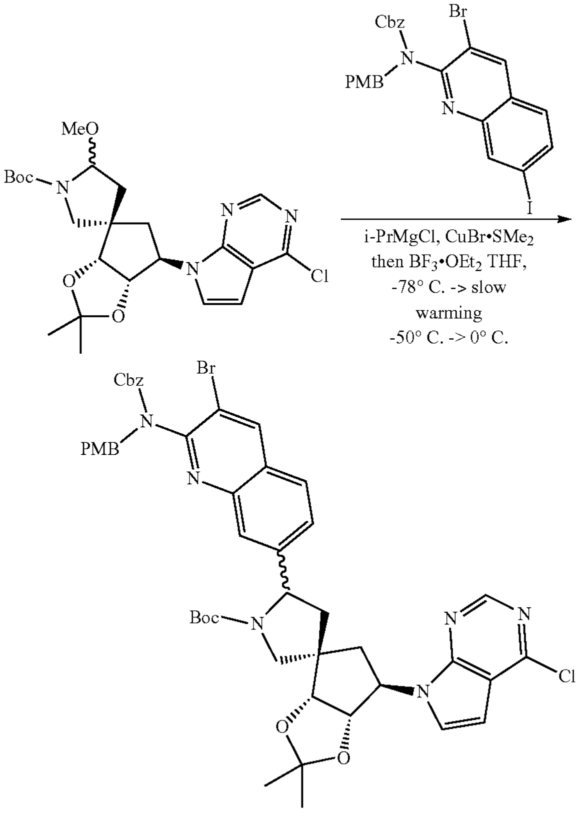

Intermediates 1-8 R&S

A flame-dried vial was charged with benzyl (3-bromo-7-iodoquinolin-2-yl)(4-methoxybenzyl)carbamate (425.0 mg, 0.737 mmol) and dry tetrahydrofuran was injected (4 mL) under an atmosphere of argon. After cooling (−78° C.) a solution of iso-propyl magnesium chloride (0.37 mL, 2 M in tetrahydrofuran, 0.74 mmol). After 60 minutes the resulting solution was transferred via cannula into a cold (−78° C.) slurry of copper(I)bromide dimethyl sulfide in tetrahydrofuran (2 mL). After 20 minutes, boron trifluoride diethyl etherate was injected (91 μL, 0.74 mmol) and after 15 additional minutes a solution of intermediate 1-6 R&S (139 mg, 0.29 mmol) in tetrahydrofuran (4 mL) was transferred in via cannula.

The reaction was maintained at −45° C. for two hours and then allowed to warm to 0° C. over two additional hours at which time LC/MS analysis indicated consumption of the starting material. The reaction was quenched with saturated aqueous ammonium chloride and ammonium hydroxide (10 mL portions). The resulting mixture was poured into a separatory funnel containing ethyl acetate (150 mL) and the organic phase was washed with water and brine (50 mL portions). The organic phase was concentrated onto silica gel and the residue was purified by chromatography (15-45% hexane/EtOAc). Two fractions were collected with the minor diastereomer eluting first (67.2 mg, 25%), followed by the major diastereomer (158.1 mg, 59% yield).

Fraction 1 of intermediates 1-8 R&S—Contains Rotomers (minor diastereomer): $^1$H NMR (500 MHz, Chloroform-d) δ 8.62 (s, 1H), 8.29 (s, 1H), 7.84 (m, 1H), 7.67 (d, J=8.5 Hz, 1H), 7.45 (t, J=9.3 Hz, 1H), 7.29 (d, J=3.6 Hz, 1H), 7.23-7.18 (m, 2H), 6.72 (d, J=8.5 Hz, 2H), 6.63 (t, J=7.9 Hz, 1H), 5.30-4.87 (m, 4H), 4.86-4.67 (m, 1H), 3.98 (d, J=11.6 Hz, 1H), 3.74-3.72 (m, 4H), 2.77-2.20 (m, 4H), 1.65-1.50 (m, 6H), 1.27 (m, 9H), 1.06 (s, 6H), 0.95-0.78 (m, 2H) ppm.

LCMS: $[M+H]^+$ m/z=923.2 amu.

Fraction 2 of intermediates 1-8 R&S—Contains Rotomers (major diastereomer): $^1$H NMR (500 MHz, Chloroform-d) δ 8.65 (s, 1H), 8.32 (d, J=10.7 Hz, 1H), 7.91 (s, 1H), 7.70 (d, J=8.5 Hz, 1H), 7.48 (s, 1H), 7.29 (m, 8H), 6.78 (d, J=8.7 Hz, 2H), 6.64 (d, J=3.7 Hz, 1H), 5.33-4.85 (m, 5H), 4.71 (dd, J=22.2, 7.4 Hz, 1H), 4.49-4.30 (m, 1H), 3.79 (s, 3H), 3.57-3.36 (m, 1H), 2.82-2.46 (m, 1H), 2.44-2.30 (m, 1H), 2.06-1.97 (m, 2H), 1.69 (m, 3H), 1.54-1.41 (m, 9H), 1.18 (s, 3H) ppm.

LCMS: $[M+H]^+$ m/z=923.2 amu.

Preparation of Compounds 5 and 6: Step 2

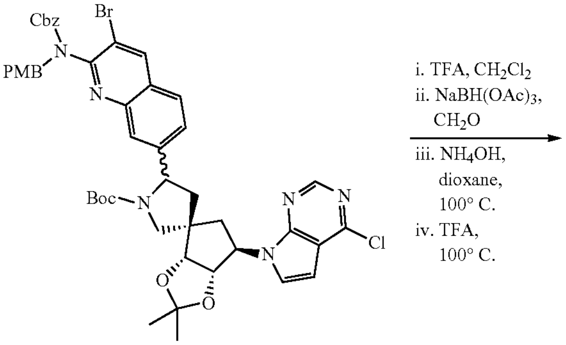

Intermediates 1-8 R&S

-continued

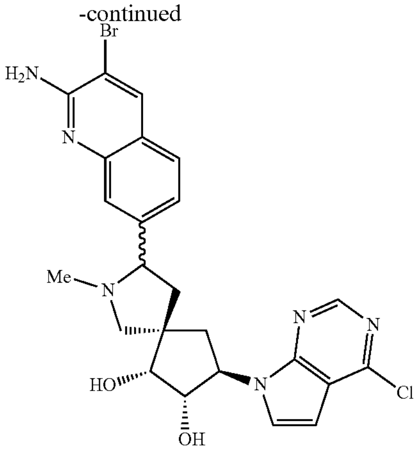

Both diastereomers prepared in step 1 above were submitted to the following general procedure. A vial containing the major diastereomer of intermediates 1-8 R&S (8.0 mg, 0.0087 mmol) was dissolved in dichloromethane (2 mL) and trifluoroacetic acid was injected (1 mL). The reaction was stirred for 90 minutes and poured into a separatory funnel containing saturated sodium bicarbonate. The organic phase was separated and the aqueous phase was washed with two additional portions of dichloromethane. The combined organic extracts were concentrated to dryness and dissolved in chloroform and methanol (1:1, 2 mL). Triacetoxyborohydride (7.0 mg, 0.03 mmol) and 37% formaldehyde (20 μL, 0.021 mmol) were added and the reaction was stirred for 60 minutes. The solution was poured into a separatory funnel containing 1 N sodium hydroxide (10 mL) and the aqueous phase was washed three times with dichloromethane.

After concentration, the crude material was dissolved in dioxane (300 μL) and treated with ammonium hydroxide (300 μL). The reaction vial was sealed and heated to 120° C. for 40 hours. The solvent was removed under a stream of nitrogen and then in vacuo. The crude solid was dissolved in trifluoroacetic acid (500 μL) and heated to 100° C. for 40 minutes. After concentration, the resulting oily solid was dissolved in DMSO and purified by reversed phase HPLC (2.5-25% acetonitrile/water+0.25% acetic acid, 20 mm×250 mm C18 column, 40 mL/min gradient over 15 minutes, 242 nM detection wavelength, 3 total injections). The product fractions were pooled, frozen and concentrated on the lyophilzer to yield the product as a white solid (2.5 mg, 55% yield).

Fraction 1 (Compound 5): $^1$H NMR (400 MHz, Acetonitrile-$d_3$) δ 8.25 (s, 1H), 8.12 (s, 1H), 7.62 (d, J=8.3 Hz, 1H), 7.53 (t, J=1.1 Hz, 1H), 7.35 (dd, J=8.3, 1.6 Hz, 1H), 7.14 (d, J=3.7 Hz, 1H), 6.47 (d, J=3.6 Hz, 1H), 5.71 (s, 2H), 5.60 (s, 2H), 4.88 (dt, J=10.0, 7.7 Hz, 1H), 4.35 (dd, J=7.3, 4.8 Hz, 1H), 3.94 (d, J=4.8 Hz, 1H), 3.73 (d, J=9.6 Hz, 1H), 3.44 (t, J=8.5 Hz, 1H), 2.48-2.36 (m, 4H), 1.96 (s, 3H) ppm. LCMS: $[M+H]^+$ m/z=524.1 amu.

Fraction 2 (Compound 6): $^1$H NMR (400 MHz, Acetonitrile-$d_3$) δ 8.29-8.17 (m, 1H), 8.09 (s, 1H), 7.58 (d, J=8.3 Hz, 1H), 7.49 (dd, J=1.6, 0.7 Hz, 1H), 7.32 (dd, J=8.3, 1.7 Hz, 1H), 7.08 (d, J=3.6 Hz, 1H), 6.44 (d, J=3.6 Hz, 1H), 5.71 (s, 2H), 5.58 (s, 2H), 4.92 (dt, J=10.0, 8.4 Hz, 1H), 4.34 (dd, J=7.4, 4.8 Hz, 1H), 3.91 (d, J=4.8 Hz, 1H), 3.36 (t, J=8.4 Hz, 1H), 3.03 (d, J=9.7 Hz, 1H), 2.77 (d, J=9.7 Hz, 1H), 2.67 (dd, J=13.5, 10.0 Hz, 1H), 2.43-2.36 (m, 2H), 2.15 (s, 3H) ppm.

LCMS: $[M+H]^+$ m/z=524.1 amu.

Preparation of Compounds 7 and 8

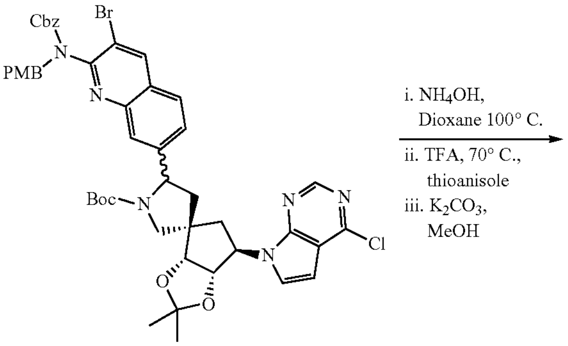

Intermediates 1-8 R&S

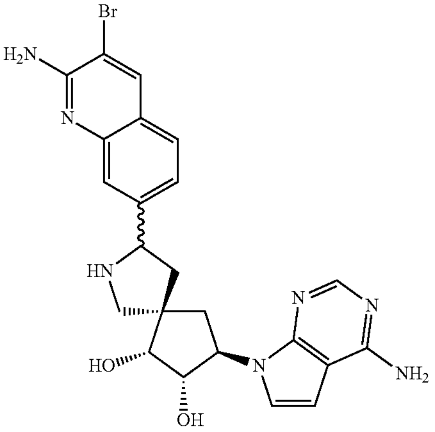

Both diastereomers prepared in step 1 of the preparation of compounds 5 and 6 were submitted to the following general procedure. A vial containing fraction 1 of intermediates 1-8 R&S was dissolved in dioxane (630 μL) and ammonium hydroxide was injected (630 μL). The reaction vial was sealed and heated to 100° C. for 27 hours. The solvent was removed under a stream of nitrogen and then in vacuo. The crude solid was dissolved in trifluoroacetic acid (910 μL), treated with thioanisole (36 μL, 0.30 mmol) and heated to 70° C. for 60 minutes.

After concentration in vacuo, the resulting oily solid was dissolved in methanol (2 mL) and treated with potassium carbonate (20.8 mg, 0.15 mmol). The mixture was stirred for one hour, filtered, concentrated, dissolved in DMSO and purified by reversed phase HPLC (3-15% acetonitrile/water+0.25% acetic acid, 20 mm×250 mm C18 column, 25 mL/min gradient over 15 minutes, 242 nM detection wavelength, 5 total injections). The product fractions were pooled, frozen and concentrated on the lyophilzer to yield the product as a white solid (10.5 mg, 60% yield over 3 steps).

Fraction 1 (Compound 7): $^1$H NMR (400 MHz, Acetonitrile-$d_3$) δ 8.23 (s, 1H), 8.14 (s, 1H), 7.71-7.49 (m, 2H), 7.34 (dd, J=8.4, 1.7 Hz, 1H), 7.19 (d, J=3.7 Hz, 1H), 6.49 (d, J=3.6 Hz, 1H), 5.71 (s, 2H), 5.57 (s, 2H), 4.92 (dt, J=9.7, 8.3 Hz, 1H), 4.44-4.30 (m, 2H), 3.91 (d, J=4.9 Hz, 1H), 3.56 (d, J=10.6 Hz, 1H), 2.83 (d, J=10.7 Hz, 1H), 2.50-2.35 (m, 2H), 1.84-1.70 (m, 2H). ppm.

LCMS: $[M+H]^+$ m/z=510.1 amu.

Fraction 2 (Compound 8): $^1$H NMR (400 MHz, Acetonitrile-$d_3$) δ 8.22 (s, 1H), 8.11 (s, 1H), 7.64-7.50 (m, 2H), 7.33 (dd, J=8.3, 1.7 Hz, 1H), 7.08 (d, J=3.6 Hz, 1H), 6.44 (d, J=3.6 Hz, 1H), 5.69 (s, 2H), 5.56 (s, 2H), 4.85 (q, J=8.9 Hz, 1H), 4.43 (dd, J=8.0, 4.9 Hz, 2H), 3.93 (d, J=5.0 Hz, 1H), 3.53 (d, J=10.7 Hz, 1H), 2.90 (d, J=10.7 Hz, 1H), 2.53-2.34 (m, 2H), 2.15-2.08 (m, 2H) ppm.

LCMS: $[M+H]^+$ m/z=510.1 amu.

To a suspension of compound 7 (10.5 mg, 0.021 mmol) in water (4 mL) was added a 0.1 N solution of methansulfonic acid (21 μL, 1.02 eq, 0.021 mmol). The mixture was sonicated for 60 minutes and became clear and homogenous, it was frozen and concentrated on the lyophilzer to yield the salt as a white fluffy powder (11.5 mg).

$^1$H NMR (400 MHz, Deuterium Oxide) δ 8.51 (s, 1H), 8.15 (s, 1H), 7.79 (d, J=8.4 Hz, 1H), 7.61 (d, J=1.6 Hz, 1H), 7.50-7.36 (m, 2H), 6.78 (d, J=3.7 Hz, 1H), 5.11 (q, J=8.9 Hz, 1H), 4.94 (dd, J=12.2, 6.3 Hz, 1H), 4.63-4.56 (m, 1H), 4.18 (d, J=4.7 Hz, 1H), 3.86 (d, J=12.5 Hz, 1H), 3.36 (d, J=12.5 Hz, 1H), 2.78-2.71 (m, 1H), 2.60 (dd, J=14.2, 10.3 Hz, 1H), 2.56-2.46 (m, 1H), 2.22 (dd, J=14.2, 8.5 Hz, 1H), 1.94 (s, 3H) ppm.

LCMS: $[M+H]^+$ m/z=510.1 amu.

Preparation of Compounds 9 and 10

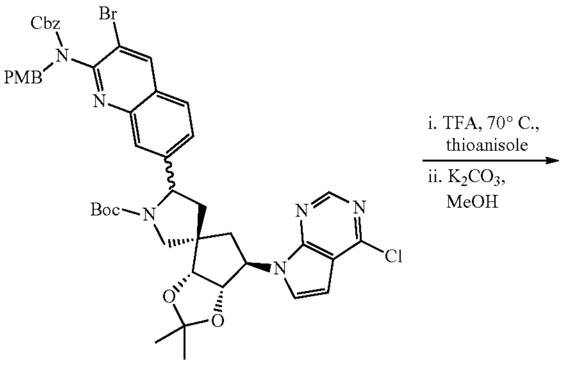

Intermediates 1-8 R&S

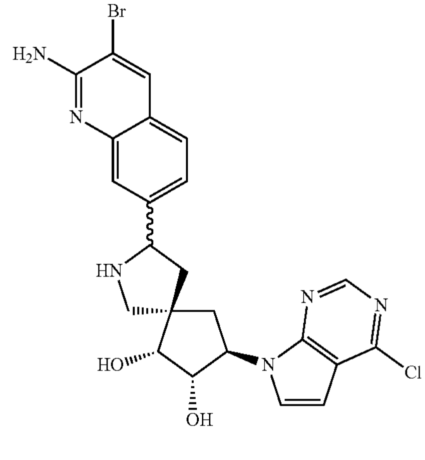

Both diastereomers prepared in step 1 for the preparation of compounds 5 and 6 were submitted to the following general procedure. A vial containing Fraction 1 of intermediates 1-8 R&S (67.2 mg, 0.072 mmol) was dissolved in trifluoroacetic acid (3.0 mL), treated with thioanisole (86 μL, 0.72 mmol) and heated to 70° C. for 60 minutes.

After concentration in vacuo the resulting oily solid was dissolved in methanol (3 mL) and treated with potassium carbonate (49.8 mg, 0.36 mmol). The mixture was stirred for one hour, filtered, concentrated, dissolved in DMSO and purified by reversed phase HPLC (5-25% acetonitrile/water+0.25% acetic acid, 20 mm×250 mm C18 column, 25 mL/min gradient over 15 minutes, 242 nM detection wavelength, 5 total injections). The product fractions were pooled, frozen and concentrated on the lyophilzer to yield the product as a white solid (19.5 mg, 51% yield over 2 steps).

Fraction 1 (Compound 9): $^1$H NMR (400 MHz, Acetonitrile-$d_3$) δ 8.58 (s, 1H), 8.23 (s, 1H), 7.65-7.51 (m, 3H), 7.35 (dd, J=8.4, 1.6 Hz, 1H), 6.67 (d, J=3.7 Hz, 1H), 5.57 (s, 2H), 5.19-5.03 (m, 1H), 4.49 (dd, J=7.9, 4.8 Hz, 1H), 4.43-4.28 (m, 1H), 3.92 (d, J=4.7 Hz, 1H), 3.57 (d, J=10.6 Hz, 1H), 2.84 (d, J=10.6 Hz, 1H), 2.55-2.37 (m, 2H), 1.85-1.75 (m, 2H) ppm.

LCMS: $[M+H]^+$ m/z=529.1 amu.

Fraction 2 (Compound 10): $^1$H NMR (400 MHz, Acetonitrile-$d_3$) δ 8.54 (s, 1H), 8.22 (d, J=0.7 Hz, 1H), 7.65-7.44 (m, 3H), 7.33 (dd, J=8.3, 1.7 Hz, 1H), 6.62 (d, J=3.7 Hz, 1H), 5.58 (s, 2H), 5.05 (dt, J=10.0, 8.8 Hz, 1H), 4.54 (dd, J=8.5, 4.7 Hz, 1H), 4.51-4.46 (m, 1H), 3.95 (d, J=4.7 Hz, 1H), 3.56 (d, J=10.7 Hz, 1H), 2.92 (d, J=10.7 Hz, 1H), 2.54-2.42 (m, 2H), 2.14-1.99 (m, 2H) ppm.

LCMS: $[M+H]^+$ m/z=529.1 amu.

To a suspension of compound 9 (9.5 mg, 0.017 mmol) in water (4 mL) was added a 0.1 N solution of methansulfonic acid (18 μL, 1.02 eq, 0.018 mmol). The mixture was sonicated for 60 minutes and became clear and homogenous, it was frozen and concentrated on the lyophilzer to yield the salt as a white fluffy powder (10.5 mg).

$^1$H NMR (400 MHz, Deuterium Oxide) δ 8.75 (s, 1H), 8.57 (s, 1H), 7.95 (d, J=8.4 Hz, 1H), 7.80-7.53 (m, 3H), 6.83 (d, J=3.7 Hz, 1H), 5.23 (q, J=8.8 Hz, 1H), 5.05 (dd, J=12.2, 6.3 Hz, 1H), 4.92-4.86 (m, 1H), 4.74 (s, 3H), 4.29 (d, J=4.7 Hz, 1H), 3.96 (d, J=12.5 Hz, 1H), 3.47 (d, J=12.5 Hz, 1H), 2.87 (dd, J=13.4, 6.3 Hz, 1H), 2.70 (dd, J=14.2, 10.3 Hz, 1H), 2.65-2.55 (m, 1H), 2.33 (dd, J=14.2, 8.5 Hz, 1H) ppm.

LCMS: $[M+H]^+$ m/z=529.1 amu.

Example 2: Syntheses of Compounds 11 Through 26

Preparation of Intermediate 2-1

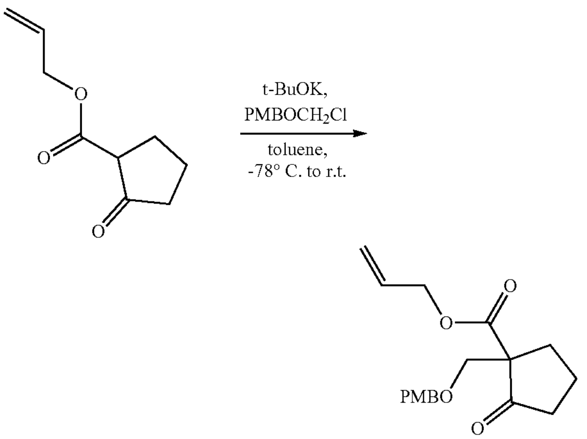

Intermediate 2-1

To a mixture of t-BuOK (139.4 g, 1.24 mol, 1.10 eq) in toluene (4.00 L) was added rac-allyl 2-oxocyclopentane-1-carboxylate (190.0 g, 1.13 mol, 1.00 eq) at approximately 0 to 10° C., and the mixture was stirred at approximately 0 to 10° C. for 30 minutes. 1-((chloromethoxy)methyl)-4- methoxybenzene (221.4 g, 1.19 mol, 1.05 eq) was added at approximately 0 to 10° C., and the mixture was stirred at 20° C. for 1 h. TLC (Petroleum ether:Ethyl acetate=10:1) showed that the starting material was consumed and one main spot was formed. The mixture was diluted with saturated brine (3.00 L) and extracted with ethyl acetate (5.00 L×2). The obtained organic phase was dried over sodium sulfate and concentrated under vacuum to give crude product. The crude product was purified by silica gel column chromatography (Petroleum ether:Ethyl acetate=50:1 to 20:1, Petroleum ether:Ethyl acetate=10:1, product $R_f$=0.22) to give allyl 1-(((4-methoxybenzyl)oxy)methyl)-2-oxocyclopentane-1-carboxylate (Intermediate 2-1; 235.82 g, 711.10 mmol, 32% yield, 96.0% purity) as a yellow oil, which was confirmed by HPLC and proton NMR.

$^1$H NMR (400 MHz, $CDCl_3$): δ 7.26-7.12 (m, 2H), 6.90-6.84 (m, 2H), 5.96-5.72 (m, 1H), 5.36-5.16 (m, 2H), 4.59 (qd, J=1.2, 5.6 Hz, 2H), 4.51-4.36 (m, 2H), 3.84-3.81 (m, 1H), 3.80 (s, 3H), 3.76-3.71 (m, 1H), 2.51-2.23 (m, 4H), 2.11-1.95 (m, 2H) ppm.

LCMS: $[M+Na]^+$ m/z=341.1 amu.

Preparation of Intermediate 2-2

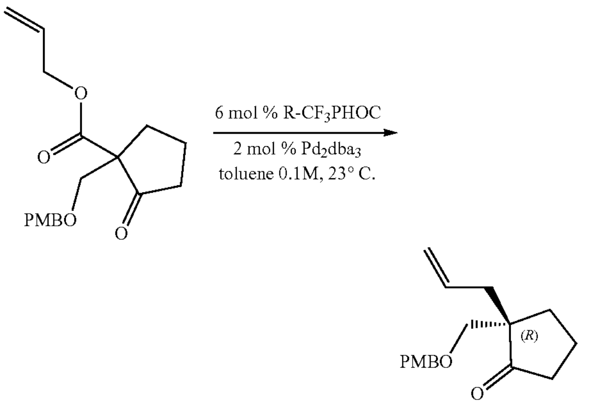

Intermediate 2-2

To an oven-dried flask under argon gas was added tris (dibenzylideneacetone)dipalladium(0) (575 mg, 0.630 mmol) and (R)-p-(CF3)3-t-BuPHOX (1.11 g, 1.88 mmoles). Sequential vacuum argon cycles (3×) were performed, and degassed toluene (450 mL) was injected to yield a dark catalyst solution that was stirred for 45 minutes. Neat Intermediate 2-1 (13.15 g, 41.31 mmol) was injected dropwise and the reaction was stirred under argon atmosphere for 17 hours. TLC analysis showed complete conversion, and the reaction was filtered through a pad of celite and concentrated to yield an oil. The oil was dissolved in DCM/Hexanes (1:1) and purified by silica gel chromatography, where the DCM/Hexanes (1:1) was exchanged to DCM, and finally to 5% EtOAc/DCM. The product fractions were pooled and concentrated to dryness to yield (R)-2-allyl-2-(((4-methoxybenzyl)oxy)methyl)cyclopentan-1-one (Intermediate 2-2; 10.45 g, 92% yield) as a clear, yellow oil. Further analysis by chiral SFC measurements (IC-Daicell; 100 bar; 40° C., 5% IPA/CO2 over 12 minutes) indicated Intermediate 2-2 to be 80% ee, and integration of the peaks confirmed a racemic sample at 210 nM. Proton NMR and LC/MS were consistent with the expected product.

$^1$H NMR (400 MHz, $CDCl_3$): δ 7.22-7.16 (m, 2H), 6.89-6.83 (m, 2H), 5.77-5.52 (m, 1H), 5.12-4.98 (m, 2H), 4.47-4.30 (m, 2H), 3.80 (s, 3H), 3.47 (d, J=8.7 Hz, 1H), 3.29 (d, J=8.8 Hz, 1H), 2.33-2.06 (m, 5H), 2.01-1.88 (m, 2H), 1.87-1.75 (m, 1H) ppm.

LCMS: [M+Na]+m/z=297.2 amu.

Preparation of Intermediate 2-3

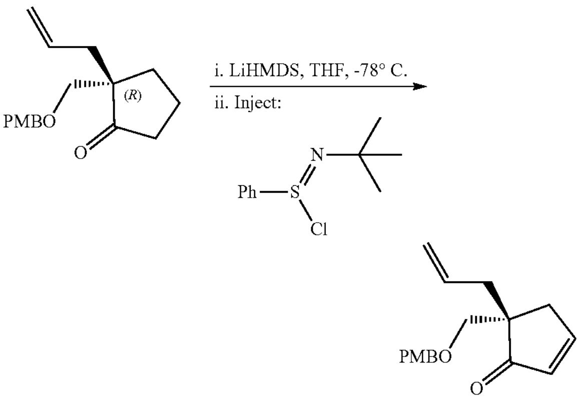

Intermediate 2-3

A solution of Intermediate 2-2 (1.89 g, 1.0 eq., 6.89 mmol) in dry tetrahydrofuran was treated dropwise via cannula with a cold (−78° C.) solution of lithium hexamethyldisilazide (8.6 mL, 1.25 eq., 8.6 mmol). After 15 minutes, a solution of sulfuryl chloride-tert-butyl imine (1.78 g, 1.20 eq., 8.26 mmol) in tetrahydrofuran was added rapidly via cannula.

After 30 minutes at constant temperature, the reaction was quenched with saturated aqueous ammonium chloride and diluted with diethyl ether. The mixture was transferred to a separatory funnel where the aqueous phase was separated and the organic phase was further washed with 0.5 N HCl, water and 3:1 brine/saturated sodium bicarbonate solution. The organic phase was dried over sodium sulfate, filtered, concentrated to give a crude oily product, and then purified via silica gel chromatography (0-100% EtOAc/Hexanes with refractive index detection) to yield (S)-5-allyl-5-(((4-methoxybenzyl)oxy)methyl)cyclopent-2-en-1-one (Intermediate 2-3). Intermediate 2-3 also stains with potassium permanganate on TLC. Proton NMR and LC/MS were consistent with the expected product.

$^1$H NMR (400 MHz, $CDCl_3$): δ 7.67 (dt, J=5.6, 2.7 Hz, 1H), 7.23-7.12 (m, 2H), 6.93-6.78 (m, 2H), 6.16 (dt, J=5.8, 2.2 Hz, 1H), 5.56 (dddd, J=16.7, 10.0, 8.2, 6.5 Hz, 1H), 5.12-4.93 (m, 2H), 4.47-4.27 (m, 2H), 3.79 (s, 3H), 3.50 (d, J=8.7 Hz, 1H), 3.36 (d, J=8.7 Hz, 1H), 2.81 (dt, J=19.2, 2.5 Hz, 1H), 2.54 (ddd, J=19.2, 2.8, 2.1 Hz, 1H), 2.26 (ddt, J=13.6, 6.5, 1.3 Hz, 1H), 2.18 (ddt, J=13.5, 8.2, 1.0 Hz, 1H) ppm.

LCMS: $[M+Na]^+$ m/z=295.2 amu.

Preparation of Intermediate 2-4

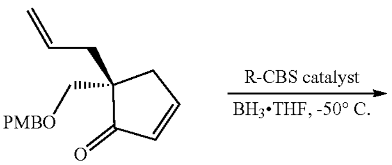

-continued

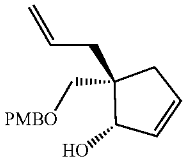

Intermediate 2-4

To a room temperature solution of Intermediate 2-3 (1.89 g, 1.0 eq., 6.93 mmol) in THE (0.1 M) was added R-CBS catalyst (2.40 g, Sigma-Aldrich, 1.25 eq., 8.67 mmol). The resulting solution was stirred vigorously for 30 minutes, cooled to −45° C. before treatment with a solution of borane in THF (8.0 mL, 1 M, 1.15 eq., 8.0 mmol). After 2 hours, TLC analysis indicated the reaction was complete (15% acetone/hexanes) and the reaction was quenched with saturated sodium bicarbonate without warming. The mixture was diluted with ethyl acetate, transferred to a separatory funnel and the organic phase was further washed with additional sodium bicarbonate and water. The organic phase was dried over sodium sulfate, filtered, concentrated to dryness and wet loaded (10% acetone/hexanes) prior to silica gel chromatography (0-20% acetone/hexanes) to afford (1S,5S)-5-allyl-5-(((4-methoxybenzyl)oxy)methyl)cyclopent-2-en-1-ol (Intermediate 2-4; 1.361 g, 72% yield), as confirmed by NMR and LC/MS analysis.

$^1$H NMR (400 MHz, $CDCl_3$): δ 7.39-7.17 (m, 2H), 6.92-6.84 (m, 2H), 5.83 (dtd, J=5.8, 2.4, 1.0 Hz, 1H), 5.80-5.66 (m, 2H), 5.11-5.00 (m, 2H), 4.47 (dtd, J=5.8, 2.2, 1.1 Hz, 1H), 4.44 (s, 1H), 3.81 (s, 3H), 3.49 (d, J=1.2 Hz, 2H), 2.98 (d, J=5.9 Hz, 1H), 2.34-2.20 (m, 2H), 2.20-2.07 (m, 2H) ppm.

LCMS: $[M+Na]^+$ m/z=297.1 amu.

Preparation of Intermediate 2-5

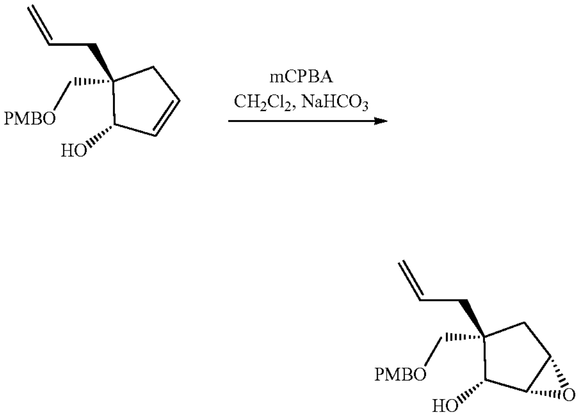

Intermediate 2-5

To a flask charged with Intermediate 2-4 (4.875 g, 1.00 eq., 17.76 mmol) was added dichloromethane (180 mL, 0.1 M), cooled to 0° C. and followed by the addition of m-CPBA (75% w/w, 6.13 g, 1.50 eq., 26.65 mmol) and sodium bicarbonate (3.73 g, 2.50 eq., 44.4 mmol). After 2 hours, TLC indicated that the reaction was not complete, and the reaction was transferred to a −15° C. circulating cold bath for overnight stirring (14 hours). After overnight stirring, TLC confirmed the reaction to be complete. The mixture was poured into sodium sulfite (250 mL, saturated) and stirred for 15 minutes prior to transfer to a separatory funnel. The mixture was diluted with diethyl ether (500 mL) and the aqueous layer was separated. The ether layer was further washed with half saturated and fully saturated sodium bicarbonate (200 mL portions). The organic phase was dried over magnesium sulfate, filtered and concentrated to dryness yielding (1R,2R,3S,5S)-3-allyl-3-(((4-methoxybenzyl)oxy)methyl)-6-oxabicyclo[3.1.0]hexan-2-ol (Intermediate 2-5; 5.50 g, crude quantitative) as a yellow oil that was pure by LC/MS and proton NMR analysis.

$^1$H NMR (400 MHz, $CDCl_3$): δ 7.25-7.19 (m, 2H), 6.90-6.84 (m, 2H), 5.70 (ddt, J=16.8, 10.3, 7.4 Hz, 1H), 5.12-5.05 (m, 2H), 4.47 (d, J=11.3 Hz, 1H), 4.34 (d, J=11.4 Hz, 1H), 4.07 (s, 1H), 3.84-3.78 (m, 5H), 3.61 (dd, J=2.9, 1.8 Hz, 1H), 3.42 (dd, J=2.9, 1.8 Hz, 1H), 3.25 (d, J=8.9 Hz, 1H), 2.53-2.41 (m, 1H), 2.12 (ddt, J=13.6, 7.2, 1.2 Hz, 1H), 1.82 (d, J=15.1 Hz, 1H), 1.69 (dd, J=15.1, 1.9 Hz, 1H) ppm.

LCMS: $[M+H]^+$ m/z=291.2 amu.

Preparation of Intermediate 2-6

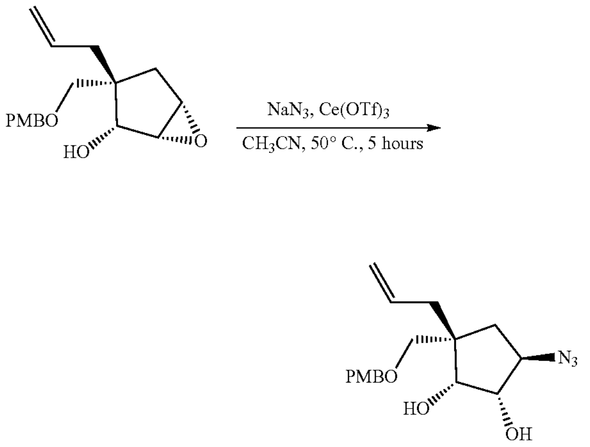

Intermediate 2-6

A round-bottomed flask was charged with Intermediate 2-5 (139.4 mg, 1.0 eq, 0.48 mmol) and dry acetonitrile (0.1 M) to yield a clear yellow solution. The reaction was stirred vigorously under nitrogen gas and sodium azide was added (150 mg, 5.0 eq., 2.3 mmol). After five minutes, cerium(III) triflate (305 mg, 1.1 eq., 0.52 mmol) was added. The reaction was warmed to 50° C. for a period of 5 hours until NMR analysis indicated that the epoxide had been consumed. The reaction was poured into 30 mL ethyl acetate plus 50% concentrated ammonium chloride (1:1). The mixture was filtered through celite and the filter cake was washed with ethyl acetate and water. The biphasic mixture was separated and the organic phase was dried over sodium sulfate. The drying agent was filtered, and the filtrate was concentrated onto silica gel and purified by flash chromatography (10-60% ethyl acetate/hexanes) to afford (1S,2R,3S,5R)-3-allyl-5-azido-3-(((4-methoxybenzyl)oxy)methyl)cyclopentane-1,2-diol (Intermediate 2-6; 70.0 mg, 45% yield), as confirmed by NMR and LC/MS analysis.

$^1$H NMR (400 MHz, $CDCl_3$): δ 7.22 (d, J=8.7 Hz, 2H), 6.90 (d, J=8.7 Hz, 2H), 5.73 (ddt, J=16.7, 10.4, 7.4 Hz, 1H), 5.18-5.03 (m, 3H), 4.54-4.38 (m, 2H), 3.91 (t, J=5.5 Hz, 1H), 3.86-3.80 (m, 4H), 3.50 (d, J=9.0 Hz, 1H), 3.41 (d, J=9.2 Hz, 1H), 3.33 (d, J=9.0 Hz, 1H), 3.09 (d, J=6.5 Hz, 1H), 2.28 (ddt, J=13.8, 7.4, 1.2 Hz, 1H), 2.11 (ddt, J=13.8, 7.3, 1.2 Hz, 1H), 1.98 (dd, J=14.2, 7.2 Hz, 1H), 1.52-1.40 (m, 1H) ppm.

LCMS: $[M+H]^+$ m/z=334.2 amu.

Preparation of Intermediate 2-7

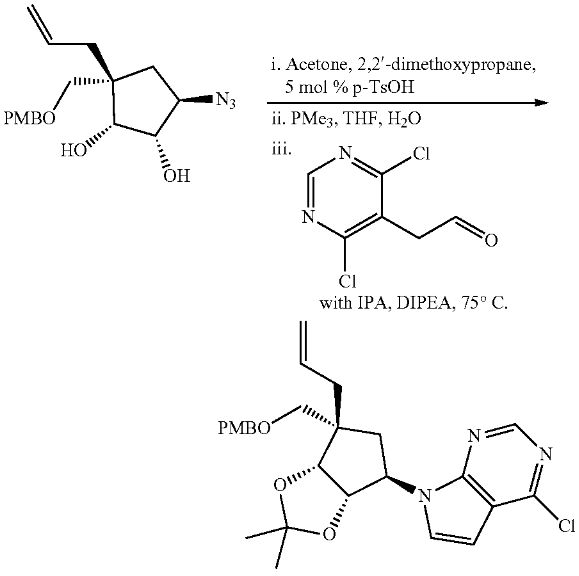

Intermediate 2-7

A flask containing Intermediate 2-6 (70.0 mg, 1.0 eq., 0.21 mmol) was charged with acetone: 2,2'-dimethoxypropane (0.2 M total, 10:1 mixture), and p-toluenesulfonic acid mono-hydrate (2.0 mg, 0.01 mmol, 5 mol %). The reaction was stirred at room temperature for 90 minutes until determined complete by TLC. The solution was diluted with ethyl acetate (15 mL), transferred to a separatory funnel and washed with sodium bicarbonate (10 mL). The organic portion was dried over sodium sulfate, filtered and concentrated to yield the crude acetonide which required no further purification (80.0 mg, crude quant.).

A mixture of the crude acetonide (185 mg, 1.0 eq., 0.495 mmol) and water (0.09 mL, 10.0 eq., 4.95 mmol) was treated with trimethylphosphine in THF (1.3 mL, 1 M, 2.5 eq., 1.23 mmol). The reaction was stirred for 2 hours and volatiles were stripped under a flow of nitrogen gas. After 1 hour at high vacuum, the residue was dissolved in isopropyl alcohol (2 mL, 0.25 M) and Hünig's base (0.65 mL, 5 eq., 3.72 mmol) was added, followed by 2-(4,6-dichloropyrimidin-5-yl)acetaldehyde (142 mg, 1.5 eq., 0.74 mmol). The reaction was sealed and heated to 75° C. for 12 hours. LC/MS analysis indicated that amine starting material remained. Additional and equal portions of Hünig's base and the aldehyde were added, and the reaction was resealed and heated to 85° C. for 5 hours.

The reaction was poured into concentrated sodium bicarbonate and ethyl acetate. The organic phase was separated, dried over sodium sulfate, filtered and concentrated to an oil that was purified by flash chromatography (0-100% ethyl acetate/hexanes). The product fractions were concentrated to dryness to yield (1S,2R,3S,5R)-3-allyl-5-(4-chloro-7H-pyrrolo[2,3-d]pyrimidin-7-yl)-3-(((4-methoxybenzyl)oxy)methyl)cyclopentane-1,2-diol (Intermediate 2-7; 137 mg, 58% yield) as a yellow oil.

$^1H$ NMR (400 MHz, $CDCl_3$): δ 8.63 (s, 1H), 7.30 (d, J=8.6 Hz, 2H), 7.24 (d, J=3.6 Hz, 1H), 6.89 (d, J=8.7 Hz, 2H), 6.60 (d, J=3.6 Hz, 1H), 5.87 (dddd, J=16.2, 10.8, 7.8, 6.9 Hz, 1H), 5.21-5.09 (m, 2H), 5.01 (ddt, J=17.1, 7.7, 5.7 Hz, 2H), 4.62 (d, J=6.8 Hz, 1H), 4.51 (s, 2H), 3.82 (s, 3H), 3.51 (s, 2H), 2.48 (ddd, J=19.3, 13.8, 7.6 Hz, 2H), 2.33-2.17 (m, 2H), 1.52 (s, 3H), 1.32-1.15 (m, 3H) ppm.

LCMS: $[M+H]^+$ m/z=484.2 amu.

Alternative Preparation of Intermediate 2-3

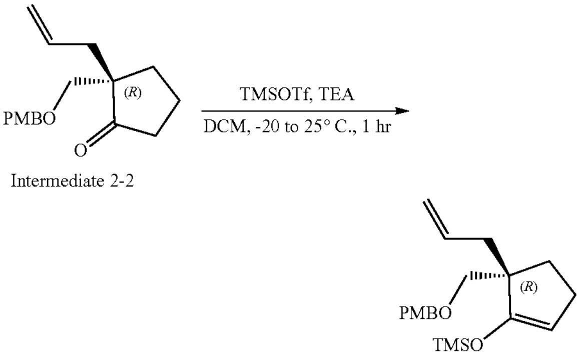

Intermediate 2-2

Intermediate 2-2a

Three reactions were carried out in parallel. To a solution of Intermediate 2-2 (32.0 g, 117 mmol, 1.00 eq.) in dichloromethane (300 mL) was added TEA (38.8 g, 383 mmol, 53.3 mL, 3.29 eq.) and TMSOTf (28.4 g, 128 mmol, 23.1 mL, 1.10 eq.) at −20° C. Then the mixture was stirred at 25° C. for 1 hr. TLC (Petroleum ether/Acetone=6/1, material $R_f$=0.5, product $R_f$=0.9) showed the reaction was complete. The reaction mixture was quenched with saturated aqueous $NaHCO_3$ (500 mL) at 0° C., and then extracted with dichloromethane (200 mL). The combined organic layers were dried over $Na_2SO_4$, filtered and concentrated under reduced pressure to give Intermediate 2-2a (123 g, crude) as a yellow oil. Crude Intermediate 2-2a was used in the next step without further purification.

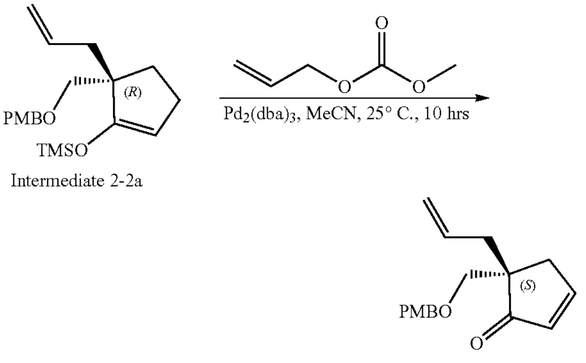

Intermediate 2-2a

Intermediate 2-3

Three reactions were carried out in parallel. To a mixture of Intermediate 2-2a (41.0 g, 118 mmol, 1.00 eq.) and allyl methyl carbonate (41.2 g, 355 mmol, 3.00 eq.) in MeCN (250 mL) was added $Pd_2(dba)_3$ (3.25 g, 3.55 mmol, 0.03 eq.). The mixture was stirred at 25° C. for 10 hours. TLC (Petroleum ether/Acetone=6/1, material $R_f$=0.9, product $R_f$=0.4) showed the reaction was complete. The reaction mixtures were combined for work-up. The combined mixture was filtered and washed with EtOAc (300 mL, 3 times). The filtrate was concentrated under reduced pressure to give a residue. The residue was purified by column chromatography ($SiO_2$, Petroleum ether/Ethyl acetate=I/O to 30/1) to give Intermediate 2-3 (53.0 g, 195 mmol, 54.8% yield) as a yellow oil.

$^1H$ NMR (400 MHz, $CDCl_3$): δ 7.67 (dt, J=5.6, 2.7 Hz, 1H), 7.23-7.12 (m, 2H), 6.93-6.78 (m, 2H), 6.16 (dt, J=5.8, 2.2 Hz, 1H), 5.56 (dddd, J=16.7, 10.0, 8.2, 6.5 Hz, 1H), 5.12-4.93 (m, 2H), 4.47-4.27 (m, 2H), 3.79 (s, 3H), 3.50 (d, J=8.7 Hz, 1H), 3.36 (d, J=8.7 Hz, 1H), 2.81 (dt, J=19.2, 2.5 Hz, 1H), 2.54 (ddd, J=19.2, 2.8, 2.1 Hz, 1H), 2.26 (ddt, J=13.6, 6.5, 1.3 Hz, 1H), 2.18 (ddt, J=13.5, 8.2, 1.0 Hz, 1H) ppm.

LCMS: $[M+Na]^+$ m/z=295.2 amu.

Alternative Preparation of Intermediate 2-4

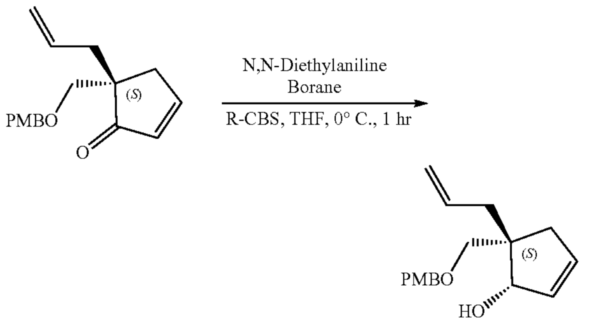

Intermediate 2-4

Four reactions were carried out in parallel. To a solution of R-CBS (5.09 g, 18.4 mmol, 5.36 mL, 0.20 eq.) and N,N-diethylaniline borane (21.0 g, 129 mmol, 22.9 mL, 1.40 eq.) in THF (200 mL) was added Intermediate 2-3 (25.0 g, 91.8 mmol, 1.00 eq.) slowly at −10° C. under nitrogen atmosphere. The mixture was stirred at −10° C. for 1 hour. TLC (Petroleum ether/Acetone=6/1, material $R_f$=0.4, product $R_f$=0.35, PMA) showed the reaction was complete. The four reactions were combined for work-up. The reaction mixture was quenched with saturated aqueous $NaHCO_3$ (1000 mL) and extracted with EtOAc (1000 mL, 2 times). The combined organic layers were washed with sat.aq $NaHCO_3$ (2000 mL) and $H_2O$ (2000 mL), dried over $Na_2SO_4$, filtered and concentrated under reduced pressure to give a residue. The residue was purified by column chromatography ($SiO_2$, Petroleum ether/Ethyl acetate=I/O to 30/1) to give Intermediate 2-4 (73.0 g, 266 mmol, 72.5% yield) as a yellow oil.

$^1H$ NMR (400 MHz, $CDCl_3$): δ 7.39-7.17 (m, 2H), 6.92-6.84 (m, 2H), 5.83 (dtd, J=5.8, 2.4, 1.0 Hz, 1H), 5.80-5.66 (m, 2H), 5.11-5.00 (m, 2H), 4.47 (dtd, J=5.8, 2.2, 1.1 Hz, 1H), 4.44 (s, 1H), 3.81 (s, 3H), 3.49 (d, J=1.2 Hz, 2H), 2.98 (d, J=5.9 Hz, 1H), 2.34-2.20 (m, 2H), 2.20-2.07 (m, 2H) ppm.

LCMS: $[M+Na]^+$ m/z=297.1 amu.

Alternative Preparation of Intermediate 2-5

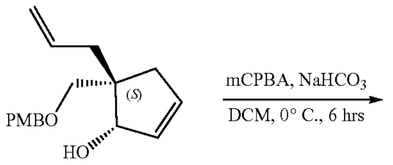

-continued

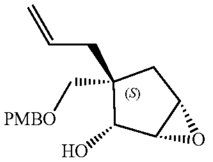

Intermediate 2-5

Two reactions were carried out in parallel. To a solution of Intermediate 2-4 (25.0 g, 91.1 mmol, 1.00 eq.) in DCM (250 mL) was added m-CPBA (27.8 g, 137 mmol, 85.0% purity, 1.50 eq.) and $NaHCO_3$ (19.1 g, 228 mmol, 8.86 mL, 2.50 eq.) at 0° C. The mixture was stirred at 0° C. for 6 hrs. TLC (Petroleum ether/Acetone=6/1, material $R_f$=0.35, product $R_f$=0.2) showed the reaction was complete. The reaction mixtures were combined for work-up. The mixture was quenched with saturated aqueous $Na_2SO_3$ (3000 mL) and extracted with EtOAc (1000 mL, 3 times). The combined organic layers were washed with saturated aqueous $NaHCO_3$ (3000 mL), dried over $Na_2SO_4$, filtered and concentrated under reduced pressure to give a crude product. The crude product (Intermediate 2-5; 66.0 g, crude) was obtained as a colorless oil and used into the next step without further purification.

$^1H$ NMR (400 MHz, $CDCl_3$): δ 7.25-7.19 (m, 2H), 6.90-6.84 (m, 2H), 5.70 (ddt, J=16.8, 10.3, 7.4 Hz, 1H), 5.12-5.05 (m, 2H), 4.47 (d, J=11.3 Hz, 1H), 4.34 (d, J=11.4 Hz, 1H), 4.07 (s, 1H), 3.84-3.78 (m, 5H), 3.61 (dd, J=2.9, 1.8 Hz, 1H), 3.42 (dd, J=2.9, 1.8 Hz, 1H), 3.25 (d, J=8.9 Hz, 1H), 2.53-2.41 (m, 1H), 2.12 (ddt, J=13.6, 7.2, 1.2 Hz, 1H), 1.82 (d, J=15.1 Hz, 1H), 1.69 (dd, J=15.1, 1.9 Hz, 1H) ppm.

LCMS: $[M+H]^+$ m/z=291.2 amu.

Alternative Preparation of Intermediate 2-6

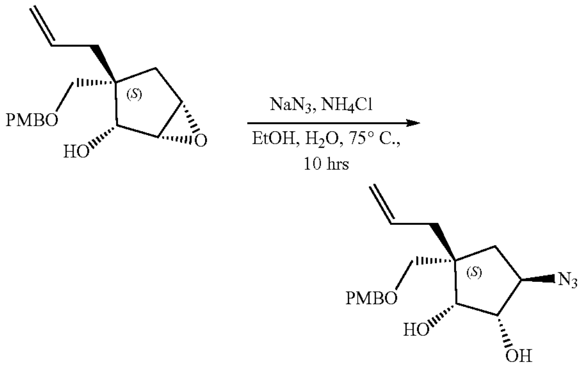

Intermediate 2-6

Two reactions were carried out in parallel. To a solution of Intermediate 2-5 (33.0 g, 114 mmol, 1.00 eq.) in EtOH (500 mL) in $H_2O$ (100 mL) was added $NaN_3$ (22.2 g, 341 mmol, 3.00 eq.) and $NH_4Cl$ (18.2 g, 341 mmol, 3.00 eq.). The mixture was stirred at 75° C. for 10 hrs. Then $NaN_3$ (5.00 g, 76.9 mmol, 6.77e-1 eq.) was added and the mixture was stirred at 75° C. for 12 hrs. HPLC (Intermediate 2-6: RT=2.110 min; starting material: RT=1.978 min) showed most of the starting material was consumed. The two batches were combined for work-up. The reaction mixture was diluted with $H_2O$ (2000 mL) and extracted with EtOAc (1000 mL, 3 times). The combined organic layers were dried over $Na_2SO_4$, filtered and concentrated under reduced pressure to give a residue. The residue was purified by column chromatography ($SiO_2$, Petroleum ether/Ethyl acetate=I/O to 10/1, TLC:Petroleum ether/Ethyl acetate=1/1, product $R_f$=0.75) to give Intermediate 2-6 (21.0 g, 63.0 mmol, 27.7% yield) as a colorless oil.

$^1$H NMR (400 MHz, $CDCl_3$): δ 7.22 (d, J=8.7 Hz, 2H), 6.90 (d, J=8.7 Hz, 2H), 5.73 (ddt, J=16.7, 10.4, 7.4 Hz, 1H), 5.18-5.03 (m, 3H), 4.54-4.38 (m, 2H), 3.91 (t, J=5.5 Hz, 1H), 3.86-3.80 (m, 4H), 3.50 (d, J=9.0 Hz, 1H), 3.41 (d, J=9.2 Hz, 1H), 3.33 (d, J=9.0 Hz, 1H), 3.09 (d, J=6.5 Hz, 1H), 2.28 (ddt, J=13.8, 7.4, 1.2 Hz, 1H), 2.11 (ddt, J=13.8, 7.3, 1.2 Hz, 1H), 1.98 (dd, J=14.2, 7.2 Hz, 1H), 1.52-1.40 (m, 1H) ppm.

LCMS: $[M+H]^+$ m/z=334.2 amu.

Alternative Preparation of Intermediate 2-7

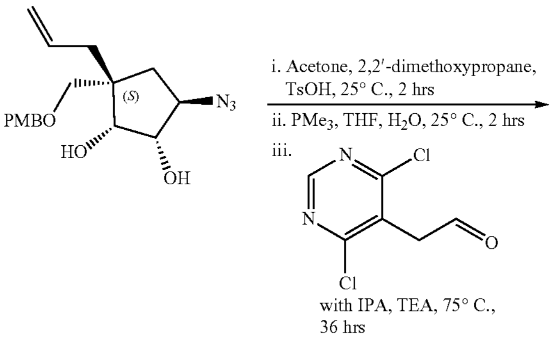

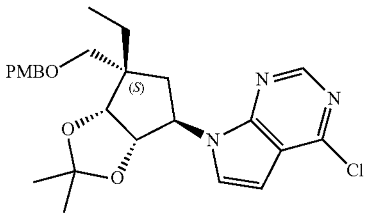

Intermediate 2-7

To a solution of Intermediate 2-6 (21.0 g, 63.0 mmol, 1.00 eq.) in acetone (300 mL) was added $TsOH{\cdot}H_2O$ (599 mg, 3.15 mmol, 0.05 eq.) and 2,2'-dimethoxypropane (65.6 g, 630 mmol, 77.2 mL, 10.0 eq.). The mixture was stirred at 25° C. for 2 hours. TLC (Petroleum ether/Ethyl acetate=1/1, material $R_f$=0.75, product $R_f$=1, $I_2$) showed the reaction was complete. The reaction mixture was diluted with saturated aqueous $NaHCO_3$ (10 mL) and $H_2O$ (200 mL), then extracted with EtOAc (200 mL, 3 times). The combined organic layers were dried over $Na_2SO_4$, filtered and concentrated under reduced pressure to give a crude product (Intermediate 2-6a). Intermediate 2-6a (23.0 g, crude) was obtained as a yellow oil and used into the next step without further purification.

To a solution of Intermediate 2-6a (23.0 g, 61.6 mmol, 1.00 eq.) in THF (50.0 mL) was added $PMe_3$ (1 M, 154 mL, 2.50 eq.) and $H_2O$ (11.1 g, 616 mmol, 11.1 mL, 10.0 eq.). The mixture was stirred at 25° C. for 2 hours. TLC (Petroleum ether/Ethyl acetate=5/1, material $R_f$=0.8, product $R_f$=0.3, $I_2$) showed the reaction was complete. The mixture was concentrated under high vacuum to give a crude product (Intermediate 2-6b). Intermediate 2-6b (25.0 g, crude) was obtained as a yellow oil and used in the next step without further purification.

To a solution of Intermediate 2-6b (20.0 g, 57.6 mmol, 1.00 eq.) and 2-(4,6-dichloropyrimidin-5-yl)acetaldehyde (27.5 g, 144 mmol, 2.50 eq.) in i-PrOH (300 mL) was added TEA (29.1 g, 288 mmol, 40.1 mL, 5.00 eq.). The mixture was stirred at 75° C. for 36 hours. LCMS showed the desired mass and TLC (Petroleum ether/Ethyl acetate=5/1, material $R_f$=0.3, product $R_f$=0.6, $I_2$) showed one main spot formed. The reaction mixture was concentrated under reduced pressure to give a residue. The residue was purified by column chromatography ($SiO_2$, Petroleum ether/Ethyl acetate=I/O to 10/1) to give Intermediate 2-7 (13.3 g, 26.6 mmol, 46.2% yield, 96.8% purity) as a yellow oil.

Intermediate 2-6b: $^1$H NMR (400 MHz, $CDCl_3$): δ 7.27-7.30 (m, 2H), 6.86-6.93 (m, 2H), 5.69-5.93 (m, 1H), 5.01-5.16 (m, 2H), 4.23-4.56 (m, 4H), 3.83 (s, 3H), 3.24-3.49 (m, 3H), 1.79-2.59 (m, 4H), 1.57 (s, 3H), 1.53 (s, 3H) ppm.

Intermediate 2-7: $^1$H NMR (400 MHz, $CDCl_3$): δ 8.63 (s, 1H), 7.30 (d, J=8.6 Hz, 2H), 7.24 (d, J=3.6 Hz, 1H), 6.89 (d, J=8.7 Hz, 2H), 6.60 (d, J=3.6 Hz, 1H), 5.87 (dddd, J=16.2, 10.8, 7.8, 6.9 Hz, 1H), 5.21-5.09 (m, 2H), 5.01 (ddt, J=17.1, 7.7, 5.7 Hz, 2H), 4.62 (d, J=6.8 Hz, 1H), 4.51 (s, 2H), 3.82 (s, 3H), 3.51 (s, 2H), 2.48 (ddd, J=19.3, 13.8, 7.6 Hz, 2H), 2.33-2.17 (m, 2H), 1.52 (s, 3H), 1.32-1.15 (m, 3H) ppm.

LCMS: $[M+H]^+$ m/z=484.2 amu.

Preparation of Intermediate 2-8 and Epi-Intermediate 2-8

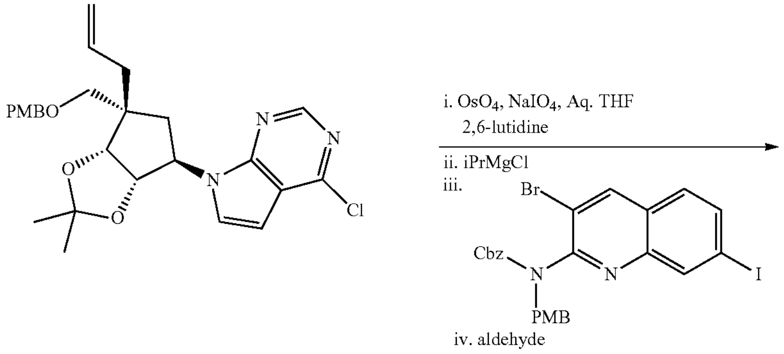

-continued

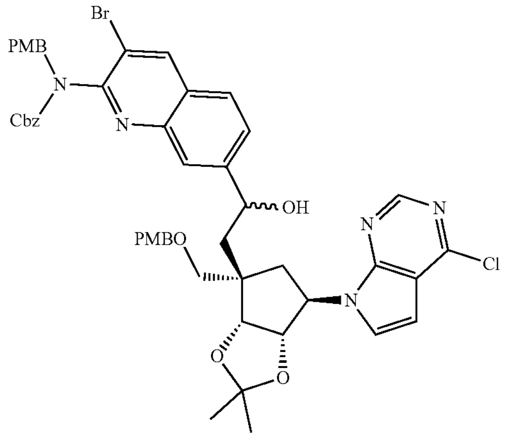

Intermediate 2-8

+

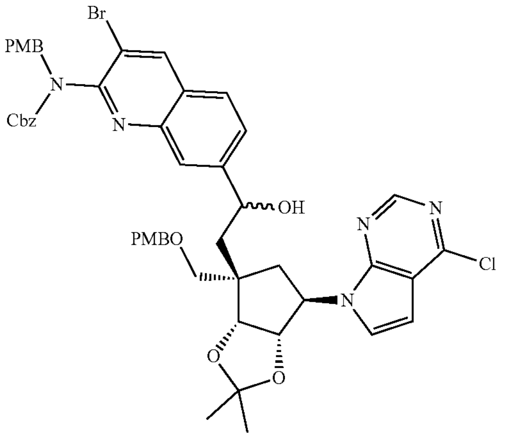

Epi-Intermediate 2-8

A flask containing Intermediate 2-7 (449 mg, 1.0 eq., 0.93 mmol) was charged with THE (3 mL), water (1 mL) and 2,6-dimethylpyridine (0.22 mL), followed with gentle heating to yield a homogenous solution. Solid sodium periodate (794 mg, 4.0 eq., 3.71 mmol) was added followed by osmium tetroxide (4% solution in water, 0.18 mL, 3 mol %, 0.03 mmol), and the reaction was stirred at ambient temperature for 2 hours. TLC analysis showed complete conversion, and the reaction was poured into 1 N aqueous sodium sulfite (2 volumes), followed by dilution with ethyl acetate (4 volumes). The aqueous phase was separated and the organic was further washed with concentrated sodium bicarbonate. The resulting organic phase was dried over sodium sulfate, filtered, concentrated to dryness and used directly in the following step.

To prepare the Grignard reagent, a dry flask was charged with benzyl(3-bromo-7-iodoquinolin-2-yl)(4-methoxybenzyl)carbamate (710 mg, 1.27 eq., 1.18 mmol) and dry THE (8 mL) was injected to yield a homogeneous solution. After cooling to −78° C., isopropyl magnesium chloride solution (2M in THF, 0.584 mL, 1.26 eq., 1.17 mmol) was injected. The reaction was stirred for one hour and then allowed to warm to ambient temperature. LC/MS confirmed the iodine-magnesium exchange and the solution was re-cooled to −78° C.

The crude aldehyde prepared above was dissolved in dry THE (8 mL), cooled to −78° C. and the Grignard reagent prepared above was transferred into the reaction flask via cannula. The resulting homogenous solution was stirred for one hour and assayed by LC/MS, which indicated consumption of the aldehyde. The cooling bath was removed, the reaction was allowed to warm for 5 minutes, and then poured into concentrated ammonium chloride solution (50 mL). The reaction flask was then washed with ethyl acetate (150 mL). After vigorous stirring, the mixture was transferred to a separatory funnel and the organic phase was separated. The organic phase was dried with sodium sulfate, filtered, concentrated to dryness and purified by reversed phase HPLC (30 mm column, 50-100% acetonitrile/water+0.25% acetic acid, 254 nM detection, 12 injections). Two fractions were collected (Fraction 1 corresponding to Intermediate 2-8, 250 mg, 28% yield; Fraction 2 corresponding to Epi-Intermediate 2-8, 200 mg, 23% yield; combined, 51% yield over 2 steps), with Fraction 1 eluting first and Fraction 2 eluting second.

Fraction 1 (Intermediate 2-8): $^1$H NMR (400 MHz, Acetonitrile-$d_3$, 70° C.): δ 8.59 (s, 1H), 8.48 (s, 1H), 7.89 (s, 1H), 7.81 (d, J=8.5 Hz, 1H), 7.65 (dd, J=8.5, 1.6 Hz, 1H), 7.59 (d, J=3.7 Hz, 1H), 7.37 (d, J=8.6 Hz, 2H), 7.34-7.23 (m, 7H), 6.98-6.89 (m, 2H), 6.80 (d, J=8.7 Hz, 2H), 6.66 (d, J=3.7 Hz, 1H), 5.44 (s, 1H), 5.23-5.08 (m, 3H), 4.99 (d, J=4.8 Hz, 3H), 4.59 (dd, J=15.8, 6.5 Hz, 3H), 3.76 (dd, J=21.6, 10.5 Hz, 6H), 3.55 (d, J=4.2 Hz, 1H), 2.57 (dd, J=13.5, 7.8 Hz, 1H), 2.42-2.33 (m, 1H), 2.12-2.06 (m, 2H), 1.77 (p, J=2.4 Hz, 1H), 1.47 (s, 3H), 1.15 (s, 3H) ppm.

LCMS: $[M+H]^+$ m/z=962.3 amu.

Fraction 2 (Epi-Intermediate 2-8): $^1$H NMR (400 MHz, Acetonitrile-$d_3$, 70° C.): δ $^1$H NMR (400 MHz, Acetonitrile-$d_3$) δ 8.58 (s, 1H), 8.52-8.40 (m, 1H), 7.96-7.83 (m, 1H), 7.77 (dd, J=8.5, 1.7 Hz, 1H), 7.64-7.51 (m, 2H), 7.43-7.19 (m, 8H), 7.02-6.85 (m, 2H), 6.86-6.73 (m, 2H), 6.73-6.60 (m, 1H), 5.44 (s, 2H), 5.22-5.13 (m, 3H), 5.05 (dd, J=7.3, 5.5 Hz, 1H), 5.00 (s, 3H), 4.86 (d, J=7.3 Hz, 1H), 4.55 (s, 2H), 3.78 (s, 3H), 3.73 (s, 3H), 2.60 (dd, J=13.2, 7.6 Hz, 1H), 2.25 (dd, J=13.3, 11.5 Hz, 1H), 2.12 (dd, J=14.5, 3.1 Hz, 1H), 2.07-1.98 (m, 2H), 1.51 (s, 3H), 1.28 (s, 3H) ppm.

LCMS: $[M+H]^+$ m/z=962.3 amu.

Preparation of Intermediate 2-8a

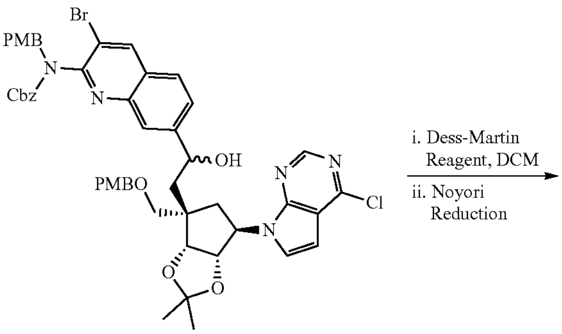

-continued

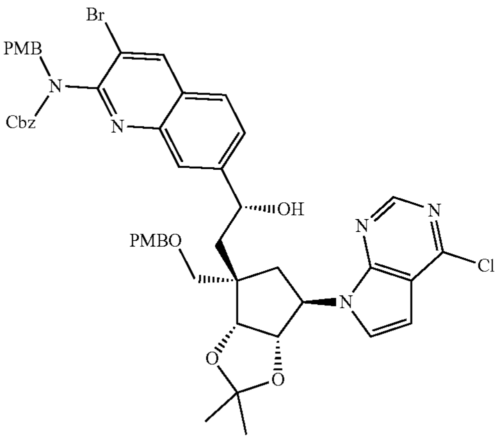

Intermediate 2-8a

A flask containing Intermediate 2-8 and Epi-Intermediate 2-8 (~1:1 mixture; 12.98 g, 13.47 mmol) was dissolved in DCM (250 mL) and solid Dess-Martin Periodinane (6.86 g, 16.17 mmol) was added in a single portion. The reaction was stirred for 3 hours at which time conversion was deemed to be complete by TLC analysis (4:1 DCM/EtOAc). The reaction mixture was diluted with 50% saturated sodium sulfite (200 mL) and stirred for 30 minutes. The volatiles were removed through evaporation, and diethyl ether (500 mL) was added.

The mixture was transferred to a separatory funnel and the organic phase was further washed with 10% sodium bicarbonate (100 mL, 2 times) and saturated sodium bicarbonate (100 mL). The aqueous phase was further washed with additional diethyl ether (200 mL) and the combined organic washings were dried over magnesium sulfate, then filtered and concentrated to yield a white foam (12.95 g, quantitative yield) that was used without further purification.

The isolated ketone was dissolved in dry DCM (120 mL) and solid RuCl[(S,S)-Tsdpen](p-cymene) was added under nitrogen atmosphere (800 mg, 0.0933 mmol). Formic acid-triethylamine azeotrope (6.18 g, 5.30 mmol) was added and the reaction was stirred at ambient temperature for 4 days. At this time LC/MS analysis indicated complete conversion and the reaction was concentrated onto silica gel.

Flash chromatography (0-30% EtOAc/DCM) was performed, yielding Intermediate 2-8a after concentration to a white foam (10.37 g, 10.765 mmol, 80% yield over two steps). By NMR analysis the diastereo-selectivity of the process was >20:1.

Intermediate 2-8a can be carried forward in the same manner described for the mixture of Intermediate 2-8 and Epi-Intermediate 2-8, delivering the bioactive stereoisomer without separation of isomeric mixtures.

$^1$H NMR (400 MHz, Acetonitrile-$d_3$): δ 8.61 (s, 1H), 8.52 (s, 1H), 7.88 (s, 1H), 7.84 (d, J=8.5 Hz, 1H), 7.70-7.63 (m, 2H), 7.43-7.36 (m, 2H), 7.36-7.24 (m, 8H), 6.99-6.91 (m, 2H), 6.87-6.78 (m, 2H), 6.69 (d, J=3.7 Hz, 1H), 5.18 (s, 3H), 5.13-5.06 (m, 1H), 5.00 (s, 2H), 4.63-4.51 (m, 2H), 3.82-3.66 (m, 9H), 2.56 (dd, J=13.4, 7.6 Hz, 1H), 2.00 (s, 6H) ppm.

LCMS: $[M+H]^+$ m/z=962.2 amu.

Preparation of Intermediate 2-9 and Epi-Intermediate 2-9

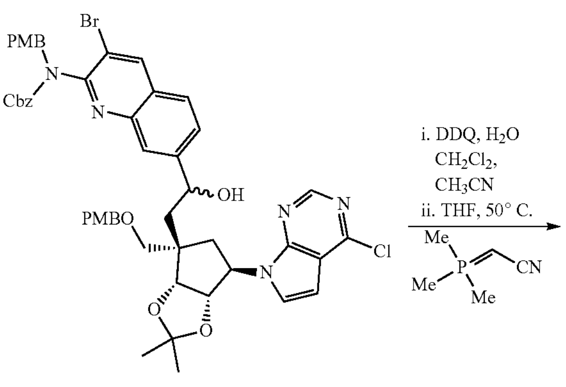

Intermediate 2-8

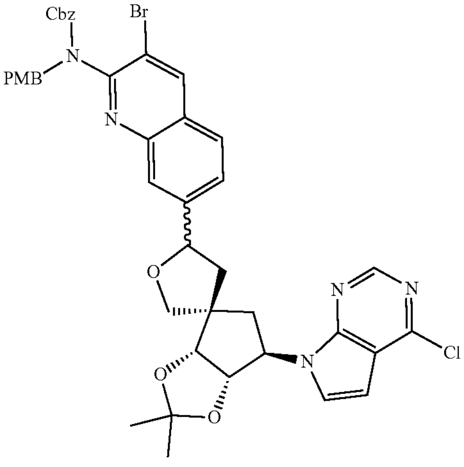

Intermediate 2-9

Epi-Intermediate 2-8 was also submitted to the following general procedure to produce the epimer of Intermediate 2-9. Intermediate 2-8 (111 mg, 1.0 eq., 0.12 mmol) was dissolved in 1:1 acetonitrile/dichloromethane (5 mL). A reaction vial was charged with pH 7 phosphate buffer (0.34 mL) and a solution of DDQ (34 mg, 1.3 eq., 0.15 mmol) in an equal volume of acetonitrile/dichloromethane (1:1, 5 mL), and the mixture was transferred into the aqueous buffer and the flask was cooled to 0° C. The substrate was transferred into the vial via pipet and partial conversion was observed after 2 hours of stirring at 0° C. The reaction was removed from the ice bath and stirred at ambient temperature for 5 hours, at which time LC/MS and TLC showed complete conversion. The reaction was poured into 0.2 N sodium carbonate (100 mL) and the aqueous phase was washed three times with DCM (50 mL portions). The combined organic washings were dried over sodium sulfate, filtered, concentrated onto silica gel and purified by flash chromatography (0-100% DCM/EtOAc) to afford the diol as a white solid (95 mg, 97%).

The diol (95 mg, 0.11 mmol) was placed under an atmosphere of nitrogen (3× high vacuum/nitrogen cycle) and a solution of (cyanomethylene)trimethylphosphorane (0.5 M, Sigma-Aldrich, 1.8 mL, 0.90 mmol) was injected. The vessel was sealed and warmed to 50° C., and the reaction was determined complete within 4 hours by LC/MS analysis. The reaction was quenched with methanol, transferred onto silica gel and concentrated to dryness. Flash chromatography (0-50% EtOAc/DCM) afforded Intermediate 2-9 as a white solid after concentration of the product fractions (78 mg, 84% yield).

$^1$H NMR (400 MHz, Acetonitrile-$d_3$): δ 8.60 (s, 1H), 8.50 (s, 1H), 7.90-7.76 (m, 2H), 7.64-7.53 (m, 2H), 7.38-7.17 (m, 7H), 6.84-6.75 (m, 2H), 6.67 (d, J=3.7 Hz, 1H), 5.22-5.01 (m, 2H), 4.97 (s, 2H), 4.70 (d, J=6.2 Hz, 1H), 4.48 (d, J=8.8 Hz, 1H), 3.81 (d, J=8.8 Hz, 1H), 3.72 (s, 3H), 2.58 (dd, J=13.4, 6.8 Hz, 1H), 2.51-2.43 (m, 1H), 2.37 (dd, J=12.5, 6.9 Hz, 1H), 2.03 (dd, J=12.6, 9.0 Hz, 1H), 1.54 (s, 3H), 1.26 (s, 3H) ppm. LCMS: $[M+H]^+$ m/z=824.2 amu.

Preparation of Intermediate 2-9a

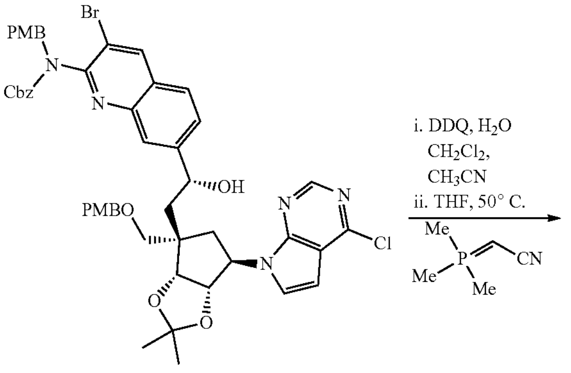

Intermediate 2-8a

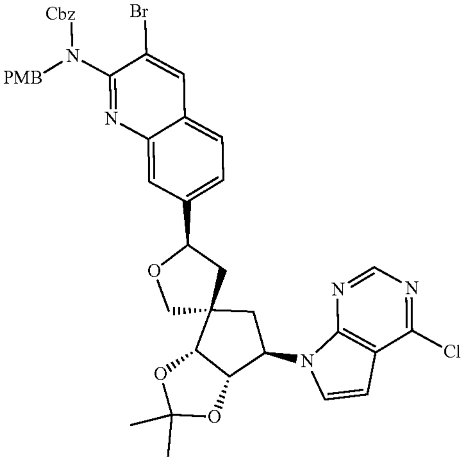

Intermediate 2-9a

Intermediate 2-9a was prepared using the same procedures used to prepare Intermediate 2-9, and was obtained as a white solid (6.40 g, 78% yield).

$^1$H NMR (400 MHz, Acetonitrile-$d_3$): δ 8.60 (s, 1H), 8.50 (s, 1H), 7.90-7.76 (m, 2H), 7.64-7.53 (m, 2H), 7.38-7.17 (m, 7H), 6.84-6.75 (m, 2H), 6.67 (d, J=3.7 Hz, 1H), 5.22-5.01 (m, 4H), 4.97 (s, 2H), 4.70 (d, J=6.2 Hz, 1H), 4.48 (d, J=8.8 Hz, 1H), 3.81 (d, J=8.8 Hz, 1H), 3.72 (s, 3H), 2.58 (dd, J=13.4, 6.8 Hz, 1H), 2.51-2.43 (m, 1H), 2.37 (dd, J=12.5, 6.9 Hz, 1H), 2.03 (dd, J=12.6, 9.0 Hz, 1H), 1.54 (s, 3H), 1.34-1.19 (s, 3H) ppm.

LCMS: $[M+H]^+$ m/z=824.2 amu.

Preparation of Intermediate 2-10 and Epi-Intermediate 2-10

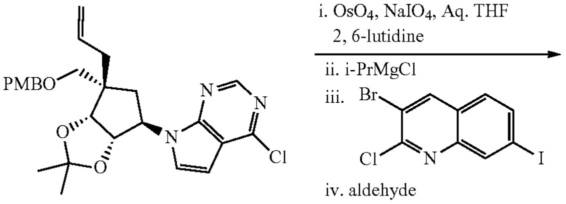

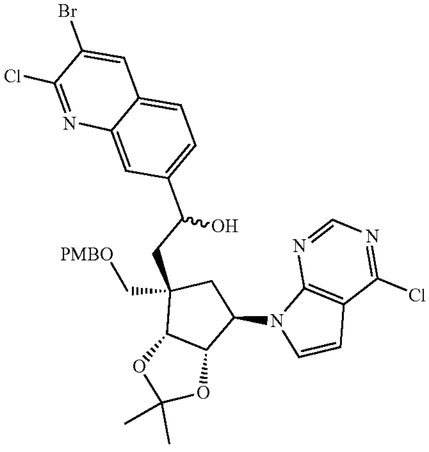

Intermediate 2-10

+

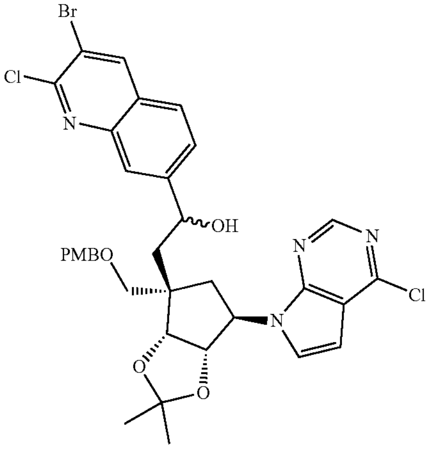

Epi-Intermediate 2-10

A flask containing Intermediate 2-7 (1.0 eq., 0.93 mmol) is charged with THE (3 mL), water (1 mL) and 2,6-dimethylpyridine (0.22 mL), followed with gentle heating to yield a homogenous solution. Solid sodium periodate (4.0 eq., 3.71 mmol) is added followed by osmium tetroxide (4% solution in water, 0.18 mL, 3 mol %, 0.03 mmol), and the reaction is stirred at ambient temperature for 2 hours. The reaction is then poured into 1 N aqueous sodium sulfite (2 volumes), followed by dilution with ethyl acetate (4 volumes). The aqueous phase is separated and the organic phase is further washed with concentrated sodium bicarbonate. The resulting organic phase is dried over sodium sulfate, filtered, concentrated to dryness and used directly in the following step.

To prepare the Grignard reagent, a dry flask is charged with benzyl(3-bromo-7-iodoquinolin-2-yl)(4-methoxybenzyl)carbamate (1.27 eq., 1.18 mmol) and dry THF (8 mL) is injected to yield a homogeneous solution. After cooling to −78° C., isopropyl magnesium chloride solution (2M in THF, 0.584 mL, 1.26 eq., 1.17 mmol) is injected. The reaction is stirred for one hour and then allowed to warm to ambient temperature. The solution is then re-cooled to −78° C.

The crude aldehyde prepared above is dissolved in dry THE (8 mL), cooled to −78° C. and the Grignard reagent prepared above is transferred into the reaction flask via cannula. The resulting homogenous solution is stirred for one hour. The cooling bath is then removed, the reaction is allowed to warm for 5 minutes, and then poured into concentrated ammonium chloride solution (50 mL). The reaction flask is then washed with ethyl acetate (150 mL). After vigorous stirring, the mixture is transferred to a separatory funnel and the organic phase is separated. The organic phase is dried with sodium sulfate, filtered, concentrated to dryness and purified by reversed phase HPLC (30 mm column, 50-100% acetonitrile/water+0.25% acetic acid, 254 nM detection, 12 injections). Two fractions are collected (Fraction 1 corresponding to Intermediate 2-10; Fraction 2 corresponding to Epi-Intermediate 2-10), with Fraction 1 eluting first and Fraction 2 eluting second.

Preparation of Intermediate 2-11 and Epi-Intermediate 2-11

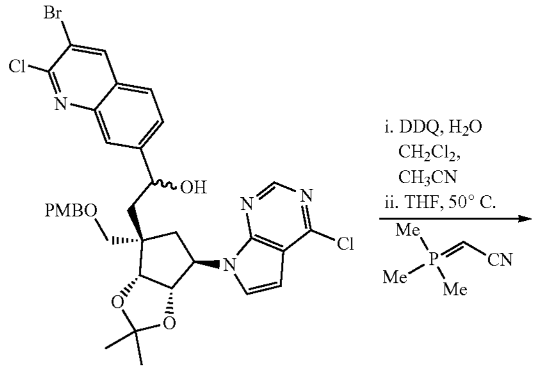

Intermediate 2-10

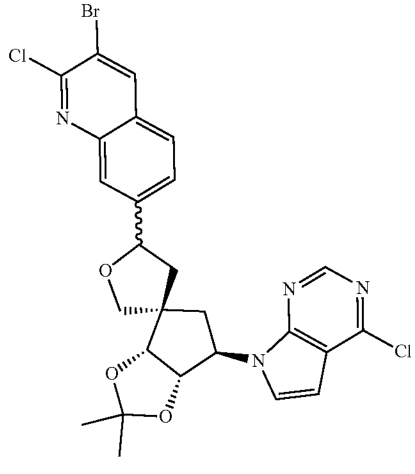

Intermediate 2-11

Epi-Intermediate 2-10 is also submitted to the following general procedure to produce the epimer of Intermediate 2-11. Intermediate 2-10 (1.0 eq., 0.12 mmol) is dissolved in 1:1 acetonitrile/dichloromethane (5 mL). A reaction vial is charged with pH 7 phosphate buffer (0.34 mL) and a solution of DDQ (1.3 eq., 0.15 mmol) in an equal volume of acetonitrile/dichloromethane (1:1, 5 mL), and the mixture is transferred into the aqueous buffer and the flask is cooled to 0° C. The substrate is transferred into the vial via pipet and is stirred for 2 hours at 0° C. The reaction is removed from the ice bath and stirred at ambient temperature for 5 hours. The reaction is poured into 0.2 N sodium carbonate (100 mL) and the aqueous phase is washed three times with DCM (50 mL portions). The combined organic washings are dried over sodium sulfate, filtered, concentrated onto silica gel and purified by flash chromatography (0-100% DCM/EtOAc) to afford the diol.

The diol (0.11 mmol) is placed under an atmosphere of nitrogen (3× high vacuum/nitrogen cycle) and a solution of (cyanomethylene)trimethylphosphorane (0.5 M, Sigma-Aldrich, 1.8 mL, 0.90 mmol) is injected. The vessel is sealed and warmed to 50° C.

The reaction is quenched with methanol, transferred onto silica gel and concentrated to dryness. Flash chromatography (0-50% EtOAc/DCM) affords Intermediate 2-11.

Preparation of Compounds 11 and 12

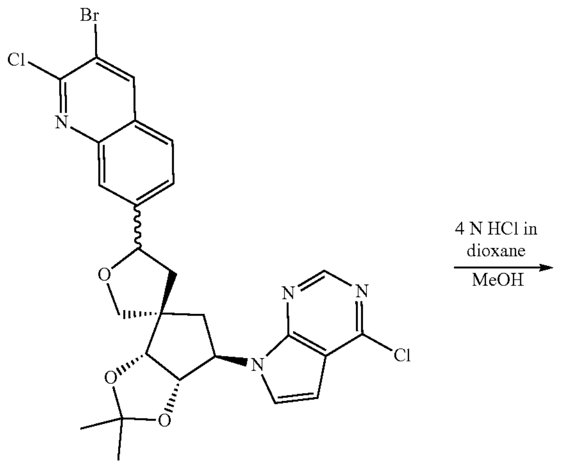

Intermediate 2-11

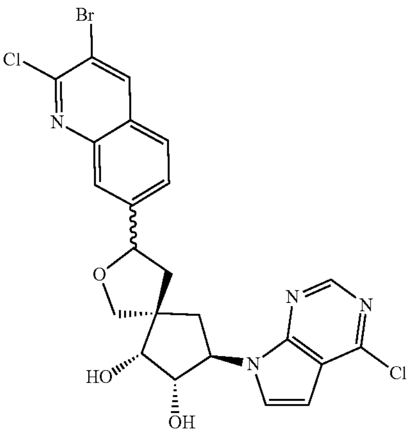

Compound 11

Epi-Intermediate 2-11 is also submitted to the following general procedures to produce Compound 12, which is the epimer of Compound 11. Intermediate 2-11 (1.0 eq.) is dissolved in methanol (0.03 M) to yield a solution, followed by 4 N hydrochloric acid in dioxane (10 eq.). The reaction is stirred at room temperature until determined complete by LC/MS analysis, concentrated to dryness and the residue is dissolved in DMSO.

After filtration, reversed phase HPLC is performed (acetonitrile/water+0.25% acetic acid, 20 mm×250 mm C18 column, 40 mL/min gradient, 242 nM detection wavelength, 3 total injections). The product fractions are pooled, frozen and concentrated on the lyophilzer to yield Compound 11.

Preparation of Compounds 13 and 14

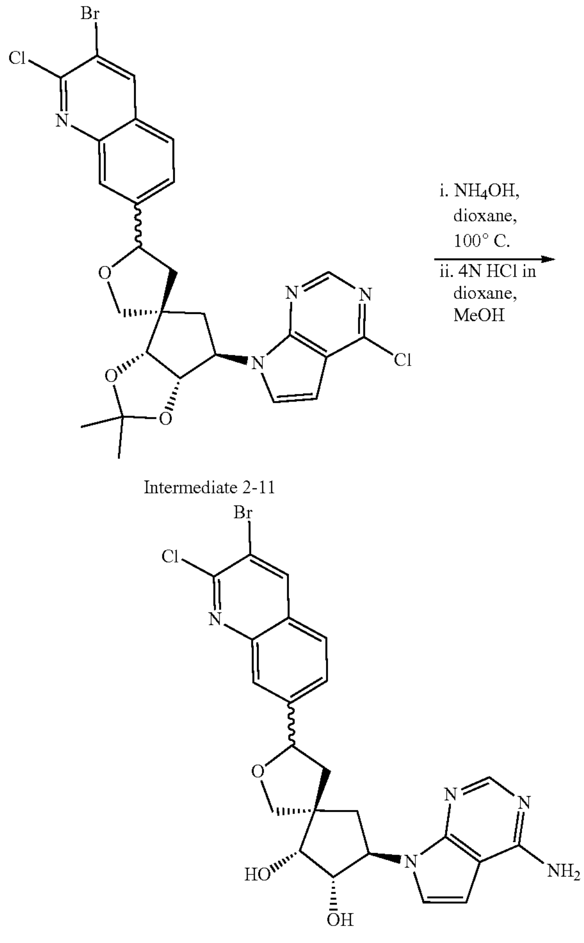

Intermediate 2-11

Compound 13

Epi-Intermediate 2-11 is also submitted to the following general procedures to produce Compound 14, which is the epimer of Compound 13. A vial of Intermediate 2-11 (1.0 eq.) is treated with dioxane (0.1 M) to yield a clear solution, followed by ammonium hydroxide (0.1 M). The reaction is stirred at 100° C. until complete, allowed to cool and the solvent is concentrated in vacuo.

To the crude material is added methanol (0.03 M) and 4 N hydrochloride acid in dioxane (10 eq.). Once determined complete by LC/MS analysis, the solution is concentrated, dissolved in DMSO, filtered and purified by reversed phase HPLC (acetonitrile/water+0.25% acetic acid, 20 mm×250 mm C18 column, 40 mL/min gradient over 15 minutes, 242 nM detection wavelength). The product fractions are pooled, frozen and concentrated on the lyophilzer to yield Compound 13.

Preparation of Compounds 15 and 16

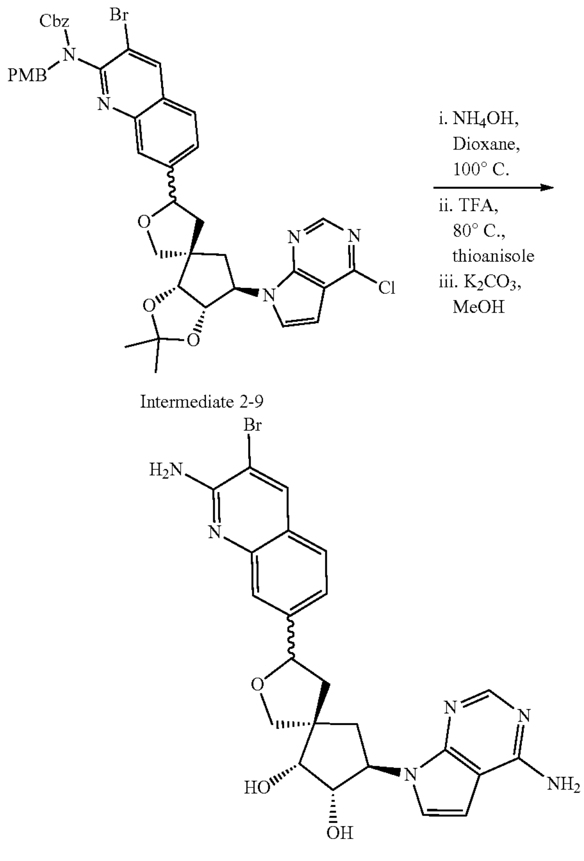

Intermediate 2-9

Compound 15

Epi-Intermediate 2-9 was also submitted to the following general procedure to produce Compound 16. Intermediate 2-9 (45 mg, 1.0 eq., 0.05 mmol) was placed in a microwave vial and dioxane was added (1.36 mL) followed by ammonium hydroxide (1.36 mL). The mixture became homogenous as it was heated to 100° C. and Intermediate 2-9 was consumed with formation of the ammonia nucleophilic substitution product over 16 hours. The solvent was then stripped, first under a stream of nitrogen, and then on high vacuum. Next, TFA was injected (1.37 mL), followed immediately by thioanisole (0.13 mL). The reaction was sealed and heated to 80° C. for a period of 75 minutes at which time LC/MS analysis showed Compound 15 and its corresponding trifluoroacetate. Solvent was removed under a stream of nitrogen and then on high vacuum for one hour. The residue was dissolved in methanol (2 mL) and potassium carbonate was added (75.4 mg, 10.0 eq., 0.55 mmol). After one hour stirring at ambient temperature, the mixture was filtered through a pad of celite and all contact surfaces were washed with a copious amount of ethyl acetate and methanol (10:1). After concentration, the residue was dissolved in DMSO with a small amount of acetic acid, filtered, and purified by reversed phase HPLC (30 mm; 45 mL/min; 254 nM; 5-25% acetonitrile/water+0.25% acetic acid). The product fractions were frozen and concentrated to dryness on the lyophilizer to yield Compound 15 as its freebase form.

Fraction 1: $^1H$ NMR (400 MHz, Acetonitrile-$d_3$+3 vol % d-TFA): δ 8.62 (s, 1H), 8.13 (s, 1H), 7.76 (d, J=8.4 Hz, 1H), 7.62 (d, J=1.7 Hz, 1H), 7.45 (dd, J=8.5, 1.4 Hz, 1H), 7.41 (d, J=3.7 Hz, 1H), 6.81 (d, J=3.7 Hz, 1H), 5.14-4.96 (m, 2H), 4.39 (dd, J=8.4, 4.4 Hz, 1H), 4.33 (d, J=8.8 Hz, 1H), 3.84 (d, J=4.4 Hz, 1H), 3.74 (d, J=8.9 Hz, 1H), 2.56 (dd, J=12.3, 6.6 Hz, 1H), 2.48 (dd, J=13.9, 10.2 Hz, 1H), 2.05-2.00 (m, 2H) ppm.

LCMS: $[M+H]^+$ m/z=511.1 amu.

Fraction 2: $^1H$ NMR (400 MHz, Acetonitrile-$d_3$+3 vol % d-TFA): δ 8.58 (s, 1H), 8.19 (s, 1H), 7.77-7.70 (m, 2H), 7.44-7.39 (m, 2H), 6.84 (dd, J=3.7, 1.0 Hz, 1H), 5.15 (m, 1H), 4.97 (m, 1H), 4.66 (m, 1H), 3.79 (m, 1H), 2.64-2.60 (m, 2H), 2.05-2.00 (m, 2H) ppm.

LCMS: $[M+H]^+$ m/z=511.1 amu.

Preparation of Compounds 17 and 18

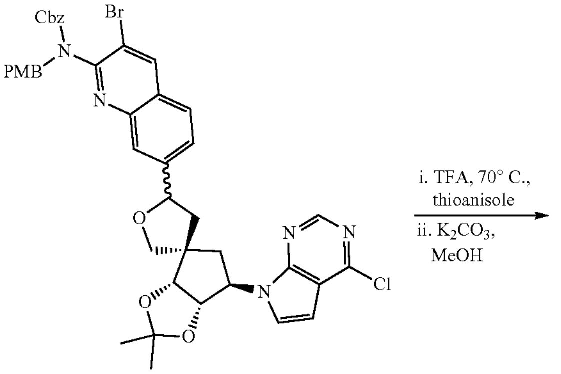

Intermediate 2-9 or Epi-Intermediate 2-9

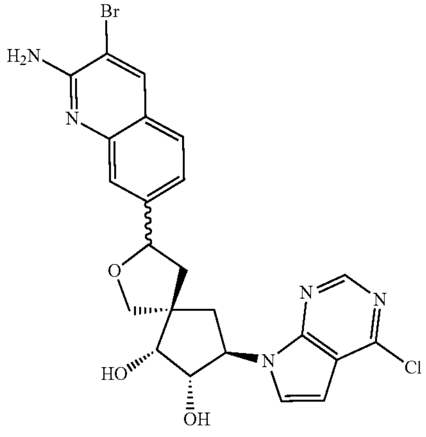

Epi-Intermediate 2-9 is also submitted to the following general procedures to produce Compound 18, which is the epimer of Compound 17. A vial containing Intermediate 2-9 (1.0 eq.) is dissolved in trifluoroacetic acid (0.05 M) and treated with thioanisole (10 eq.). After concentration in vacuo, the resulting crude solid is dissolved in methanol (0.03 M) and treated with potassium carbonate (5.0 eq.). The mixture is stirred for one hour, filtered, concentrated, dissolved in DMSO and purified by reversed phase HPLC (acetonitrile/water+0.25% acetic acid, 20 mm×250 mm C18 column, 242 nM detection wavelength). The product fractions are pooled, frozen and concentrated on the lyophilzer to yield Compound 17.

Preparation of Mesylate Salt of Compound 15

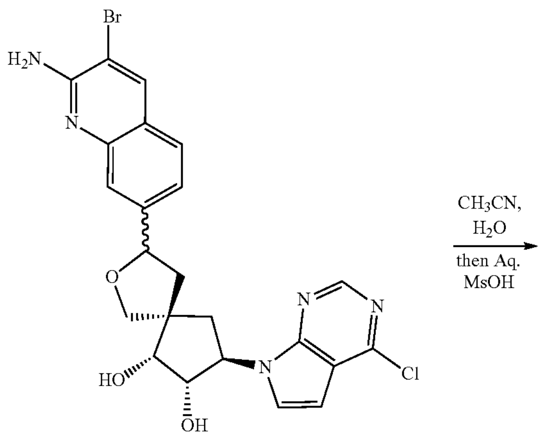

Compound 15

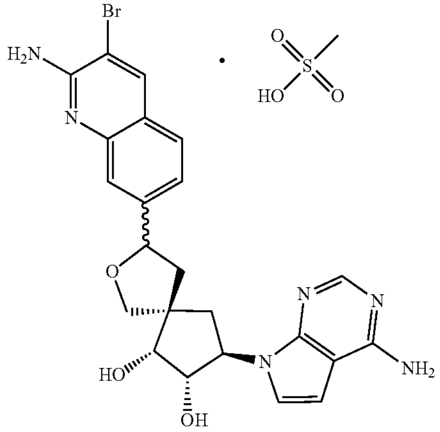

Compound 15-MS

The freebase of Compound 15 was suspended in water, and methansulfonic acid was added (32 mg in 2 mL water). The resulting solution was gently heated and sonicated until a homogenous solution resulted, which was frozen and concentrated to dryness on the lyophilzer. The oily solid that resulted was re-dissolved in water, frozen and concentrated in the same manner to give a water soluble white solid (~3 mg/mL). Further experiments were more easily conducted with this salt (32.0 mg, 91% yield over 2 steps).

$^1H$ NMR (400 MHz, Deuterium Oxide) δ 8.69 (d, J=0.9 Hz, 1H), 8.23 (d, J=0.7 Hz, 1H), 7.84 (d, J=8.3 Hz, 1H), 7.68-7.59 (m, 1H), 7.58-7.46 (m, 2H), 6.88 (d, J=3.6 Hz, 1H), 5.29-5.12 (m, 2H), 4.61 (dd, J=9.2, 4.3 Hz, 1H), 4.45 (d, J=8.9 Hz, 1H), 4.05 (d, J=4.3 Hz, 1H), 3.91 (d, J=9.0 Hz, 1H), 2.68-2.58 (m, 2H), 2.24-2.02 (m, 2H) ppm.

LC/MS: $[M+H]^+$ m/z=511.1 amu.

Preparation of Compound 19

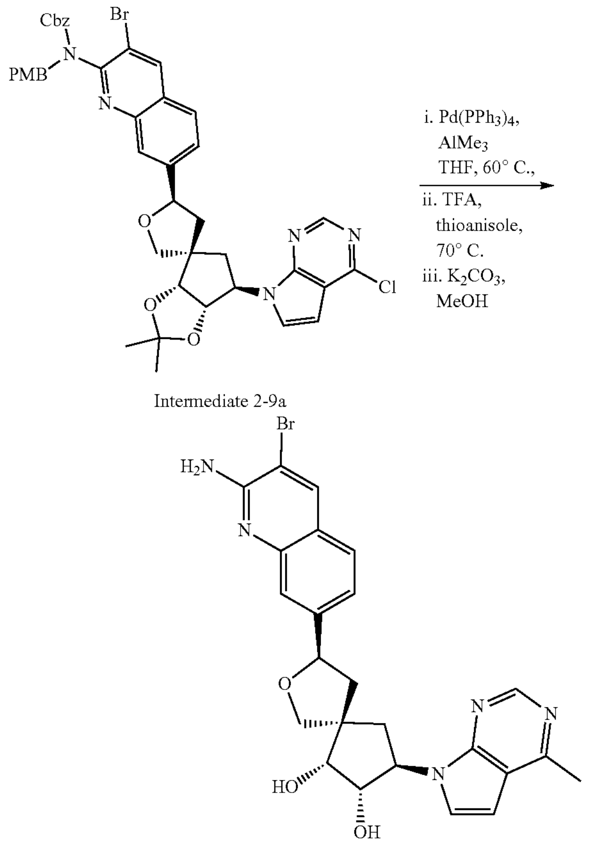

Intermediate 2-9a

Compound 19

A vial was charged with tetrakis(triphenylphosphine)palladium(0) (35 mg, 0.0303 mmol) and Intermediate 2-9a, and dissolved in THE (3 mL). $Me_3Al$ (2M in toluene, 0.33 mL) was then injected and the reaction was heated at 60° C. for 2 hours. The reaction was determined as complete by LC/MS analysis, and it was allowed to cool to ambient temperature at which time 1 mL of methanol was added.

Solvent was removed under a stream of nitrogen gas, followed by vacuum. The residue was dissolved in TFA (5 mL) and thioanisole (5 eq., 0.20 mL) was injected, followed by heating to 65° C. for 1 hour. LC/MS analysis showed that the conversion was not complete, and 5 mL additional TFA was injected and the reaction heated to 80° C. for an additional 1 hour in a sealed vessel. Subsequently, LC/MS analysis showed the reaction was complete.

Solvent was removed under a stream of nitrogen gas, followed by vacuum, and the residue was dissolved in MeOH (3 mL), and then $K_2CO_3$ (3 eq., 140 mg) in $H_2O$ (1 mL) was injected. The reaction was stirred for 1 hour, then neutralized with 0.5 mL AcOH and filtered. The filtrate was then purified by HPLC (10-20% $H_2O/CH_3CN$+0.25% AcOH).

The combined HPLC fractions were concentrated 50% by evaporation and aqueous 2M $Na_2CO_3$ (25 mL) was added to precipitate the product, which was collected by filtration. The filtrate was dried by lyophilisation and transferred to a vial to yield Compound 19 (113 mg, 0.2214 mmol, 65.64% yield) as a white solid.

$^1$H NMR (400 MHz, Acetonitrile-$d_3$+1% d-TFA): δ 8.93 (s, 1H), 8.61 (s, 1H), 7.84-7.67 (m, 3H), 7.50 (dd, J=8.3, 1.6 Hz, 1H), 7.03 (d, J=3.8 Hz, 1H), 5.31-5.08 (m, 2H), 4.54 (dd, J=8.7, 4.3 Hz, 1H), 4.43 (d, J=8.9 Hz, 1H), 3.92 (d, J=4.2 Hz, 1H), 3.80 (d, J=8.9 Hz, 1H), 2.93 (s, 3H), 2.69 (dd, J=12.3, 6.5 Hz, 1H), 2.58 (dd, J=14.0, 10.4 Hz, 1H), 2.21 (dd, J=14.0, 8.4 Hz, 1H) ppm.

LC/MS: $[M+H]^+$ m/z=510.1 amu.

Preparation of Compounds 20 and 21

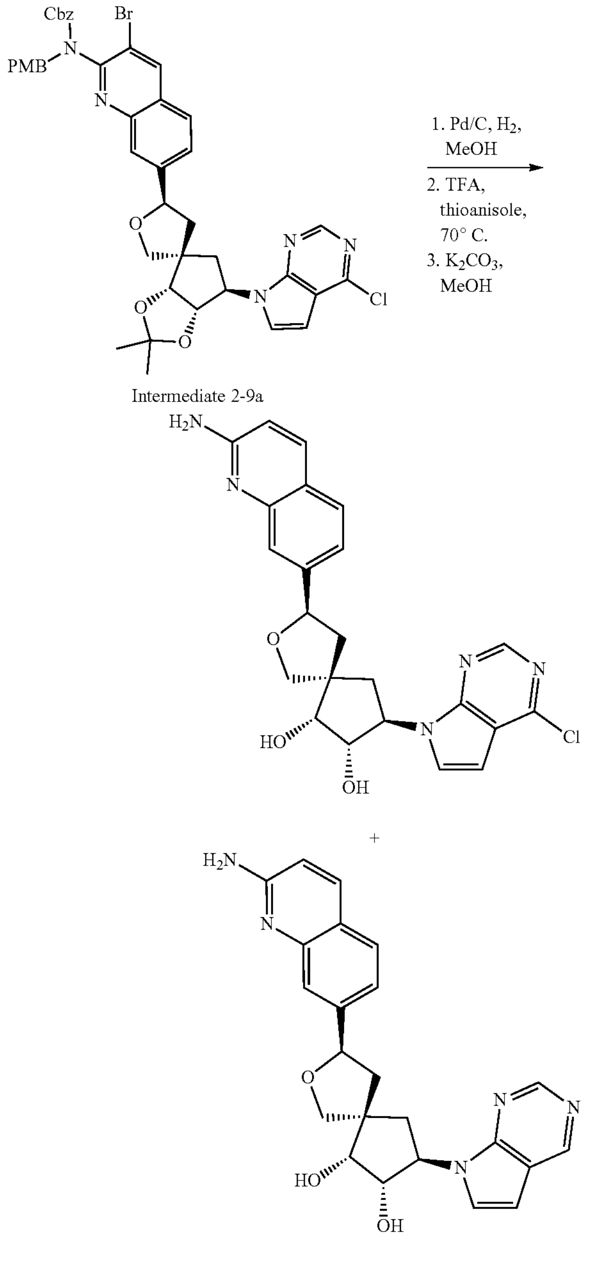

Intermediate 2-9a

Compound 20 & 21

A microwave vial was charged with Intermediate 2-9a (12.4 mg, 0.015 mmol) and palladium on carbon (10%, 4 mg), and methanol was injected under an atmosphere of nitrogen gas. The reaction was placed under hydrogen gas (balloon, atmospheric pressure) and monitored by LC/MS.

After 2 hours, additional palladium on carbon (10%, 4 mg) was added and hydrogenation was continued for 2 hours. The reaction was filtered and concentrated. The filtrate was dissolved in TFA (1 mL) and thioaniosole (50 μL, 5 vol %) was injected. The reaction was sealed and heated to 70° C. for 1 hour.

The solvent was removed under a stream of nitrogen. The residue was dissolved in MeOH (1 mL) and stirred with aqueous 2N $K_2CO_3$ (50 μL, 5 vol %) for 1 hour. The reaction was filtered, and the filtrate was washed with MeOH (1 mL) and purified by HPLC (20 mm, 23 mL/min, 10-30% water/ACN+0.25% TFA buffer). Active fractions were frozen and lyophilized to yield Compounds 20 and 21.

Compound 20:

$^1$H NMR (400 MHz, Acetonitrile-$d_3$): δ 8.51 (d, J=1.5 Hz, 1H), 8.17 (dt, J=9.2, 1.0 Hz, 1H), 7.76 (dd, J=8.4, 1.5 Hz, 1H), 7.62-7.51 (m, 2H), 7.41 (dd, J=8.2, 1.7 Hz, 1H), 6.97-6.83 (m, 1H), 6.68-6.51 (m, 1H), 5.31-4.88 (m, 2H), 4.56-4.44 (m, 1H), 4.36 (dd, J=8.8, 1.5 Hz, 1H), 3.83 (d, J=4.3 Hz, 1H), 3.73 (dd, J=8.9, 1.5 Hz, 1H), 2.65 (dd, J=12.4, 6.7 Hz, 1H), 2.49 (dd, J=13.9, 10.4 Hz, 1H), 2.20-2.04 (m, 1H) ppm. LC/MS: $[M+H]^+$ m/z=452.1 amu.

Compound 21:

$^1$H NMR (400 MHz, Acetonitrile-$d_3$): δ 9.00 (s, 1H), 8.86 (s, 1H), 8.15-8.09 (m, 1H), 7.74 (d, J=8.3 Hz, 1H), 7.69 (d, J=3.7 Hz, 1H), 7.62 (d, J=1.5 Hz, 1H), 7.38 (dd, J=8.3, 1.6 Hz, 1H), 6.88 (d, J=9.3 Hz, 1H), 6.81 (d, J=3.7 Hz, 1H), 5.17-5.04 (m, 2H), 4.46 (dd, J=8.6, 4.3 Hz, 1H), 4.36 (d, J=8.9 Hz, 1H), 3.83 (d, J=4.3 Hz, 1H), 3.71 (d, J=8.9 Hz, 1H), 2.61 (dd, J=12.3, 6.6 Hz, 1H), 2.49 (dd, J=13.9, 10.4 Hz, 1H), 2.15-2.10 (m, 2H) ppm.

LC/MS: $[M+H]^+$ m/z=418.2 amu.

Preparation of Compound 22

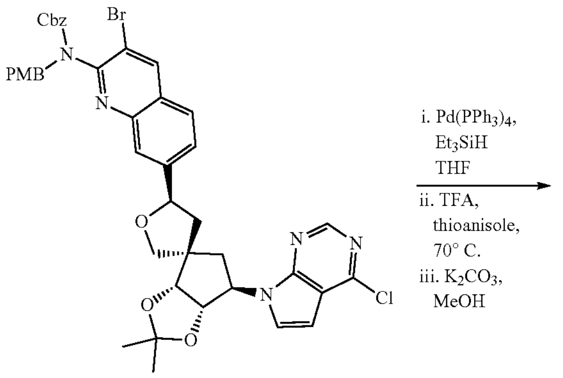

Intermediate 2-9a

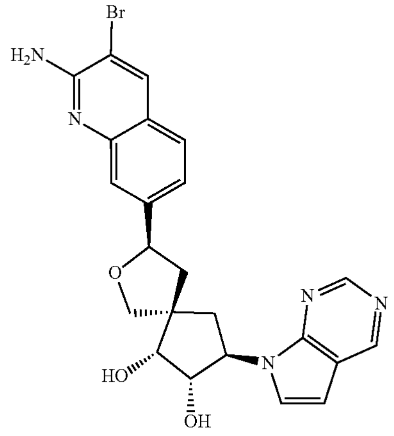

Compound 22

A microwave vial was charged with Intermediate 2-9a (22 mg, 0.0267 mmol) and tetrakis(triphenylphosphine)palladium(0) (5 mg, 0.0043 mmol), and THE (0.3 mL) was injected under argon. Triethylsilane was then injected (5 μL) and after 5 hours, the reaction was filtered and concentrated.

The filtrate was dissolved in TFA (1 mL) and thioaniosole (50 μL, 5 vol %) was injected. The reaction was sealed and heated to 70° C. for 1 hour. Solvent was then removed under a flow of nitrogen gas, followed by vacuum. The crude residue was dissolved in MeOH (1 mL) and stirred with aqueous 2N $K_2CO_3$ (50 μL, 5 vol %) for 1 hour.

The mixture was filtered, and the filtrate was washed with MeOH (1 mL) and purified by HPLC (20 mm, 23 mL/min, 10-30% water/ACN+0.25% TFA buffer). Active fractions were frozen and lyophilized to yield Compound 22 (5.0 mg, 37% yield) as a white solid.

$^1$H NMR (400 MHz, Acetonitrile-$d_3$): δ 8.98 (s, 1H), 8.83 (s, 1H), 8.53 (s, 1H), 7.73-7.63 (m, 3H), 7.42 (dd, J=8.3, 1.5 Hz, 1H), 6.81 (dd, J=3.7, 1.0 Hz, 1H), 5.20-5.00 (m, 2H), 4.47 (dd, J=8.6, 4.3 Hz, 1H), 4.36 (d, J=8.9 Hz, 1H), 3.83 (d, J=4.3 Hz, 1H), 3.73 (d, J=8.8 Hz, 1H), 2.55-2.43 (m, 3H), 2.13 (dd, J=13.9, 8.4 Hz, 1H) ppm.

LC/MS: $[M+H]^+$ m/z=496.1 amu.

Preparation of Compound 23

Compound 23 was synthesized with the general procedures used for Compound 15, using Intermediate 2-9a as the starting material, and using the corresponding amine nucleophile (2N methylamine in methanol). Compound 23 was obtained as a white solid.

$^1$H NMR (500 MHz, Methanol-$d_4$): δ 8.34 (d, J=2.9 Hz, 1H), 8.19 (s, 1H), 7.71-7.60 (m, 2H), 7.36 (dt, J=8.4, 1.9 Hz, 1H), 7.29 (dd, J=3.7, 1.5 Hz, 1H), 6.63 (d, J=3.5 Hz, 1H), 5.20-5.10 (m, 2H), 4.61 (dd, J=8.3, 4.4 Hz, 1H), 4.56 (d, J=8.8 Hz, 1H), 4.02 (d, J=4.4 Hz, 1H), 3.89 (d, J=7.6 Hz, 1H), 3.11 (s, 3H), 2.73-2.61 (m, 2H), 2.18 (dd, J=13.4, 8.3 Hz, 1H), 2.10-2.04 (m, 1H) ppm.

LCMS: $[M+H]^+$ m/z=525.1 amu.

Preparation of Compound 24

Compound 24 was synthesized with the general procedures used for Compound 15, using Intermediate 2-9a as the starting material, and using the corresponding amine nucleophile (2N ethylamine in methanol). Compound 24 was obtained as a white solid.

$^1$H NMR (400 MHz, DMSO-$d_6$): δ 8.53 (s, 1H), 8.25 (s, 1H), 7.67 (d, J=8.3 Hz, 1H), 7.58 (s, 1H), 7.49 (s, 1H), 7.30-7.20 (m, 1H), 6.90-6.80 (m, 1H), 5.05-4.92 (m, 2H), 4.32 (dd, J=8.8, 4.0 Hz, 1H), 4.25 (d, J=8.7 Hz, 1H), 3.70 (d, J=4.0 Hz, 1H), 3.60 (d, J=8.8 Hz, 1H), 2.51 (dd, J=12.1, 6.3 Hz, 1H), 2.35 (dd, J=13.8, 10.5 Hz, 1H), 1.92-1.70 (m, 2H), 1.19 (t, J=7.2 Hz, 3H) ppm.

LCMS: $[M+H]^+$ m/z=539.1 amu.

Preparation of Compound 25

Compound 25 was synthesized with the general procedures used for Compound 15, using Intermediate 2-9a as the starting material, and using the corresponding amine nucleophile (isopropylamine). Compound 25 was obtained as a white solid.

$^1$H NMR (400 MHz, DMSO-$d_6$): δ 8.54 (s, 1H), 8.26 (s, 1H), 7.69 (d, J=8.3 Hz, 1H), 7.59 (s, 1H), 7.51 (s, 1H), 7.30-7.22 (m, 1H), 6.96-6.87 (m, 1H), 5.08-4.89 (m, 2H), 4.34 (dd, J=8.8, 4.0 Hz, 1H), 4.26 (d, J=8.8 Hz, 1H), 4.20-4.10 (m, 1H), 3.72 (d, J=4.0 Hz, 1H), 3.61 (d, J=8.8 Hz, 1H), 2.52 (dd, J=12.2, 6.3 Hz, 1H), 2.41-2.31 (m, 1H), 1.89 (dd, J=13.7, 8.1 Hz, 1H), 1.79 (dd, J=12.2, 9.6 Hz, 1H), 1.24 (d, J=6.4 Hz, 6H) ppm.

LCMS: $[M+H]^+$ m/z=553.1 amu.

Preparation of Compound 26

Compound 26 was synthesized with the general procedures used for Compound 15, using Intermediate 2-9a as the starting material, and using the corresponding amine nucleophile (n-propylamine). Compound 26 was obtained as a white solid.

$^1$H NMR (400 MHz, DMSO-$d_6$): δ 8.54 (s, 1H), 8.27 (s, 1H), 7.69 (d, J=8.3 Hz, 1H), 7.64-7.40 (m, 2H), 7.27 (dd, J=8.3, 1.6 Hz, 1H), 6.99-6.73 (m, 1H), 5.07-4.92 (m, 2H), 4.40-4.30 (m, 1H), 4.26 (d, J=8.8 Hz, 1H), 3.72 (d, J=4.0 Hz, 1H), 3.61 (d, J=8.8 Hz, 1H), 2.52 (dd, J=12.2, 6.3 Hz, 1H), 2.37 (dd, J=13.8, 10.6 Hz, 1H), 1.96-1.73 (m, 2H), 1.60 (q, J=7.3 Hz, 2H), 0.90 (t, J=7.4 Hz, 3H) ppm.

LCMS: $[M+H]^+$ m/z=553.1 amu.

Example 3: Syntheses of Other Compounds

General Route 1

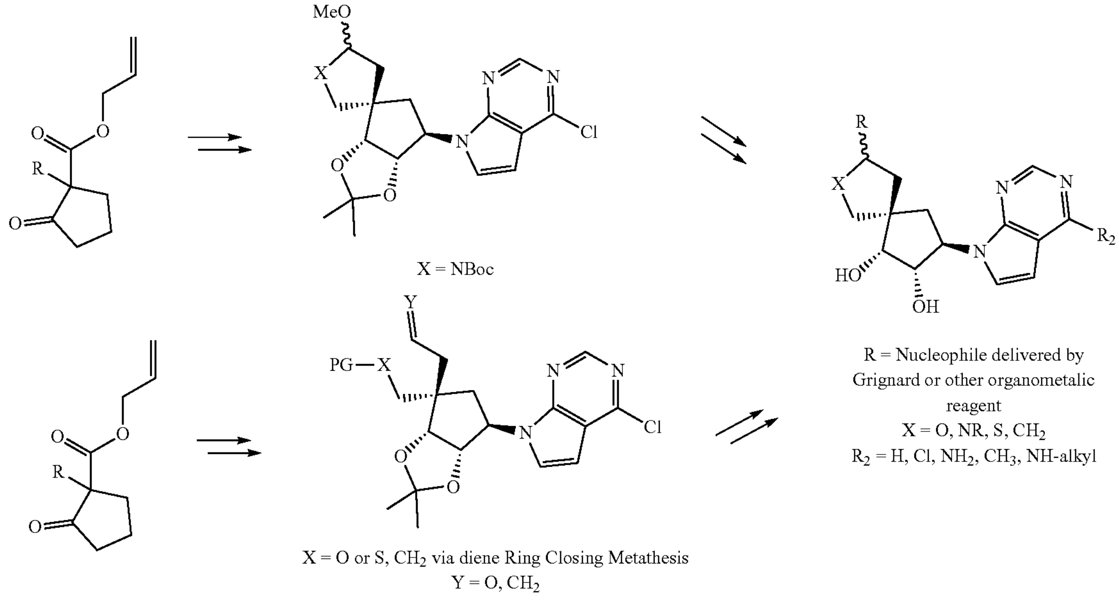

This general approach can be used to synthesize a variety of compounds hereof. The installation of a variety of groups in the R position is compatible with the starting allyl 2-oxocyclopentane-1-carboxylate compound, and is accomplished prior to decarboxylative enantioselective allylic alkylation. The installation of the nucleoside can then be accompanied by cyclization of a hetereocyclyl or cycloalkyl, followed by nucleophilic addition with a Grignard or other organometallic reagent, or nucleophile.

In other embodiments, compounds of the invention have nucleosides containing a spiro-carbocycle or spiro-heterocyclyl, with ring sizes from 5-6 members, and can also be synthesized with this general approach. The hetereoatom in the spiro-heterocyclyl is selected from oxygen, nitrogen and sulfur. The spiro ring can have either stereo-configuration, and a substitution pattern as described herein. In preferred embodiments, the R group is an optionally substituted aryl or heteroaryl, wherein one, two, or three optional substituents are independently selected from H, F, Cl, Br, methyl, $NH_2$, $N(CH_3)_2$, OH or $O(CH_3)$.

General Route 2

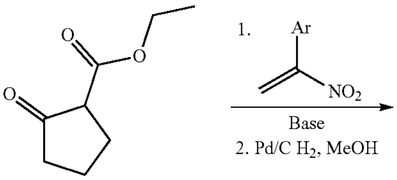

-continued

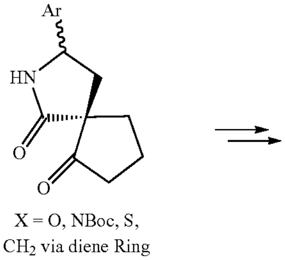

X = O, NBoc, S, CH2 via diene Ring Closing Metathesis

-continued

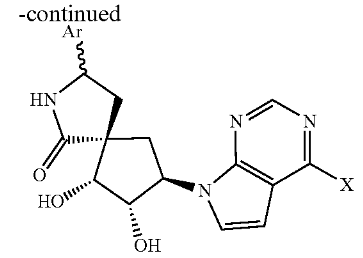

X = H, Cl, $NH_2$

Alternatively, the approach of General Route 1 is not limited to the employment of decarboxylative enantioselective allylic alkylation. The beta-ketoester building block may alternatively be employed in nucleophilic addition chemistry to a variety of electrophiles. Specifically, the beta-ketoester can undergo nucleophilic addition to unsaturated nitro compounds. Following reduction and spontaneous lactam formation, compounds bearing a lactam at the indicated position in the General Route 2 scheme can be obtained.

General Route 3

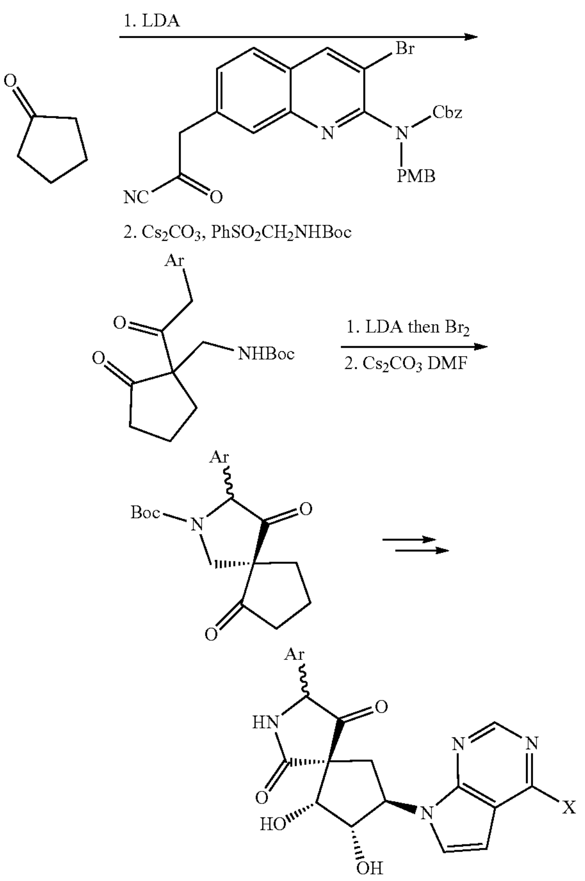

X = H, Cl, $NH_2$

The carbonyl of compounds obtained through General Route 2 could be transposed through modification of the aryl fragment. A ketone could be introduced via Negishi coupling of benzyl (3-bromo-7-iodoquinolin-2-yl)(4-methoxybenzyl)carbamate with 2-tert-butoxy-2-oxoethylzinc bromide. The ester is converted to its corresponding Mander's reagent and reacts in the presence of the lithium enolate of cyclopentanone to yield a new 1,3-dicarbonyl species known to participate in the Mannich chemistry referenced in Y. Numajiri, B. P. Pritchett, K. Chiyoda, and B. M. Stoltz published in *J. Am. Chem. Soc.* in 2015, volume 137, on pages 1040-1043. From here, selective bromination of the benzylic ketone and cyclization yields the corresponding bicyclic species, which is readily converted to its corresponding nucleoside analog.

Biological Experiments

PRMT5 Enzymatic Inhibition Assay

A chemiluminescence immunoassay (CLIA) measuring the amount of PRMT5-mediated histone methylation was performed in a 96-well plate format according to the manufacturer's protocol (BPS Biosciences, Cat #52002L). A 96-well plate precoated with histone H4 peptide was rehydrated prior to use. A master mix containing PRMT5 substrate S-adenosylmethionine, reaction buffer, and purified PRMT5 enzyme was added to create reaction-competent wells. Wells lacking either S-adenosylmethionine substrate or PRMT5 enzyme were created as negative controls. 10 test concentrations, ranging from 100 μM to 10 nM, of the test compound were prepared using a 1:3 serial dilution in $dH_2O$. 5 μL of each test concentration was added into a reaction-competent well. 5 μL of a 1% DMSO aqueous solution lacking inhibitor was added into negative control wells and into a reaction-competent well, creating a positive control well. The final reaction volume in each well was 50 μL, and the final concentration of the test compound in each well ranged from 10 μM to 1 nM. A known inhibitor of PRMT5, EPZ015666, was tested in parallel reaction wells as an assay validation control. The 96-well plate was incubated for 1 hour at room temperature.

Upon completion of the incubation, the reaction supernatant in each well was discarded. Wells were washed with 1×TBST and incubated in blocking buffer for 1 hour. The wells were incubated with a primary antibody recognizing methylated Arg3 residues on Histone H4 for 1 hour. The wells were washed with 1×TBST again and subsequently incubated with an HRP-conjugated secondary antibody for 30 minutes. The wells were washed again with 1×TBST, and equal parts of the chemiluminescence reagents were added into each well. Quantification of luminescence was measured in a plate reader.

Luminescence values were normalized against the positive and negative controls to convert the data into % PRMT5 activity. An inhibitor concentration-dependent curve was plotted against % PRMT5 activity and am $IC_{50}$ value was determined for each compound. See Table 3. "A" represents an $IC_{50}$ of 100 nM or less, "B" represents an $IC_{50}$ of 101 nM to 500 nM, and "C" represents an $IC_{50}$ of greater than 500 nM.

Cell Line Growth Retardation Assay

Cells were seeded at densities of 1,000-5,000 cells per well in 48-well tissue culture plates. After a 24 h rest period, cells were treated with compound at 1 μM, 0.2 μM, 0.04 μM, 0.008 μM, 0.0016 μM, and 0.00032 μM. A group of cells were treated with the vehicle in which the compound was prepared and served as a control. Prior to treatment, cells were counted and this count was used as a baseline for the calculation of growth inhibition. The cells were grown in the presence of compounds for 6 days and were counted on day 6. All cell counting was performed using a Synentec Cellavista plate imager. Growth inhibition was calculated as a ratio of cell population doublings in the presence of compound versus the absence of compound and expressed as the maximum percentage growth inhibition achieved across the range of tested concentrations of the compound ("maximum effect" or "ME") calculated by fitting curves to data points from each dose-response assay using the Proc NLIN function in SAS for Windows version 9.2 (SAS Institute, Inc.).

Designation of Sensitive and Resistant Cohorts and Calculation of Average Maximum Effect Values Human cancer cell lines were grouped as "sensitive" or "resistant" to PRMT5 inhibition based on whether their growth was retarded by JNJ-64619178 (i.e., (1S,2R,3R,5R)-3-(2-(2-amino-3-bromoquinolin-7-yl)ethyl)-5-(4-amino-7H-pyrrolo[2,3-d]pyrimidin-7-yl)cyclopentane-1,2-diol) (data not shown; see Table 4). These sensitive and resistant cohorts were interrogated for response to each compound, and ME was calculated for each cell line using the same technique described above. Average MEs for the sensitive and resistant cohorts were calculated as arithmetic means of the group. See Table 3. "A" represents a percent of maximum effect of 60% or greater, "B" represents a percent of maximum effect of 30% to 59%, and "C" represents a percent of maximum effect of 29% or lower.

Caco-2 Assay ($P_{app}$ A to B)

The degree of bi-directional human intestinal permeability for compounds was estimated using a Caco-2 cell permeability assay. Caco-2 cells were seeded onto polyethylene membranes in 96-well plates. The growth medium was refreshed every 4 to 5 days until cells formed a confluent cell monolayer. HBSS with 10 mM HEPES at pH 7.4 was used as the transport buffer. Compounds were tested at 2 μM bi-directionally in duplicate. Digoxin, nadolol and metoprolol were included as standards. Digoxin was tested at 10 μM bi-directionally in duplicate, while nadolol and metoprolol were tested at 2 μM in the A to B direction in duplicate. The final DMSO concentration was adjusted to less than 1% for all experiments. The plate was incubated for 2 hours in a $CO_2$ incubator at 37° C., with 5% $CO_2$ at saturated humidity. After incubation, all wells were mixed with acetonitrile containing an internal standard, and the plate was centrifuged at 4,000 rpm for 10 minutes. 100 μL supernatant was collected from each well and diluted with 100 μL distilled water for LC/MS/MS analysis. Concentrations of test and control compounds in starting solution, donor solution, and receiver solution were quantified by LC/MS/MS, using peak area ratio of analyte/internal standard.

The apparent permeability coefficient $P_{app}$ (cm/s) was calculated using the equation:

$$P_{app}=(dC_r/dt)\times V_r/(A\times C_0),$$

where $dC_r/dt$ is the cumulative concentration of compound in the receiver chamber as a function of time (μM/s); $V_r$ is the solution volume in the receiver chamber (0.075 mL on the apical side, 0.25 mL on the basolateral side); A is the surface area for the transport, which is 0.0804 $cm^2$ for the area of the monolayer; and Co is the initial concentration in the donor chamber (μM). $P_{app}$ scores for example compounds are presented in Table 3. "A" represents a score of 1 or greater, "B" represents a score of 0.2 to 0.99, and "C" represents a score of less than 0.2.

The efflux ratio was calculated using the equation:

$$\text{Efflux Ratio}=P_{app}(BA)/P_{app}(AB)$$

Percent recovery was calculated using the equation:

$$\%\ \text{Recovery}=100\times[(V_r\times C_r)+(V_d\times C_d)]/(V_d\times C_0),$$

where Vd is the volume in the donor chambers, which are 0.075 mL on the apical side and 0.25 mL on the basolateral side; and $C_d$ and $C_r$ are the final concentrations of transport compound in donor and receiver chambers, respectively.

Measurement of Compound Metabolic Stability

The metabolic stability of compounds was determined in hepatocytes from human, mice and rats. Compounds were diluted to 5 μM in Williams' Medium E from 10 mM stock solutions. 10 μL of each compound was aliquoted into a well of a 96-well plate and reactions were started by aliquoting 40 μL of a 625,000 cells/mL suspension into each well. The plate was incubated at 37° C. with 5% $CO_2$. At each corresponding time point, the reaction was stopped by quenching with ACN containing internal standards (IS) at a 1:3. Plates were shaken at 500 rpm for 10 min, and then centrifuged at 3,220×g for 20 minutes. Supernatants were transferred to another 96-well plate containing a dilution solution. Supernatants were analyzed by LC/MS/MS. The Half-lives (in minutes) and $CL_{int}$ values (in μL/min/$10^6$ cells) of example compounds, as measured in mouse hepatocytes, are presented in Table 3. For half-life, "A" represents greater than 50 minutes, "B" represents 15 to 50 minutes, and "C" represents less than 15 minutes. For $CL_{int}$, "A" represents greater than 100 μL/min/$10^6$ cells, "B" represents 50 to 100 μL/min/$10^6$ cells, and "C" represents less than 50 μL/min/$10^6$ cells.

The remaining percent of compound after incubation was calculated using the following equation:

% Remaining Compound=Peak Area Ratios of Tested Compound vs. Internal Standard at End Point Peak Area Ratios of Tested Compound vs. Internal Standard at Start Point Compound half-life and $CL_{int}$ were calculated using the following equations:

$C_t=C_0*e^{-k*t}$(first order kinetics); when $C_t=12C_0$, $t_{1/2}=\ln 2/k=0.693/k$; and $CL_{int}=k/(1{,}000{,}000\ \text{cells/mL})$ Activity-Guided Selection of Inhibitors Subgenera of PRMT5 inhibitors having desirable properties were identified using a combination of in vitro data.

In particular, the results from the assays described above (e.g., Cell Line Growth Retardation Assay, PRMT5 Enzymatic Inhibition Assay, Caco-2 Assay ($P_{app}$ A to B), Measurement of Compound Metabolic Stability, and Designation of Sensitivity and Resistant Cohorts and Calculation of Average Maximum Effect) were used to select compounds having structural and functional features defined in the subgenera of Formula (V).

In particular, a desirable property of compounds examined in sensitive and resistant cell lines, as described above, is having an average ME for the drug-sensitive cell lines of Table 4 of at least 60% or greater and having an average ME for the drug-resistant cell lines of Table 4 of about 60% or less.

The skilled artisan would readily recognize that the results of additional in vitro assays (e.g., CYP enzymatic inhibition, hERG inhibition, compound solubility, target-specificity analysis), as well as the results of in vivo assays (e.g., rodent xenograft studies, rodent pharmacokinetic and single-dose saturation studies, rodent maximum tolerated dose studies, and oral bioavailability) could be used to identify other subgenera of PRMT5 inhibitors, or to narrow subgenera determined using other results, for example, the subgenera of Formula (V).

Example of Predicted Binding Affinities for PRMT5 of Example Compounds

The structure of Compound 15 bound to PRMT5:MEP50 was determined by X-ray crystallography:

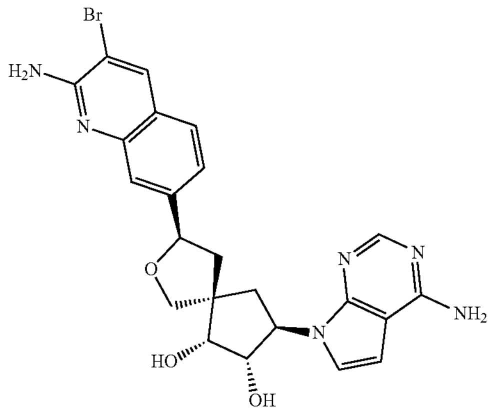 [SMILES: Nc1nc2cc([C@H]3C[C@@]4(CO3)C[C@@H](n3ccc5c(N)ncnc53)[C@H](O)[C@@H]4O)ccc2cc1Br]

Using version 2019.0102 of the Molecular Operating Environment (MOE) software package (Chemical Computing Group, Montreal, Canada), conformational ensembles of example compounds were generated via flexible alignment to the central core structure of Compound 15 as found in the X-ray structure. This furnished an ensemble of energetically accessible conformers of all substituent groups of interest.

Energy minimization in the crystal structure of PRMT5:MEP50 and the predicted, approximate binding affinities were determined utilizing two methods: (i) implementing GB-IV using the AMBER10:EHT force field in the aforementioned MOE software package ("Method 1"); and (ii) implementing MMGB-SA using the OPLS3e force field in the Prime module of the Schrodinger software suite (v. 2020-1, Schrodinger LLC, New York, New York) ("Method 2").

In some embodiments, compounds of the invention have predicted binding affinities that are superior to that of Compound 15 as determined by one of the methods. In preferred embodiments, compounds of the invention have predicted binding affinities that are superior to that of Compound 15 as determined by both of the methods.

Predicted binding affinity values for example compounds as determined with each method are presented in Table 5. Values are in arbitrary units ("A.U."), where more negative values correspond to higher predicted affinities. The predicted binding affinity of Compound 15 when using Method 1 is −8.84, and when using Method 2 is −15.08.

TABLE 3

| Cmpd | PRMT5 $IC_{50}$ (nM) | AvgSens ME (%) | AvgRes ME (%) | $P_{app}$ A-to-B | Half-life (mins) | $CL_{int}$ (μL/min/$10^6$) |
|---|---|---|---|---|---|---|
| 1 | C | C | C | | | |
| 2 | C | C | C | | | |
| 3 | C | C | C | | | |
| 4 | B | C | C | | | |
| 5 | B | C | C | | | |
| 6 | C | C | C | | | |
| 7 | A | A | B | | | |
| 8 | B | C | C | C | | |
| 9 | A | B | C | C | | |
| 10 | B | C | C | | | |
| 15 | A | A | B | C | A | C |
| 16 | A | A | B | | | |
| 17 | A | A | B | B | B | B |
| 18 | A | C | C | | | |
| 19 | A | A | B | A | A | C |
| 20 | A | A | B | | C | A |
| 21 | A | A | B | | C | A |
| 22 | A | A | B | A | C | A |
| 23 | A | A | B | B | A | C |
| 24 | A | A | B | A | B | B |
| 25 | A | B | C | | | |
| 26 | A | B | B | | | |

TABLE 4

| Cell Line Name | Cohort |
|---|---|
| EFM-19 | Sensitive |
| MV4-11 | Sensitive |
| HUPT4 | Sensitive |
| SKCO1 | Sensitive |
| JIMT-1 | Sensitive |
| HCC1954 | Sensitive |
| NCI-H929 | Sensitive |
| OVCAR3 | Sensitive |
| OPM-2 | Sensitive |
| NCIH747 | Sensitive |
| MDA-MB-453 | Sensitive |
| SW480 | Sensitive |
| M275 | Sensitive |
| HT29 | Sensitive |
| NCI-H2286 | Sensitive |
| KMS-27 | Resistant |
| ML-2 | Resistant |
| UMUC-15 | Resistant |
| NCI-H1581 | Resistant |
| OVCA429 | Resistant |
| CAL-51 | Resistant |
| UMUC-7 | Resistant |
| NCI-H23 | Resistant |
| NCI-H647 | Resistant |
| NCI-H1650 | Resistant |
| Cha-Go-K-1 | Resistant |
| SW48 | Resistant |
| MDA-MB-231 | Resistant |
| DU4475 | Resistant |
| EFM-192A | Resistant |

TABLE 5
| Compound Structure | Method 1 (A.U.) | Method 2 (A.U.) |
| --- | --- | --- |
| 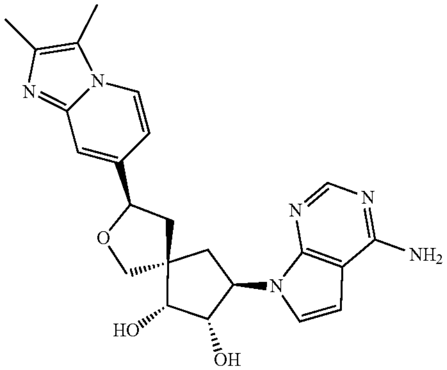 [SMILES: Cc1nc2cc([C@H]3C[C@@]4(CO3)C[C@@H](n3ccc5c(N)ncnc53)[C@H](O)[C@@H]4O)ccn2c1C] | −9.81 | −37.26 |
| 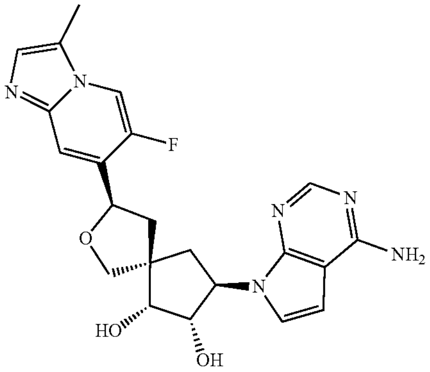 [SMILES: Cc1cnc2cc([C@H]3C[C@@]4(CO3)C[C@@H](n3ccc5c(N)ncnc53)[C@H](O)[C@@H]4O)c(F)cn12] | −9.58 | −35.10 |
| 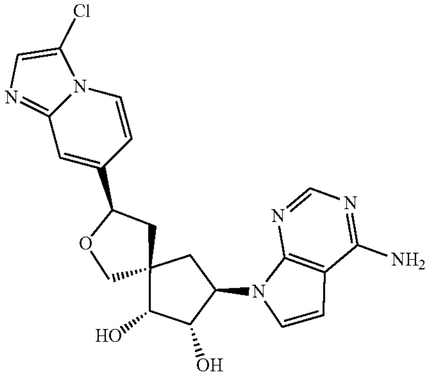 | −9.48 | −55.19 |
| 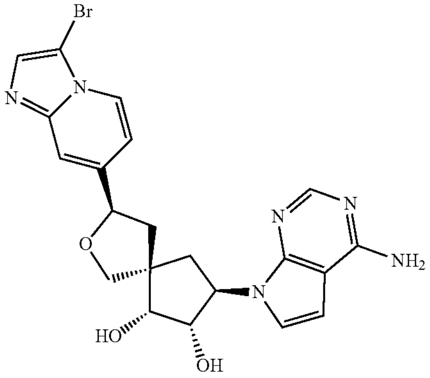 [SMILES: Nc1ncnc2c1ccn2[C@@H]1C[C@@]2(CO[C@@H](c3ccn4c(Cl)cnc4c3)C2)[C@@H](O)[C@H]1O] | −9.45 | −51.96 |

TABLE 5-continued
| Compound Structure | Method 1 (A.U.) | Method 2 (A.U.) |
|---|---|---|
| 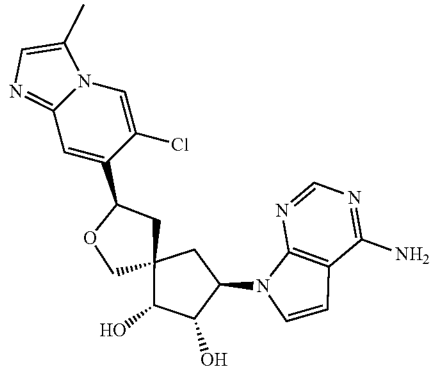 | −9.78 | −29.44 |
| 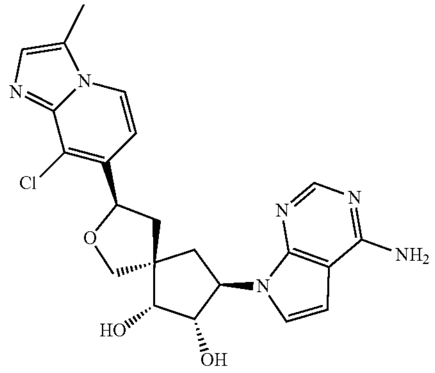 [SMILES: Cc1cnc2c(Cl)c([C@H]3C[C@@]4(CO3)C[C@@H](n3ccc5c(N)ncnc53)[C@H](O)[C@@H]4O)ccn12] | −8.60 | 2.36 |
| 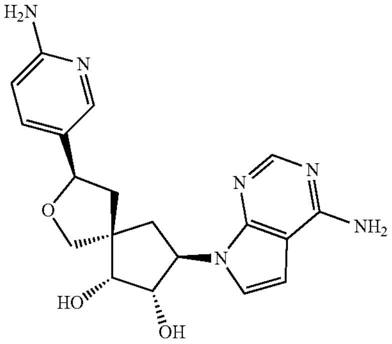 [SMILES: Nc1ccc([C@H]2C[C@@]3(CO2)C[C@@H](n2ccc4c(N)ncnc42)[C@H](O)[C@@H]3O)cn1] | −9.25 | −34.32 |
| 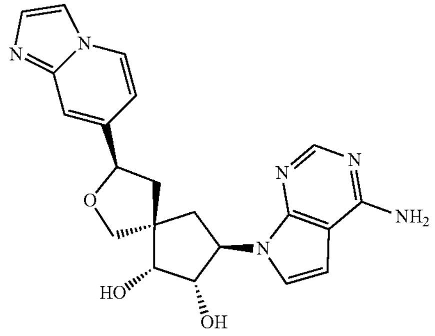 [SMILES: Nc1ncnc2c1ccn2[C@@H]1C[C@@]2(CO[C@@H](c3ccn4ccnc4c3)C2)[C@@H](O)[C@H]1O] | −9.21 | −28.00 |

TABLE 5-continued
| Compound Structure | Method 1 (A.U.) | Method 2 (A.U.) |
|---|---|---|
| 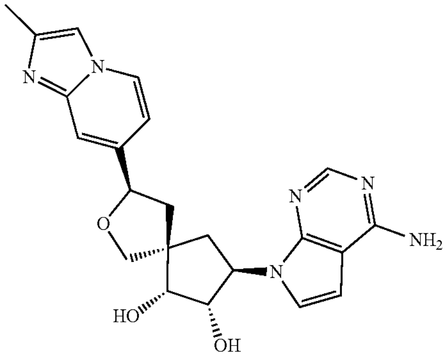 [SMILES: Cc1cn2ccc([C@H]3C[C@@]4(CO3)C[C@@H](n3ccc5c(N)ncnc53)[C@H](O)[C@@H]4O)cc2n1] | −9.41 | −27.19 |
| 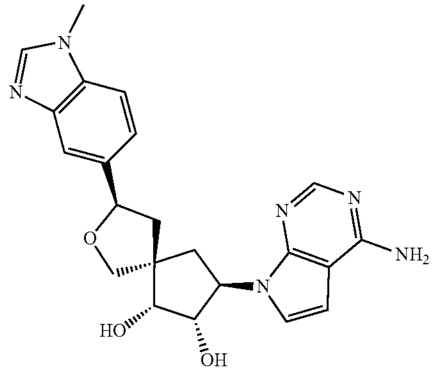 [SMILES: Cn1cnc2cc([C@H]3C[C@@]4(CO3)C[C@@H](n3ccc5c(N)ncnc53)[C@H](O)[C@@H]4O)ccc21] | −9.47 | −52.92 |
| 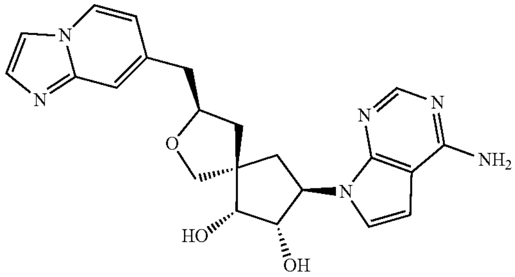 [SMILES: Nc1ncnc2c1ccn2[C@@H]1C[C@@]2(CO[C@@H](Cc3ccn4ccnc4c3)C2)[C@@H](O)[C@H]1O] | −10.48 | −50.07 |
| 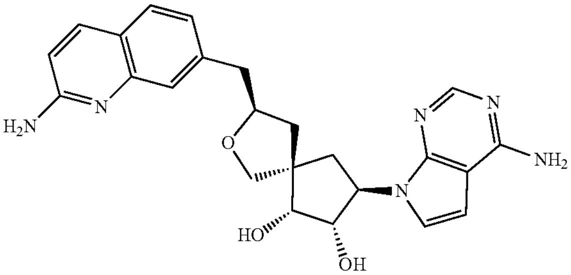 [SMILES: Nc1ccc2ccc(C[C@H]3C[C@@]4(CO3)C[C@@H](n3ccc5c(N)ncnc53)[C@H](O)[C@@H]4O)cc2n1] | −4.13 | 142.75 |
| 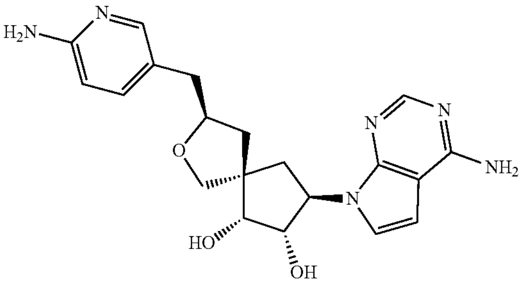 [SMILES: Nc1ccc(C[C@H]2C[C@@]3(CO2)C[C@@H](n2ccc4c(N)ncnc42)[C@H](O)[C@@H]3O)cn1] | −9.91 | −18.55 |

TABLE 5-continued
| Compound Structure | Method 1 (A.U.) | Method 2 (A.U.) |
|---|---|---|
| 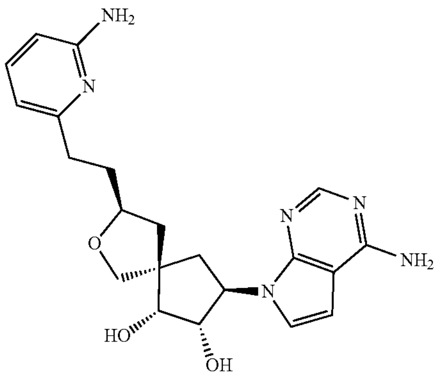 [SMILES: Nc1cccc(CC[C@H]2C[C@@]3(CO2)C[C@@H](n2ccc4c(N)ncnc42)[C@H](O)[C@@H]3O)n1] | −9.90 | −52.45 |
| 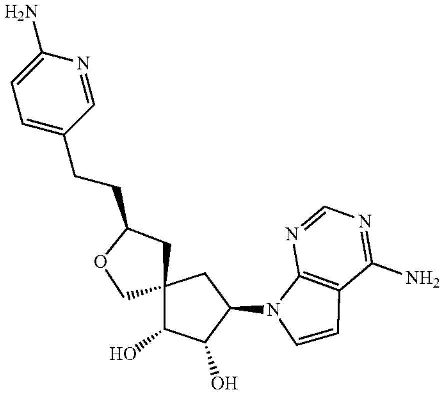 [SMILES: Nc1ccc(CC[C@H]2C[C@@]3(CO2)C[C@@H](n2ccc4c(N)ncnc42)[C@H](O)[C@@H]3O)cn1] | −9.95 | −51.74 |
| 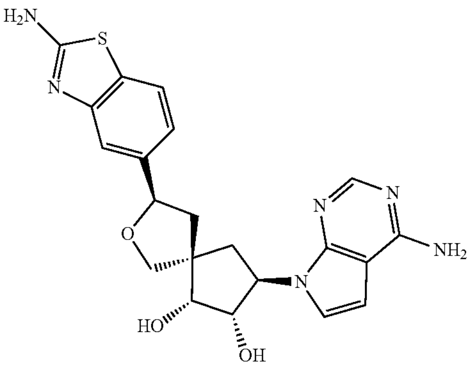 [SMILES: Nc1nc2cc([C@H]3C[C@@]4(CO3)C[C@@H](n3ccc5c(N)ncnc53)[C@H](O)[C@@H]4O)ccc2s1] | −9.39 | −21.66 |
| 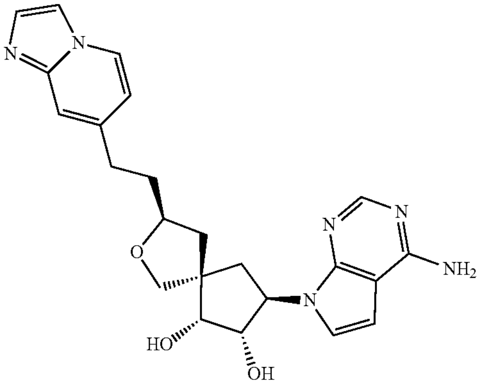 [SMILES: Nc1ncnc2c1ccn2[C@@H]1C[C@@]2(CO[C@@H](CCc3ccn4ccnc4c3)C2)[C@@H](O)[C@H]1O] | −10.24 | −50.13 |

TABLE 5-continued
| Compound Structure | Method 1 (A.U.) | Method 2 (A.U.) |
|---|---|---|
| 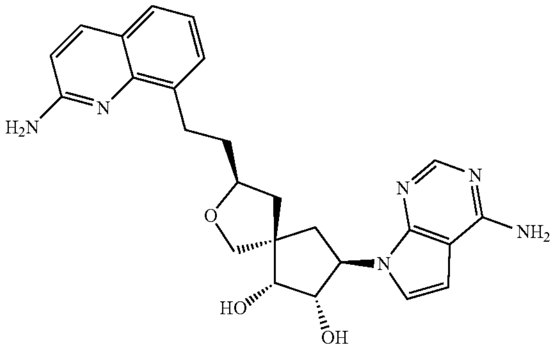 [SMILES: Nc1ccc2cccc(CC[C@H]3C[C@@]4(CO3)C[C@@H](n3ccc5c(N)ncnc53)[C@H](O)[C@@H]4O)c2n1] | −8.69 | −8.81 |
| 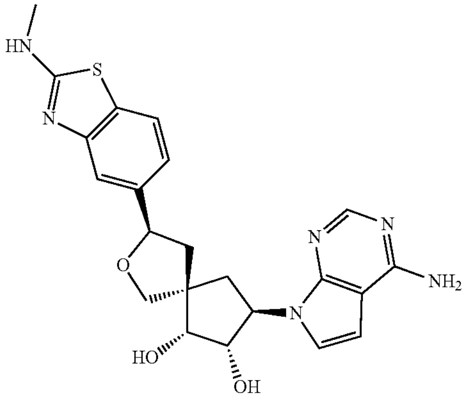 [SMILES: CNc1nc2cc([C@H]3C[C@@]4(CO3)C[C@@H](n3ccc5c(N)ncnc53)[C@H](O)[C@@H]4O)ccc2s1] | −9.70 | −20.00 |
| 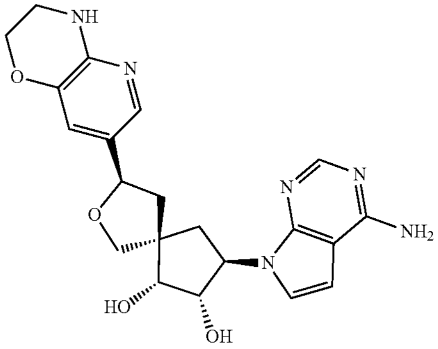 [SMILES: Nc1ncnc2c1ccn2[C@@H]1C[C@@]2(CO[C@@H](c3cnc4c(c3)OCCN4)C2)[C@@H](O)[C@H]1O] | −10.10 | −33.48 |
| 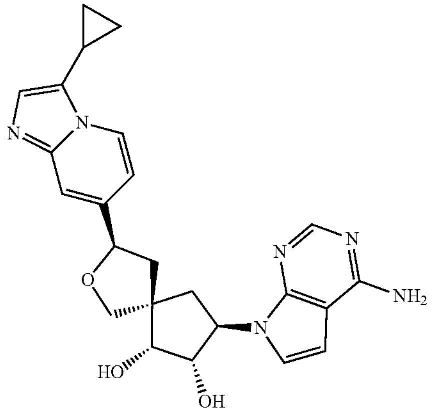 [SMILES: Nc1ncnc2c1ccn2[C@@H]1C[C@@]2(CO[C@@H](c3ccn4c(C5CC5)cnc4c3)C2)[C@@H](O)[C@H]1O] | −8.39 | −26.78 |

TABLE 5-continued
| Compound Structure | Method 1 (A.U.) | Method 2 (A.U.) |
|---|---|---|
| 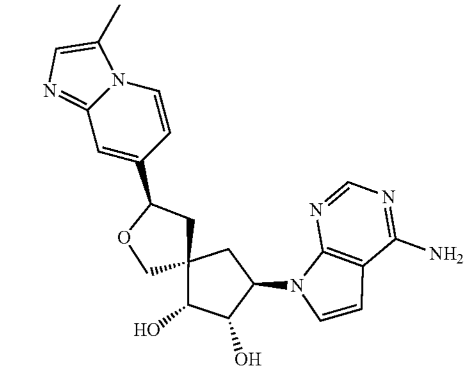 [SMILES: Cc1cnc2cc([C@H]3C[C@@]4(CO3)C[C@@H](n3ccc5c(N)ncnc53)[C@H](O)[C@@H]4O)ccn12] | −9.87 | −50.30 |
| 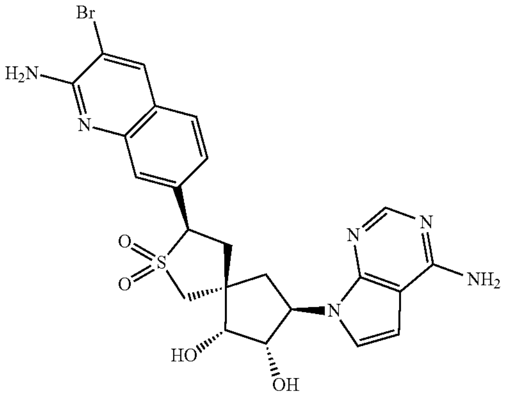 [SMILES: Nc1nc2cc([C@H]3C[C@]4(C[C@@H](n5ccc6c(N)ncnc65)[C@H](O)[C@@H]4O)CS3(=O)=O)ccc2cc1Br] | −8.29 | −15.42 |
| 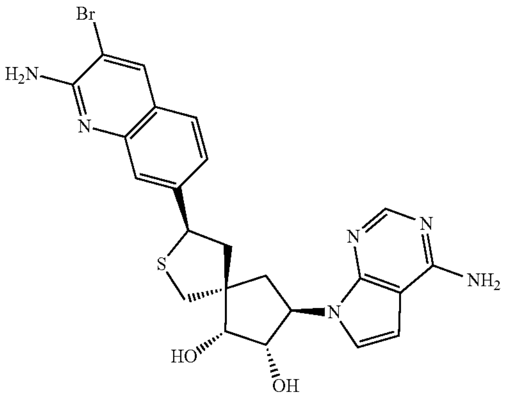 [SMILES: Nc1nc2cc([C@H]3C[C@@]4(CS3)C[C@@H](n3ccc5c(N)ncnc53)[C@H](O)[C@@H]4O)ccc2cc1Br] | −7.69 | −10.32 |

We claim:

1. A compound having the structure of Formula II:

(Formula II)

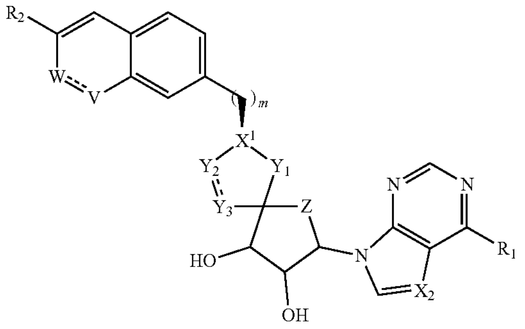

or a pharmaceutically acceptable salt thereof, wherein:

⋱ in each instance is independently a double bond or a single bond;

$R_1$ is H, halogen, $C_1$-$C_4$ alkyl, $C_2$-$C_4$ alkenyl, —O($R_a$), $C_3$-$C_6$ cycloalkyl, $C_3$-$C_7$ heterocyclyl or N($R_a$)$_2$;

$R_2$ is H, halogen, hydroxyl, cyano, —C(O)$NH_2$, —C(O)N($R_a$)$_2$, —C(O)O($R_a$), —C(O)$R_a$, —N($R_a$)$_2$, —O($R_a$), $C_3$-$C_6$ cycloalkyl, $C_3$-$C_7$ heterocyclyl, optionally substituted $C_1$-$C_4$ alkyl or optionally substituted $C_2$-$C_6$ alkenyl;

W is C($R_b$) or C(O), with the proviso that V is NH and the ⋱ between W and V is a single bond when W is C(O);

V is CH, NH or N, with the proviso that W is C($R_b$) and the ⋱ between W and V is a double bond when V is CH or N;

$X_1$ and $X_2$ are each independently CH or N;

$Y_1$ is ($CH_2$), or C(O), with the proviso that $Y_1$ cannot be C(O) when $Y_2$ or $Y_3$ is C(O);

$Y_2$ is $CH_2$, C(O), S, $SO_2$, O or $NR_a$, with the provisos that:

$Y_2$ cannot be C(O) when $Y_1$ or $Y_3$ is C(O); and the ⋱ between $Y_2$ and $Y_3$ is a single bond;

$Y_3$ is $CH_2$ or C(O), with the provisos that:

$Y_3$ cannot be C(O) when $Y_1$ or $Y_2$ is C(O); and the ⋱ between $Y_2$ and $Y_3$ is a single bond; or $Y_2$ and $Y_3$ are CH and the ⋱ between $Y_2$ and $Y_3$ is a double bond;

Z is $CH_2$, O, S or NH;

$R_a$ in each instance is independently H, $C_1$-$C_4$ alkyl or $C_3$-$C_6$ cycloalkyl;

$R_b$ is H, halogen, hydroxyl, cyano, —C(O)$NH_2$, —C(O)N($R_a$)$_2$, —C(O)O($R_a$), —C(O)$R_a$, —N($R_a$)$_2$, —O($R_a$), $C_3$-$C_6$ cycloalkyl, $C_3$-$C_7$ heterocyclyl, optionally substituted $C_1$-$C_4$ alkyl or optionally substituted $C_2$-$C_6$ alkenyl;

m is 0, 1, 2 or 3; and n is 1 or 2.

2. The compound of claim 1 having the structure of Formula IIa:

(Formula IIa)

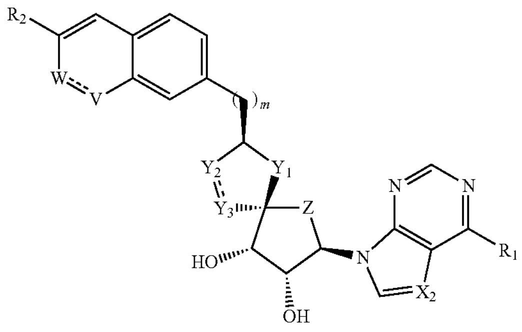

or a pharmaceutically acceptable salt thereof.

3. The compound of claim 1 having the structure of Formula IV:

(Formula IV)

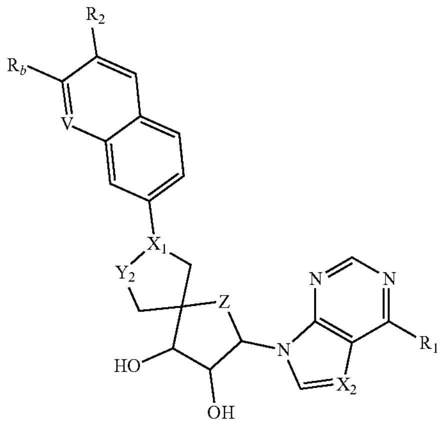

or a pharmaceutically acceptable salt thereof, wherein:

V is CH or N; and $Y_2$ is $CH_2$, S, O or N($R_a$).

4. The compound of claim 3 having the structure of Formula IVa:

(Formula IVa)

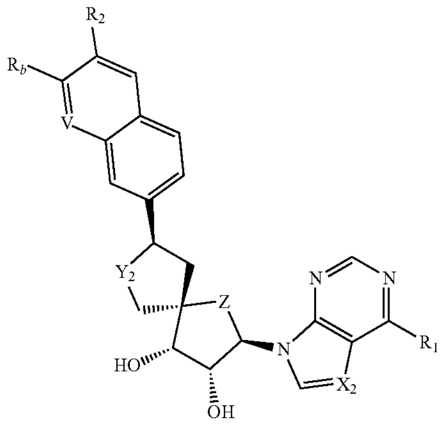

or a pharmaceutically acceptable salt thereof.

5. The compound of claim 1 having the structure of Formula V:

(Formula V)

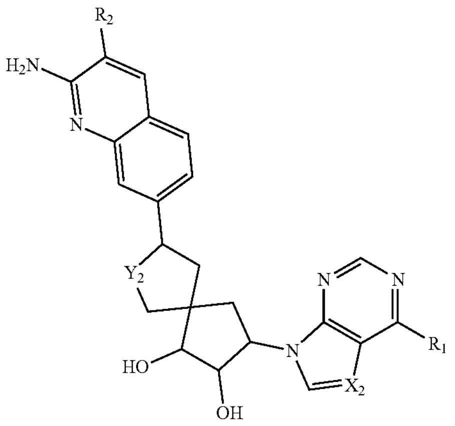

or a pharmaceutically acceptable salt thereof, wherein:

$Y_2$ is $CH_2$, S, O or $N(R_a)$; and wherein the compound has a PRMT5 $IC_{50}$ of about 100 nM or lower.

6. The compound of claim 5, wherein the compound has an average percent of maximum effect of about 60% or lower for the drug-resistant cell lines of the table below:

| Cell Line Name | Cohort |
|---|---|
| KMS-27 | Resistant |
| ML-2 | Resistant |
| UMUC-15 | Resistant |
| NCI-H1581 | Resistant |
| OVCA429 | Resistant |
| CAL-51 | Resistant |
| UMUC-7 | Resistant |
| NCI-H23 | Resistant |
| NCI-H647 | Resistant |
| NCI-H1650 | Resistant |
| Cha-Go-K-1 | Resistant |
| SW48 | Resistant |
| MDA-MB-231 | Resistant |
| DU4475 | Resistant |
| EFM-192A | Resistant |

and/or the compound has an average percent of maximum effect of about 60% or greater for the drug-sensitive cell lines of the table below:

| Cell Line Name | Cohort |
|---|---|
| EFM-19 | Sensitive |
| MV4-11 | Sensitive |
| HUPT4 | Sensitive |
| SKCO1 | Sensitive |
| JIMT-1 | Sensitive |
| HCC1954 | Sensitive |
| NCI-H929 | Sensitive |
| OVCAR3 | Sensitive |
| OPM-2 | Sensitive |
| NCIH747 | Sensitive |
| MDA-MB-453 | Sensitive |

-continued

| Cell Line Name | Cohort |
|---|---|
| SW480 | Sensitive |
| M275 | Sensitive |
| HT29 | Sensitive |
| NCI-H2286 | Sensitive |

7. The compound of claim 5 having the structure of Formula Va:

(Formula Va)

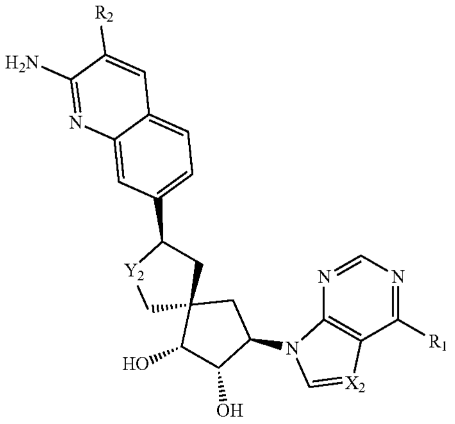

or a pharmaceutically acceptable salt thereof.

8. The compound of claim 1, wherein $X_1$ is CH.

9. The compound of claim 1, wherein $X_2$ is CH.

10. The compound of claim 1, wherein V is N.

11. The compound of claim 1, wherein $R_b$ is $NH_2$.

12. The compound of claim 1, wherein Z is $CH_2$.

13. The compound of claim 1, wherein $Y_2$ is N(H) or O.

14. The compound of claim 1, wherein $R_1$ is Cl or $NH_2$.

15. The compound of claim 1, wherein $R_2$ is Br.

16. The compound of claim 1, selected from:

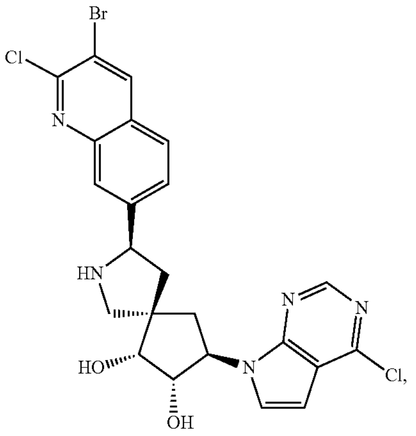

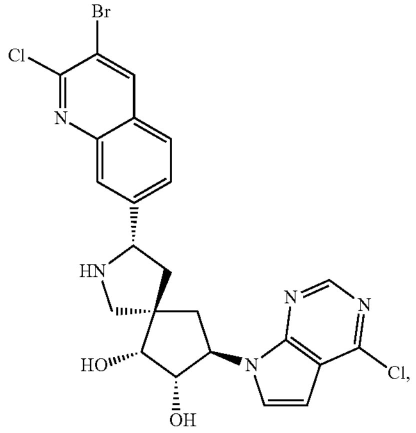,
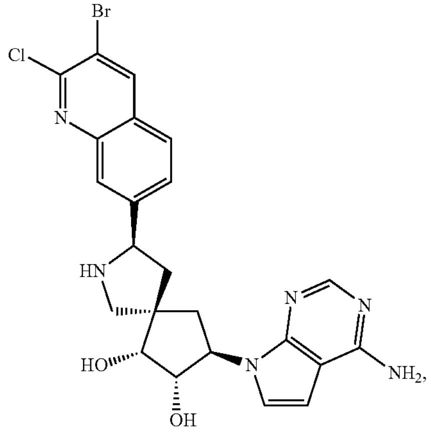,
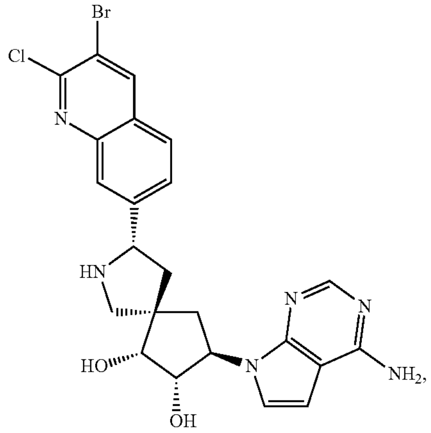,
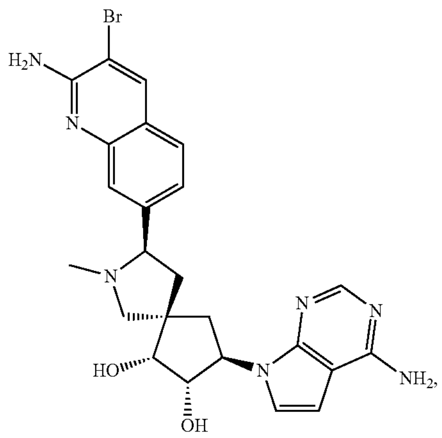,
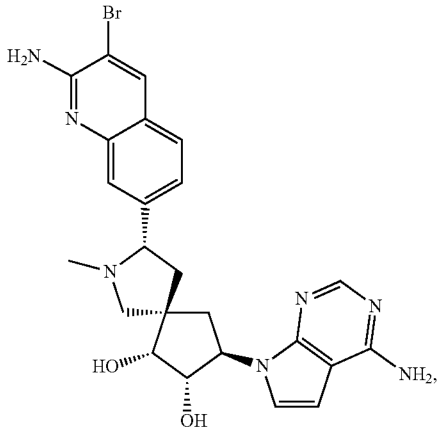,
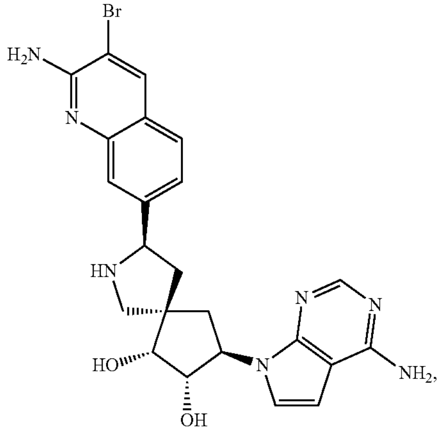,
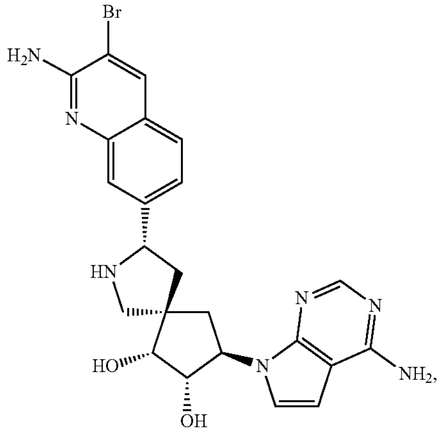,
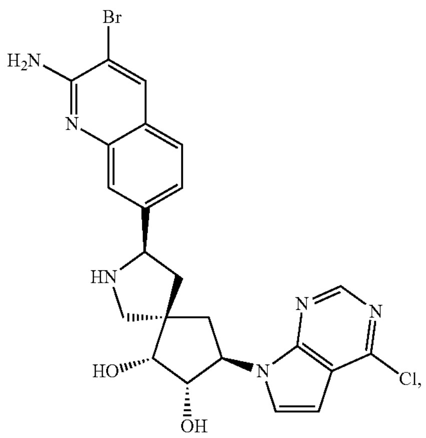, -continued
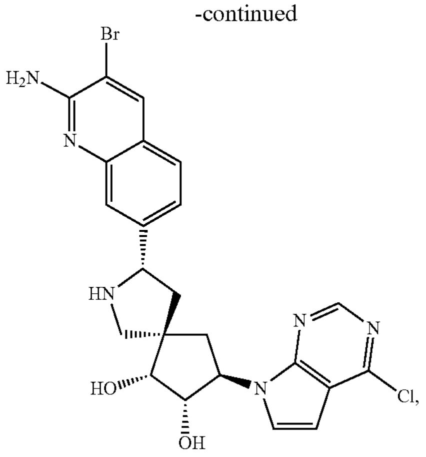
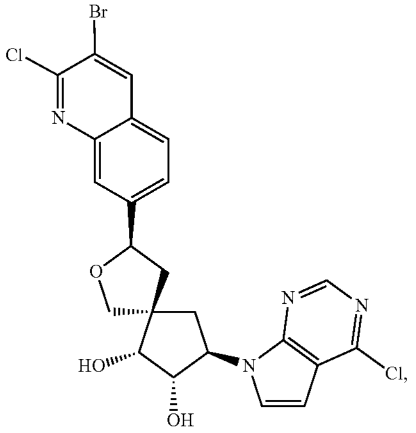
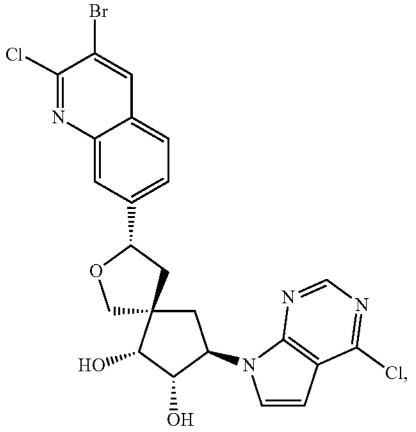
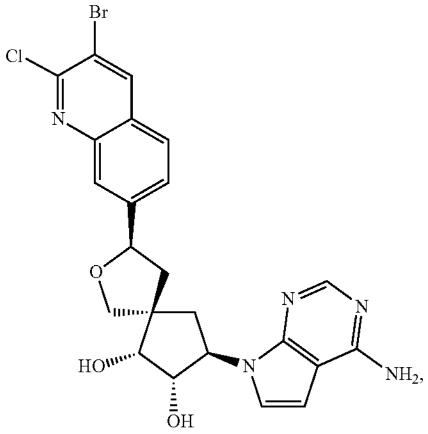
-continued
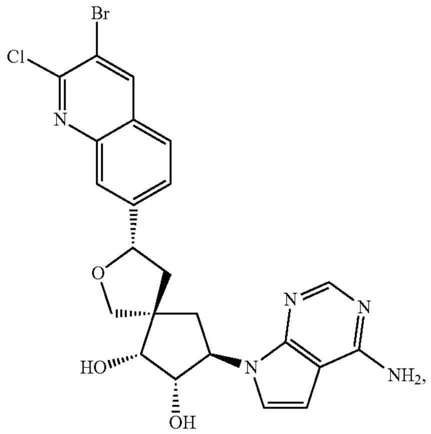
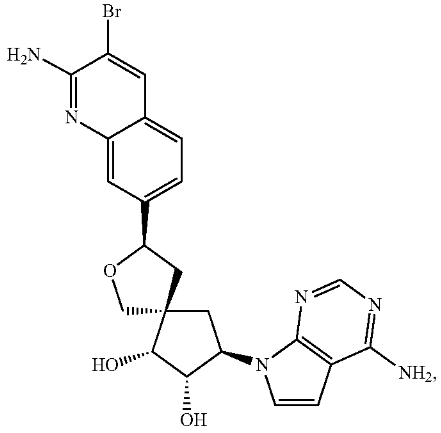
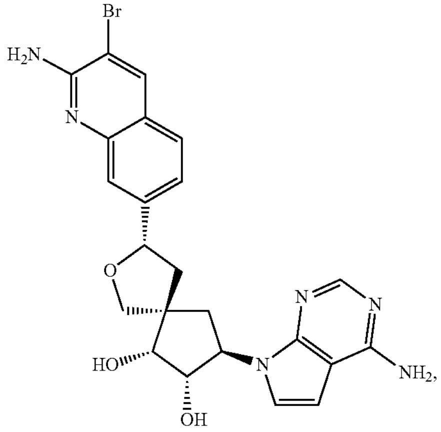
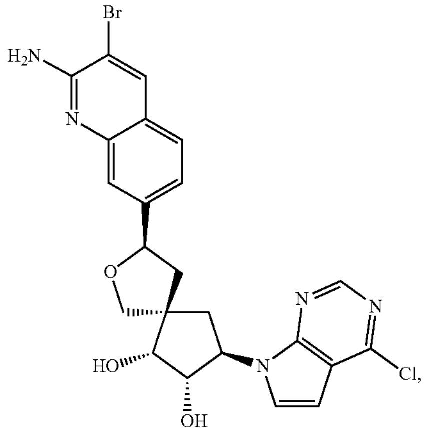

-continued
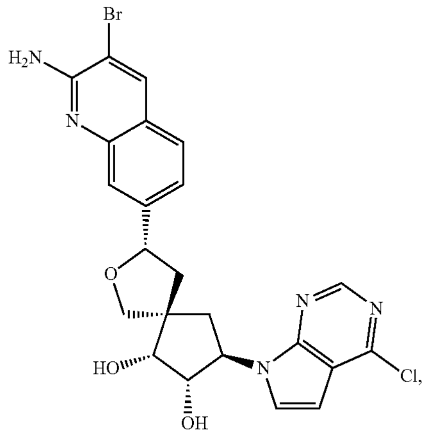
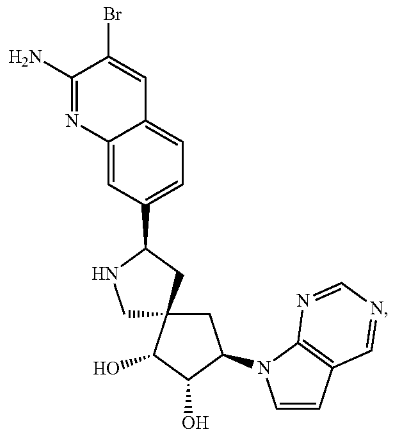
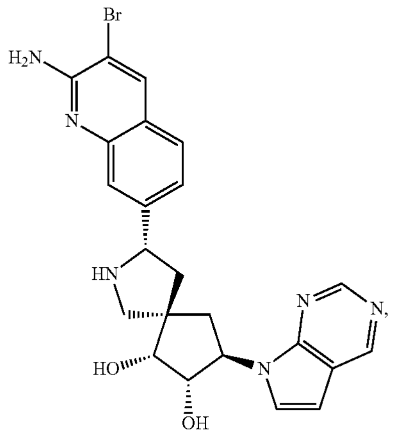
-continued
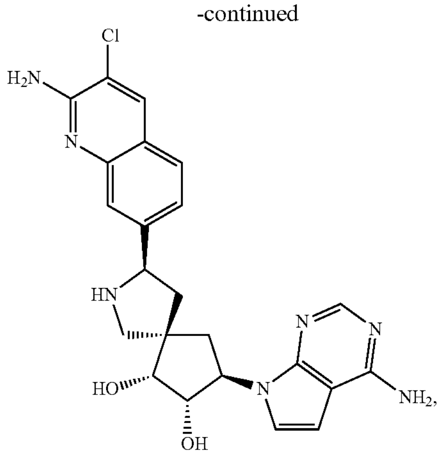
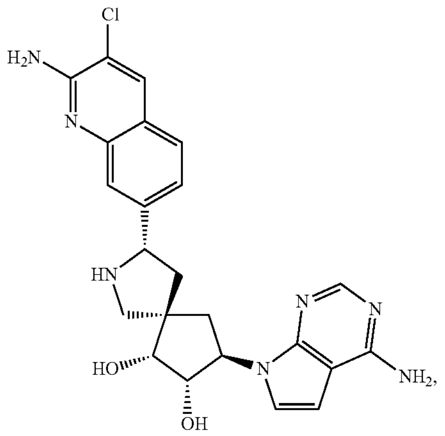
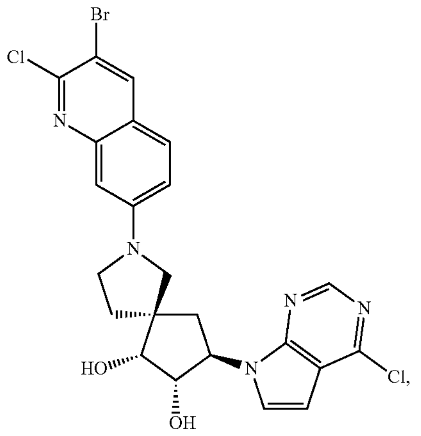
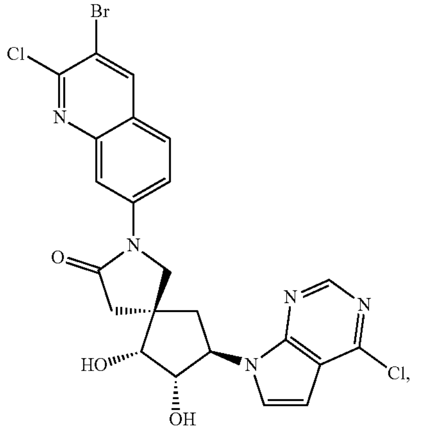

-continued
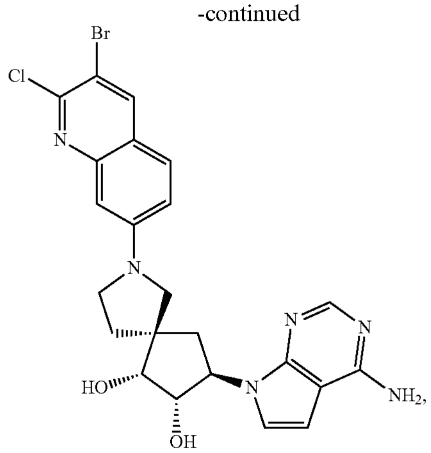
,
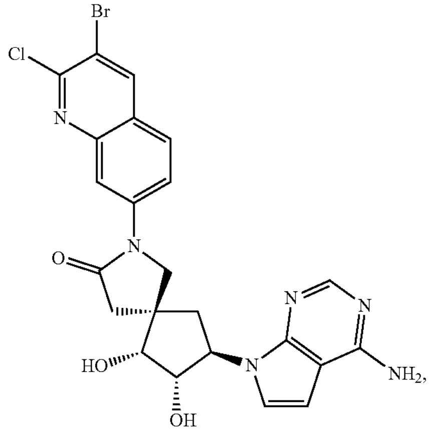
,
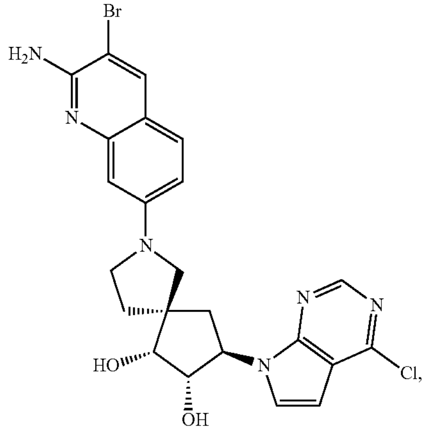
,
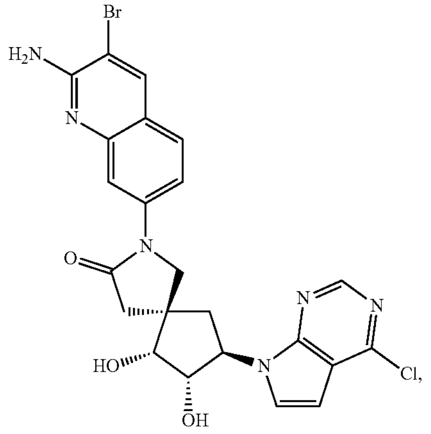
,
-continued
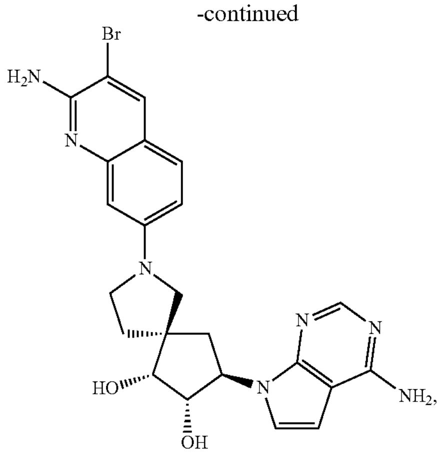
,
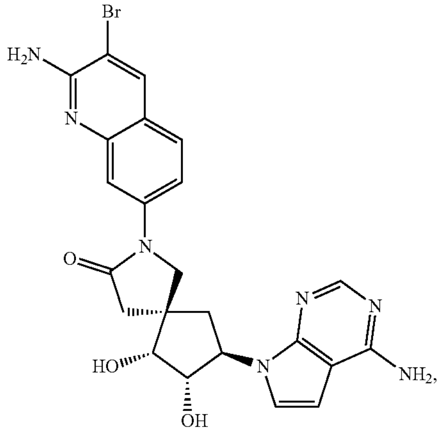
,
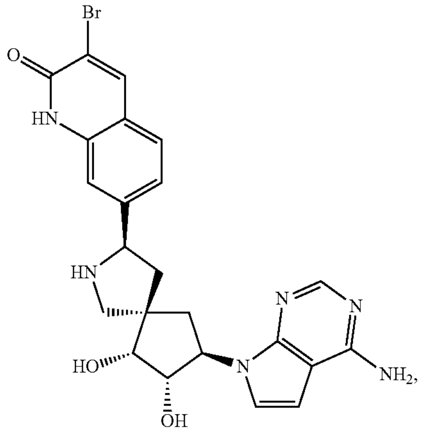
,
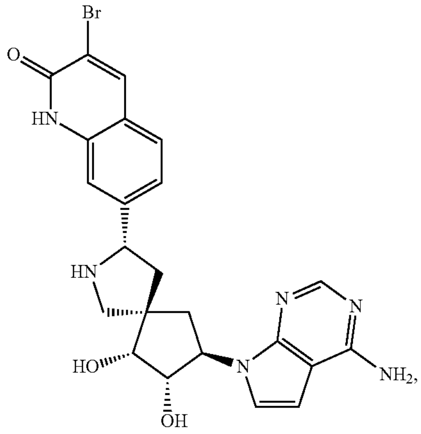
, -continued
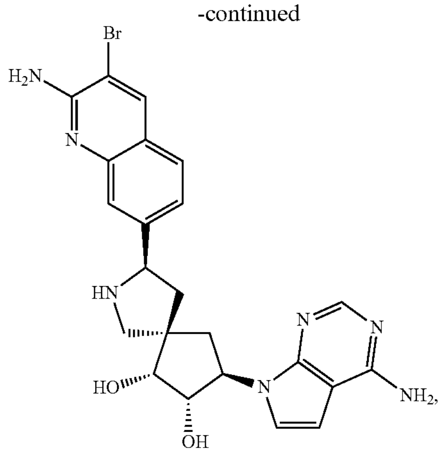
,
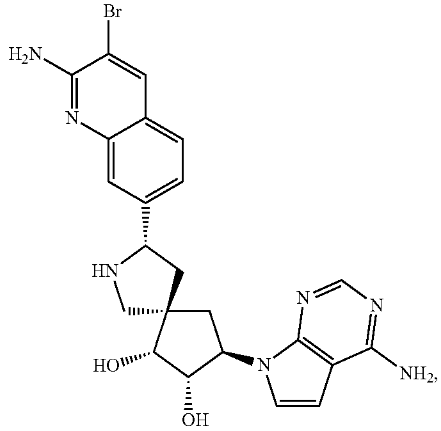
,
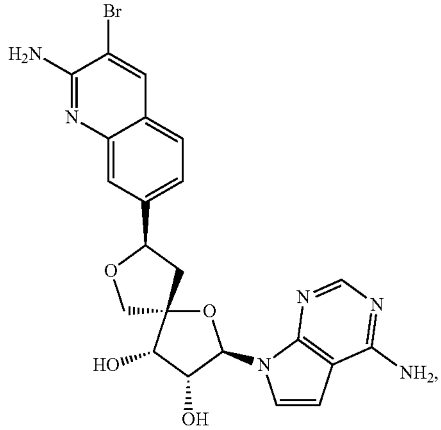
,
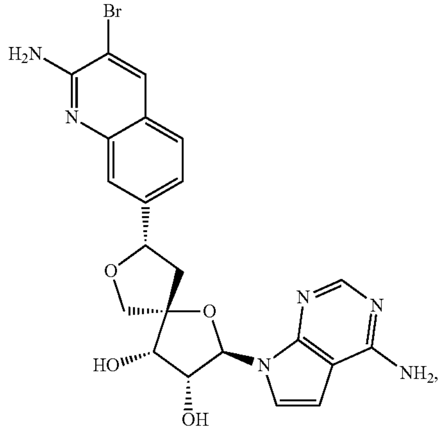
,
-continued
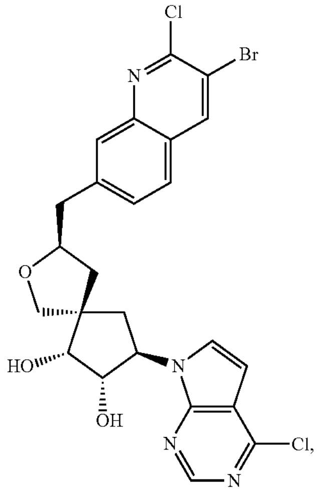
,
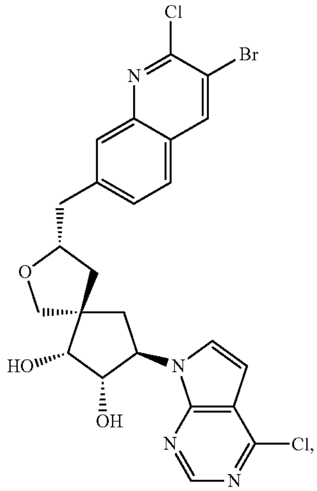
,
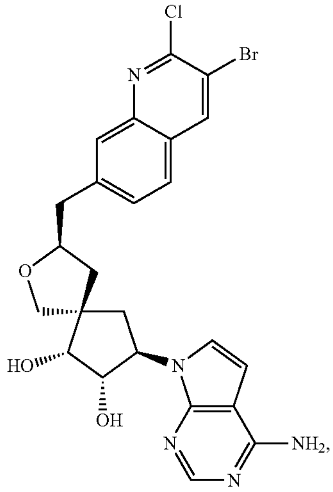
, -continued
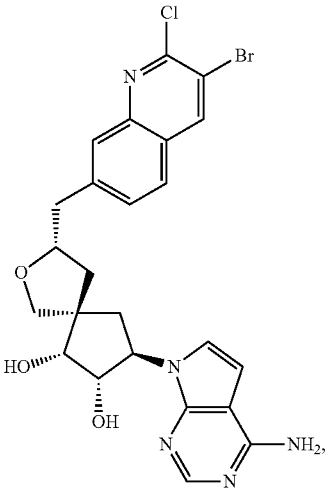
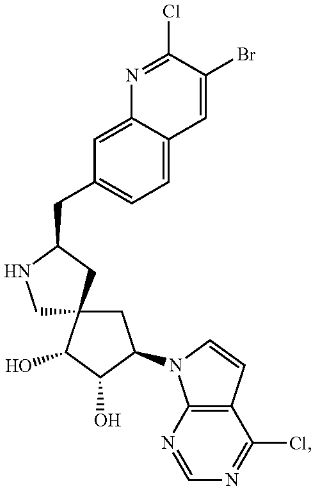
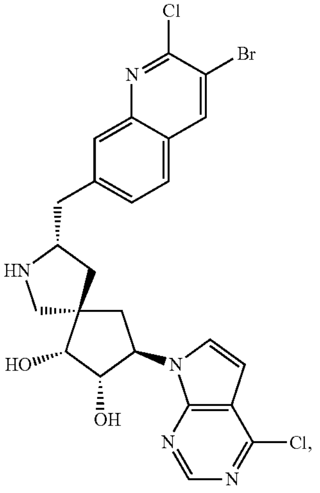
-continued
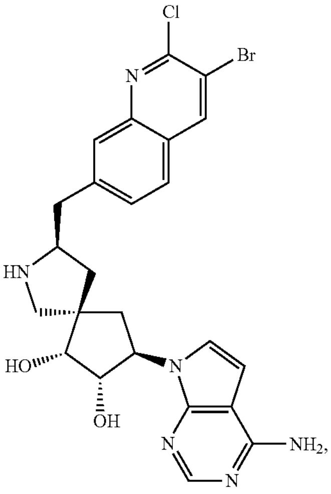
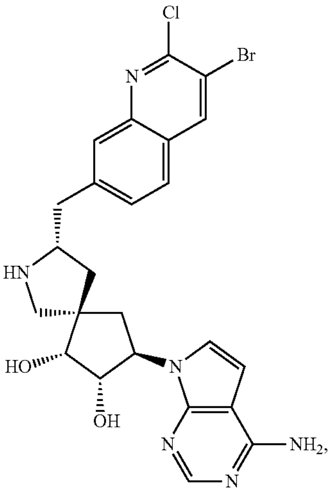
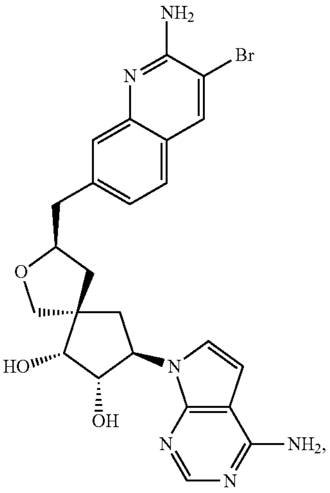

-continued
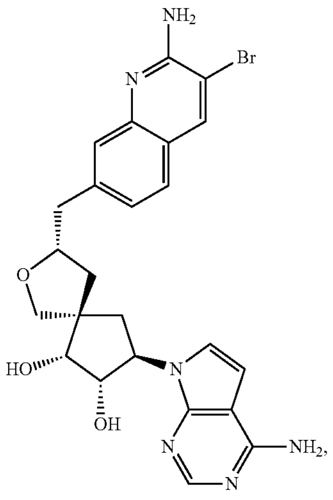
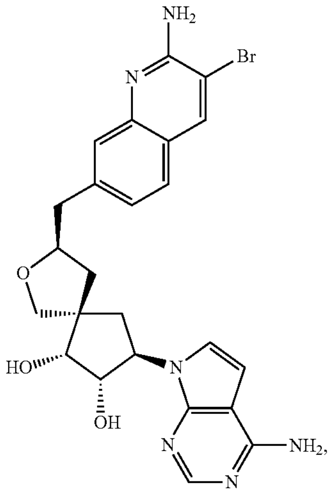
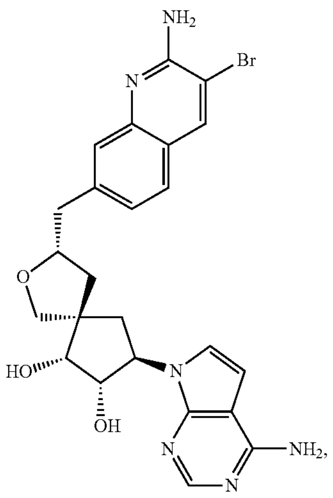
-continued
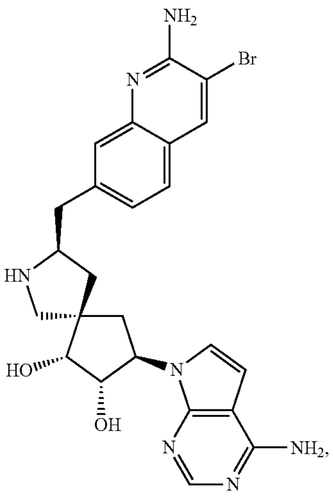
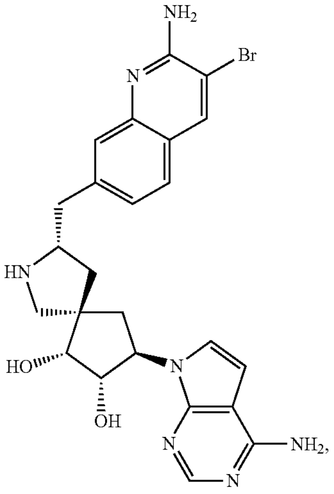
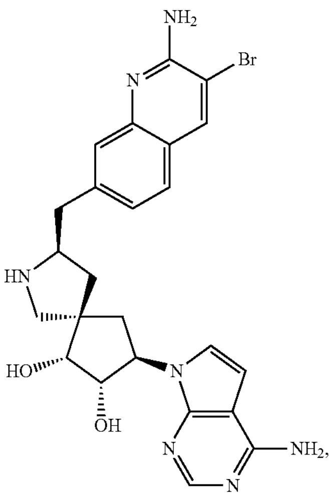

-continued
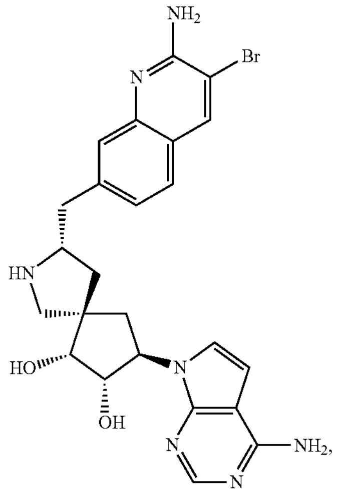
,
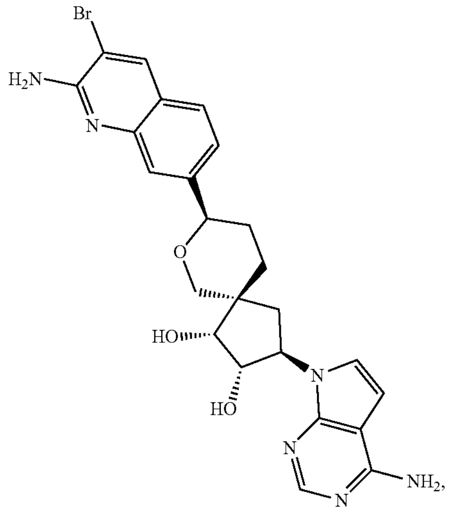
,
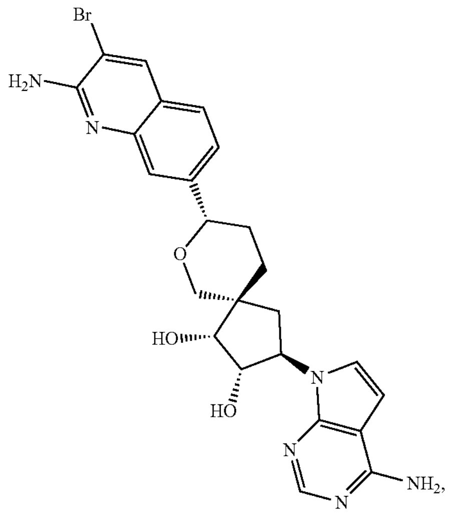
,
-continued
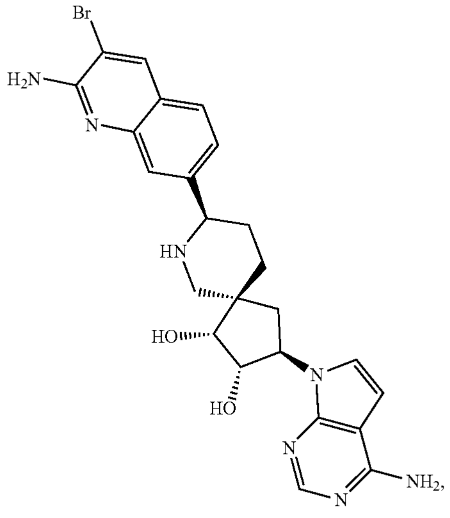
,
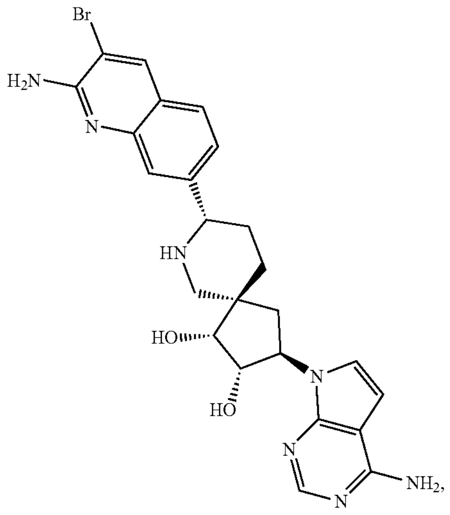
,
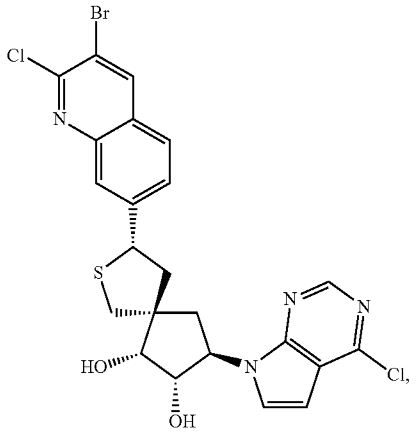
, -continued
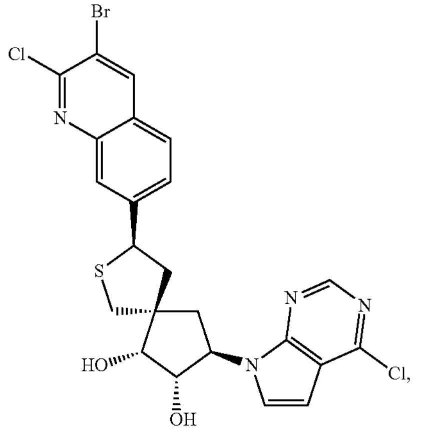
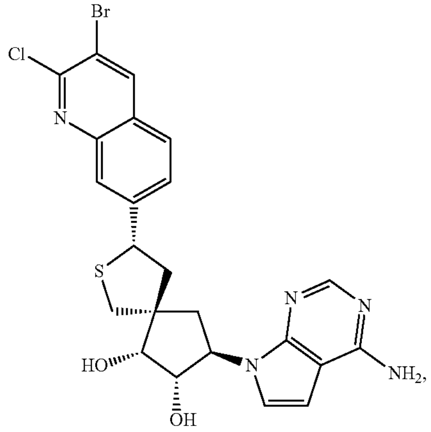
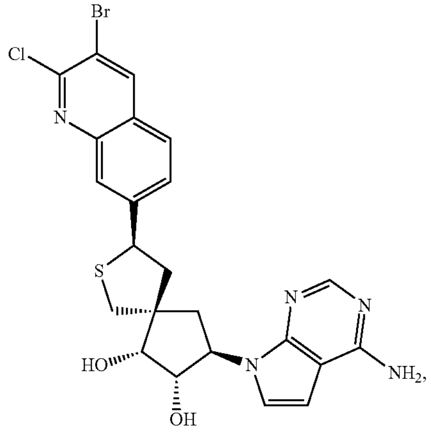
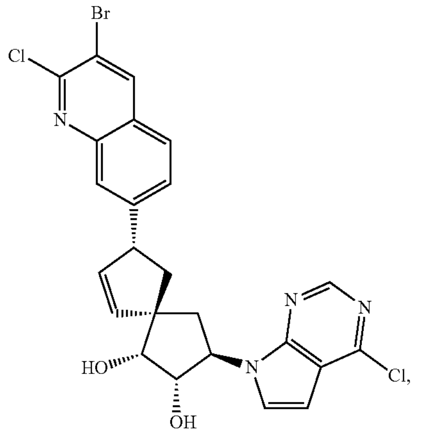
-continued
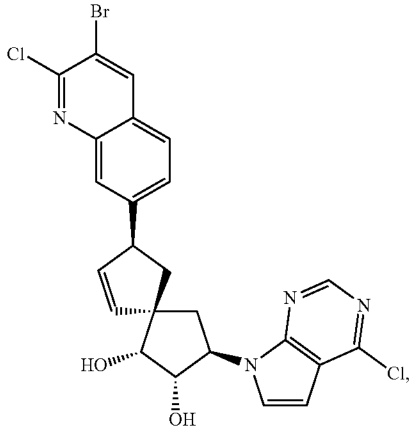
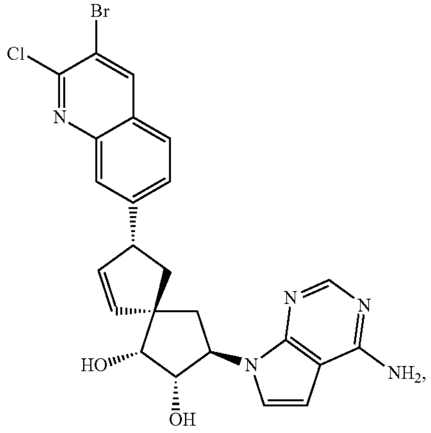
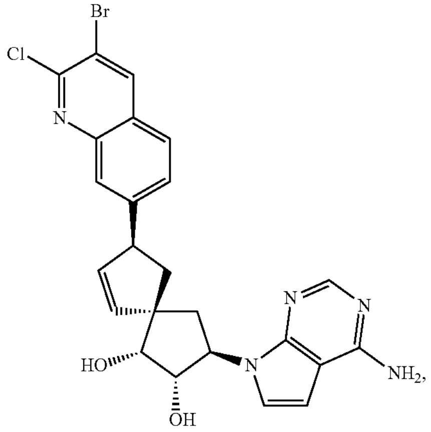
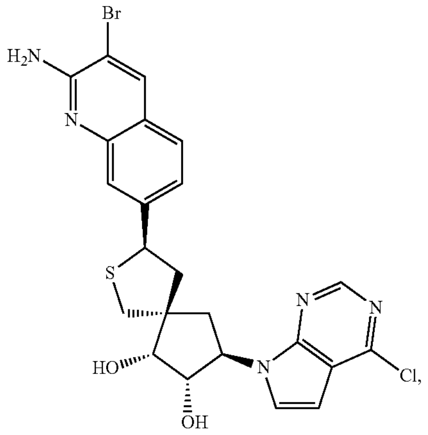

-continued
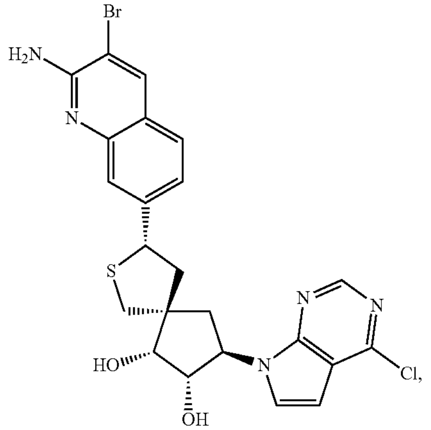
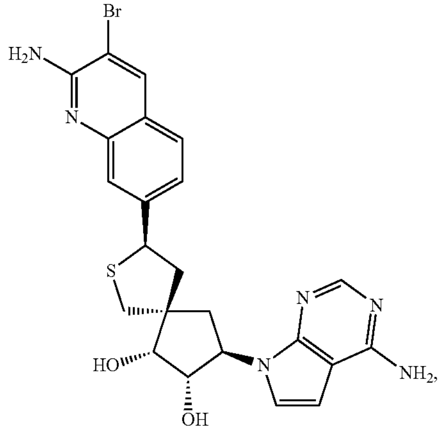
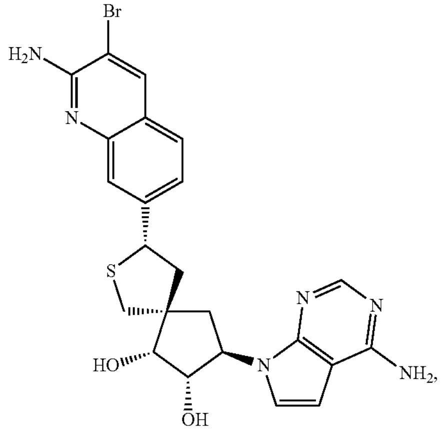
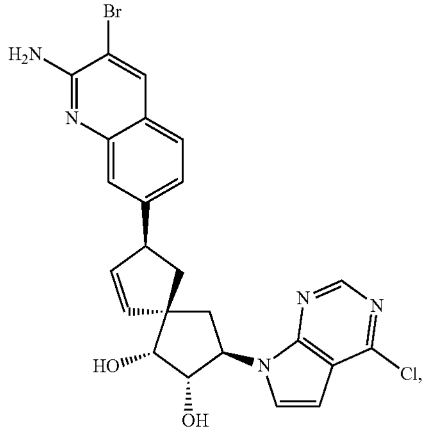
-continued
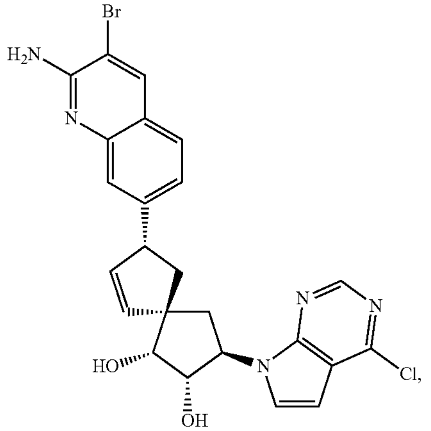
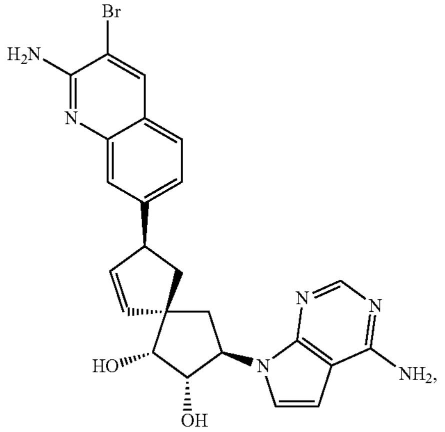
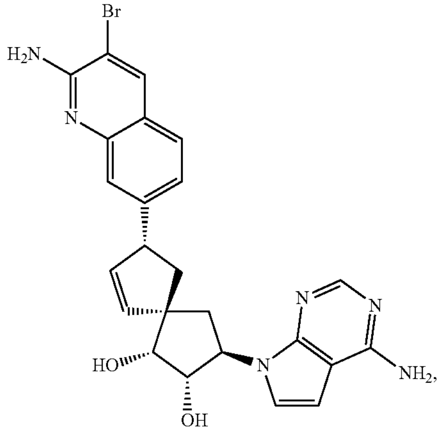
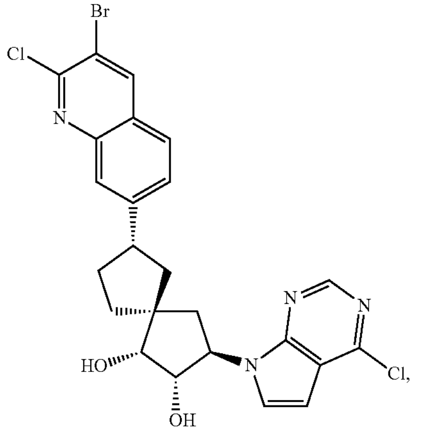

-continued
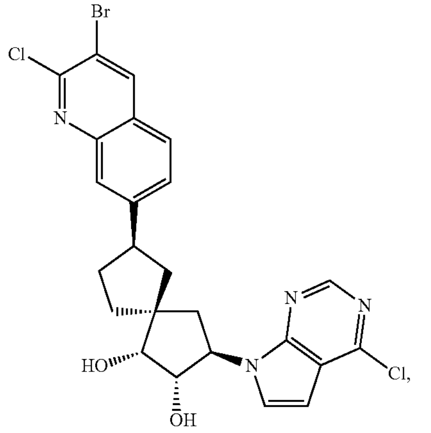
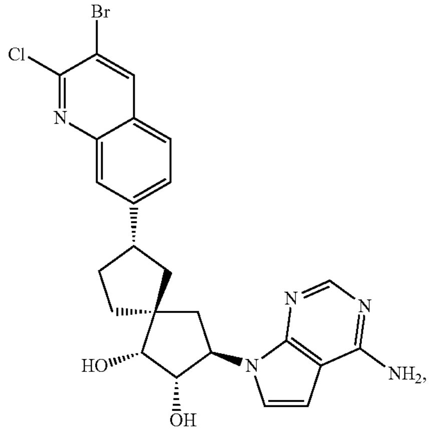
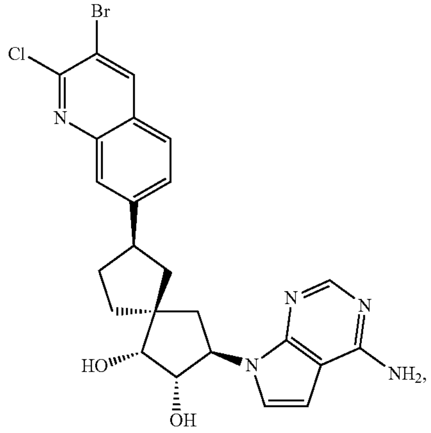
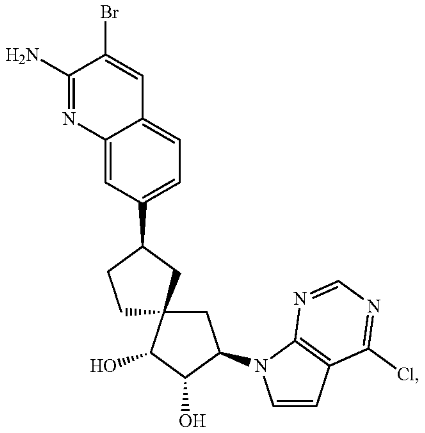
-continued
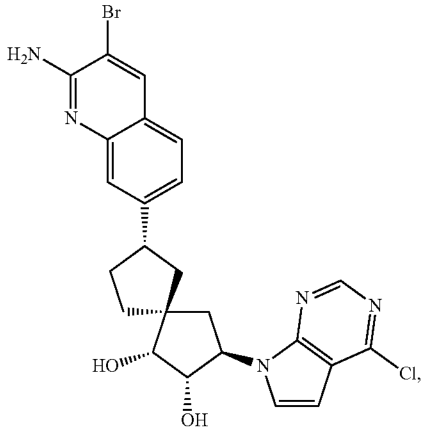
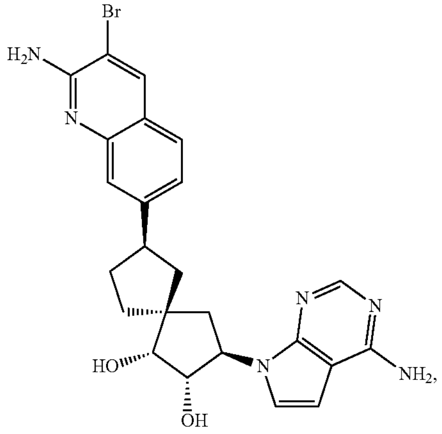
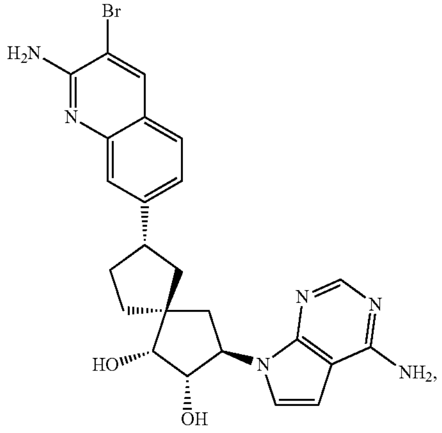
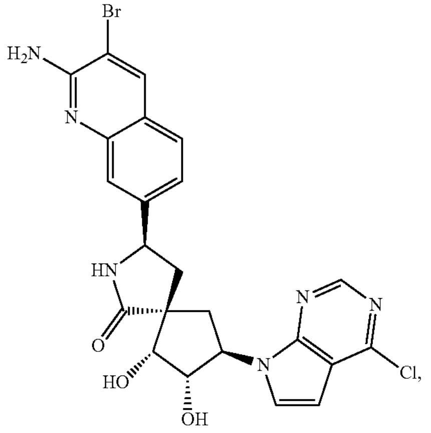

-continued
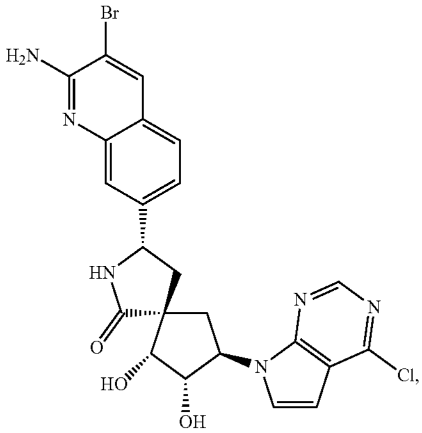
,
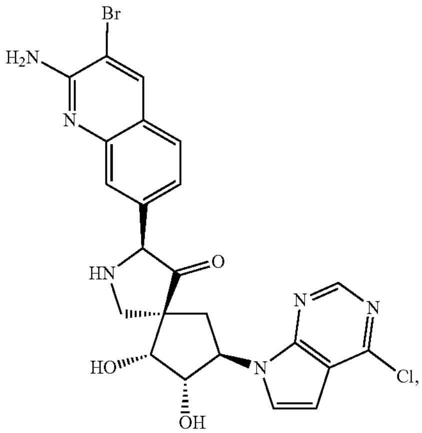
,
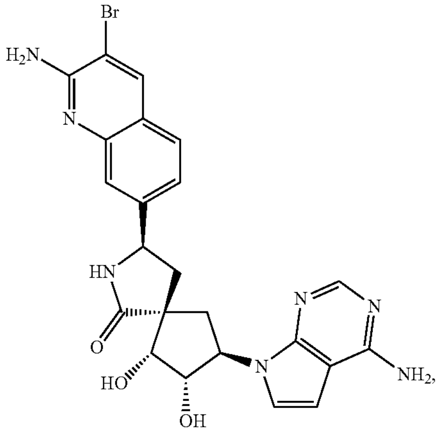
,
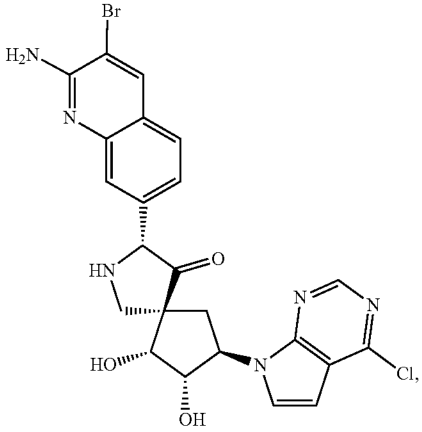
,
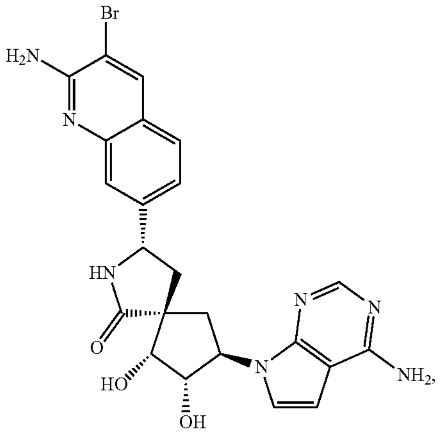
,
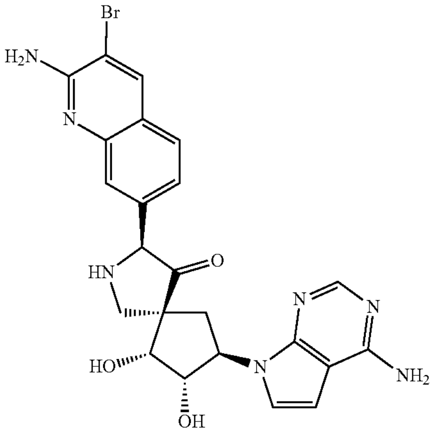
and -continued
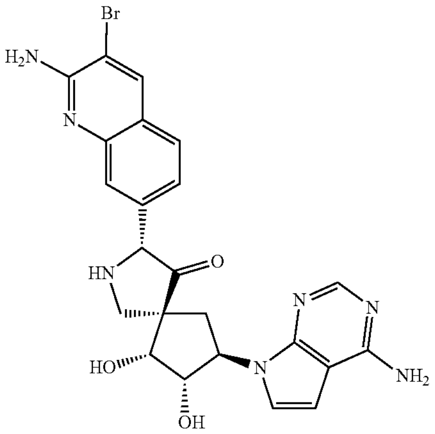
or a pharmaceutically acceptable salt thereof.
17. The compound of claim 1, selected from:
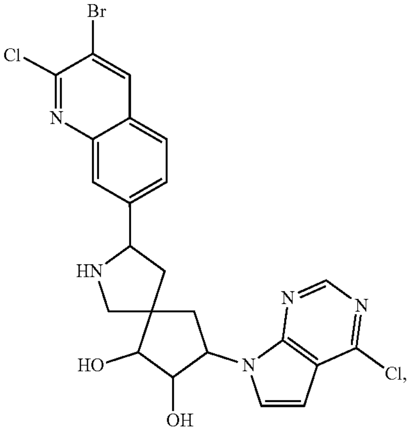
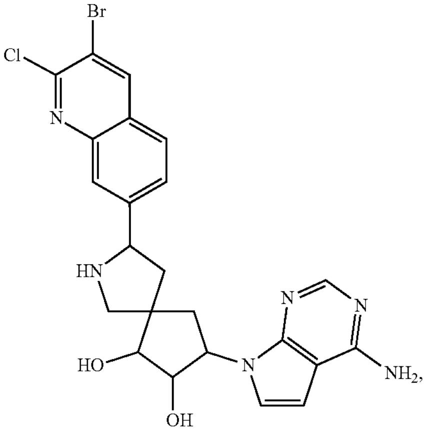
-continued
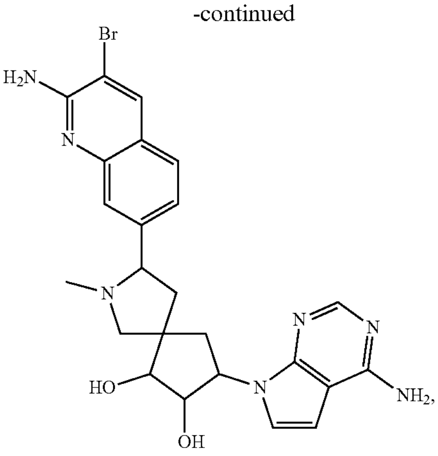
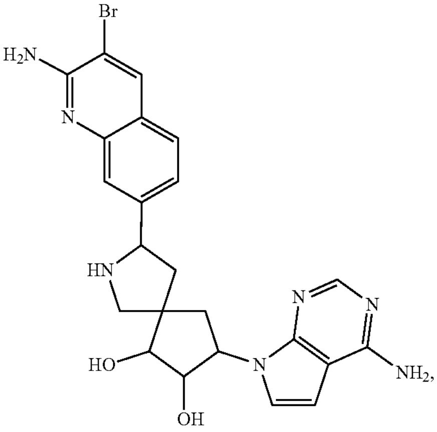
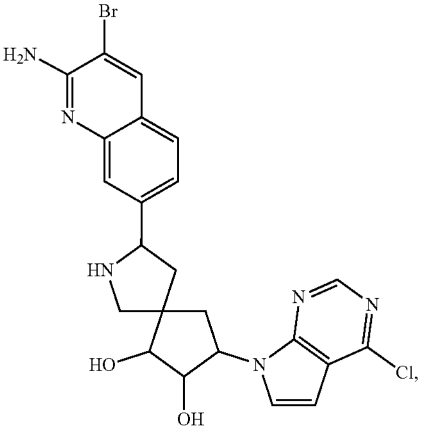
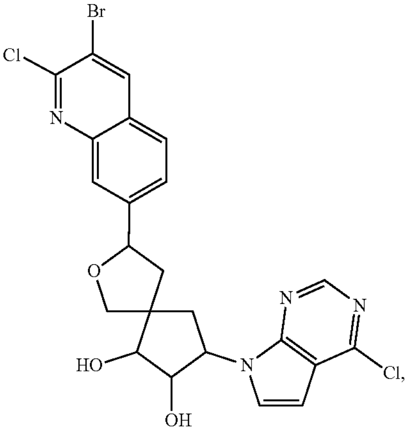

-continued
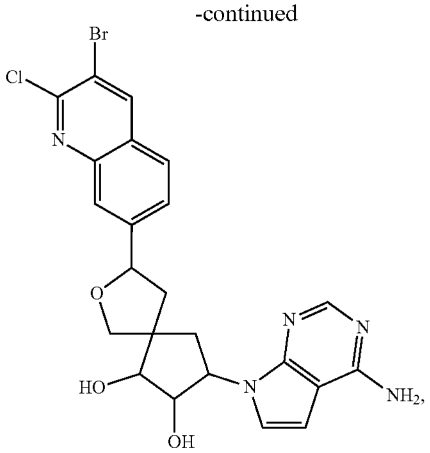
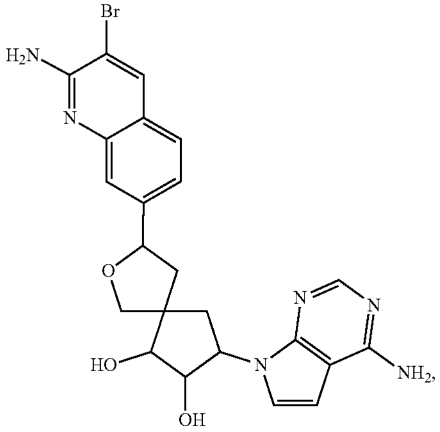
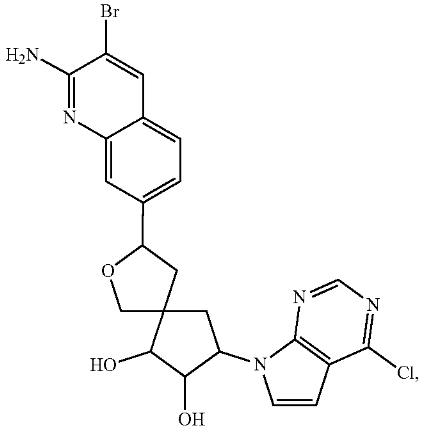
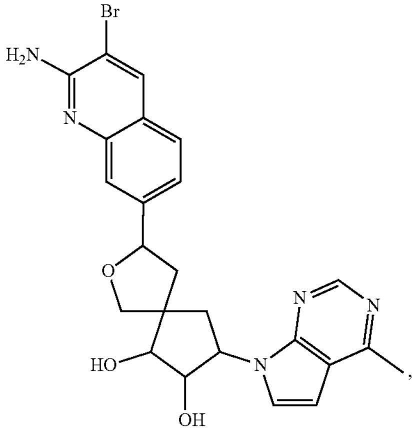
-continued
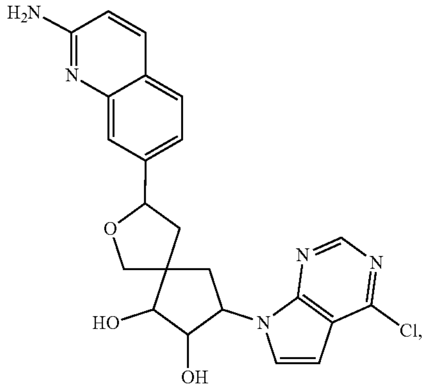
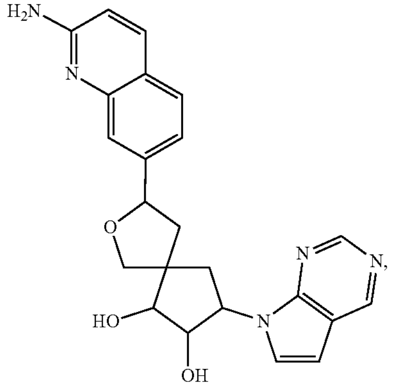
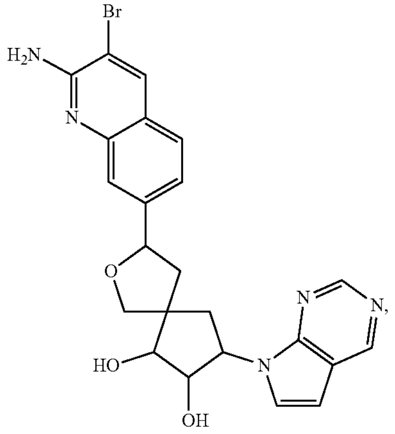
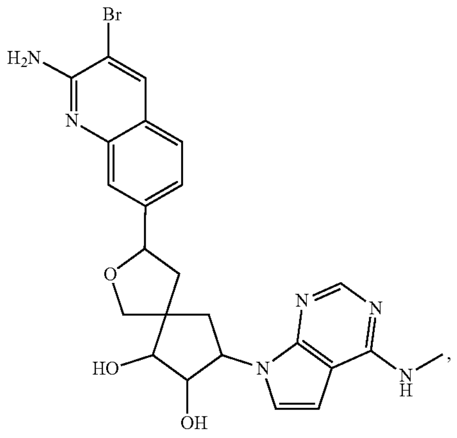

-continued
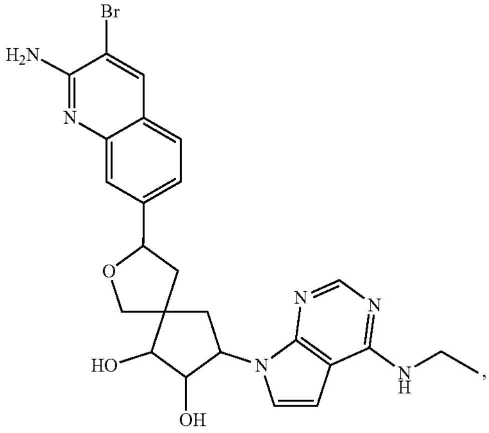
,
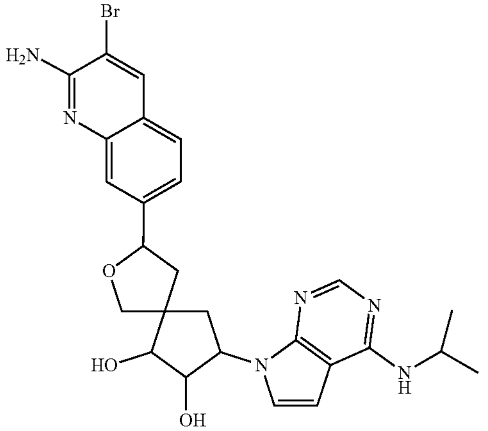
,
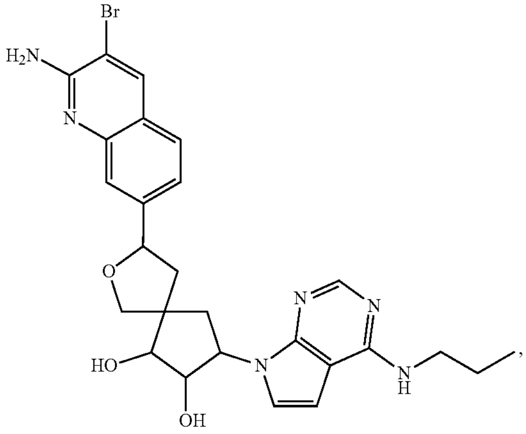 [SMILES: CCCNc1ncnc2c1ccn2C1CC2(COC(c3ccc4cc(Br)c(N)nc4c3)C2)C(O)C1O]
,
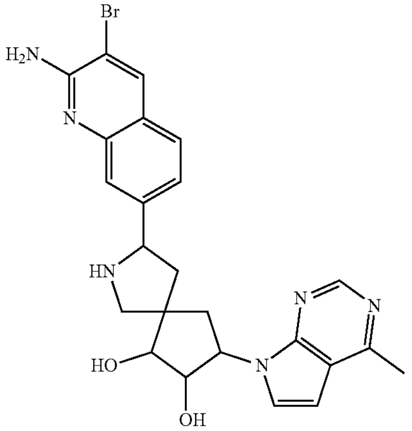
,
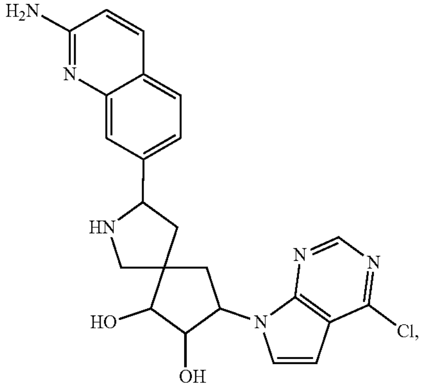
,
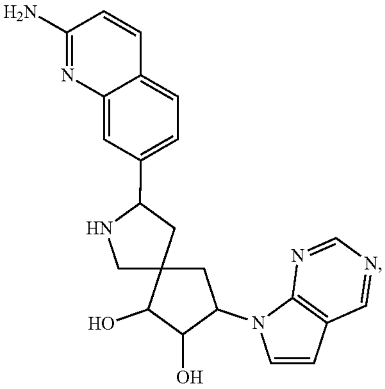
,
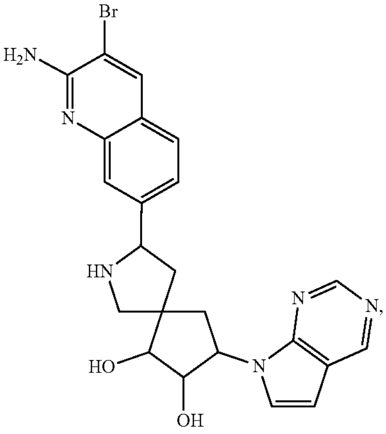
, -continued
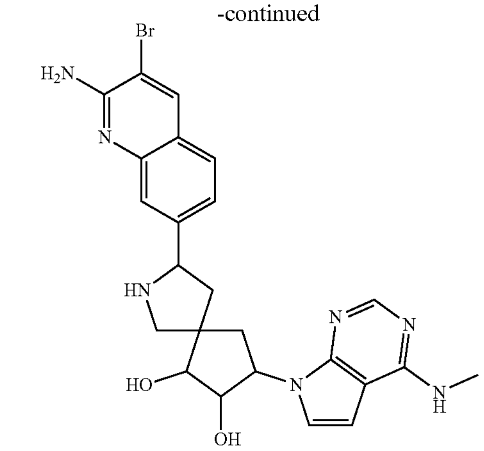
,
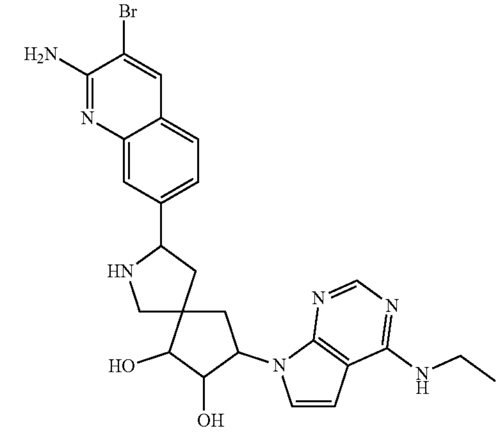
,
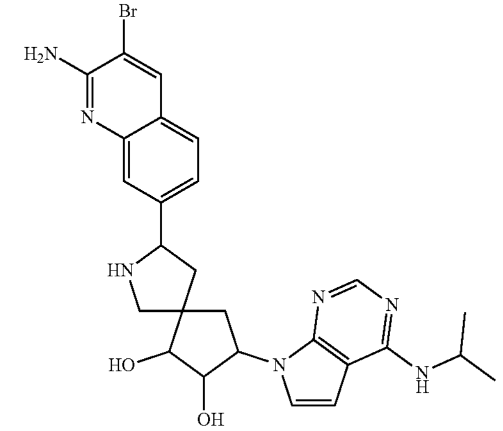
,
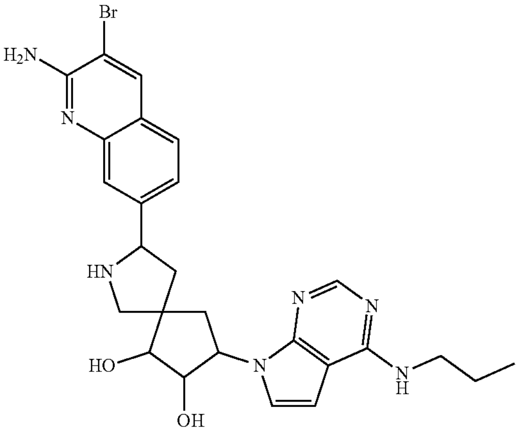
,
-continued
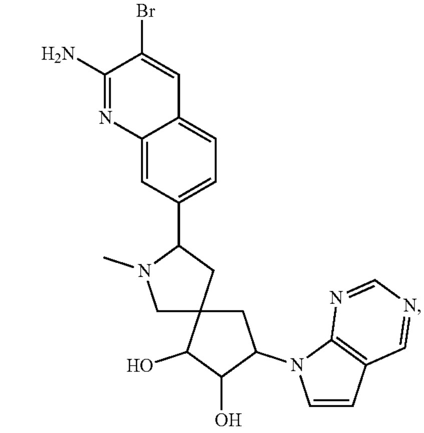
,
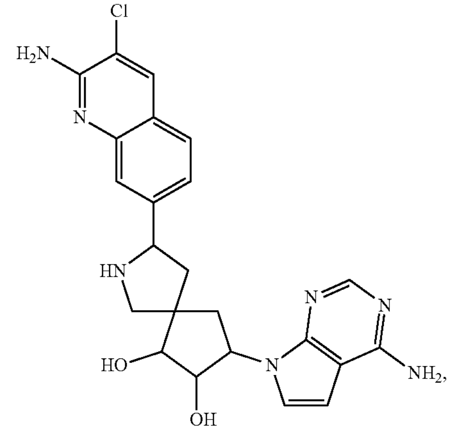
,
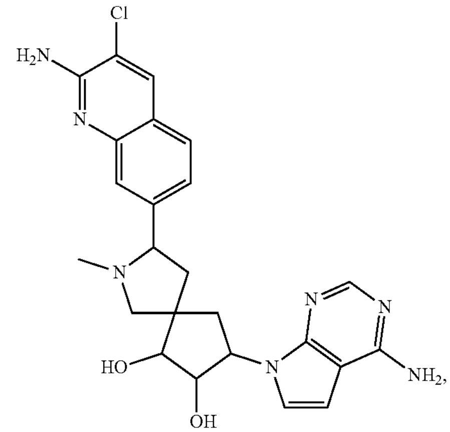
,
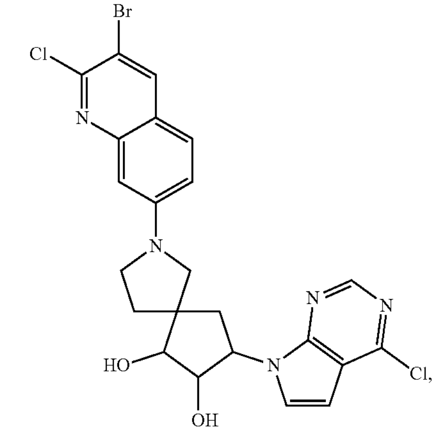
, -continued
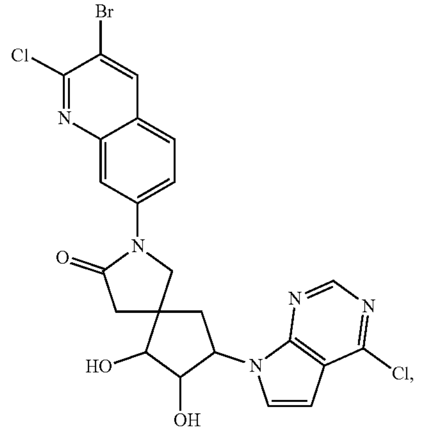
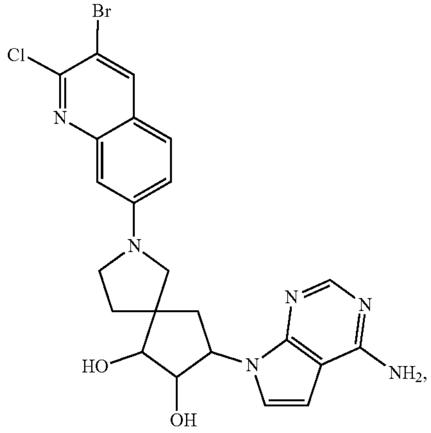
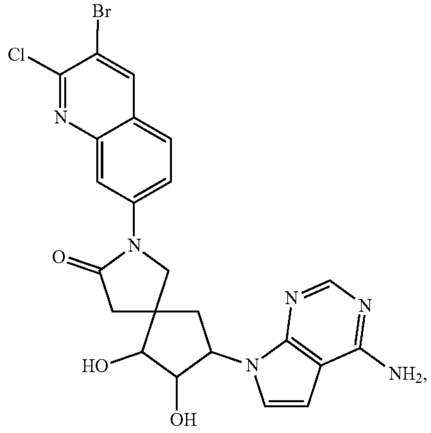
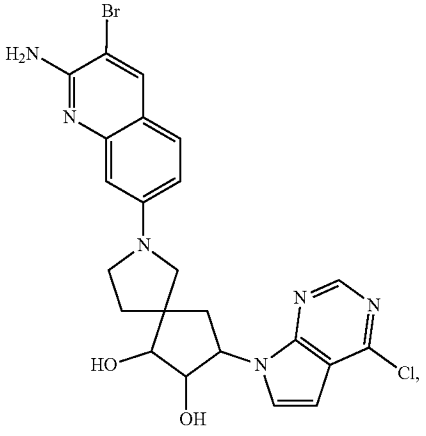
-continued
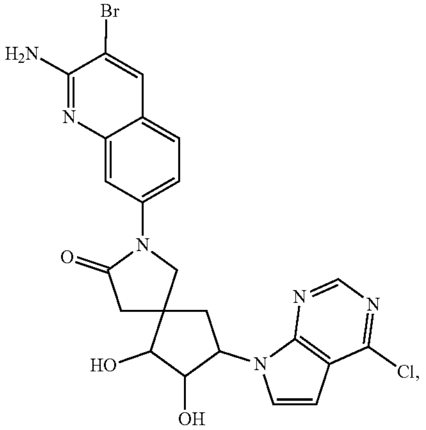
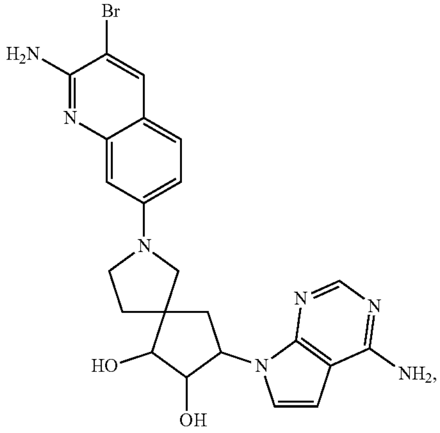
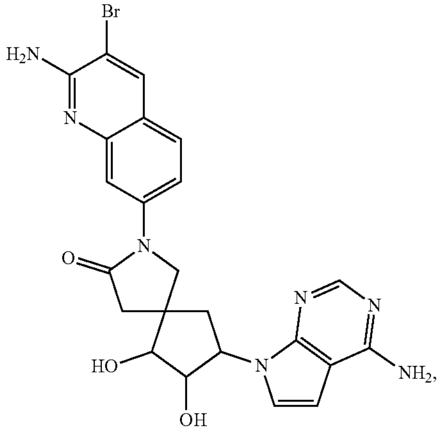
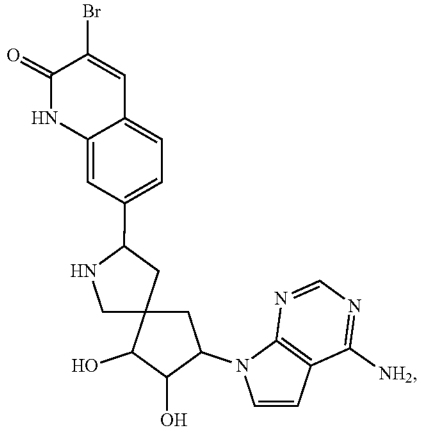

-continued
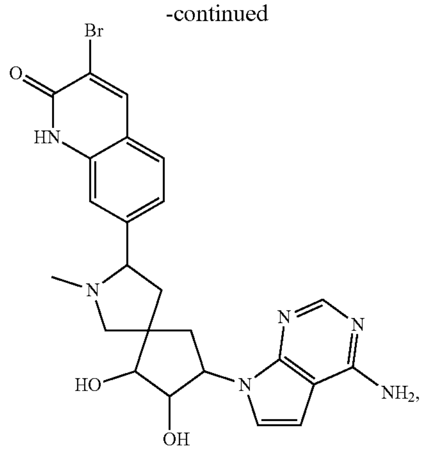
,
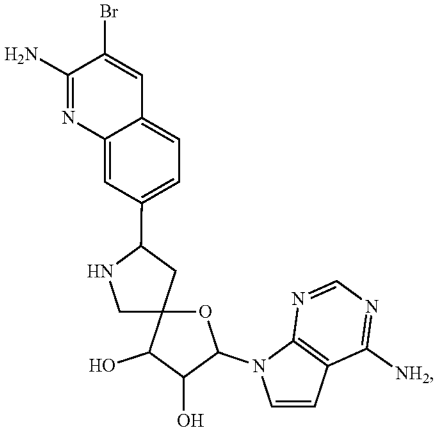
,
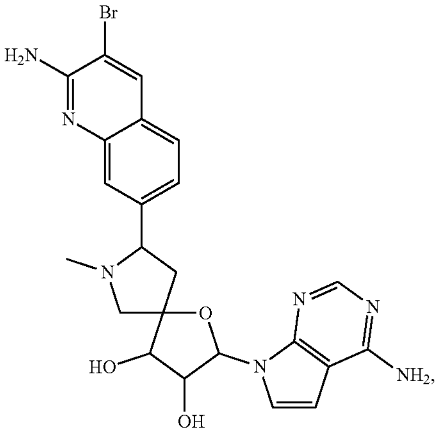
,
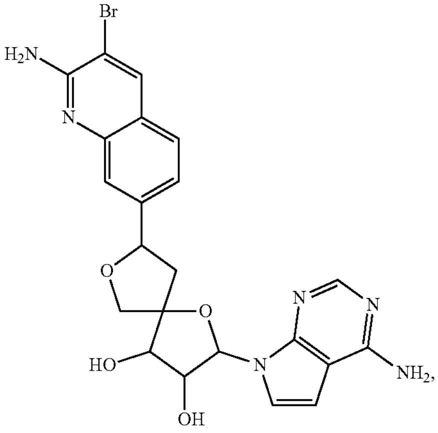
,
-continued
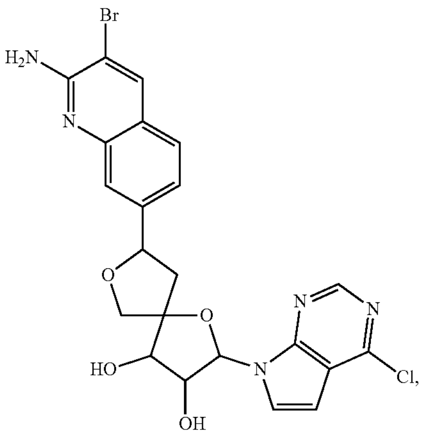
,
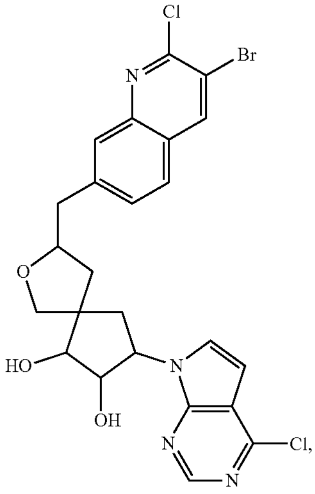
,
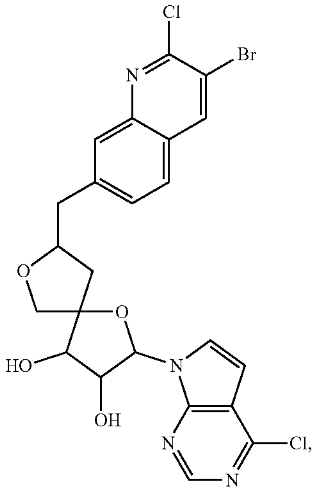
, -continued
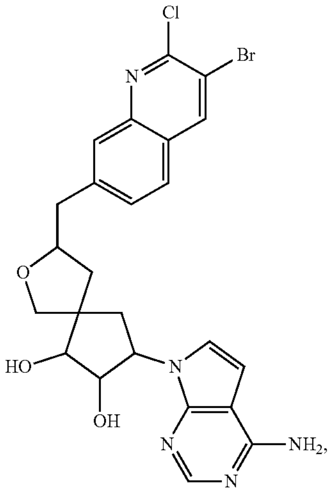
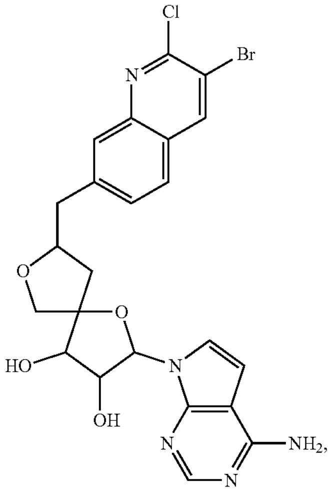
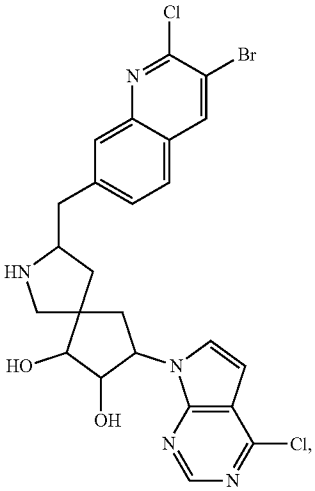
-continued
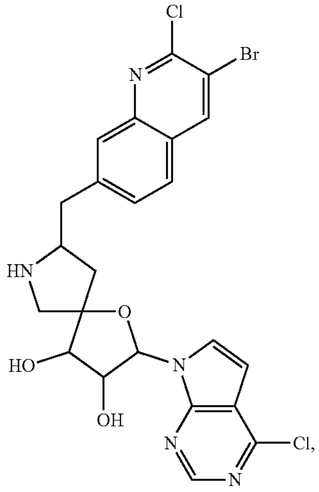
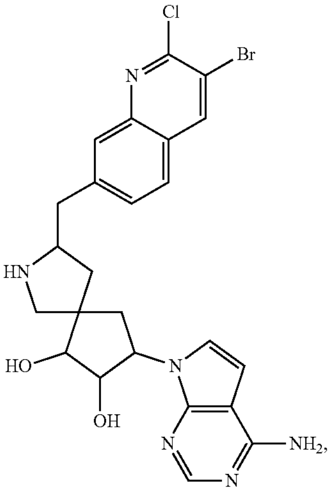
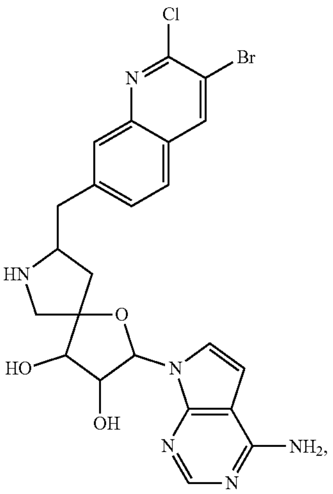

-continued
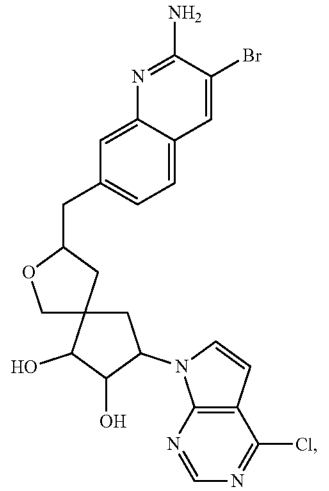
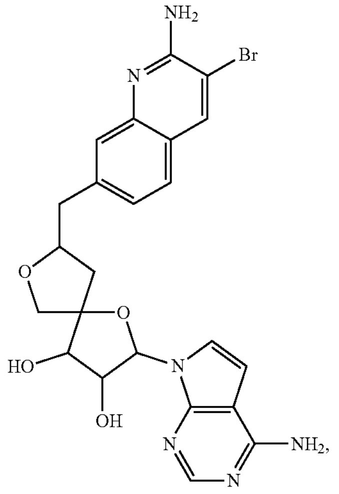
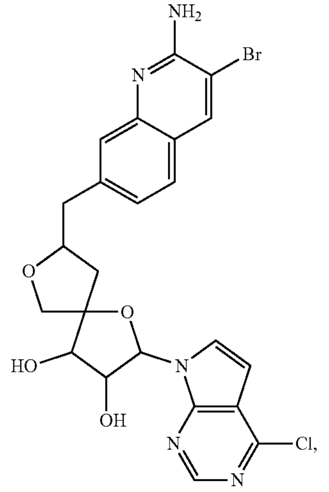
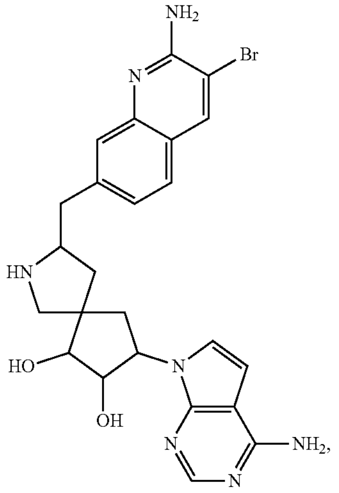
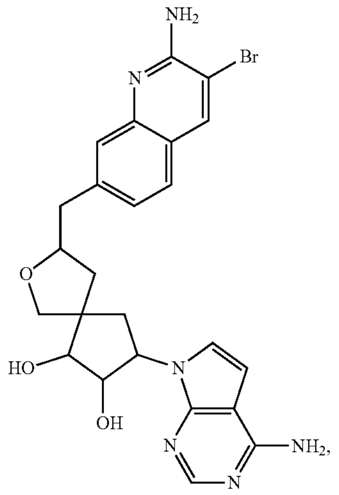
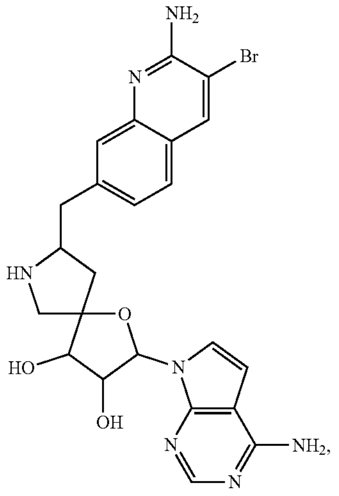

-continued
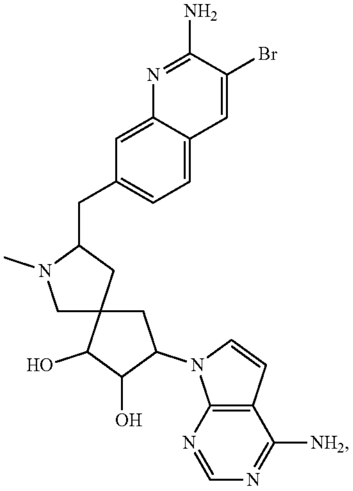
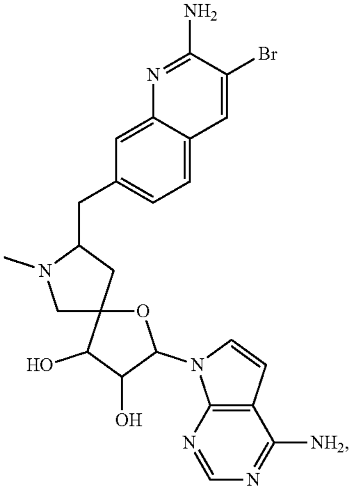
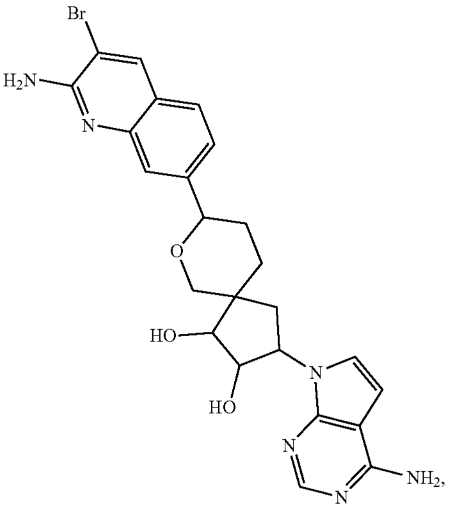
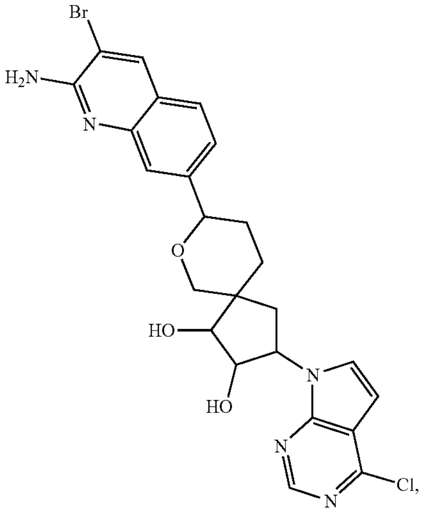
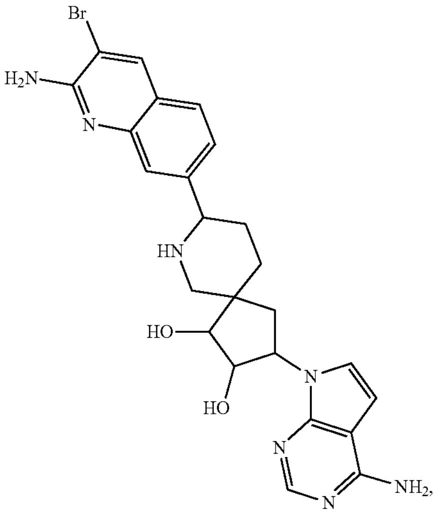
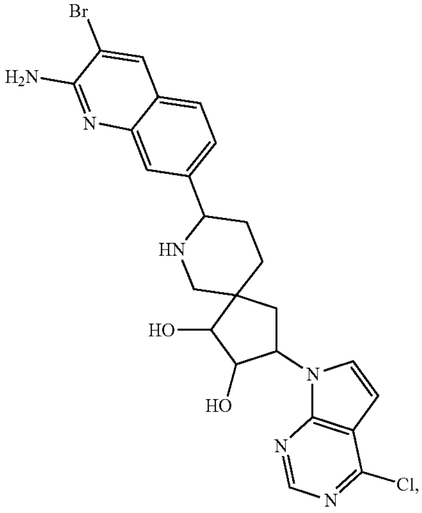
-continued -continued
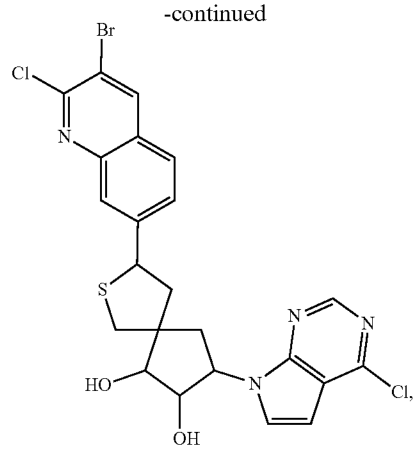
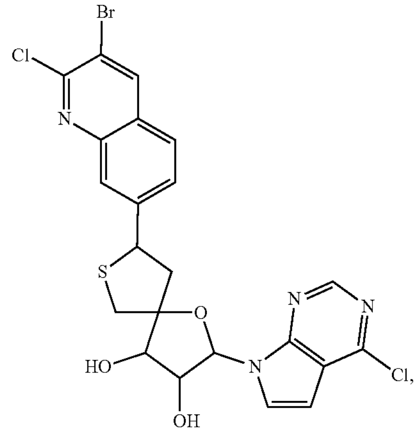
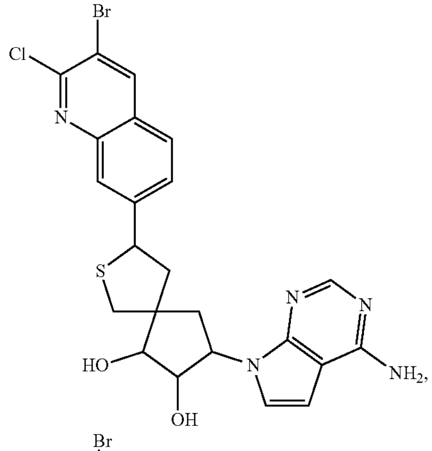
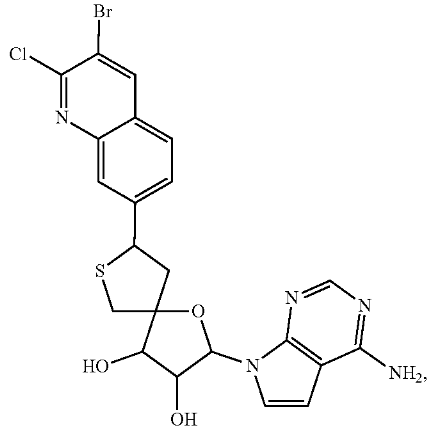
-continued
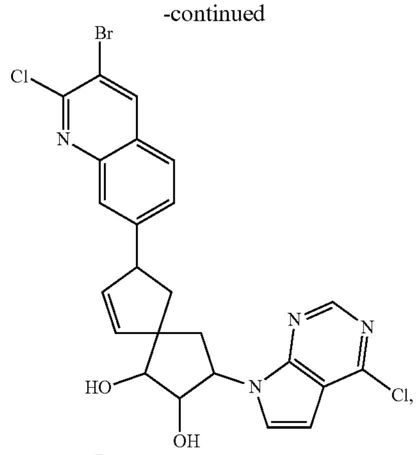
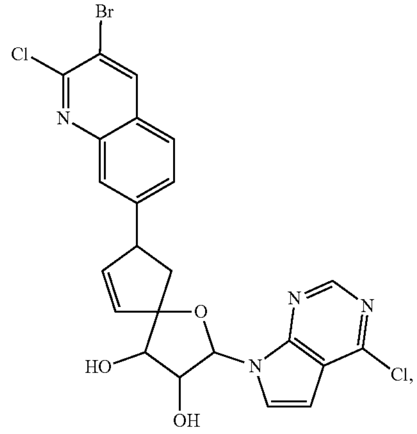
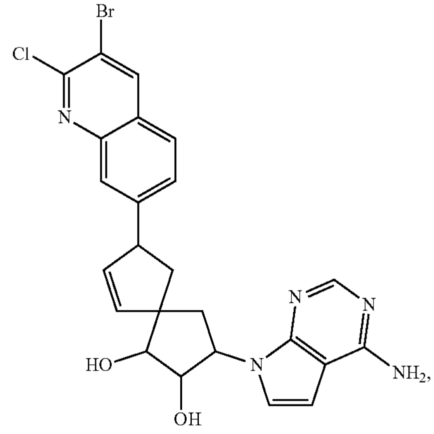
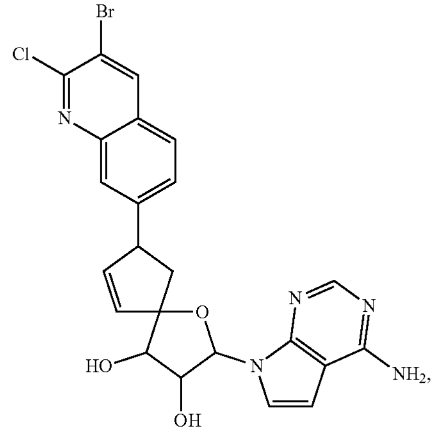

-continued
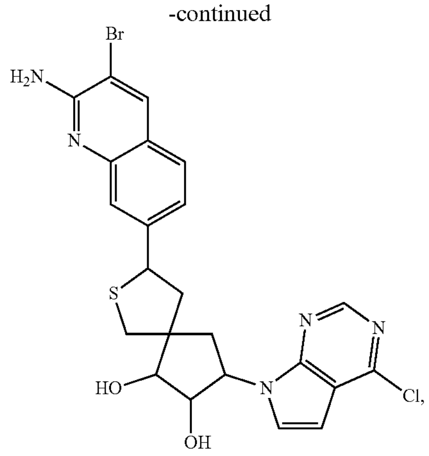
,
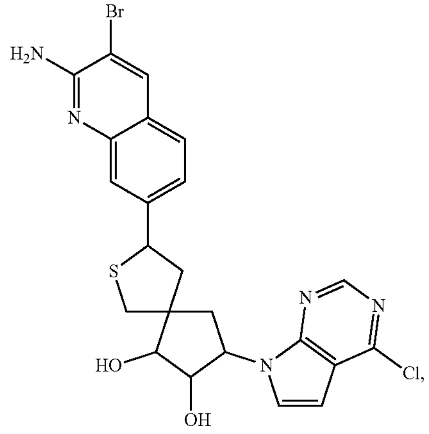
,
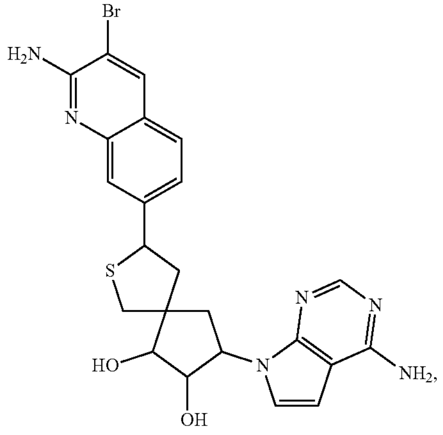
,
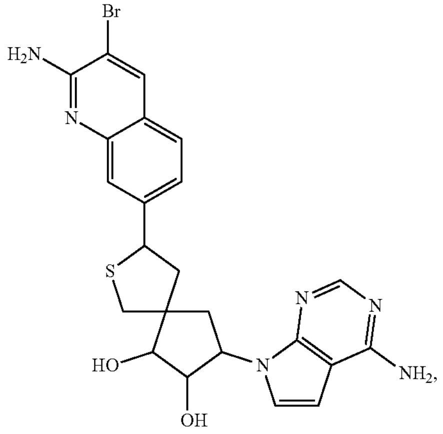
,
-continued
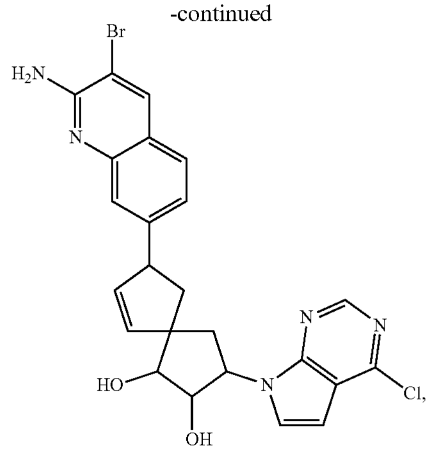
,
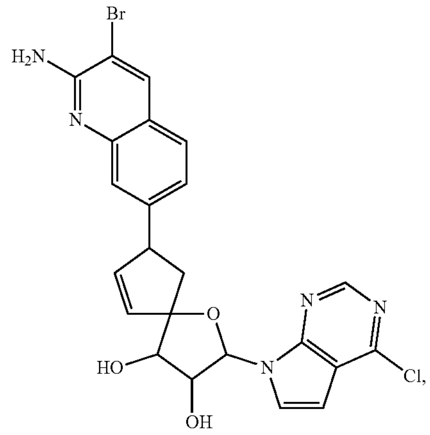
,
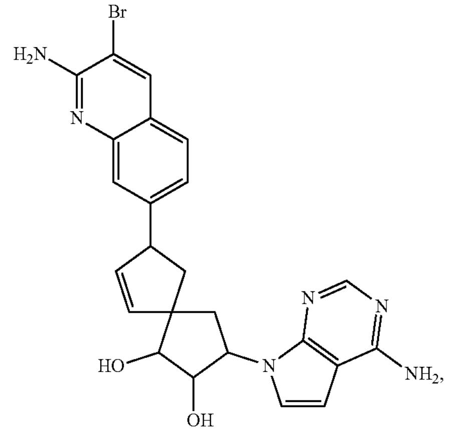
,
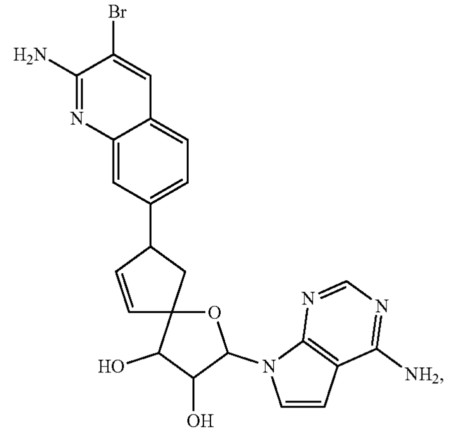
, -continued
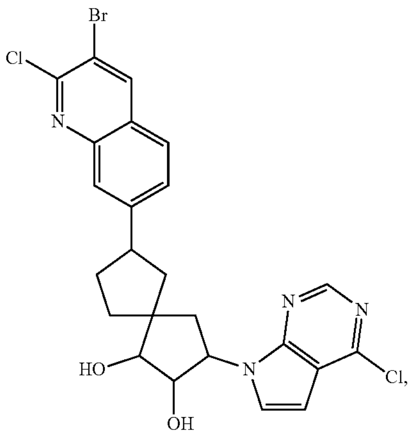
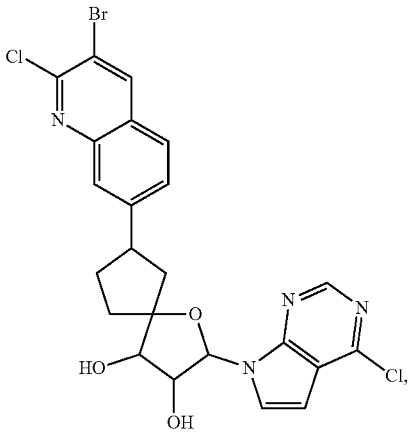
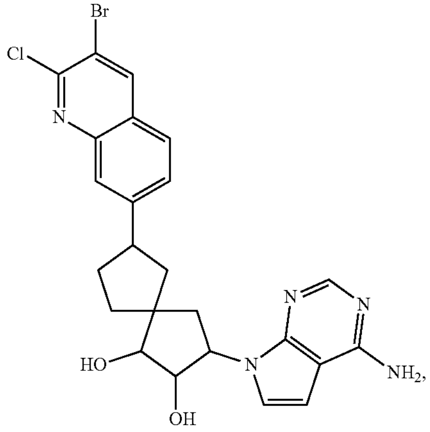
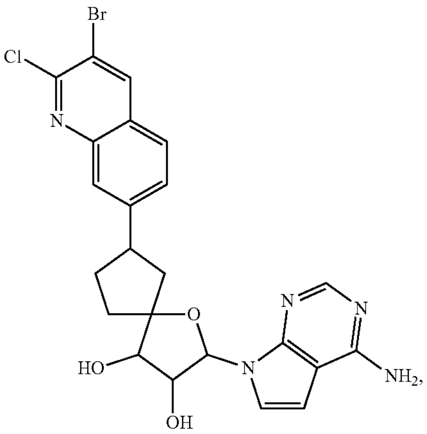
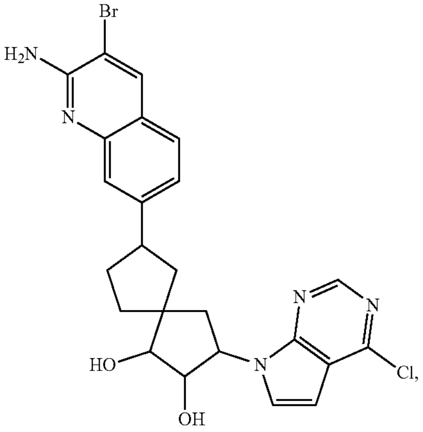
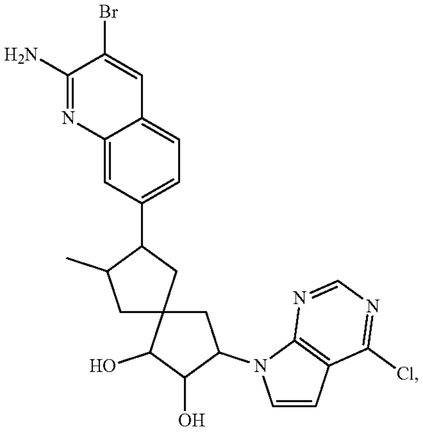
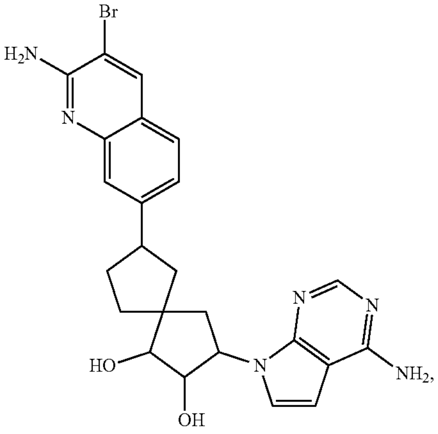

-continued
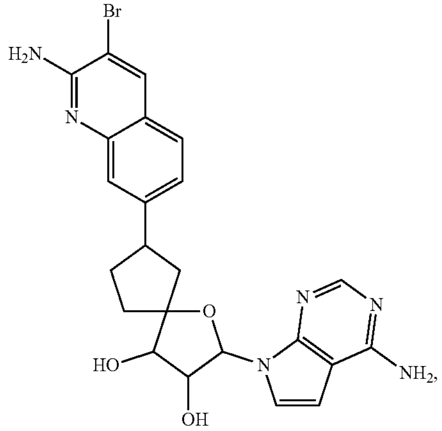,
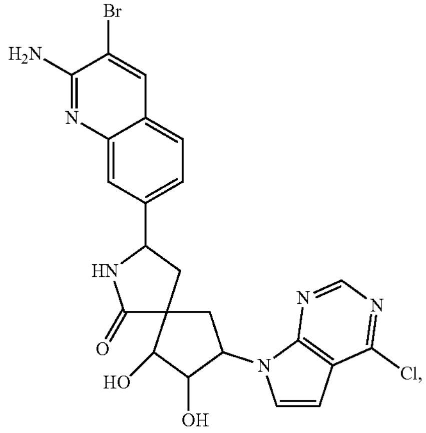,
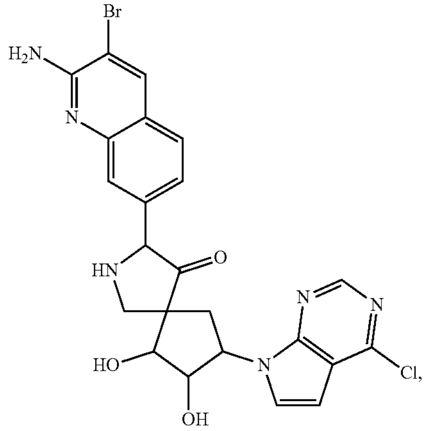,
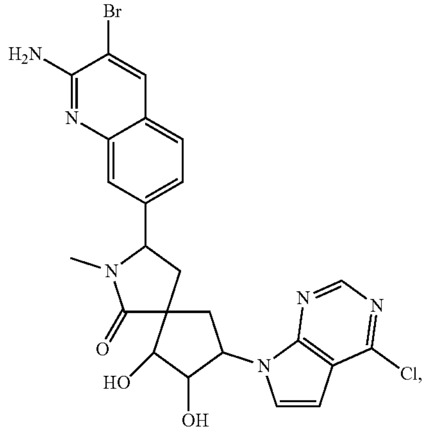,
-continued
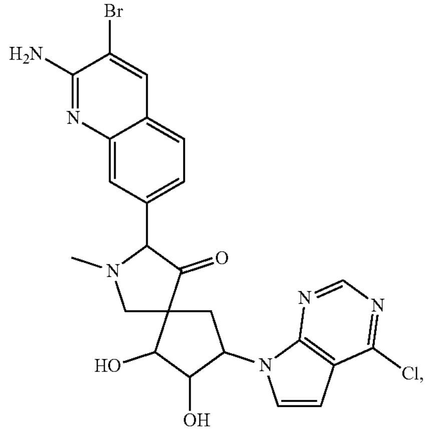,
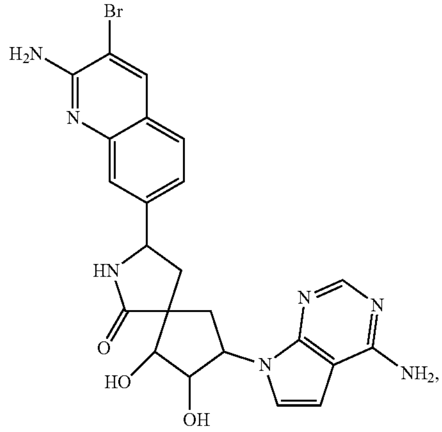,
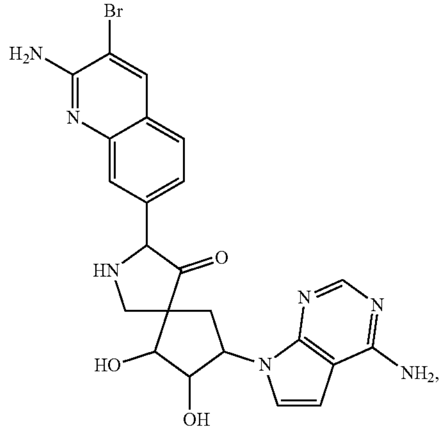,
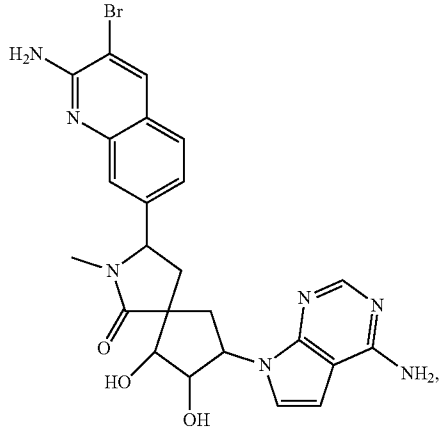, -continued
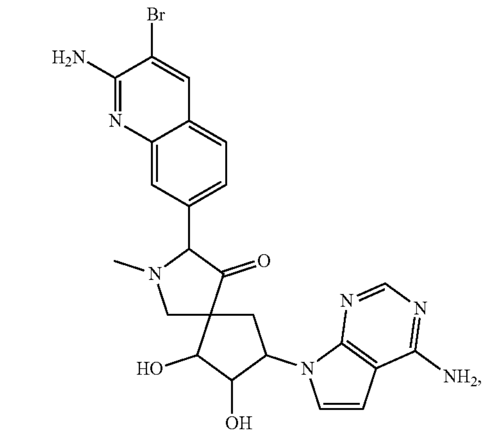
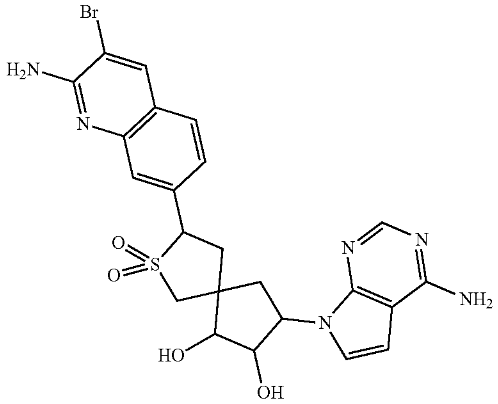
and
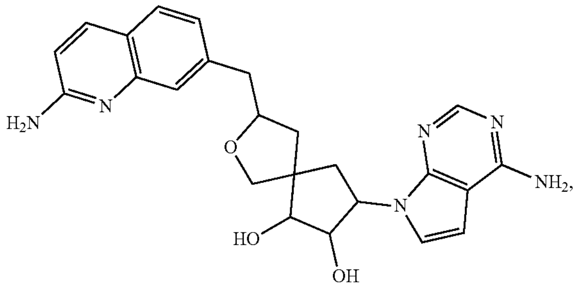
or a pharmaceutically salt thereof.
18. The compound of claim 1, selected from:
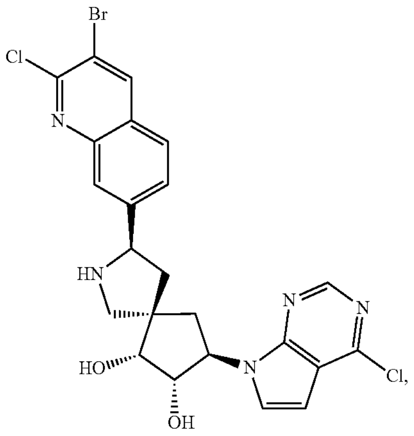
-continued
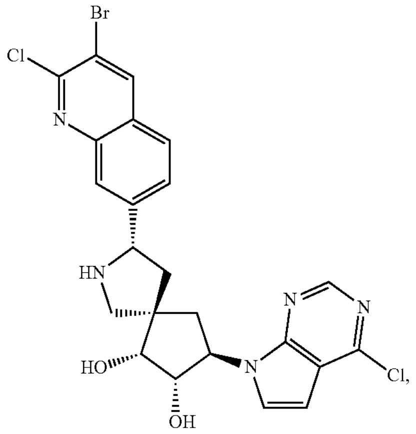
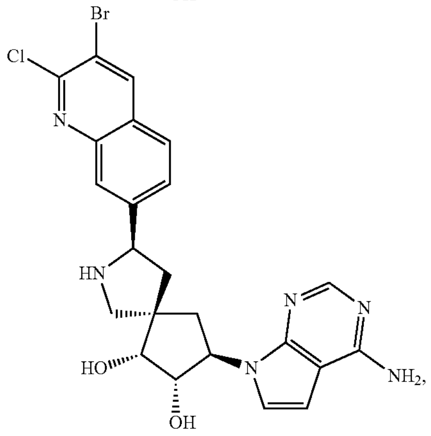
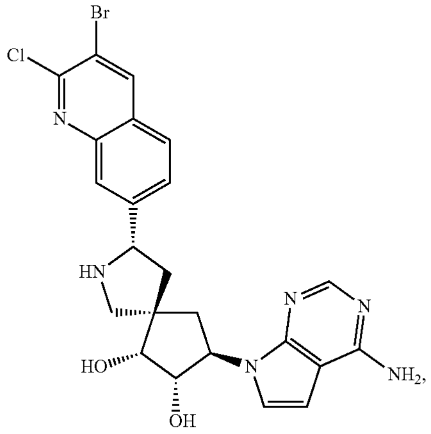
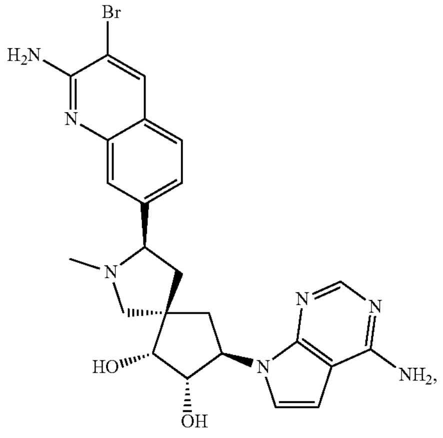

-continued
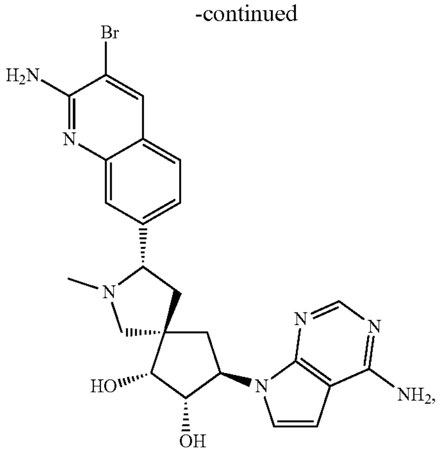
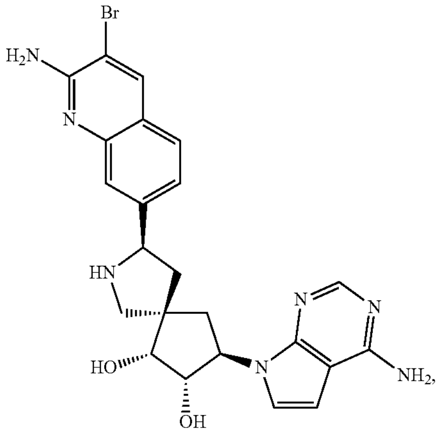
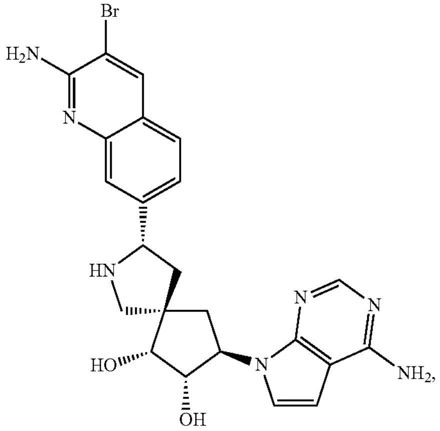
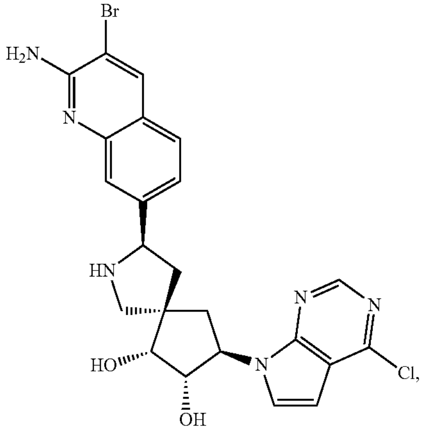
-continued
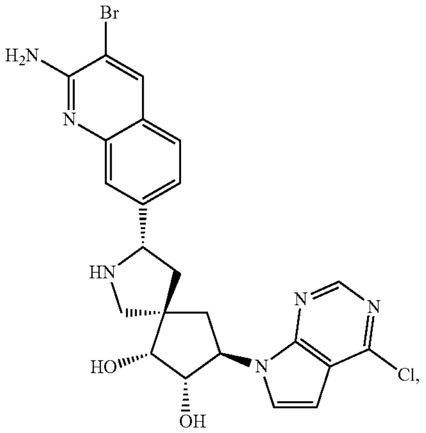
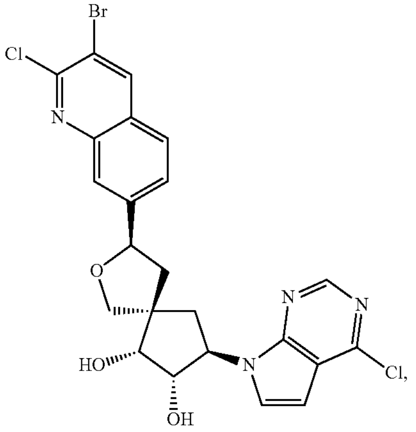
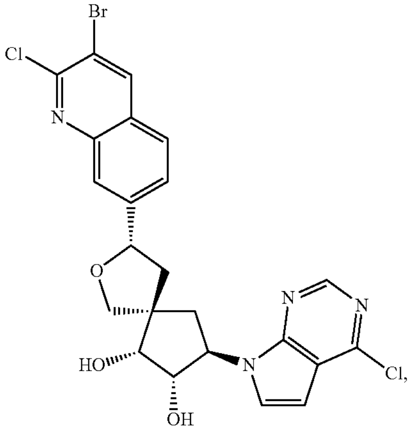
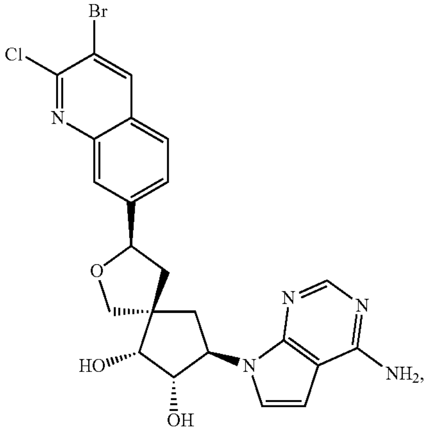

-continued
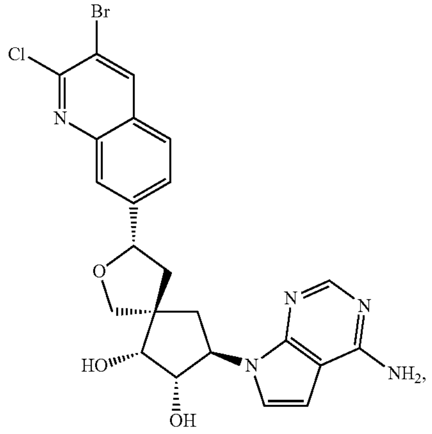
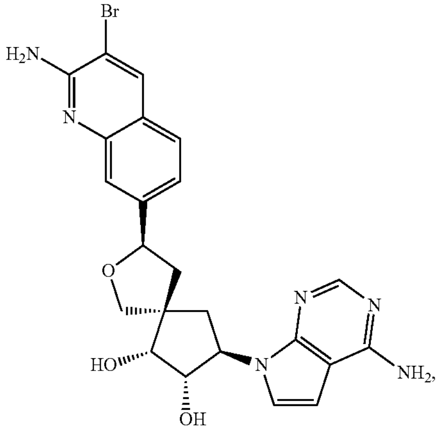
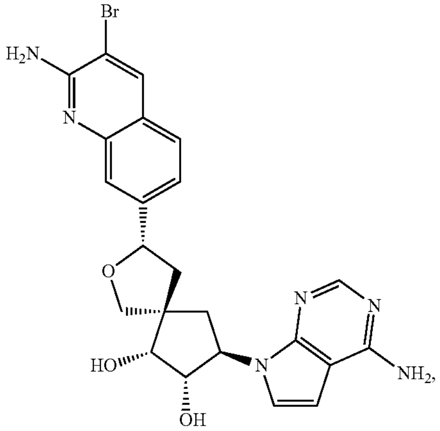
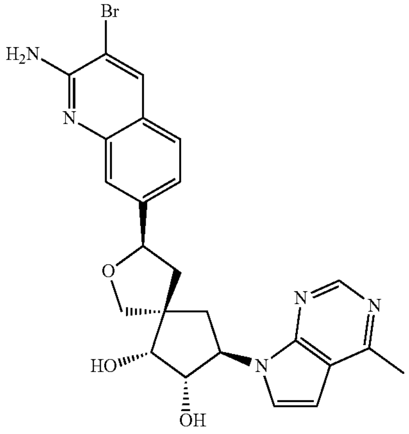
,
-continued
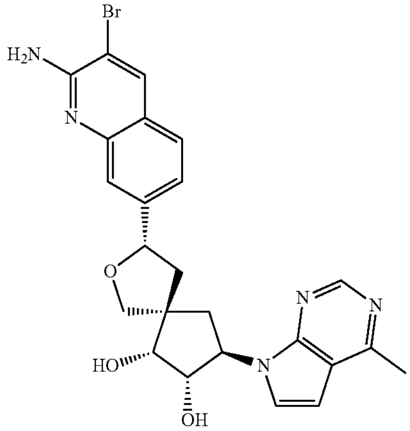
,
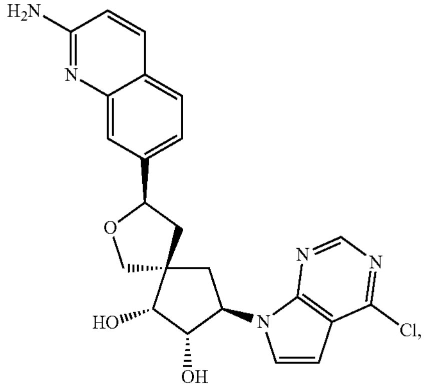
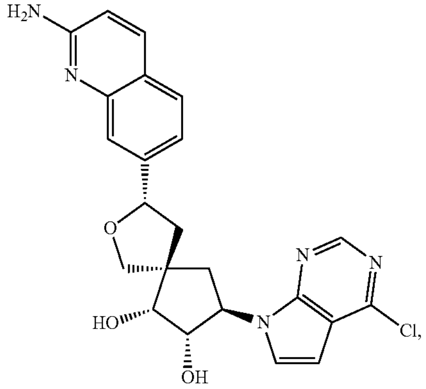
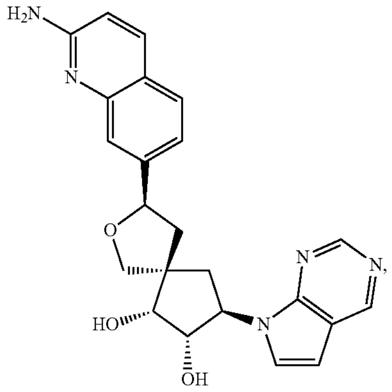

-continued
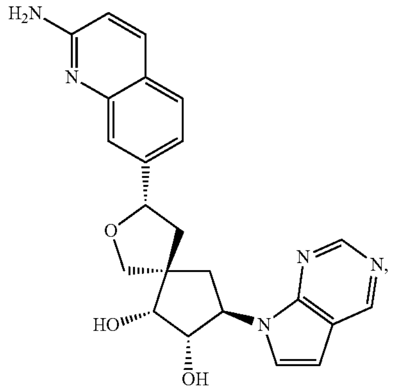
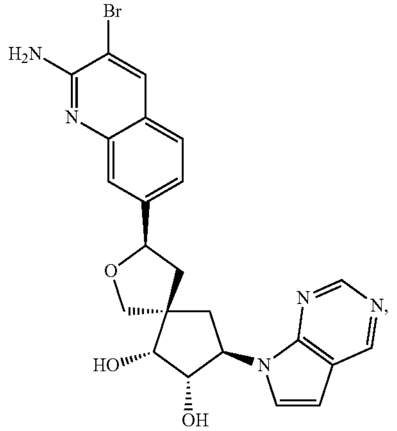
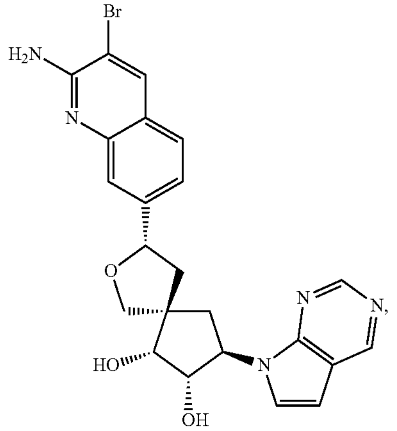
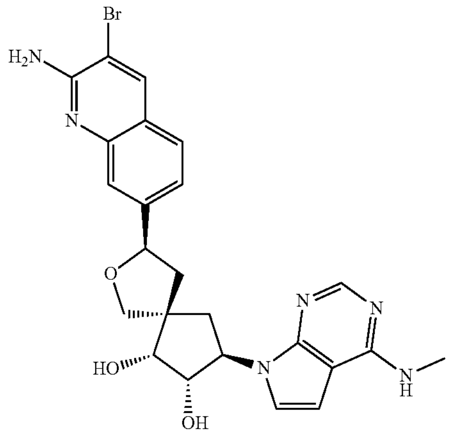
,
-continued
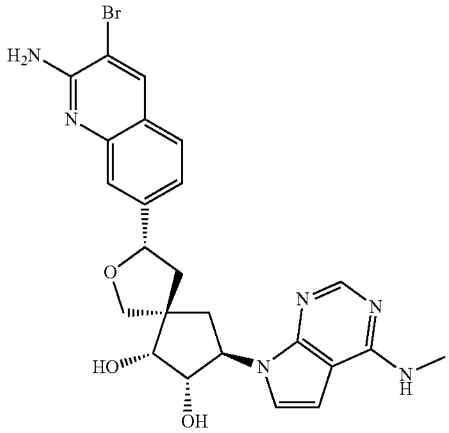
,
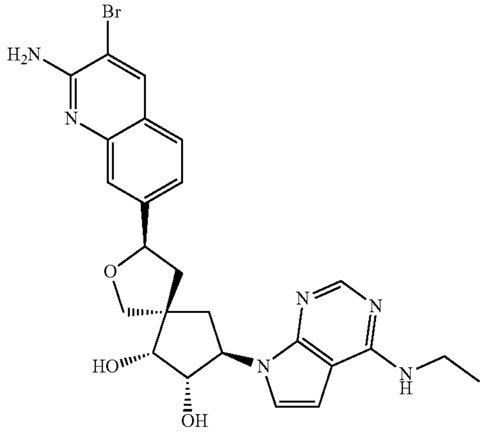
,
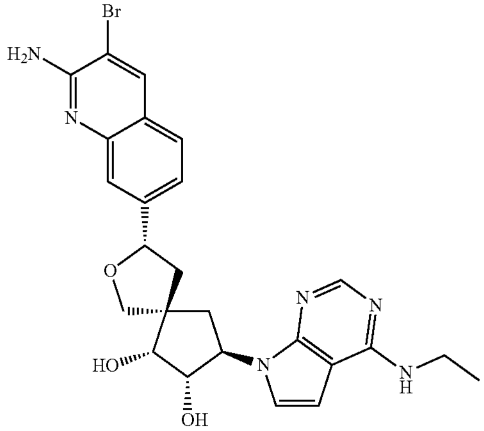
,
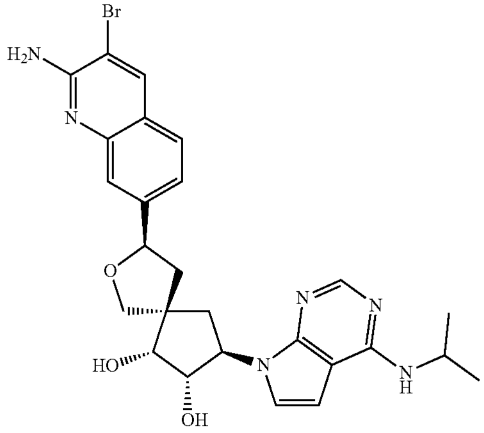
, -continued
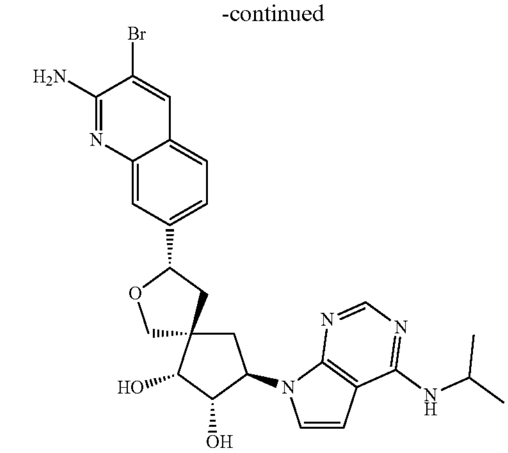
,
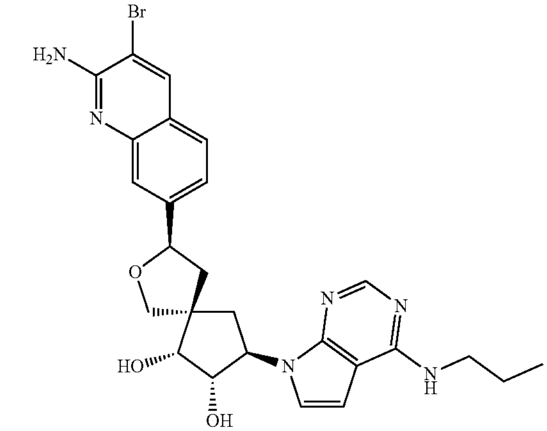
,
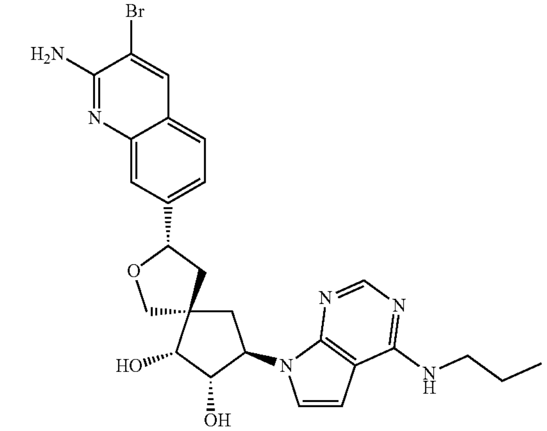
,
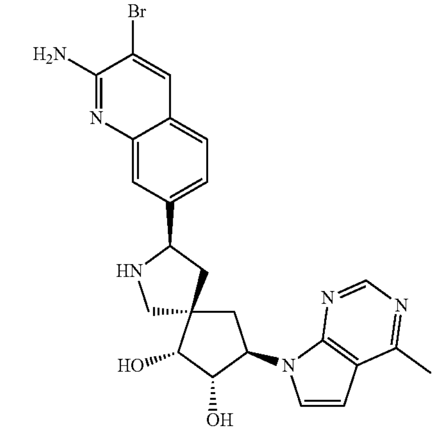
,
-continued
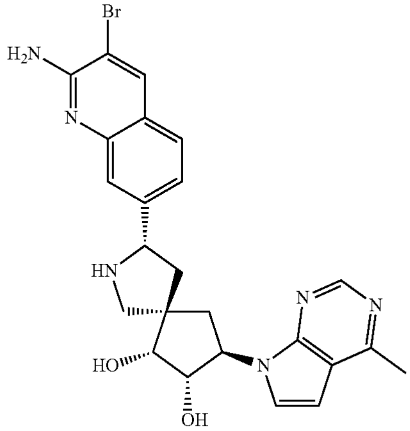
,
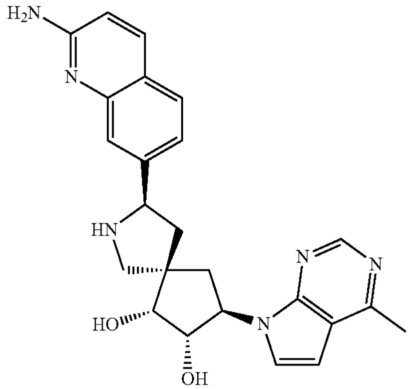
,
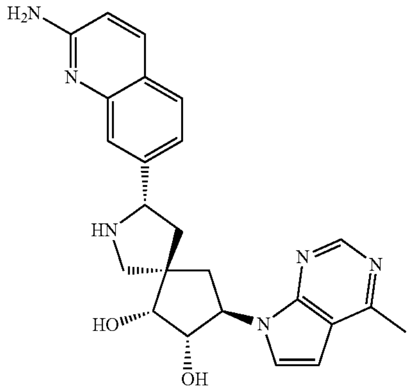
,
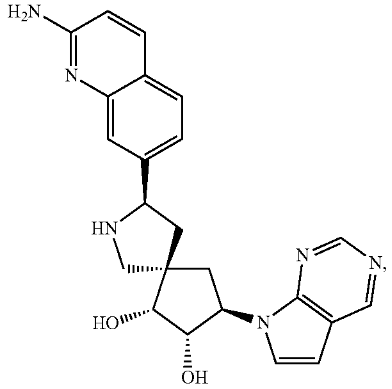

-continued
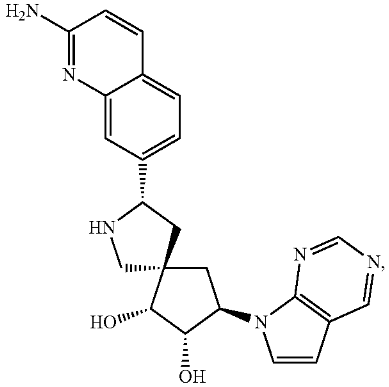
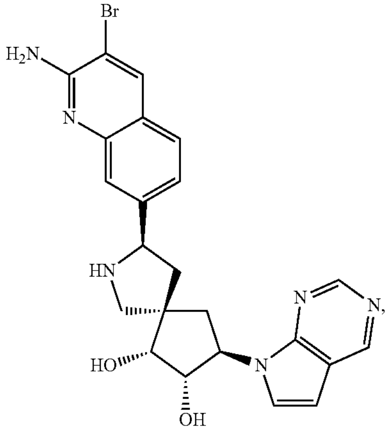
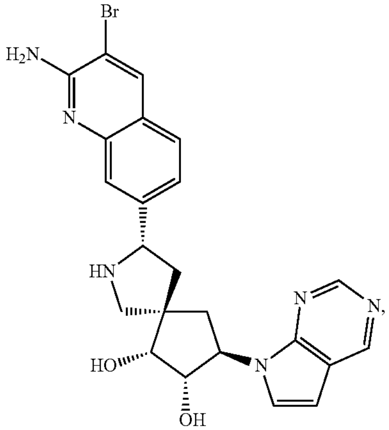
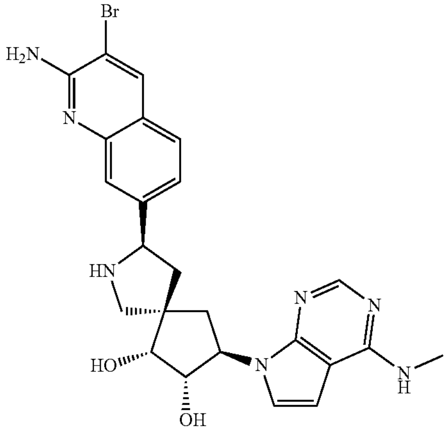
,
-continued
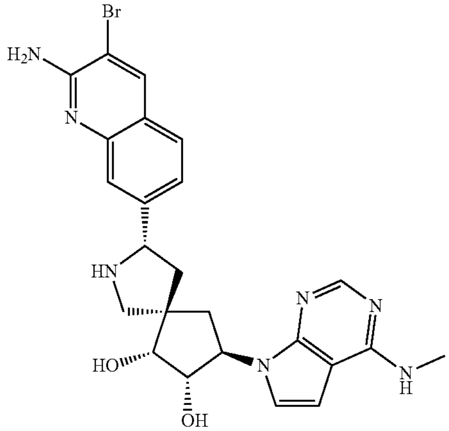
,
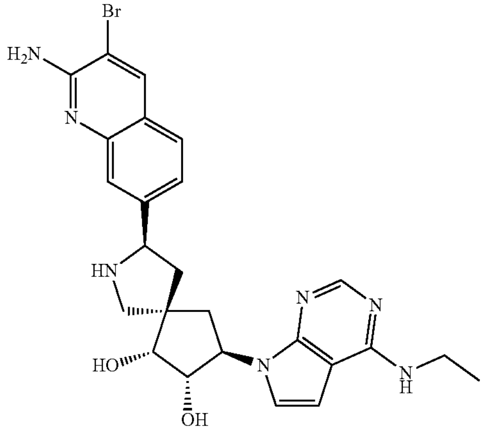
,
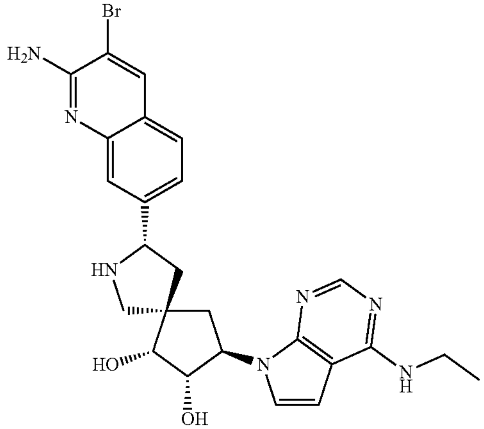
,
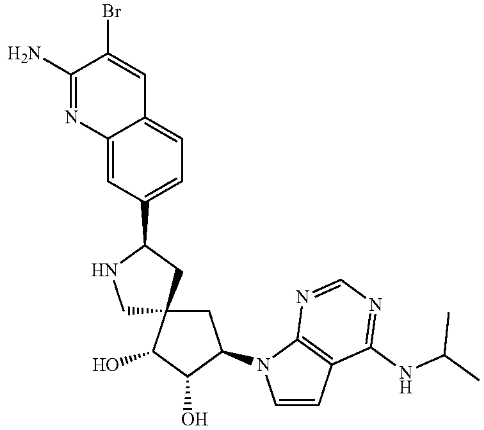
, -continued
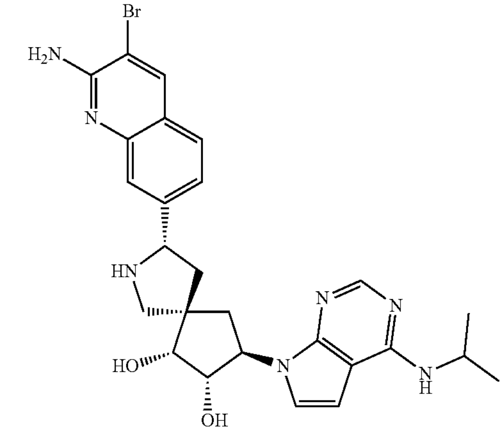
,
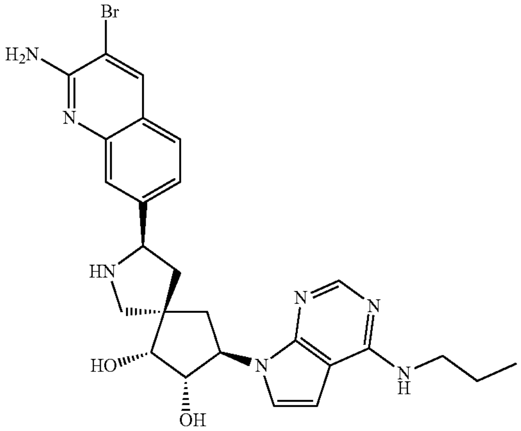
,
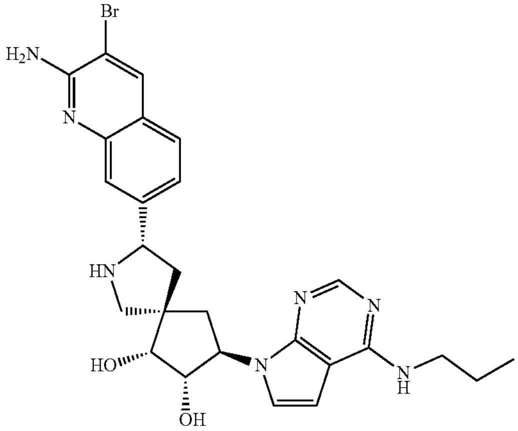
,
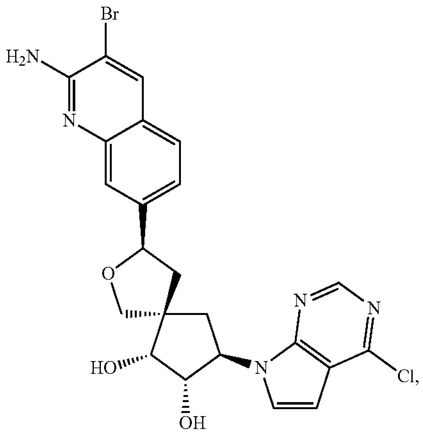
-continued
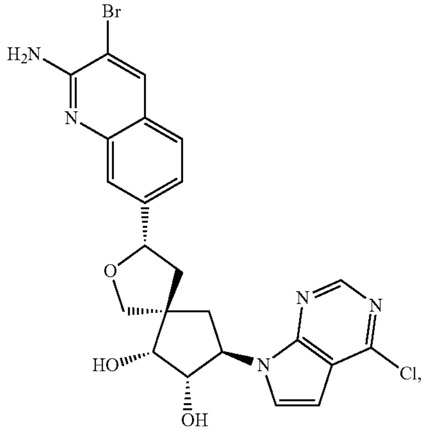
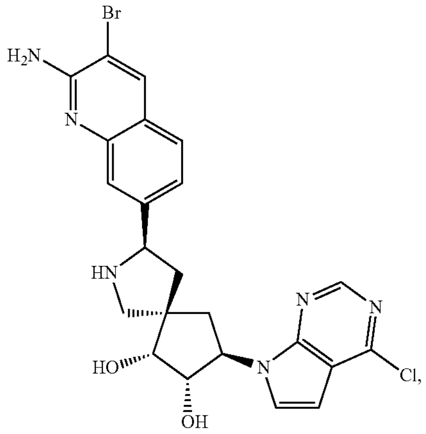
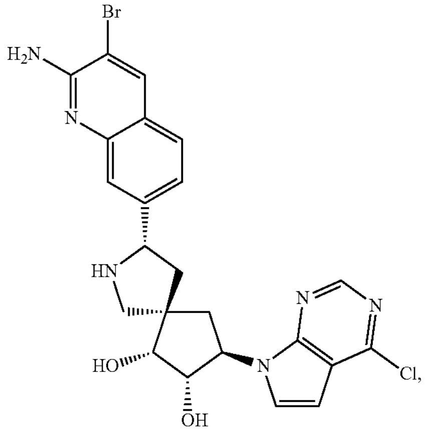
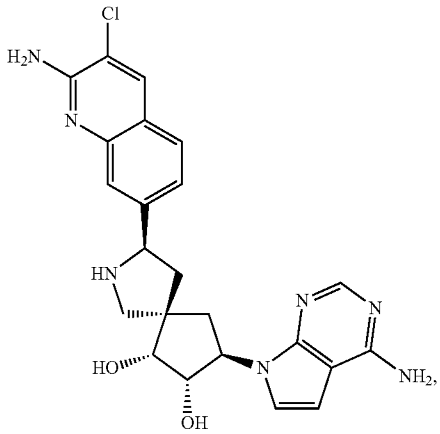

-continued
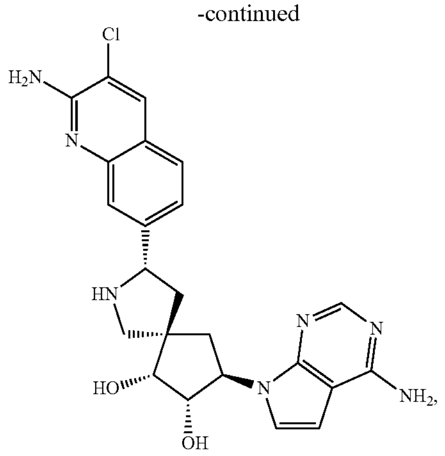
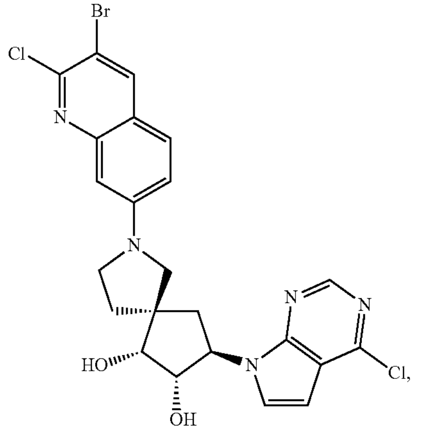
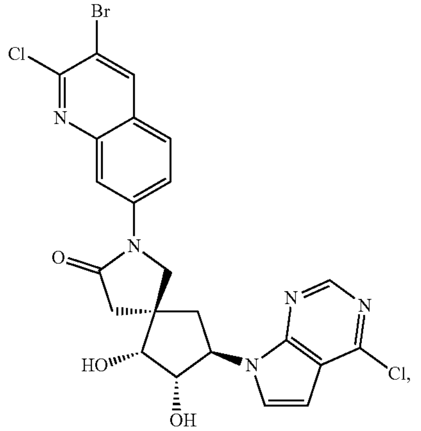
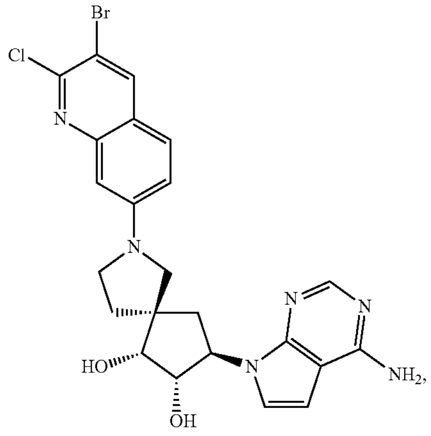
-continued
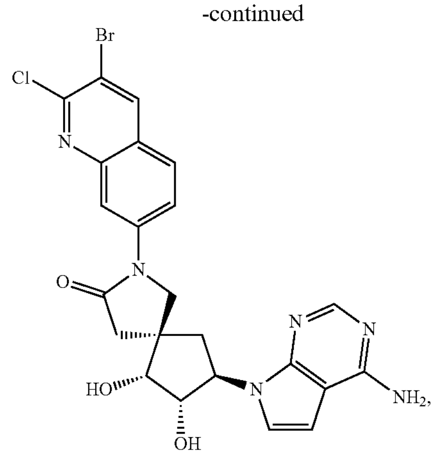
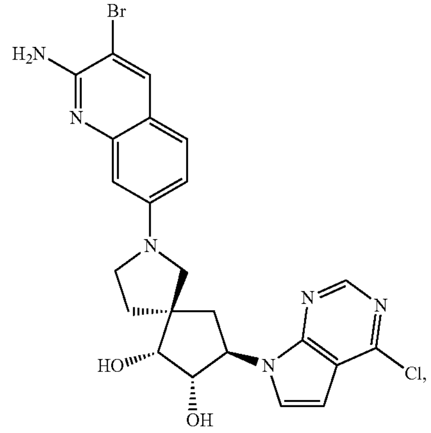
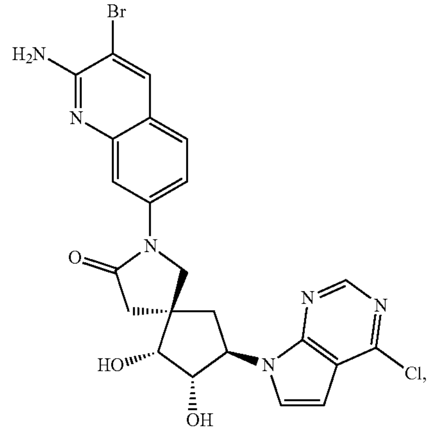
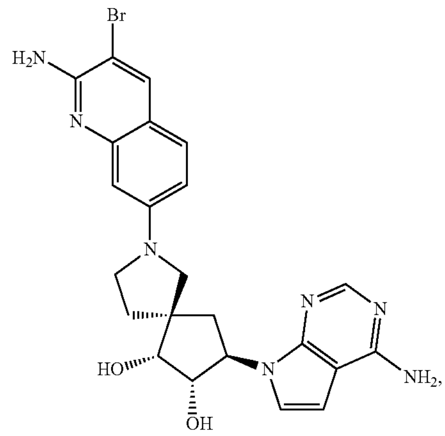

-continued
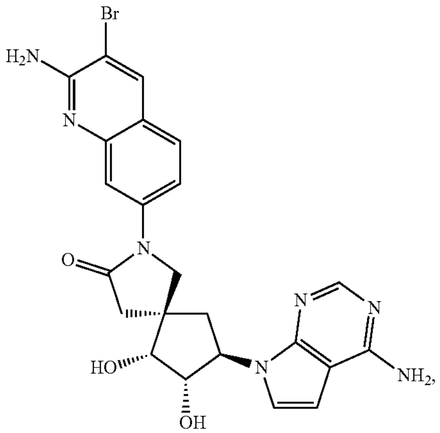
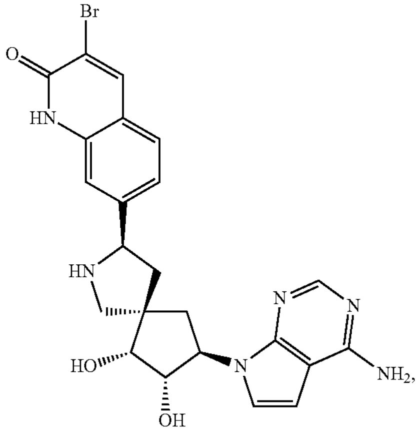
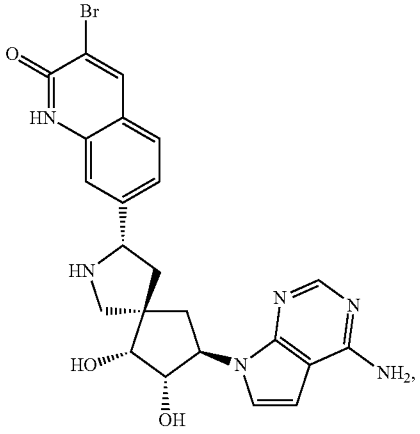
-continued
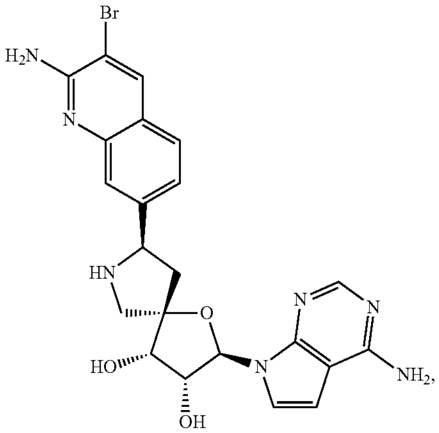
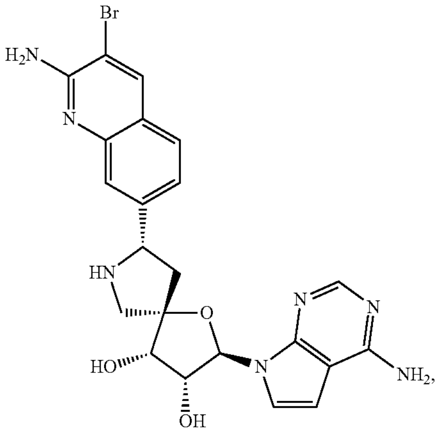
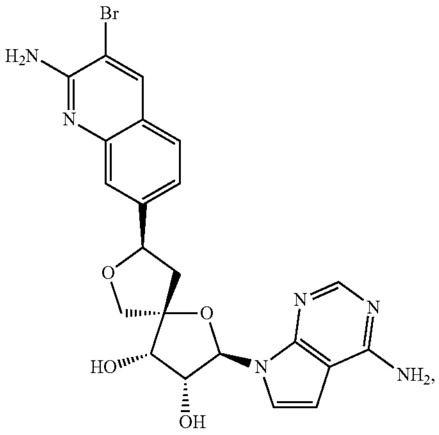

-continued
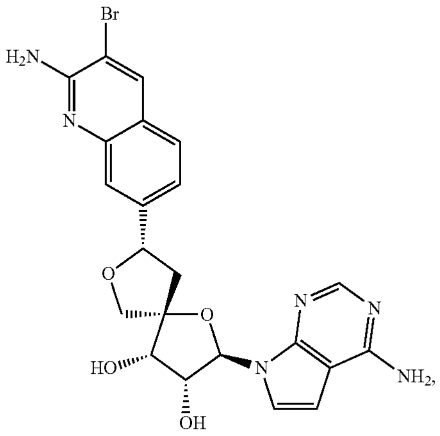
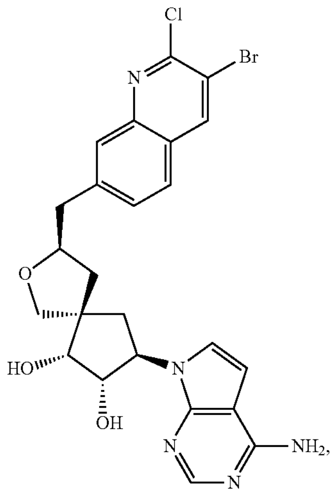
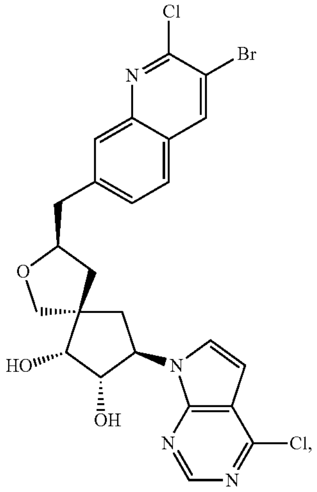
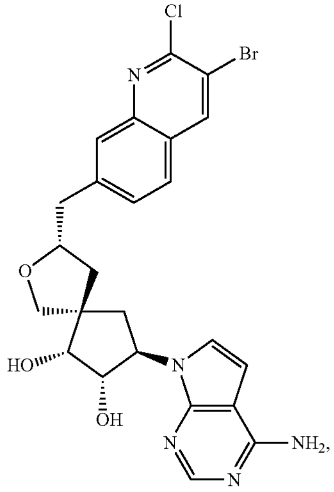
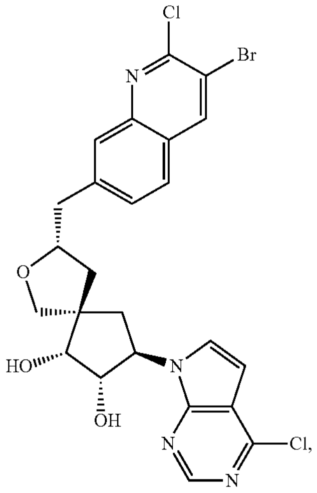
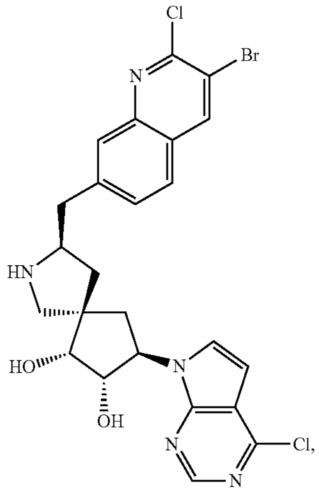

-continued
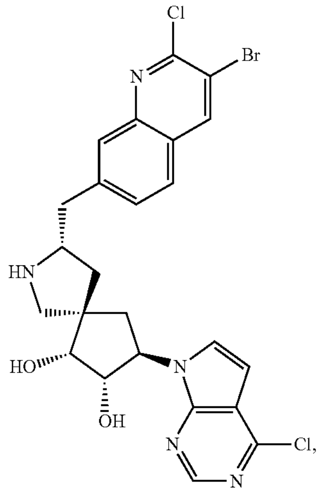
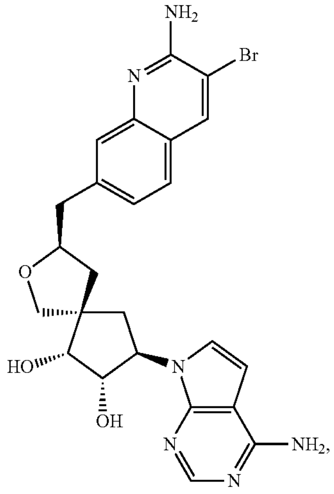
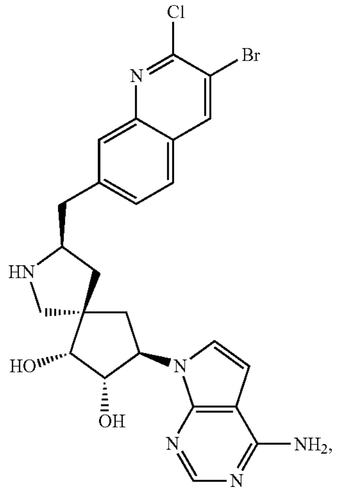
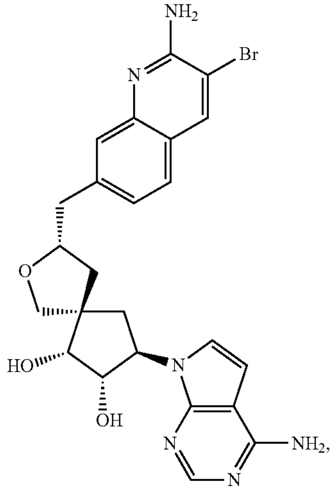
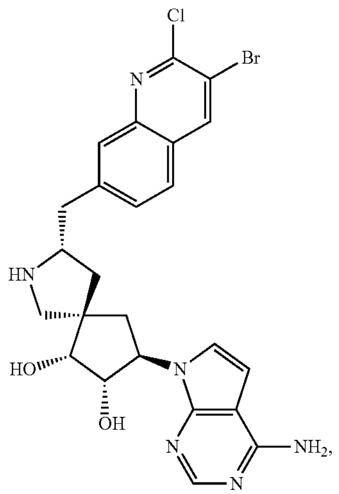
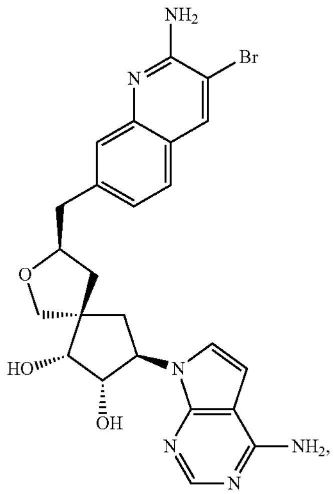

-continued
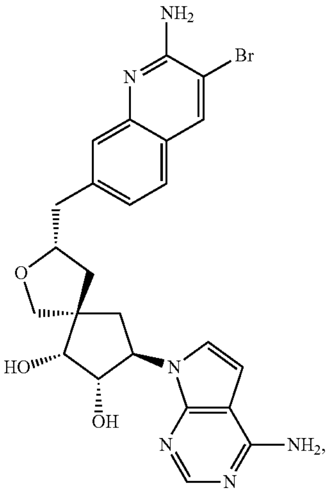
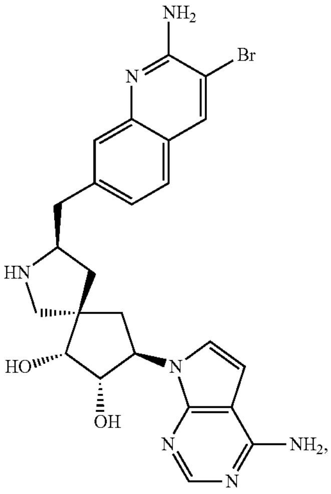
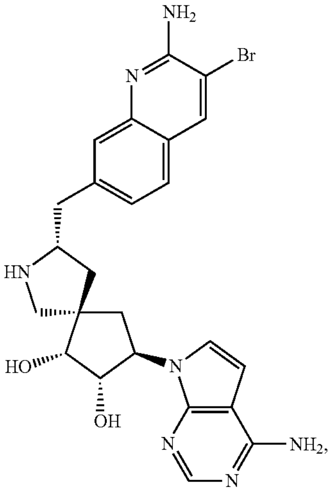
-continued
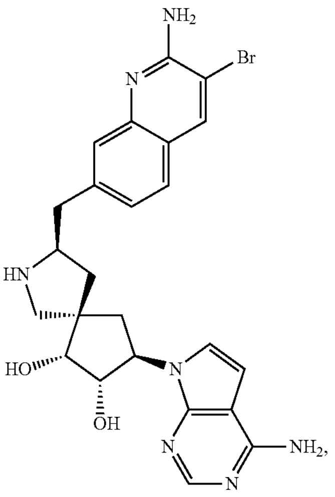
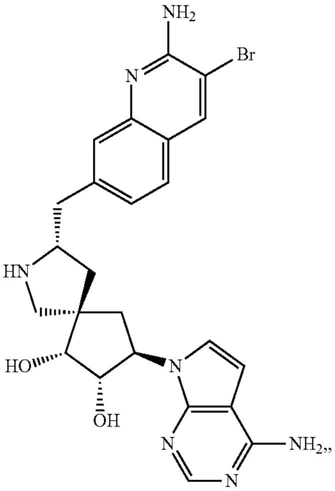 [SMILES: Nc1nc2cc(C[C@@H]3C[C@@]4(CN3)C[C@@H](n3ccc5c(N)ncnc53)[C@H](O)[C@@H]4O)ccc2cc1Br]
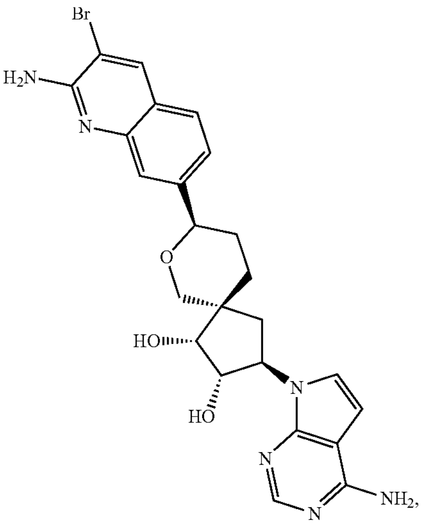

-continued
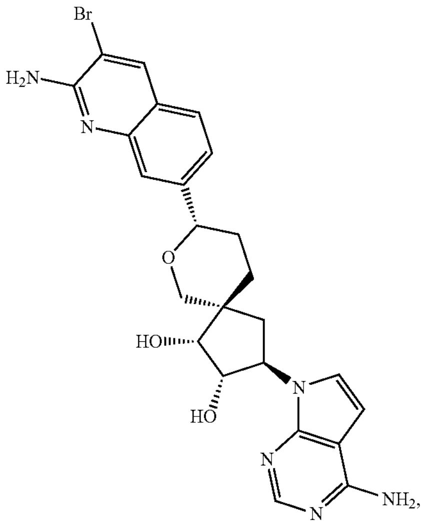
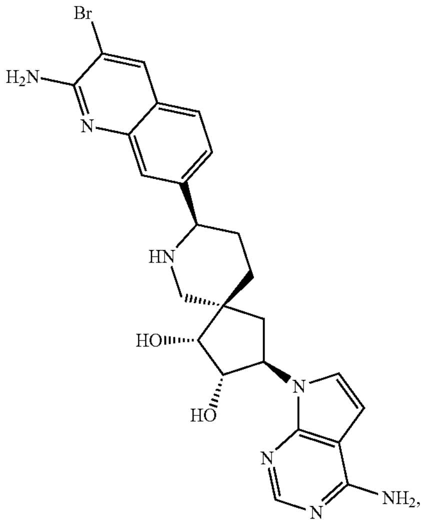 [SMILES: Nc1nc2cc([C@H]3CC[C@@]4(CN3)C[C@@H](n3ccc5c(N)ncnc53)[C@H](O)[C@@H]4O)ccc2cc1Br]
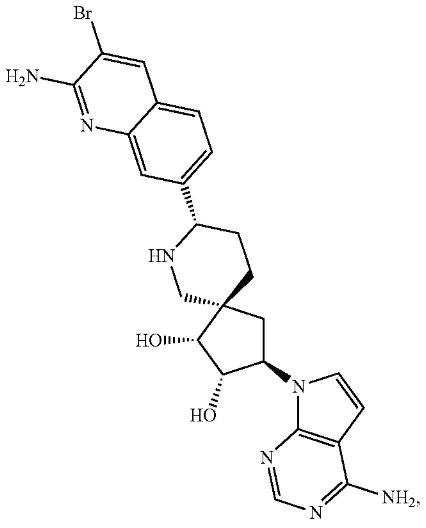 [SMILES: Nc1nc2cc([C@@H]3CC[C@@]4(CN3)C[C@@H](n3ccc5c(N)ncnc53)[C@H](O)[C@@H]4O)ccc2cc1Br]
-continued
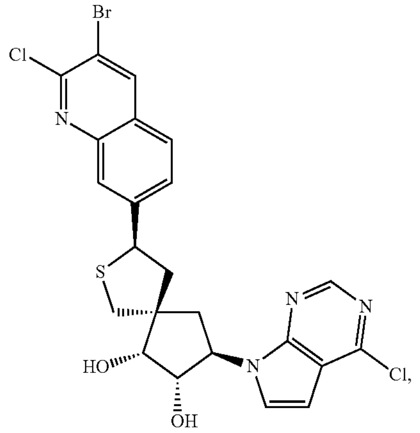
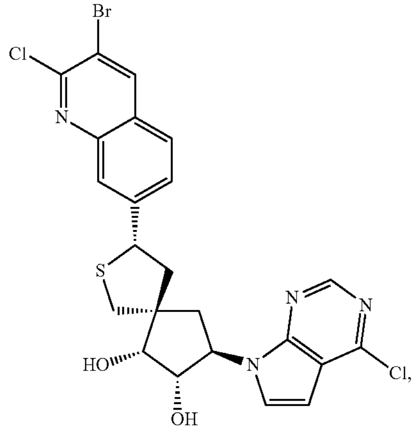
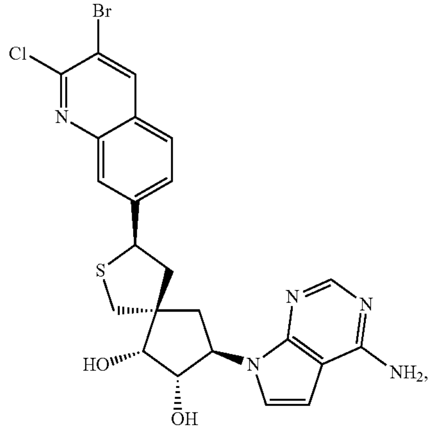
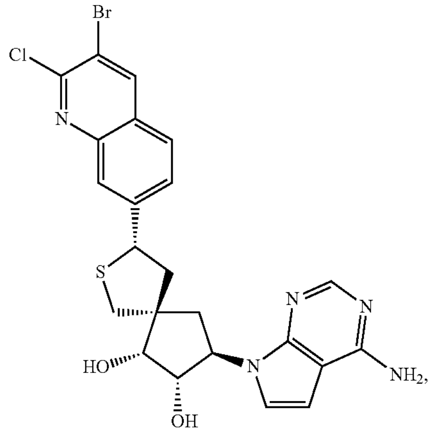

-continued
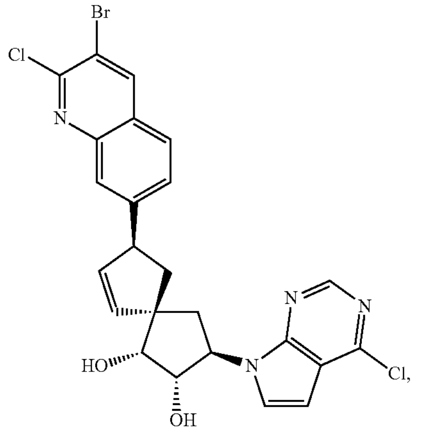
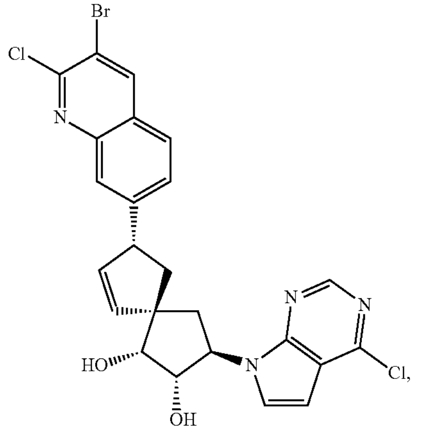
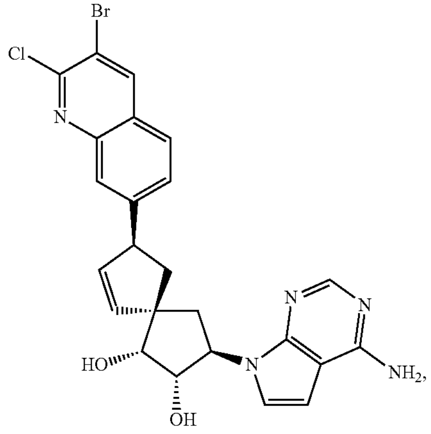
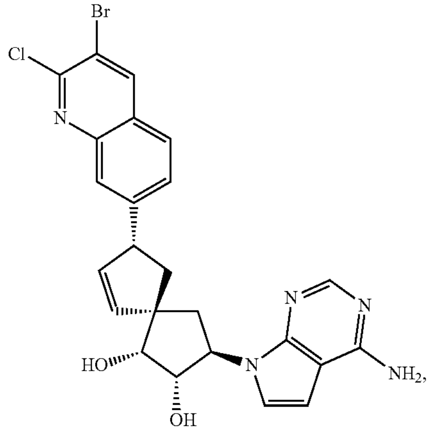
-continued
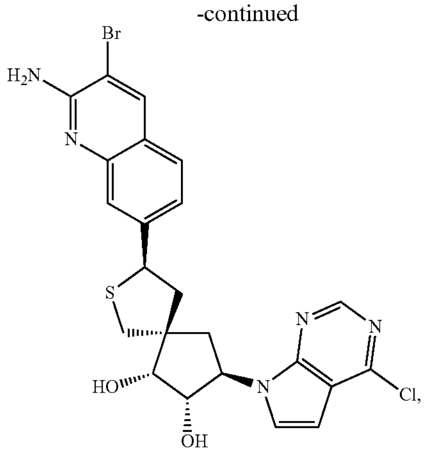
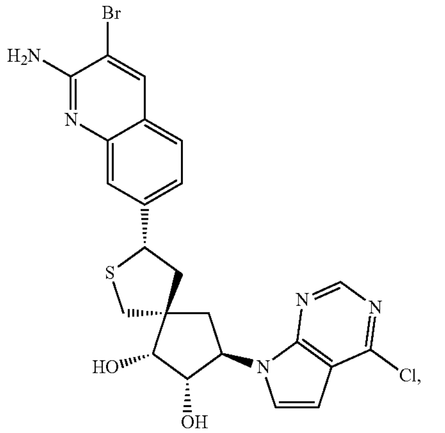
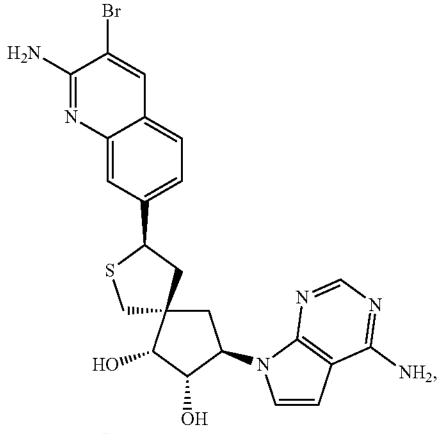
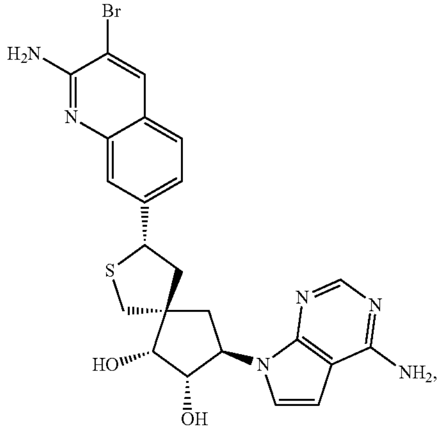

-continued
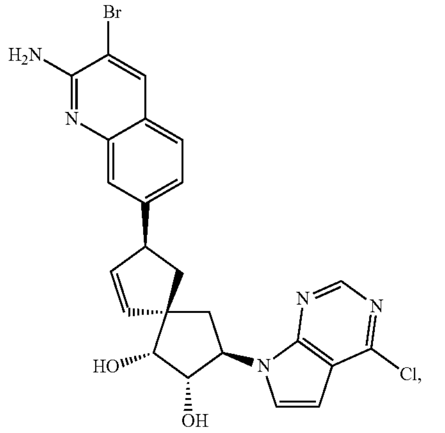
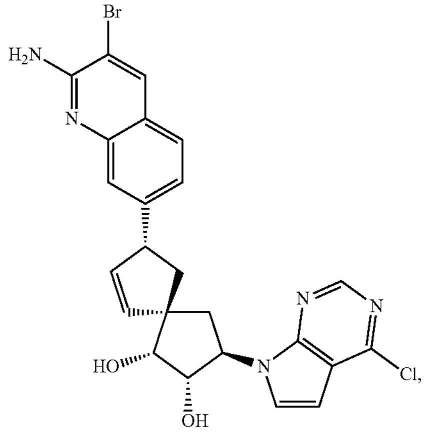
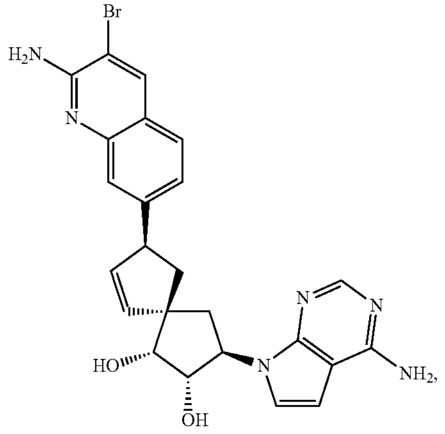
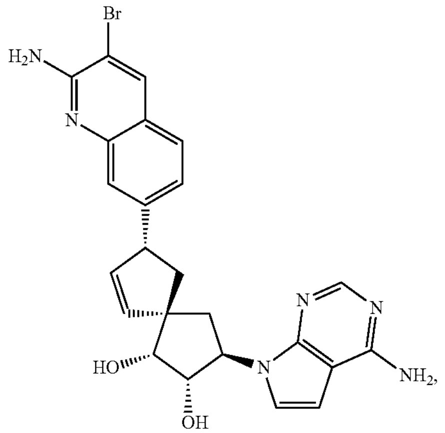
-continued
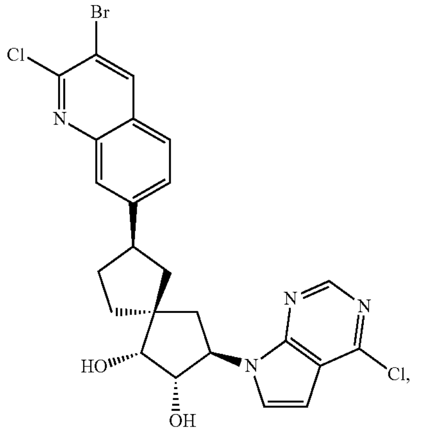
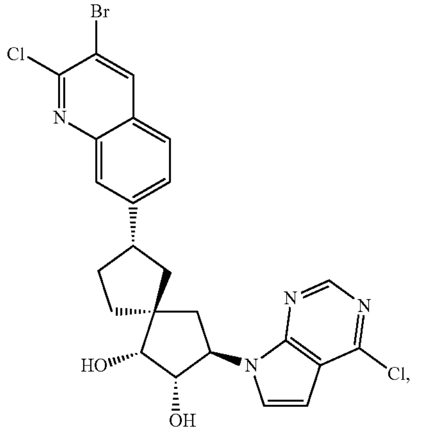
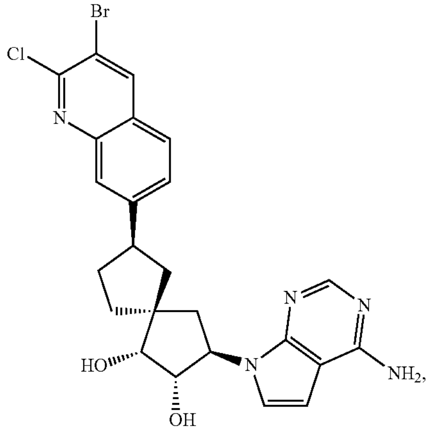
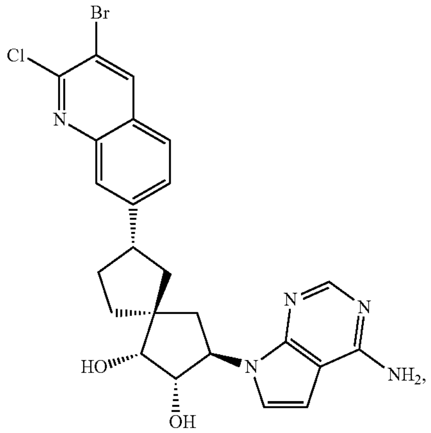

-continued
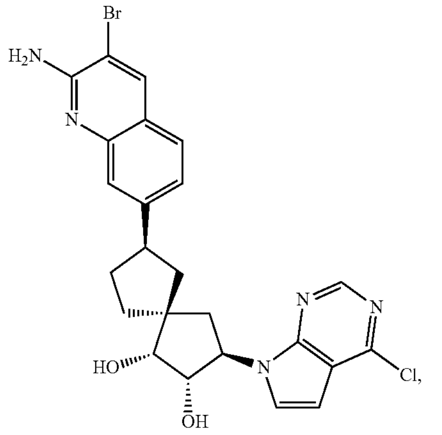
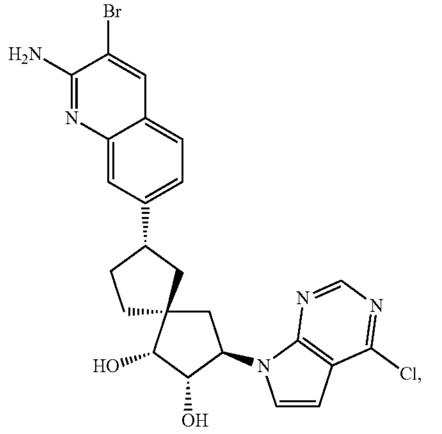
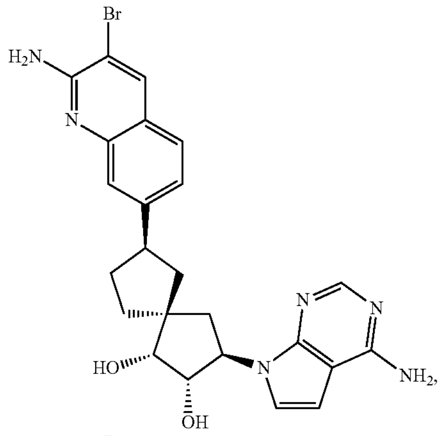
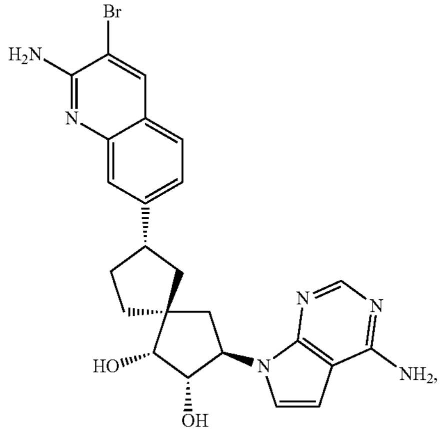
-continued
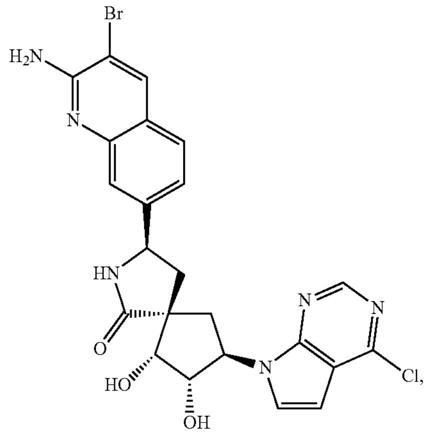
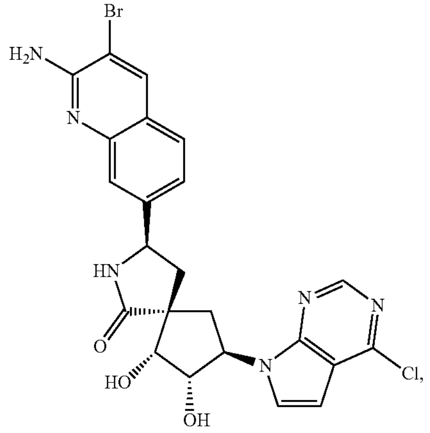
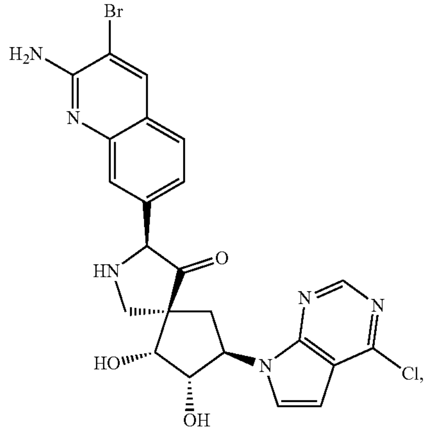
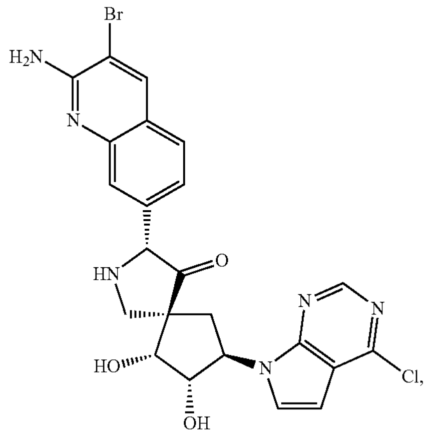

-continued
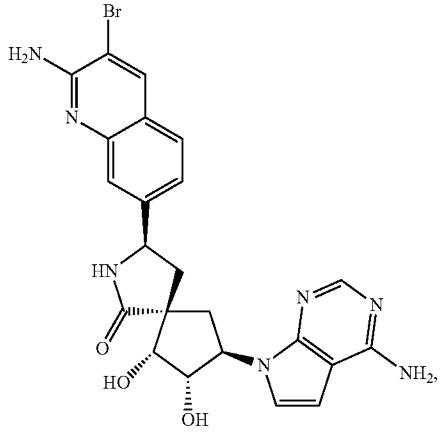
,
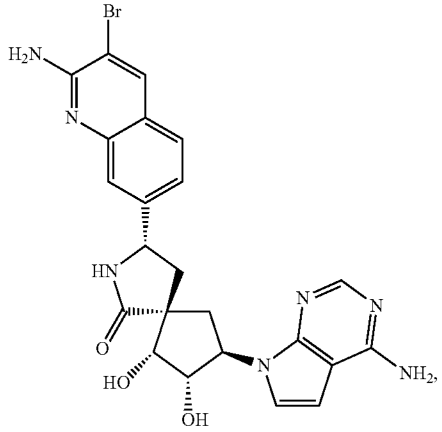
,
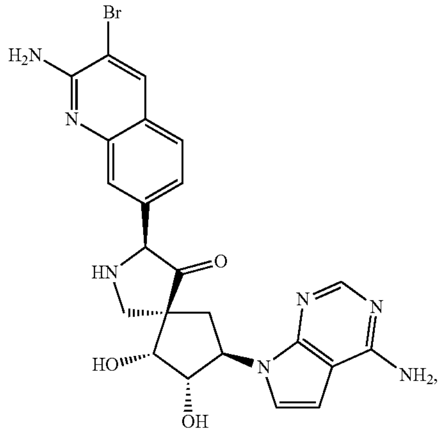
,
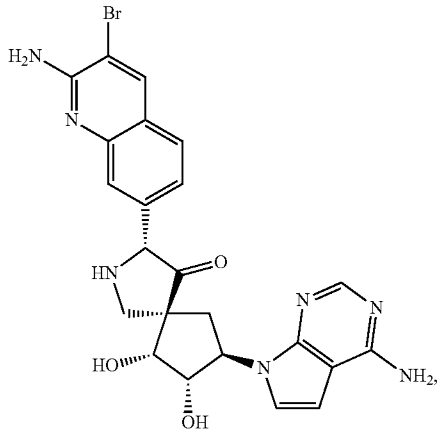
,
-continued
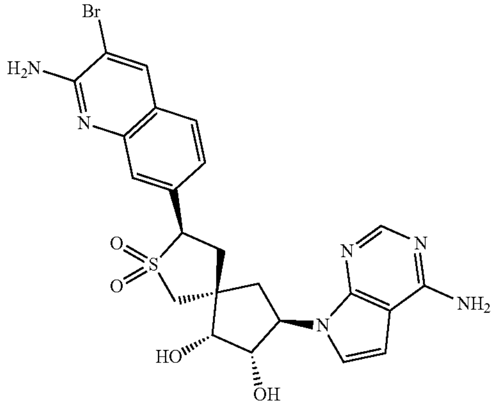
and
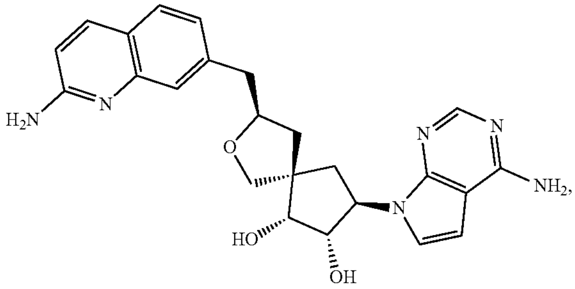 [SMILES: Nc1ccc2ccc(C[C@H]3C[C@@]4(CO3)C[C@@H](n3ccc5c(N)ncnc53)[C@H](O)[C@@H]4O)cc2n1]
,
or a pharmaceutically salt thereof.
19. The compound of claim 1, selected from:
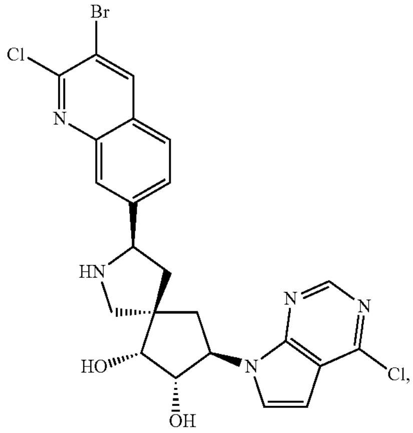
,
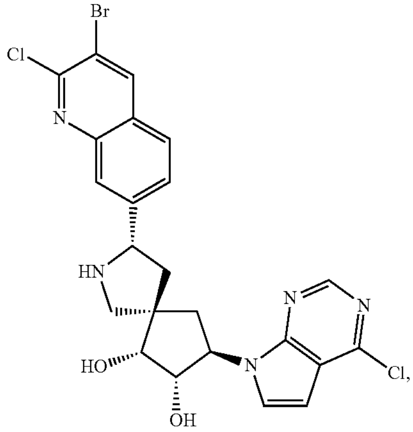
, -continued
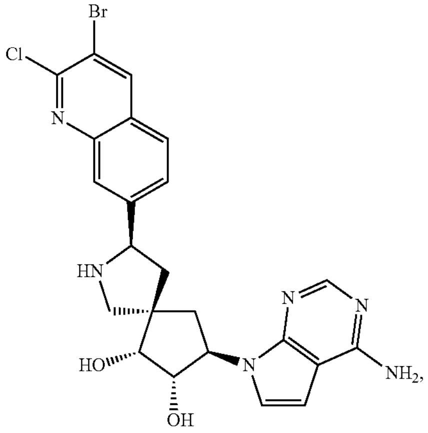
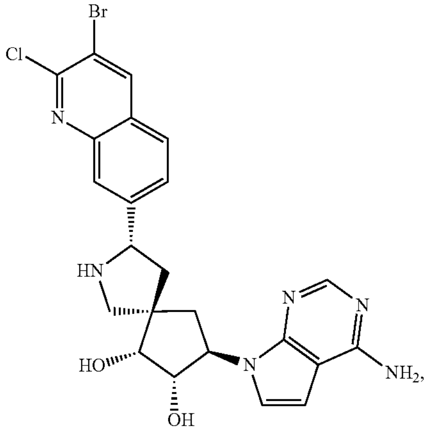
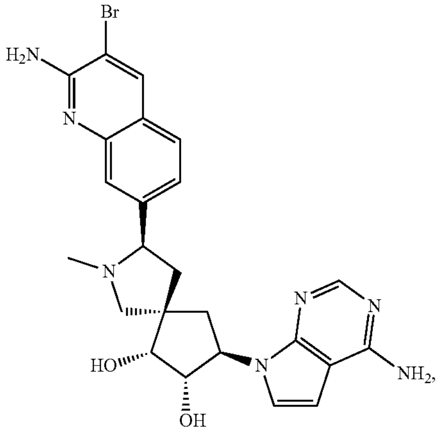
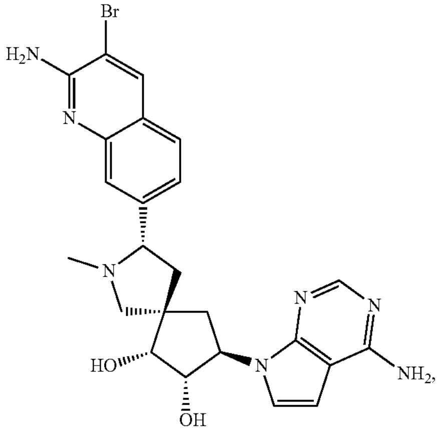
-continued
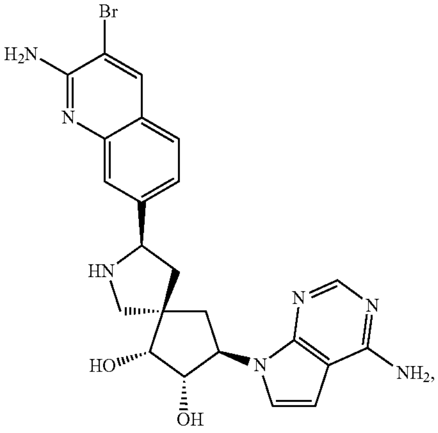
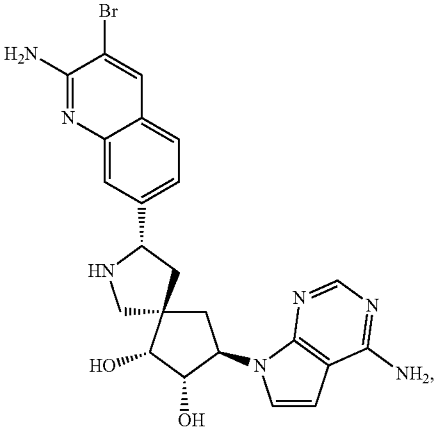
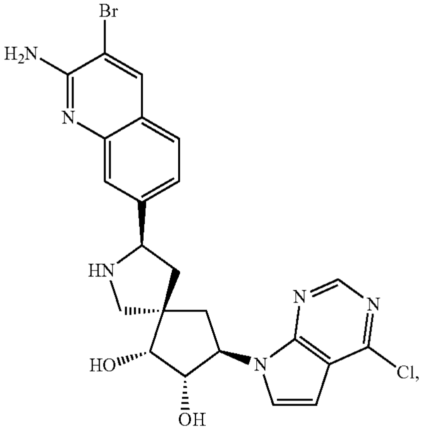
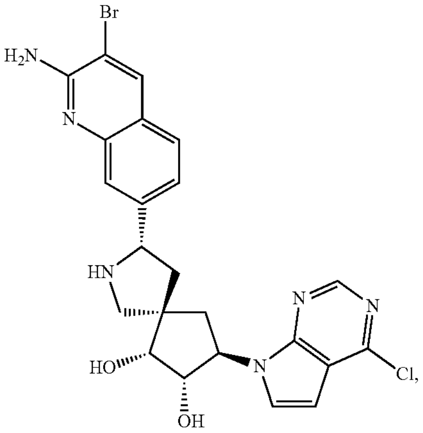

-continued
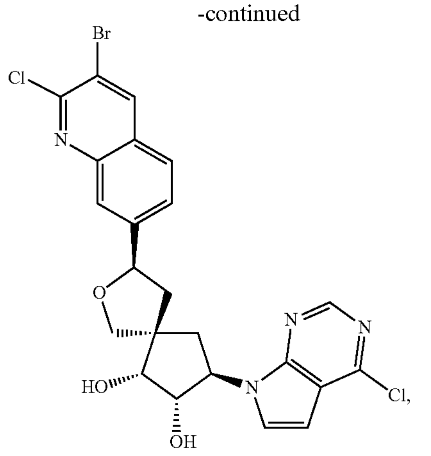
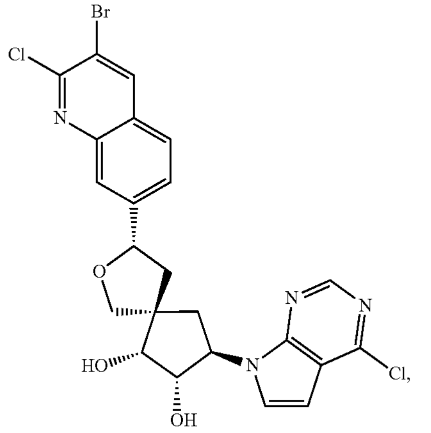
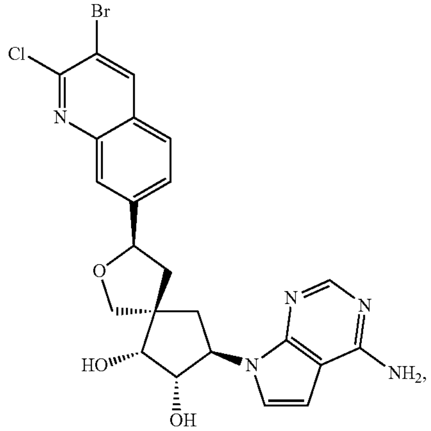
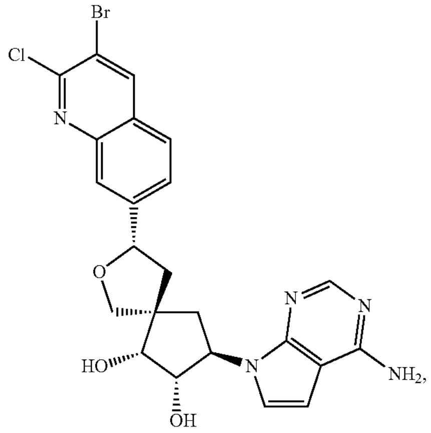
-continued
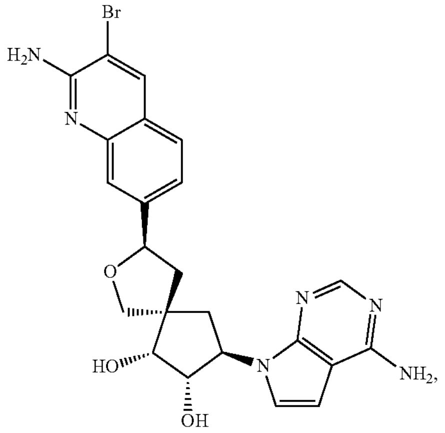
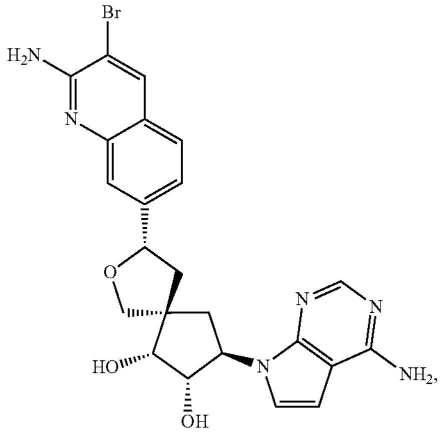
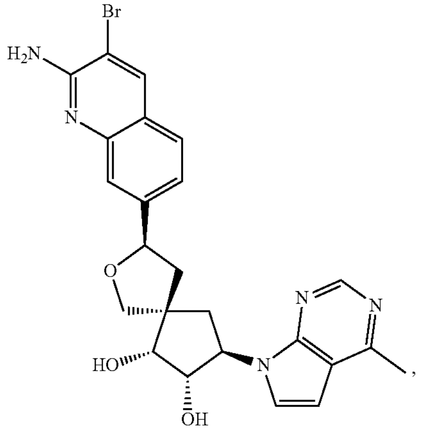
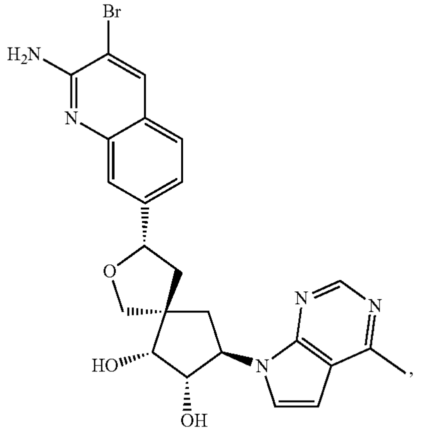

-continued
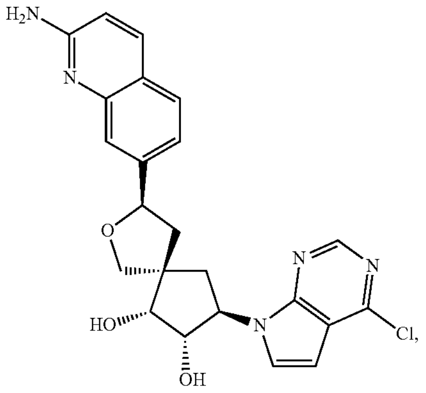
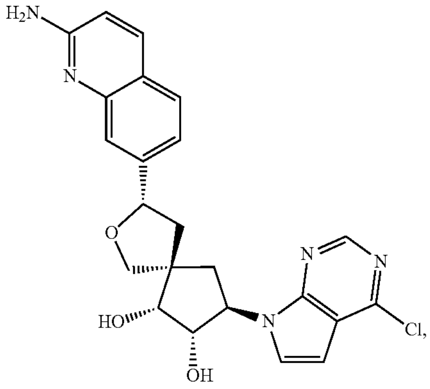
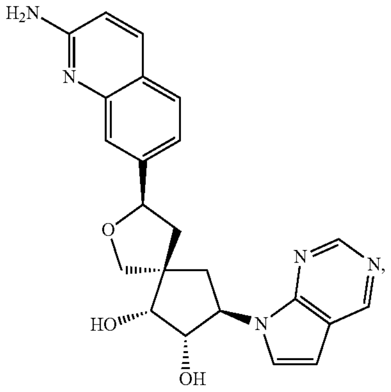
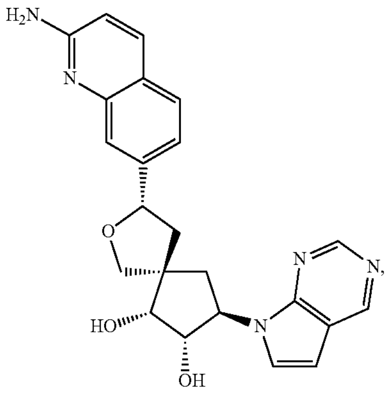
-continued
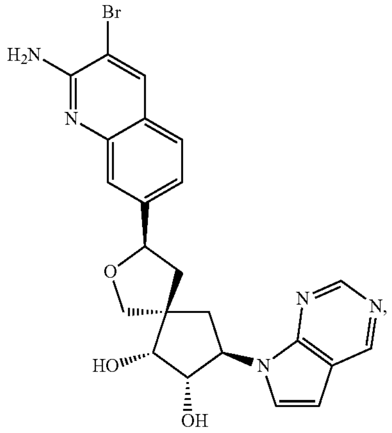
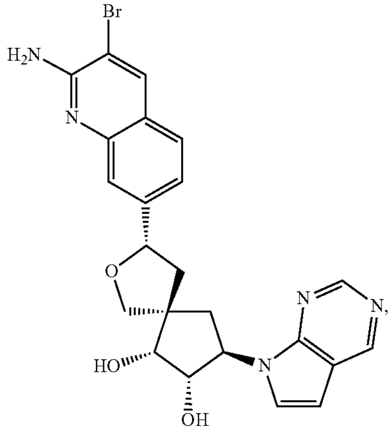
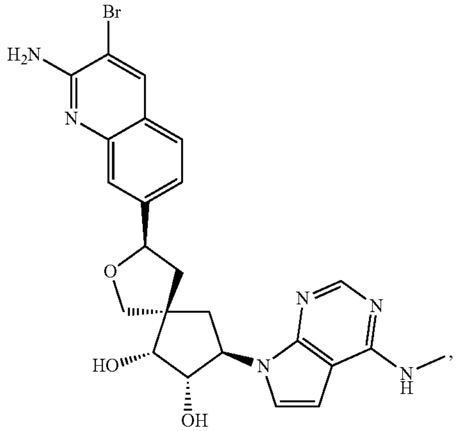
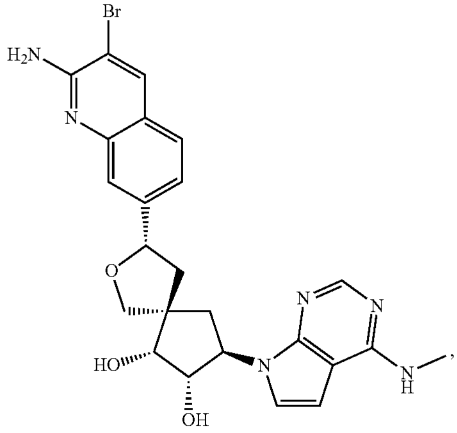

-continued

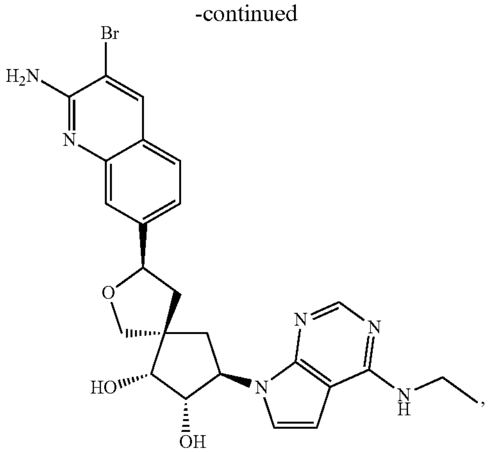

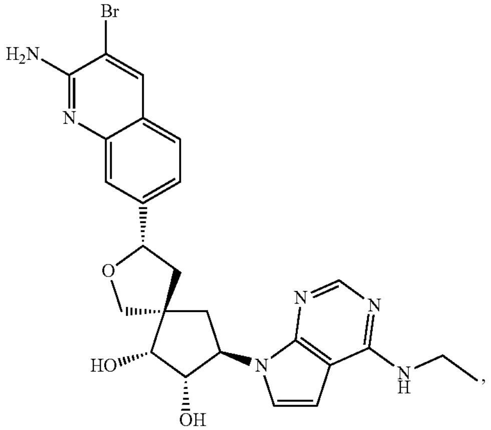

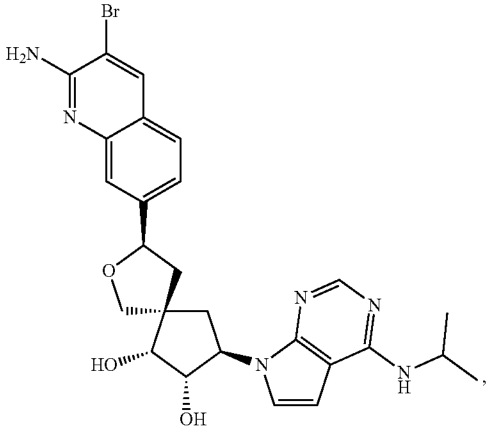

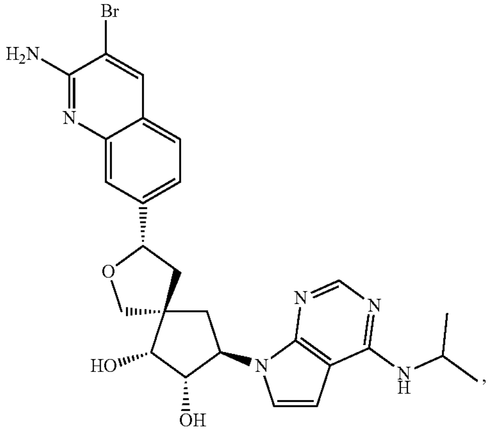

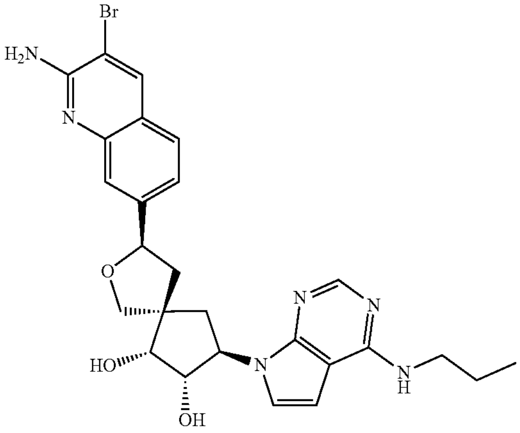

and

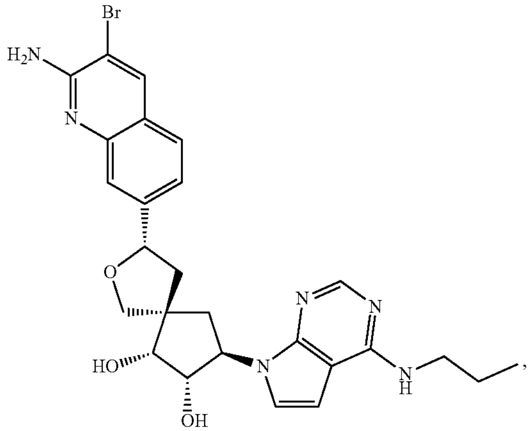

or a pharmaceutically salt thereof.

20. A pharmaceutical composition comprising a compound of claim 1 and a pharmaceutically acceptable diluent or excipient.

21. A method of treating a disease characterized by increased expression of PRMT5 in a subject, comprising administering to the subject in recognized need of such treatment, an effective amount of a compound of claim 4 or a pharmaceutically acceptable salt thereof, optionally wherein the disease is selected from cancers, metabolic diseases, and blood diseases;

wherein the cancers are selected from carcinoma; sarcoma; kidney; epidermis; liver; lung; esophagus; gallbladder; ovary; pancreas; stomach; cervix; thyroid; head and neck; prostate; skin; human breast cancers; familial melanoma; melanoma; hematopoietic tumors of lymphoid lineage; hematopoietic tumors of myeloid lineage; a tumor of the central or peripheral nervous system; seminoma; teratocarcinoma; retinoblastoma; keratoacanthoma; and thyroid follicular cancer.

22. The compound of claim 1, selected from:

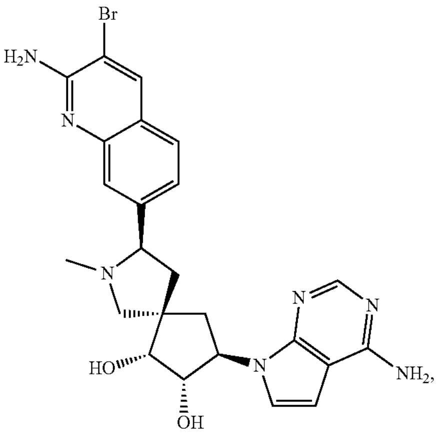

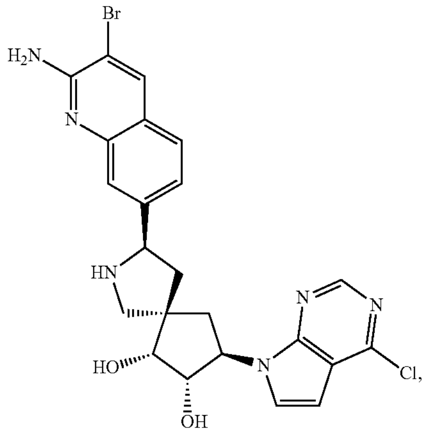

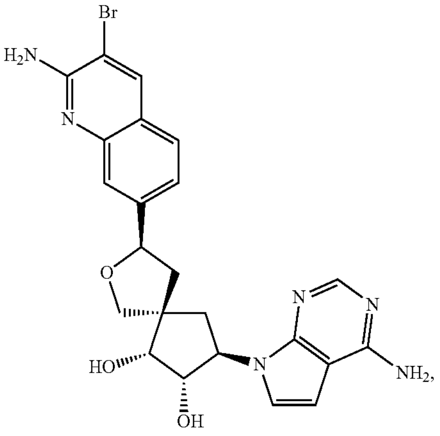

-continued

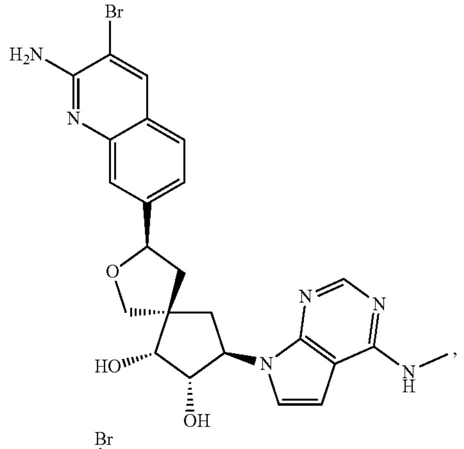

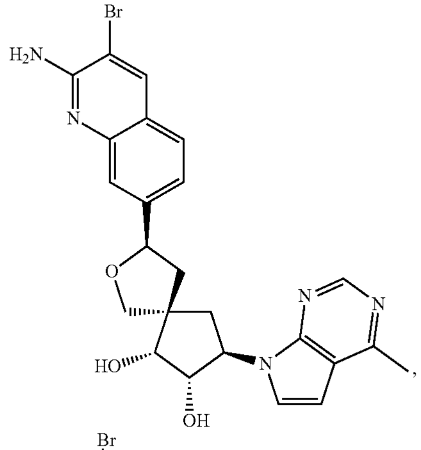

and

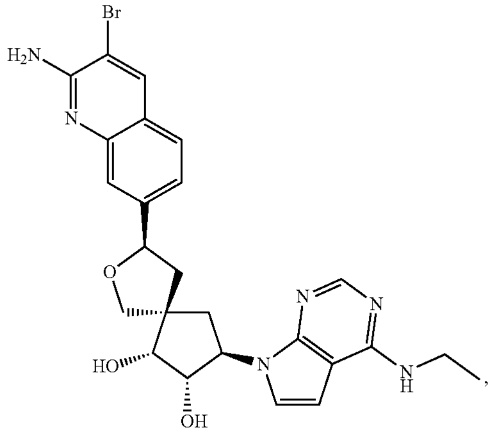

or a pharmaceutically salt thereof.

23. A pharmaceutical composition comprising a compound of claim 22 and a pharmaceutically acceptable diluent or excipient.

24. The method of claim 21, wherein the cancer is selected from:

a carcinoma of the endometrium, bladder, breast, or colon, wherein the colon carcinoma is colon adenocarcinoma or colon adenoma;

a sarcoma selected from Kaposi's, osteosarcoma, and tumor of mesenchymal origin, wherein the tumor of mesenchymal origin is fibrosarcoma or rhabdomyosarcoma;

a lung carcinoma selected from adenocarcinoma, small cell lung cancer, and non-small cell lung carcinomas;

a pancreas carcinoma, wherein the pancreas carcinoma is exocrine pancreatic carcinoma;

a skin carcinoma, wherein the skin carcinoma is squamous cell carcinoma;

human breast cancer, wherein the human breast cancer is selected from primary breast tumors, node-negative breast cancer, invasive duct adenocarcinomas of the breast, and non-endometrioid breast cancers;

hematopoietic tumors of lymphoid lineage, wherein hematopoietic tumors of lymphoid lineage are selected from leukemia, acute lymphocytic leukemia, mantle cell lymphoma, chronic lymphocytic leukemia, and B-cell lymphoma, wherein B-cell lymphoma is selected from diffuse large B cell lymphoma; T-cell lymphoma, multiple myeloma, Hodgkin's lymphoma, non-Hodgkin's lymphoma, hairy cell lymphoma, and Burkett's lymphoma;

hematopoietic tumors of myeloid lineage, wherein the hematopoietic tumors of myeloid lineage are selected from acute and chronic myelogenous leukemias, myelodysplastic syndrome, and promyelocytic leukemia; and a tumor of the central or peripheral nervous system, wherein the tumor of the central or peripheral nervous system is astrocytoma, neuroblastoma, glioma or schwannoma.

* * * * *